US006172255B1

(12) United States Patent
Fischer et al.

(10) Patent No.: US 6,172,255 B1
(45) Date of Patent: Jan. 9, 2001

(54) ALKOXY-ALKYL-SUBSTITUTED 1-H-3-ARYL-PYRROLIDINE-2,4-DIONES USED AS HERBICIDES AND PESTICIDES

(75) Inventors: Reiner Fischer, Monheim; Thomas Bretschneider, Lohmar; Bernd-Wieland Krüger, Bergisch Gladbach; Michael Ruther, Monheim; Christoph Erdelen, Leichlingen; Ulrike Wachendorff-Neumann, Neuwied; Hans-Joachim Santel; Markus Dollinger, both of Leverkusen, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/127,279

(22) Filed: Jul. 31, 1998

Related U.S. Application Data

(62) Division of application No. 08/716,200, filed as application No. PCT/EP95/01100 on Mar. 23, 1995, now Pat. No. 5,830,826.

(30) Foreign Application Priority Data

Apr. 5, 1994 (DE) .............................................. 44 11 669
Nov. 14, 1994 (DE) .............................................. 44 40 594

(51) Int. Cl.[7] ...................... C07C 233/31; C07C 231/02; C07C 231/06

(52) U.S. Cl. ................................................................ 560/24

(58) Field of Search ................................................ 560/24

(56) References Cited

FOREIGN PATENT DOCUMENTS 0 456 063 A2 * 11/1991 (EP) .
0 521 334 A1 * 1/1993 (EP) .

* cited by examiner

*Primary Examiner*—Fiona T. Powers
(74) *Attorney, Agent, or Firm*—Norris, McLaughlin & Marcus, P.A.

(57) ABSTRACT

The present invention relates to novel 1H-3-aryl-pyrrolidine-2,4-dione derivatives of the formula (I)

(I)

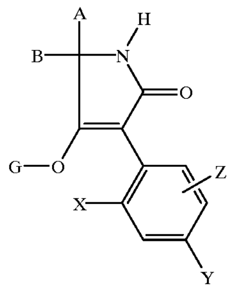

in which

A, B, G, X, Y and Z have the meaning given in the description, to processes for their preparation and to intermediates for this purpose. The compounds of the formula (I) are used as pesticides and herbicides.

2 Claims, No Drawings

ALKOXY-ALKYL-SUBSTITUTED 1-H-3-ARYL-PYRROLIDINE-2,4-DIONES USED AS HERBICIDES AND PESTICIDES

This is a divisional application of Ser. No. 08/716,200 filed on Sep. 27, 1996, now U.S. Pat. No. 5,830,826, which is a 371 of PCT/EP95/01100 filed on Mar. 23, 1995.

The invention relates to novel 1H-3-aryl-pyrrolidine-2,4-dione derivatives, to a number of processes for their preparation and to their use as pesticides, especially as insecticides and acaricides.

Pharmaceutical properties of 3-acyl-pyrrolidine-2,4-diones have been described before (S. Suzuki et al. Chem. Pharm. Bull. 15 1120 (1967)). In addition, N-phenylpyrrolidine-2,4-diones have been synthesized by R. Schmierer and H. Mildenberger (Liebigs Ann. Chem. 1985 1095). No biological activity of these compounds has been described.

EP-A 0 262 399 and GB-A 2 266 888 disclose compounds of similar structure (3-aryl-pyrrolidine-2,4-diones) for which, however, no herbicidal, insecticidal or acaricidal action has been disclosed. Compounds which are known to have herbicidal, insecticidal or acaricidal action are unsubstituted, bicyclic 3-aryl-pyrrolidine-2,4-dione derivatives (EP-A 355 599 and EP 415 211) and substituted, monocyclic 3-aryl-pyrrolidine-2,4-dione derivatives (EP-A 377 893 and EP 442 077).

Polycyclic 3-aryl-pyrrolidine-2,4-dione derivatives (EP 442 073) and 1H-3-aryl-pyrrolidine-dione derivatives (EP 456 063 and EP 521 334) are also known.

Novel substituted 1H-3-aryl-pyrrolidine-2,4-dione derivatives have now been found of the formula (I)

(I)

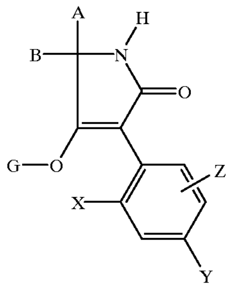

in which

A represents hydrogen, in each case optionally halogeno-substituted alkyl, alkenyl, alkoxyalkyl, polyalkoxyalkyl or alkylthioalkyl, cycloalkyl which is optionally interrupted by at least one heteroatom and optionally substituted, or represents in each case optionally halogen-, alkyl-, halogenoalkyl-, alkoxy- or nitro-substituted aryl, arylalkyl or hetaryl, B represents alkyl or alkoxyalkyl, or A and B together with the carbon atom to which they are attached represent a saturated or unsaturated, unsubstituted or substituted ring which is optionally interrupted by at least one heteroatom, X represents alkyl or alkoxy, Y represents hydrogen, alkyl or alkoxy, Z represents hydrogen, alkyl or alkoxy, G represents hydrogen (a) or represents the groups (b)

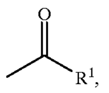

(c)

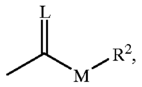

(d)

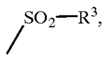

(e)

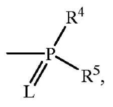

(f)

E or (g)

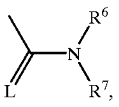

E represents a metal ion equivalent or an ammonium ion,

L represents oxygen or sulfur,

M represents oxygen or sulfur, $R^1$ represents in each case optionally halogeno-substituted alkyl, alkenyl, alkoxyalkyl, alkylthioalkyl or polyalkoxyalkyl, or optionally halogen- or alkyl-substituted cycloalkyl which may be interrupted by at least one heteroatom, or represents in each case optionally substituted phenyl, phenylalkyl, hetaryl, phenoxyalkyl or hetaryloxyalkyl, $R^2$ represents in each case optionally halogeno-substituted alkyl, alkenyl, alkoxyalkyl or polyalkoxyalkyl, or represents in each case optionally substituted cycloalkyl, phenyl or benzyl, $R^3$, $R^4$ and $R^5$ independently of one another represent in each case optionally halogeno-substituted alkyl, alkoxy, alkylamino, dialkylamino, alkylthio, alkenylthio or cycloalkylthio or represent in each case optionally substituted phenyl, phenoxy or phenylthio, $R^6$ and $R^7$ independently of one another represent hydrogen, represent in each case optionally halogeno-substituted alkyl, cycloalkyl, alkenyl, alkoxy or alkoxyalkyl, represent optionally substituted phenyl, represent optionally substituted benzyl, or together with N atom to which they are attached represent a ring which is optionally interrupted by oxygen or sulfur, with the proviso that at least one of the substituents Y and Z represents alkoxy if X represents alkyl.

Taking into account the various meanings (a), (b), (c), (d), (e), (f) and (g) of the group G results in the following principal structures (Ia) to (Ig):

(Ia)

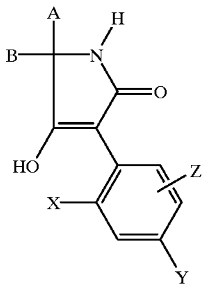

(Ib)

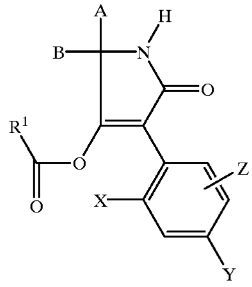

(Ic)

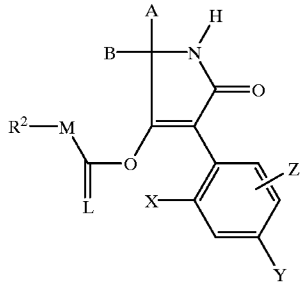

(Id)

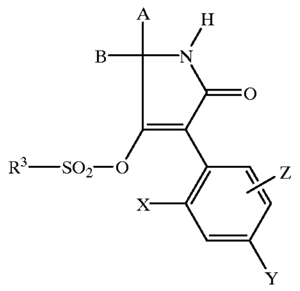

-continued (Ie)

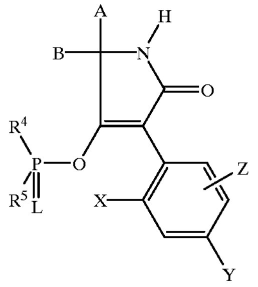

(If)

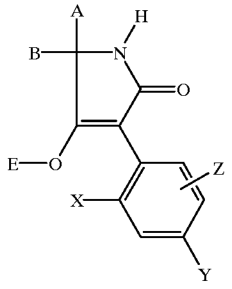

(Ig)

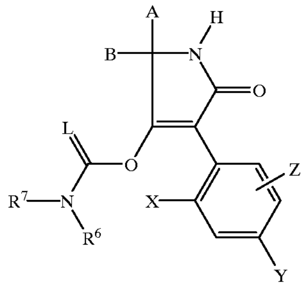

in which

A, B, E, L, M, X, Y, Z, $R^1$, $R^2$, $R^3$, $R^4$, $R^5$, $R^6$ and $R^7$ possess the meanings given above.

Because of one or more centres of chirality, the compounds of the formulae (Ia)–(Ig) are generally obtained as a mixture of stereoisomers, which can be separated if desired in a conventional manner. They may be used both in the form of their diastereomer mixtures and as pure diastereomers or enantiomers. For simplicity, the text below always uses the term compounds of the formula (Ia) to (Ig) although this refers not only to the pure compounds but also to the mixtures with different proportions of isomeric, enantiomeric and stereomeric compounds.

It has also been found that novel substituted 1H-3-aryl-pyrrolidine-2,4-dione derivatives of the formula (I) are obtained by one of the processes described below.

(A) 1H-3-Aryl-pyrrolidine-2,4-diones and/or their enols, of the formula (Ia)

(Ia)

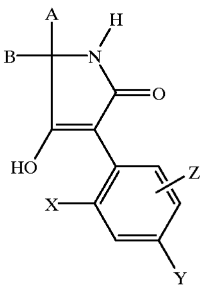

in which

A, B, X, Y and Z have the meaning given above, are obtained if

N-acylamino acid esters of the formula (II)

(II)

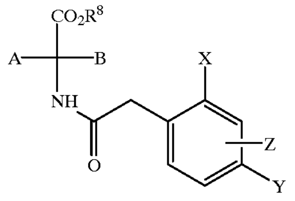

in which

A, B, X, Y and Z have the meaning given above, and $R^8$ represents alkyl, especially $C_1$–$C_6$-alkyl are subjected to intramolecular condensation in the presence of a diluent and in the presence of a base;

or (B) compounds of the formula (Ib)

(Ib)

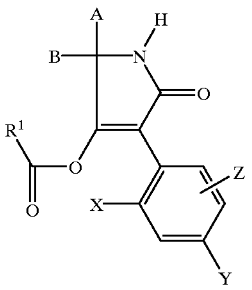

in which

A, B, X, Y, Z and $R^1$ have the meaning given above, are obtained if compounds of the formula (Ia)

(Ia)

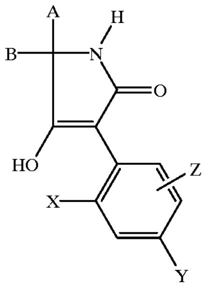

in which

A, B, X, Y and Z have the meaning given above,

α) are reacted with acid halides of the formula (III)

(III)

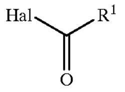

in which $R^1$ has the meaning given above and

Hal represents halogen, especially chlorine or bromine, optionally in the presence of a diluent and optionally in the presence of an acid-binding agent, or β) are reacted with carboxylic anhydrides of the formula (IV)

$R^1$—CO—O—CO—$R^1$ (IV)

in which $R^1$ has the meaning given above, optionally in the presence of a diluent and optionally in the presence of an acid-binding agent;

or (C) compounds of the formula (Ic-a)

(Ic-a)

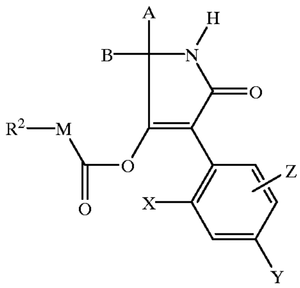

in which

A, B, X, Y, Z and $R^2$ have the meaning given above, and

M represents oxygen or sulfur are obtained if compounds of the formula (Ia)

(Ia)

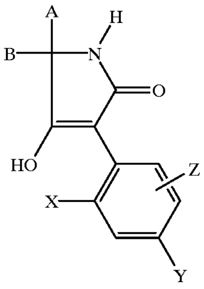

in which

A, B, X, Y and Z have the meaning given above are reacted with chloroformic esters or chloroformic thioesters of the formula (V)

$R^2$—M—CO—Cl (V)

in which $R^2$ and M have the meaning given above, optionally in the presence of a diluent and optionally in the presence of an acid-binding agent;

or (D) compounds of the formula (Ic-b)

(Ic-b)

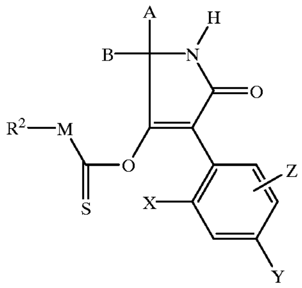

in which

A, B, $R^2$, X, Y and Z have the meaning given above and

M represents oxygen or sulfur are obtained if compounds of the formula (Ia)

(Ia)

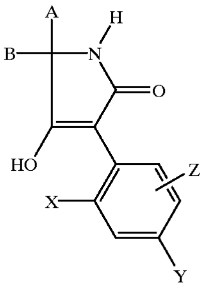

in which

A, B, X, Y and Z have the meaning given above,

α) are reacted with chloromonothioformic esters or chlorodithioformic esters of the formula (VI)

(VI)

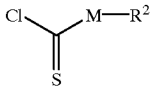

in which

M and $R^2$ have the meaning given above optionally in the presence of a diluent and optionally in the presence of an acid-binding agent, or β) are reacted with carbon disulfide and then with alkyl halides of the formula (VII)

$R^2$—Hal (VII)

in which $R^2$ has the meaning given above and

Hal represents chlorine, bromine or iodine optionally in the presence of a diluent and optionally in the presence of a base;

or (E) compounds of the formula (Id)

(Id)

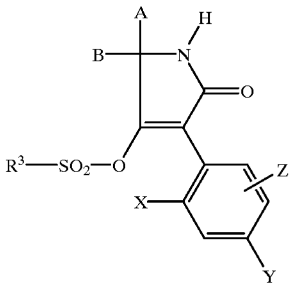

in which

A, B, X, Y, Z and $R^3$ have the meaning given above are obtained if compounds of the formula (Ia)

(Ia)

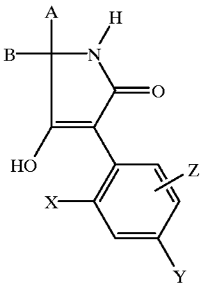

in which

A, B, X, Y and Z have the meaning given above are reacted with sulfonyl chlorides of the formula (VIII)

$R^3$—$SO_2$—Cl (VIII)

in which $R^3$ has the meaning given above optionally in the presence of a diluent and optionally in the presence of an acid-binding agent;

or (F) 3-aryl-pyrrolidine-2,4-diones of the formula (Ie)

(Ie)

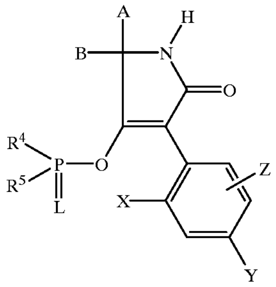

in which

A, B, L, X, Y, Z, $R^4$ and Rs have the meaning given above are obtained if 1H-3-aryl-pyrrolidine-2,4-diones of the formula (Ia) and/or their enols (Ia)

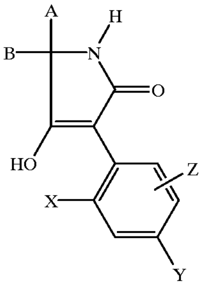

in which

A, B, X, Y and Z have the meaning given above are reacted with phosphorus compounds of the formula (IX)

(IX)

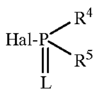

in which

L, $R^4$ and $R^5$ have the meaning given above and

Hal represents halogen, especially chlorine or bromine, optionally in the presence of a diluent and optionally in the presence of an acid-binding agent;

or (G) compounds of the formula (If)

(I-f)

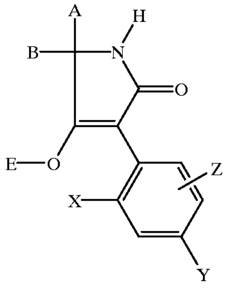

in which

A, B, X, Y and Z have the meaning given above and

E represents a metal ion equivalent or an ammonium ion are obtained if compounds of the formula (ia)

(Ia)

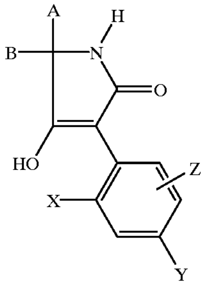

in which

A, B, X, Y and Z have the meaning given above are reacted with metal hydroxides, metal alkoxides or amines of the formulae (X) and (XI)

(X)

$Me(OR^{10})_t$ (XI)

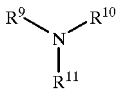

in which

Me represents mono- or divalent metal ions such as, for example, lithium, sodium, potassium, magnesium or calcium, t represents the number 1 or 2 and $R^9$, $R^{10}$ and $R^{11}$ independently of one another represent hydrogen and/or alkyl, especially $C_1$–$C_6$-alkyl, optionally in the presence of a diluent.

(H) It has also been found that compounds of the formula (Ig)

(Ig)

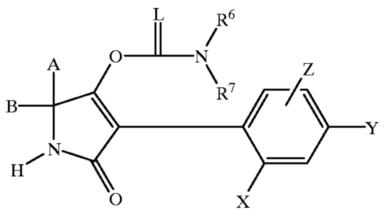

in which

A, B, L, X, Y, Z, $R^6$ and $R^7$ have the meaning given above are obtained if compounds of the formula (Ia)

(Ia)

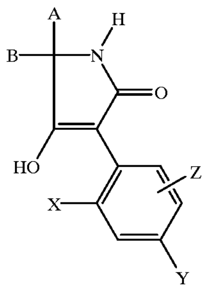

in which

A, B, X, Y and Z have the meaning given above

α) are reacted with isocyanates or isothiocyanates of the formula (XII)

$R^6—N=C=L$ (XII)

in which $R^6$ has the meaning given above optionally in the presence of a diluent and optionally in the presence of a catalyst or β) are reacted with carbamoyl chlorides or thiocarbamoyl chlorides of the formula (XIII)

(XIII)

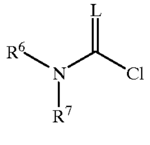

in which

L, $R^6$ and $R^7$ have the meaning given above optionally in the presence of a diluent and optionally in the presence of an acid-binding agent.

It has also been found that the novel 1H-3-aryl-pyrrolidine-2,4-dione derivatives of the formula (I) are distinguished by outstanding insecticidal, acaricidal and herbicidal actions.

The text below indicates preferred substituents and/or ranges for the radicals listed in the formulae mentioned above and below.

A preferably represents hydrogen or represents in each case optionally mono- or poly-halogeno-substituted $C_1$–$C_{12}$-alkyl, $C_2$–$C_8$-alkenyl, $C_1$–$C_{10}$-alkoxy-$C_1$–$C_8$-alkyl, $C_1$–$C_8$-polyalkoxy-$C_1$–$C_8$-alkyl or $C_1$–$C_{10}$-alkylthio-$C_1$–$C_6$-alkyl, optionally halogen-, $C_1$–$C_4$-alkyl- or $C_1$–$C_4$-alkoxy-substituted cycloalkyl having 3 to 8 ring atoms which may be interrupted by oxygen and/or sulfur, or represents in each case optionally mono- to poly-halogen-, $C_1$–$C_6$-alkyl-, $C_1$–$C_6$-halogenoalkyl-, $C_1$–$C_6$-alkoxy- and/or -nitro-substituted phenyl, naphthyl, pyridyl, imidazoyl, indolyl, thiazolyl, furanyl, thienyl, phenyl-$C_1$–$C_6$-alkyl or naphthyl-$C_1$–$C_6$-alkyl.

B preferably represents $C_1$–$C_{12}$-alkyl or $C_1$–$C_8$-alkoxy-$C_1$–$C_6$-alkyl, or A, B and the carbon atom to which they are attached preferably represent a saturated or unsaturated $C_3$–$C_{10}$ spirocyclic radical which is optionally mono-substituted or polysubstituted by $C_1$–$C_6$-alkyl, $C_3$–$C_8$-cycloalkyl, $C_1$–$C_4$-halogenoalkyl, $C_1$–$C_6$-alkoxy, $C_1$–$C_6$-alkylthio, halogen or phenyl and is optionally interrupted by oxygen or sulfur, or A, B and the carbon atom to which they are attached preferably represent a $C_3$–$C_6$ spirocyclic radical which is substituted by an alkylenediyl group optionally interrupted by one or two oxygen and/or sulfur atoms, or is substituted by an alkylenedioxy or an alkylenedithio group which forms, with the carbon to which it is attached, a further five- to eight-membered spirocyclic ring, or A, B and the carbon atom to which they are attached preferably represent a $C_3$–$C_8$ spirocyclic radical in which two substituents together represent a saturated or unsaturated five- to eight-membered ring which is optionally substituted by $C_1$–$C_4$-alkyl, $C_1$–$C_4$-alkoxy or halogen and may be interrupted by oxygen or sulfur.

A particularly preferably represents hydrogen, represents in each case optionally mono- to hexa-fluoro- or chloro-substituted $C_1$–$C_{10}$-alkyl, $C_2$–$C_6$-alkenyl, $C_1$–$C_8$-alkoxy-$C_1$–$C_6$-alkyl, $C_1$–$C_6$-polyalkoxy-$C_1$–$C_6$-alkyl or $C_1$–$C_8$-alkylthio-$C_1$–$C_6$-alkyl, represents optionally fluoro-, chloro-, $C_1$–$C_3$-alkyl- or $C_1$–$C_3$-alkoxy-substituted cycloalkyl having 3 to 7 ring atoms which may be interrupted by 1 or 2 oxygen and/or sulfur atoms, or represents in each case optionally mono- or di-fluoro-, chloro-, bromo-, -$C_1$–$C_4$-alkyl-, -$C_1$–$C_4$-halogenoalkyl-, -$C_1$–$C_4$-alkoxy- or -nitro-substituted phenyl, pyridyl, thienyl, furanyl, imidazolyl, indolyl or phenyl-$C_1$–$C_4$-alkyl.

B particularly preferably represents $C_1$–$C_{10}$-alkyl or $C_1$–$C_6$-alkoxy-$C_1$–$C_4$-alkyl, or A, B and the carbon atom to which they are attached particularly preferably represent a saturated or unsaturated $C_3$–$C_9$ spirocyclic radical which is optionally substituted one or more times by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl and is optionally interrupted by oxygen or sulfur, or A, B and the carbon atom to which they are attached particularly preferably represent a $C_3$–$C_6$ spirocyclic radical which is substituted by an alkylenediyl group optionally interrupted by one or two oxygen or sulfur atoms, or is substituted by an alkylenedioxy or by an alkylenedithio group which forms, with the carbon to which it is attached, a further five- to seven-membered spirocyclic ring, or A, B and the carbon atom to which they are attached particularly preferably represent a $C_3$–$C_6$ spirocyclic radical in which two substituents together represent a saturated or unsaturated five- to seven-membered ring which is optionally substituted by $C_1$–$C_3$-alkyl, $C_1$–$C_3$-alkoxy, fluorine, chlorine or bromine and may be interrupted by oxygen or sulfur.

A very particularly preferably represents hydrogen, in each case optionally mono- to tri-fluoro- and/or -chloro-substituted $C_1$–$C_8$-alkyl, $C_2$–$C_4$-alkenyl, $C_1$–$C_6$-alkoxy-$C_{-C_4}$-alkyl, $C_1$–$C_4$-polyalkoxy-$C_1$–$C_4$-alkyl or $C_1$–$C_6$-alkylthio-$C_1$–$C_4$-alkyl, optionally fluoro-, chloro-, methyl-, ethyl-, methoxy- or ethoxy-substituted cycloalkyl having 3 to 6 ring atoms which may be interrupted by 1 or 2 oxygen and/or sulfur atoms, or in each case optionally mono- or di-fluoro-, -chloro-, -bromo-, methyl-, -ethyl-, -propyl-, -isopropyl, -methoxy-, -ethoxy-, -trifluoromethyl- and/or -nitro-substituted phenyl, furanyl, thienyl, imidazolyl, indolyl, pyridyl or benzyl.

B very particularly preferably represents $C_1$–$C_8$-alkyl or $C_1$–$C_4$-alkoxy-$C_1$–$C_2$-alkyl, or A, B and the carbon atom to which they are attached very particularly preferably represent a saturated or unsaturated $C_3$–$C_8$ spirocyclic radical which is optionally substituted one or more times by methyl, ethyl, propyl, isopropyl, butyl, isobutyl, sec-butyl, tert-butyl, cyclohexyl, trifluoromethyl, methoxy, ethoxy, propoxy, isopropoxy, butoxy, isobutoxy, sec-butoxy, tert-butoxy, methylthio, ethylthio, fluorine, chlorine or phenyl and is optionally interrupted by oxygen or sulfur, or A, B and the carbon atom to which they are attached very particularly preferably represent a $C_5$–$C_6$ spirocyclic radical which is substituted by an alkylenediyl group optionally interrupted by an oxygen or sulfur atom, or is substituted by an alkylenedioxy group which forms, with the carbon atom to which it is attached, a further five- to seven-membered spirocyclic radical, or A, B and the carbon atom to which they are attached very particularly preferably represent a $C_3$–$C_6$ spirocyclic radical in which two substituents together represent a saturated or unsaturated five- or six-membered ring which may be interrupted by oxygen or sulfur.

X preferably represents $C_1$–$C_6$-alkyl or $C_1$–$C_6$-alkoxy.

X particularly preferably represents $C_1$–$C_5$-alkyl or $C_1$–$C_4$-alkoxy.

X very particularly preferably represents methyl, ethyl, propyl, isopropyl, methoxy, ethoxy, propoxy or isopropoxy.

Y preferably represents hydrogen, $C_1$–$C_6$-alkyl or $C_1$–$C_6$-alkoxy.

Y particularly preferably represents hydrogen, $C_1$–$C_5$-alkyl or $C_1$–$C_4$-alkoxy.

Y very particularly preferably represents hydrogen, methyl, ethyl, propyl, isopropyl, butyl, isobutyl, sec-butyl, tert-butyl, methoxy, ethoxy, propoxy or isopropoxy.

Z preferably represents hydrogen, $C_1$–$C_6$-alkyl or $C_1$–$C_6$-alkoxy.

Z particularly preferably represents hydrogen, $C_1$–$C_4$-alkyl or $C_1$–$C_4$-alkoxy.

Z very particularly preferably represents hydrogen, methyl, ethyl, propyl, isopropyl, methoxy, ethoxy, propoxy or isopropoxy.

In this context it is valid that at least one of the substituents Y and Z represents alkoxy if X represents alkyl.

G preferably represents hydrogen (a) or represents the groups (b)

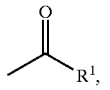

(c)

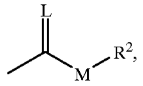

(d)

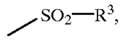

(e)

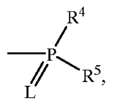

(f)

E or (g)

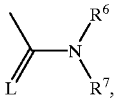

in which

E represents a metal ion equivalent or an ammonium ion,

L represents oxygen or sulfur, and

M represents oxygen or sulfur.

$R^1$ preferably represents in each case optionally mono- or poly-halogeno-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl or optionally halogen- or $C_1$–$C_6$-alkyl-substituted cycloalkyl having 3 to 8 ring atoms, which may be interrupted by at least one oxygen and/or sulfur atom, represents optionally mono- to penta- halogeno-, -nitro-, -$C_1$–$C_6$-alkyl-, -$C_1$–$C_6$-alkoxy-, -$C_1$–$C_6$-halogenoalkyl-, -$C_1$–$C_6$-halogenoalkoxy-, -$C_1$–$C_6$-halogeno-alkylthio- or -$C_1$–$C_6$-alkylsulfonyl-substituted phenyl, represents optionally mono- to penta- halogeno-, $C_1$–$C_6$-alkyl-, -$C_1$–$C_6$-alkoxy-, -$C_1$–$C_6$-halogenoalkyl- or -$C_1$–$C_6$-halogenoalkoxy-substituted phenyl-$C_1$–$C_6$-alkyl, represents optionally mono- to tri-halogeno- or -$C_1$–$C_6$-alkyl-substituted pyridyl, thienyl, furanyl, pyrazolyl, pyrimidyl or thiazolyl, represents optionally mono- to tri- halogeno- or -$C_1$–$C_6$-alkyl-substituted phenoxy-$C_1$–$C_6$-alkyl, or represents optionally mono- or di-halogeno-, -amino- or -$C_1$–$C_6$-alkyl-substituted pyridinyloxy-$C_1$–$C_6$-alkyl, pyrimidinyloxy-$C_1$–$C_6$-alkyl or thiazolyloxy-$C_1$–$C_6$-alkyl.

$R^2$ preferably represents in each case optionally mono- or poly-halogeno-substituted $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, represents optionally mono- or poly-halogeno-, $C_1$–$C_4$-alkyl- and/or -$C_1$–$C_4$-alkoxy-substituted $C_3$–$C_8$-cycloalkyl, or represents optionally mono- or tri-halogeno-, -nitro-, -$C_1$–$C_6$-alkyl-, -$C_1$–$C_6$-alkoxy- or -$C_1$–$C_6$-halogenoalkyl-substituted phenyl or benzyl, $R^3$, $R^4$ and $R^5$ independently of one another preferably represent in each case optionally mono- or poly-halogeno-substituted $C_1$–$C_8$-alkyl, $C_1$–$C_8$-alkoxy, $C_1$–$C_8$- alkylamino, di-($C_1$–$C_8$)-alkylamino, $C_1$–$C_8$-alkylthio, $C_3$–$C_6$-alkenylthio or $C_3$–$C_7$-cycloalkylthio, or represent phenyl, phenoxy or phenylthio each of which is optionally mono- or poly-substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, represent in each case optionally mono- or poly-halogeno-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, represent optionally mono- to tri-halogeno-, -$C_1$–$C_8$-halogenoalkyl-, $C_1$–$C_8$-alkyl- or $C_1$–$C_8$-alkoxy-substituted phenyl, optionally mono- to tri-halogeno-, -$C_1$–$C_8$-alkyl-, -$C_1$–$C_8$-halogenoalkyl- or -$C_1$–$C_8$-alkoxy-substituted benzyl, or together represent a $C_3$–$C_6$-alkylene radical which is optionally interrupted by oxygen or sulfur.

G particularly preferably represents hydrogen (a) or represents the groups (b)

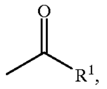

(c)

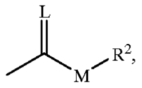

(d)

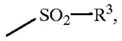

(e)

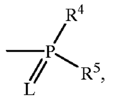

(f)

E or (g)

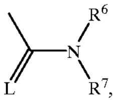

in which

E represents a metal ion equivalent or an ammonium ion,

L represents oxygen or sulfur, and

M represents oxygen or sulfur.

$R^1$ particularly preferably represents in each case optionally mono- to hexa-fluoro- or chloro-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_2$–$C_6$ -alkyl or optionally fluoro-, chloro- or $C_1$–$C_5$-alkyl-substituted cycloalkyl having 3 to 7 ring atoms, which may be interrupted by 1 or 2 oxygen and/or sulfur atoms, represents optionally mono- to tri-fluoro-, -chloro-, -bromo-, -nitro-, -$C_1$–$C_4$-alkyl-, -$C_1$–$C_4$-alkoxy-, -$C_1$–$C_3$-halogenoalkyl-, -$C_1$–$C_3$-halogenoalkoxy-, -$C_1$–$C_4$-alkylthio- or $C_1$–$C_4$-alkylsulfonyl-substituted phenyl, represents optionally mono- to tri-fluoro-, -chloro-, -bromo-, -$C_1$–$C_4$-alkyl-, -$C_1$–$C_4$-alkoxy-, -$C_1$–$C_3$-halogeno-alkyl-, or -$C_1$–$C_3$-halogenoalkoxy-substituted phenyl-$C_1$–$C_4$-alkyl, represents optionally mono- or di-fluoro-, -chloro-, -bromo- or -$C_1$–$C_4$-alkyl-substituted pyridyl, thienyl, furanyl, pyrazolyl, pyrimidyl or thiazolyl, represents optionally mono- or di-fluoro-, -chloro-, -bromo- or -$C_1$–$C_4$-alkyl-substituted phenoxy-$C_1$–$C_5$-alkyl, or represents optionally mono- or di-fluoro-, -chloro-, -bromo-, -amino- or -$C_1$–$C_4$-alkyl-substituted pyrimidinyloxy-$C_1$–$C_5$-alkyl, pyridyloxy-$C_1$–$C_5$-alkyl or thiazolyloxy-$C_1$–$C_5$-alkyl.

$R^2$ particularly preferably represents in each case optionally mono- to hexa-fluoro- or -chloro-substituted $C_1$–$C_{16}$-alkyl, $C_3$–$C_{16}$-alkenyl, $C_1$–$C_6$-alkoxy-$C_2$–$C_6$-alkyl or $C_1$–$C_6$-polyalkoxy-$C_2$–$C_6$-alkyl, represents optionally mono- to hexa-fluoro-, -chloro-, -$C_1$–$C_3$-alkyl- or -$C_1$–$C_3$-alkoxy-substituted $C_3$–$C_7$-cyclo-alkyl, represents optionally mono- or di-fluoro-, -chloro-, -bromo-, -nitro-, -$C_1$–$C_4$-alkyl-, -$C_1$–$C_3$-alkoxy- or -$C_1$–$C_3$-halogenoalkyl-substituted phenyl or benzyl.

$R_3$, $R^4$ and $R_5$ independently of one another particularly preferably represent in each case optionally mono- to hexa-fluoro- or -chloro-substituted $C_1$–$C_6$-alkyl, $C_1$–$C_6$-alkoxy-, $C_1$–$C_6$-alkylamino, di-($C_1$–$C_6$)-alkylamino, $C_1$–$C_6$-alkylthio, $C_3$–$C_4$-alkenylthio or $C_3$–$C_6$-cycloalkylthio, or represent phenyl, phenoxy or phenylthio each of which is optionally substituted once or twice by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, in each case optionally mono- to hexa-fluoro- or -chloro-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent phenyl which is optionally substituted once or twice by fluorine, chlorine, bromine, -$C_1$–$C_5$-halogenoalkyl-, $C_1$–$C_5$-alkyl- and/or $C_1$–$C_5$-alkoxy, represent benzyl which is optionally substituted once or twice by fluorine, chlorine, bromine, $C_1$–$C_5$-alkyl, $C_1$–$C_5$-halogenoalkyl or $C_1$–$C_5$-alkoxy, or together represent a $C_3$–$C_6$-alkylene radical which is optionally interrupted by oxygen or sulfur.

G very particularly preferably represents hydrogen (a) or represents the groups (b)

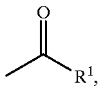

(c)

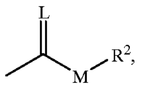

(d)

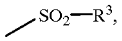

(e)

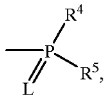

(f)

E or

-continued (g)

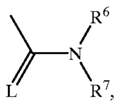

in which

E represents a metal ion equivalent or an ammonium ion,

L represents oxygen or sulfur, and

M represents oxygen or sulfur.

$R^1$ very particularly preferably represents in each case optionally mono- to tri-fluoro- or -chloro-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, or $C_1$–$C_4$-polyalkoxy-$C_2$–$C_4$-alkyl, or represents optionally fluoro-, chloro-, methyl-, ethyl-, propyl-, 2-propyl-, butyl-, isobutyl- or t-butyl-substituted cycloalkyl having 3 to 6 ring atoms, which may be interrupted by 1 or 2 oxygen and/or sulfur atoms, represents optionally mono- or di-fluoro-, -chloro-, -bromo-, -methyl-, -ethyl-, -propyl-, -isopropyl-, -methoxy-, -ethoxy-, -trifluoromethyl-, -trifluoromethoxy-, -methylthio-, -ethylthio-, -methylsulfonyl-, -ethylsulfonyl- or -nitro-substituted phenyl, represents optionally mono- or di-fluoro-, -chloro-, -bromo-, -methyl-, -ethyl-, -propyl-, -isopropyl-, -methoxy-, -ethoxy-, -trifluoromethyl-, or -trifluoromethoxy-substituted phenyl-$C_1$–$C_3$-alkyl, represents optionally mono- or di-fluoro-, -chloro-, -bromo-, -methyl- or -ethyl-substituted thienyl, furanyl or pyridyl, represents optionally mono- or di-fluoro-, -chloro-, -methyl- or -ethyl-substituted phenoxy-$C_1$–$C_4$-alkyl, or represents in each case optionally mono- or di-fluoro-, -chloro-, -amino-, -methyl- or -ethyl-substituted pyridyloxy-$C_1$–$C_4$-alkyl, pyrimidinyloxy-$C_1$–$C_4$-alkyl or thiazolyloxy-$C_1$–$C_4$-alkyl.

$R^2$ very particular preferably represents in each case optionally mono- to tri-fluoro- or -chloro-substituted $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, represents optionally mono- to tri-fluoro-, -chloro-, -methyl-, -ethyl-, -propyl-, -isopropyl- or -methoxy-substituted $C_3$–$C_6$-cycloalkyl, or represents in each case optionally mono- or di-fluoro-, -chloro-, -nitro-, -methyl-, -ethyl-, -propyl-, -isopropyl-, -methoxy-, -ethoxy- or -trifluoromethyl-substituted phenyl or benzyl.

$R^3$, $R^4$, and $R^5$ independently of one another very particularly preferably represent in each case optionally mono- to tri-fluoro- or -chloro-substituted $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, or represent phenyl, phenoxy or phenylthio each of which is optionally mono- or di-substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio, $C_1$–$C_2$-alkyl or $C_1$–$C_2$-fluoroalkyl.

$R_6$ and $R^7$ independently of one another very particularly preferably represent hydrogen, represent in each case optionally mono- to tri-fluoro- or -chloro-substituted $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_2$–$C_4$-alkyl, represent phenyl which is optionally substituted once or twice by fluorine, chlorine, bromine, $C_1$–$C_4$-halogenoalkyl, $C_1$–$C_4$-alkyl or $C_1$–$C_4$-alkoxy, represent benzyl which is optionally substituted once or twice by fluorine, chlorine, bromine, $C_1$–$C_4$-alkyl, $C_1$–$C_4$-halogenoalkyl or $C_1$–$C_4$-alkoxy, or together represent a $C_3$–$C_6$-alkylene radical which is optionally interrupted by oxygen or sulfur.

In the above definitions, where possible, saturated or unsaturated alkyl radical—both alone and in conjunction with heteroatoms, such as, for example, alkoxy or alkylthio—may be straight-chain or branched.

The optionally polysubstituted radicals may be substituted by identical or different substituents from among those specified for these radicals.

The definitions and/or explanations of radicals which are given above, given in general or within preferred ranges, may be combined with one another—ie. also between the respective ranges and preferred ranges—as desired. They apply correspondingly to the end products and also to the precursors and intermediates.

In accordance with the invention, preference is given to those compounds of the general formula (I) in which there is a combination of the meanings given above as being preferred (preferable).

In accordance with the invention, particular preference is given to the compounds of the general formula (I) in which there is a combination of the meanings given above as being particularly preferred.

In accordance with the invention, very particular preference is given to the compounds of the general formula (I) in which there is a combination of the meanings given above as being very particularly preferred.

A group of compounds which is also preferred comprises those compounds of the formula (Ih)

(Ih)

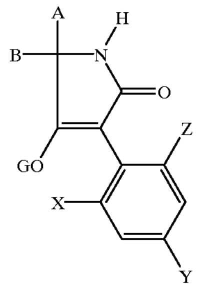

which

X and Z represent alkyl,

Y represents alkoxy, and

A, B and G have the meanings specified above.

Preference is also given to compounds of the formula (Ih) shown above in which

X and Y represent alkyl,

Z represents alkoxy, and

A, B and G have the meanings specified above.

Preference is additionally given to compounds of the formula (Ih) shown above in which X represent alkyl, Y represents hydrogen, Z represents alkoxy, and A, B and G have the meanings specified above.

A further group of preferred compounds comprise those of the formula (Ih) shown above in which X represents alkyl, Y represents alkoxy, Z represents hydrogen, and A, B and G have the meanings specified above.

A further group of preferred compounds comprise those of the formula (Ih) shown above in which X represents alkoxy, Y represents alkyl, Z represents hydrogen, and A, B and G have the meanings specified above.

Specific mention may be made, in addition to the compounds specified in the Preparation Examples, of the following compounds of the formula (Ia):

(Ia)

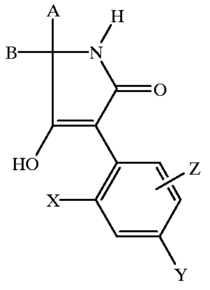

| X | Y | Z | A | B |
|---|---|---|---|---|
| $CH_3$ | $OCH_3$ | H | $CH_3$ | H |
| $CH_3$ | $OCH_3$ | H | $C_2H_5$ | H |
| $CH_3$ | $OCH_3$ | H | $C_3H_7$ | H |
| $CH_3$ | $OCH_3$ | H | i-$C_3H_7$ | H |
| $CH_3$ | $OCH_3$ | H | $C_4H_9$ | H |
| $CH_3$ | $OCH_3$ | H | i-$C_4H_9$ | H |
| $CH_3$ | $OCH_3$ | H | s-$C_4H_9$ | H |
| $CH_3$ | $OCH_3$ | H | t-$C_4H_9$ | H |
| $CH_3$ | $OCH_3$ | H | $CH_3$ | $CH_3$ |
| $CH_3$ | $OCH_3$ | H | $C_2H_5$ | $CH_3$ |
| $CH_3$ | $OCH_3$ | H | $C_3H_7$ | $CH_3$ |
| $CH_3$ | $OCH_3$ | H | i-$C_3H_7$ | $CH_3$ |
| $CH_3$ | $OCH_3$ | H | $C_4H_9$ | $CH_3$ |
| $CH_3$ | $OCH_3$ | H | i-$C_4H_9$ | $CH_3$ |
| $CH_3$ | $OCH_3$ | H | s-$C_4H_9$ | $CH_3$ |
| $CH_3$ | $OCH_3$ | H | t-$C_4H_9$ | $CH_3$ |
| $CH_3$ | $OCH_3$ | H | $C_2H_5$ | $C_2H_5$ |
| $CH_3$ | $OCH_3$ | H | $C_3H_7$ | $C_3H_7$ |
| $CH_3$ | $OCH_3$ | H | 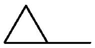 | $CH_3$ |
| $CH_3$ | $OCH_3$ | H | 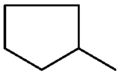 | $CH_3$ |
| /$CH_3$ | $OCH_3$ | H | 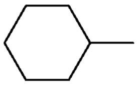 | $CH_3$ |
| $CH_3$ | H | 6-$OCH_3$ | $CH_3$ | H |
| $CH_3$ | H | 6-$OCH_3$ | $C_2H_5$ | H |
| $CH_3$ | H | 6-$OCH_3$ | $C_3H_7$ | H |
| $CH_3$ | H | 6-$OCH_3$ | i-$C_3H_7$ | H |
| $CH_3$ | H | 6-$OCH_3$ | $C_4H_9$ | H |
| $CH_3$ | H | 6-$OCH_3$ | i-$C_4H_9$ | H |
| $CH_3$ | H | 6-$OCH_3$ | s-$C_4H_9$ | H |
| $CH_3$ | H | 6-$OCH_3$ | t-$C_4H_9$ | H |
| $CH_3$ | H | 6-$OCH_3$ | $CH_3$ | $CH_3$ |
| $CH_3$ | H | 6-$OCH_3$ | $C_2H_5$ | $CH_3$ |
| $CH_3$ | H | 6-$OCH_3$ | $C_3H_7$ | $CH_3$ |
| $CH_3$ | H | 6-$OCH_3$ | i-$C_3H_7$ | $CH_3$ |
| $CH_3$ | H | 6-$OCH_3$ | $C_4H_9$ | $CH_3$ |
| $CH_3$ | H | 6-$OCH_3$ | i-$C_4H_9$ | $CH_3$ |
| $CH_3$ | H | 6-$OCH_3$ | s-$C_4H_9$ | $CH_3$ |
| $CH_3$ | H | 6-$OCH_3$ | t-$C_4H_9$ | $CH_3$ |
| $CH_3$ | H | 6-$OCH_3$ | $C_2H_5$ | $C_2H_5$ |

-continued

| | | | | |
|---|---|---|---|---|
| $CH_3$ | H | 6-$OCH_3$ | $C_3H_7$ | $C_3H_7$ |
| $CH_3$ | H | 6-$OCH_3$ | 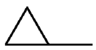 | $CH_3$ |
| $CH_3$ | H | 6-$OCH_3$ | 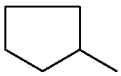 | $CH_3$ |
| $CH_3$ | H | 6-$OCH_3$ | 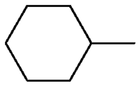 | $CH_3$ |
| $CH_3$ | $CH_3$ | 6-$OCH_3$ | $CH_3$ | H |
| $CH_3$ | $CH_3$ | 6-$OCH_3$ | $C_2H_5$ | H |
| $CH_3$ | $CH_3$ | 6-$OCH_3$ | $C_3H_7$ | H |
| $CH_3$ | $CH_3$ | 6-$OCH_3$ | i-$C_3H_7$ | H |
| $CH_3$ | $CH_3$ | 6-$OCH_3$ | $C_4H_9$ | H |
| $CH_3$ | $CH_3$ | 6-$OCH_3$ | i-$C_4H_9$ | H |
| $CH_3$ | $CH_3$ | 6-$OCH_3$ | s-$C_4H_9$ | H |
| $CH_3$ | $CH_3$ | 6-$OCH_3$ | t-$C_4H_9$ | H |
| $CH_3$ | $CH_3$ | 6-$OCH_3$ | $CH_3$ | $CH_3$ |
| $CH_3$ | $CH_3$ | 6-$OCH_3$ | $C_2H_5$ | $CH_3$ |
| $CH_3$ | $CH_3$ | 6-$OCH_3$ | $C_3H_7$ | $CH_3$ |
| $CH_3$ | $CH_3$ | 6-$OCH_3$ | i-$C_3H_7$ | $CH_3$ |
| $CH_3$ | $CH_3$ | 6-$OCH_3$ | $C_4H_9$ | $CH_3$ |
| $CH_3$ | $CH_3$ | 6-$OCH_3$ | i-$C_4H_9$ | $CH_3$ |
| $CH_3$ | $CH_3$ | 6-$OCH_3$ | s-$C_4H_9$ | $CH_3$ |
| $CH_3$ | $CH_3$ | 6-$OCH_3$ | t-$C_4H_9$ | $CH_3$ |
| $CH_3$ | $CH_3$ | 6-$OCH_3$ | $C_2H_5$ | $C_2H_5$ |
| $CH_3$ | $CH_3$ | 6-$OCH_3$ | $C_3H_7$ | $C_3H_7$ |
| $CH_3$ | $CH_3$ | 6-$OCH_3$ | 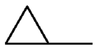 | $CH_3$ |
| $CH_3$ | $CH_3$ | 6-$OCH_3$ | 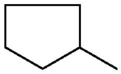 | $CH_3$ |
| $CH_3$ | $CH_3$ | 6-$OCH_3$ | 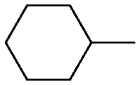 | $CH_3$ |
| $CH_3$ | $OCH_3$ | 6-$CH_3$ | $CH_3$ | H |
| $CH_3$ | $OCH_3$ | 6-$CH_3$ | $C_2H_5$ | H |
| $CH_3$ | $OCH_3$ | 6-$CH_3$ | $C_3H_7$ | H |
| $CH_3$ | $OCH_3$ | 6-$CH_3$ | i-$C_3H_7$ | H |
| $CH_3$ | $OCH_3$ | 6-$CH_3$ | $C_4H_9$ | H |
| $CH_3$ | $OCH_3$ | 6-$CH_3$ | i-$C_4H_9$ | H |
| $CH_3$ | $OCH_3$ | 6-$CH_3$ | s-$C_4H_9$ | H |
| $CH_3$ | $OCH_3$ | 6-$CH_3$ | t-$C_4H_9$ | H |
| $CH_3$ | $OCH_3$ | 6-$CH_3$ | $CH_3$ | $CH_3$ |
| $CH_3$ | $OCH_3$ | 6-$CH_3$ | $C_2H_5$ | $CH_3$ |
| $CH_3$ | $OCH_3$ | 6-$CH_3$ | $C_3H_7$ | $CH_3$ |
| $CH_3$ | $OCH_3$ | 6-$CH_3$ | i-$C_3H_7$ | $CH_3$ |
| $CH_3$ | $OCH_3$ | 6-$CH_3$ | $C_4H_9$ | $CH_3$ |
| $CH_3$ | $OCH_3$ | 6-$CH_3$ | i-$C_4H_9$ | $CH_3$ |
| $CH_3$ | $OCH_3$ | 6-$CH_3$ | s-$C_4H_9$ | $CH_3$ |
| $CH_3$ | $OCH_3$ | 6-$CH_3$ | t-$C_4H_9$ | $CH_3$ |
| $CH_3$ | $OCH_3$ | 6-$CH_3$ | $C_2H_5$ | $C_2H_5$ |
| $CH_3$ | $OCH_3$ | 6-$CH_3$ | $C_3H_7$ | $C_3H_7$ |
| $CH_3$ | $OCH_3$ | 6-$CH_3$ | 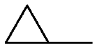 | $CH_3$ |
| $CH_3$ | $OCH_3$ | 6-$CH_3$ | 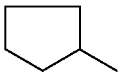 | $CH_3$ |

-continued

| | | | | |
|---|---|---|---|---|
| $CH_3$ | $OCH_3$ | 6-$CH_3$ | 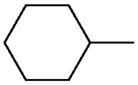 | $CH_3$ |

-continued

| X | Y | Z | A | B |
|---|---|---|---|---|
| $CH_3$ | $OCH_3$ | H | | $-(CH_2)_2-$ |
| $CH_3$ | $OCH_3$ | H | | $-(CH_2)_4-$ |
| $CH_3$ | $OCH_3$ | H | | $-(CH_2)_5-$ |
| $CH_3$ | $OCH_3$ | H | | $-(CH_2)_6-$ |
| $CH_3$ | $OCH_3$ | H | | $-(CH_2)_7-$ |
| $CH_3$ | $OCH_3$ | H | | $-(CH_2)_2-O-(CH_2)_2-$ |
| $CH_3$ | $OCH_3$ | H | | $-(CH_2)_2-S-(CH_2)_2-$ |
| $CH_3$ | $OCH_3$ | H | | $-CH_2-CHCH_3-(CH_2)_3-$ |
| $CH_3$ | $OCH_3$ | H | | $-(CH_2)_2-CHCH_3-(CH_2)_2-$ |
| $CH_3$ | $OCH_3$ | H | | $-(CH_2)_2-CHC_2H_5-(CH_2)_2-$ |
| $CH_3$ | $OCH_3$ | H | | $-(CH_2)_2-CHC_3H_7-(CH_2)_2-$ |
| $CH_3$ | $OCH_3$ | H | | $-(CH_2)_2-CHi\text{-}C_3H_7-(CH_2)_2-$ |
| $CH_3$ | $OCH_3$ | H | | $-(CH_2)_2-CHOCH_3-(CH_2)_2-$ |
| $CH_3$ | $OCH_3$ | H | | $-(CH_2)_2-CHOC_2H_5-(CH_2)_2-$ |
| $CH_3$ | $OCH_3$ | H | | $-(CH_2)_2-CHOC_3H_7-(CH_2)_2-$ |
| $CH_3$ | $OCH_3$ | H | | $-(CH_2)_2-CHi\text{-}OC_3H_7-(CH_2)_2-$ |
| $CH_3$ | $OCH_3$ | H | | $-(CH_2)_2-C(CH_3)_2-(CH_2)_2-$ |
| $CH_3$ | $OCH_3$ | H | | $-CH_2-(CHCH_3)_2-(CH_2)_2-$ |
| $CH_3$ | $OCH_3$ | H | | 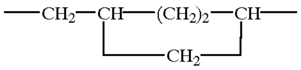 |
| $CH_3$ | $OCH_3$ | H | | 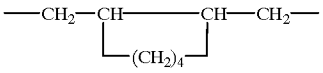 |
| $CH_3$ | $OCH_3$ | H | | 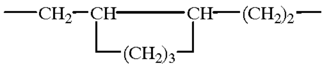 |
| $CH_3$ | H | 6-$OCH_3$ | | $-(CH_2)_2-$ |
| $CH_3$ | H | 6-$OCH_3$ | | $-(CH_2)_4-$ |
| $CH_3$ | H | 6-$OCH_3$ | | $-(CH_2)_5-$ |
| $CH_3$ | H | 6-$OCH_3$ | | $-(CH_2)_6-$ |
| $CH_3$ | H | 6-$OCH_3$ | | $-(CH_2)_7-$ |
| $CH_3$ | H | 6-$OCH_3$ | | $-(CH_2)_2-O-(CH_2)_2-$ |
| $CH_3$ | H | 6-$OCH_3$ | | $-(CH_2)_2-S-(CH_2)_2-$ |
| $CH_3$ | H | 6-$OCH_3$ | | $-CH_2-CHCH_3-(CH_2)_3-$ |
| $CH_3$ | H | 6-$OCH_3$ | | $-(CH_2)_2-CHCH_3-(CH_2)_2-$ |
| $CH_3$ | H | 6-$OCH_3$ | | $-(CH_2)_2-CHC_2H_5-(CH_2)_2-$ |
| $CH_3$ | H | 6-$OCH_3$ | | $-(CH_2)_2-CHC_3H_7-(CH_2)_2-$ |
| $CH_3$ | H | 6-$OCH_3$ | | $-(CH_2)_2-CHi\text{-}C_3H_7-(CH_2)_2-$ |
| $CH_3$ | H | 6-$OCH_3$ | | $-(CH_2)_2-CHOCH_3-(CH_2)_2-$ |
| $CH_3$ | H | 6-$OCH_3$ | | $-(CH_2)_2-CHOC_2H_5-(CH_2)_2-$ |
| $CH_3$ | H | 6-$OCH_3$ | | $-(CH_2)_2-CHOC_3H_7-(CH_2)_2-$ |
| $CH_3$ | H | 6-$OCH_3$ | | $-(CH_2)_2-CHi\text{-}OC_3H_7-(CH_2)_2-$ |
| $CH_3$ | H | 6-$OCH_3$ | | $-(CH_2)_2-C(CH_3)_2-(CH_2)_2-$ |
| $CH_3$ | H | 6-$OCH_3$ | | $-CH_2-(CHCH_3)_2-(CH_2)_2-$ |
| $CH_3$ | H | 6-$OCH_3$ | | 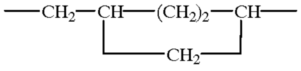 |
| $CH_3$ | H | 6-$OCH_3$ | | 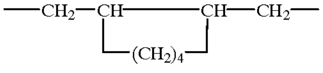 |
| $CH_3$ | H | 6-$OCH_3$ | | 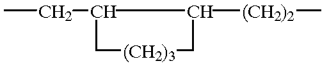 |
| $CH_3$ | $CH_3$ | 6-$OCH_3$ | | $-(CH_2)_2-$ |
| $CH_3$ | $CH_3$ | 6-$OCH_3$ | | $-(CH_2)_4-$ |
| $CH_3$ | $CH_3$ | 6-$OCH_3$ | | $-(CH_2)_5-$ |
| $CH_3$ | $CH_3$ | 6-$OCH_3$ | | $-(CH_2)_6-$ |
| $CH_3$ | $CH_3$ | 6-$OCH_3$ | | $-(CH_2)_7-$ |
| $CH_3$ | $CH_3$ | 6-$OCH_3$ | | $-(CH_2)_2-O-(CH_2)_2-$ |
| $CH_3$ | $CH_3$ | 6-$OCH_3$ | | $-(CH_2)_2-S-(CH_2)_2-$ |
| $CH_3$ | $CH_3$ | 6-$OCH_3$ | | $-CH_2-CHCH_3-(CH_2)_3-$ |
| $CH_3$ | $CH_3$ | 6-$OCH_3$ | | $-(CH_2)_2-CHCH_3-(CH_2)_2-$ |
| $CH_3$ | $CH_3$ | 6-$OCH_3$ | | $-(CH_2)_2-CHC_2H_5-(CH_2)_2-$ |
| $CH_3$ | $CH_3$ | 6-$OCH_3$ | | $-(CH_2)_2-CHC_3H_7-(CH_2)_2-$ |
| $CH_3$ | $CH_3$ | 6-$OCH_3$ | | $-(CH_2)_2-CHi\text{-}C_3H_7-(CH_2)_2-$ |
| $CH_3$ | $CH_3$ | 6-$OCH_3$ | | $-(CH_2)_2-CHOCH_3-(CH_2)_2-$ |
| $CH_3$ | $CH_3$ | 6-$OCH_3$ | | $-(CH_2)_2-CHOC_2H_5-(CH_2)_2-$ |
| $CH_3$ | $CH_3$ | 6-$OCH_3$ | | $-(CH_2)_2-CHOC_3H_7-(CH_2)_2-$ |
| $CH_3$ | $CH_3$ | 6-$OCH_3$ | | $-(CH_2)_2-CHi\text{-}OC_3H_7-(CH_2)_2-$ |
| $CH_3$ | $CH_3$ | 6-$OCH_3$ | | $-(CH_2)_2-C(CH_3)_2-(CH_2)_2-$ |
| $CH_3$ | $CH_3$ | 6-$OCH_3$ | | $-CH_2-(CHCH_3)_2-(CH_2)_2-$ |
| $CH_3$ | $CH_3$ | 6-$OCH_3$ | | 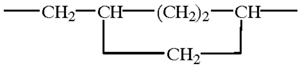 |
| $CH_3$ | $CH_3$ | 6-$OCH_3$ | | 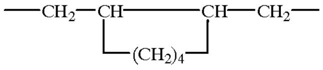 |
| $CH_3$ | $CH_3$ | 6-$OCH_3$ | | 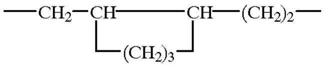 |
| $CH_3$ | $OCH_3$ | 6-$CH_3$ | | $-(CH_2)_2-$ |
| $CH_3$ | $OCH_3$ | 6-$CH_3$ | | $-(CH_2)_4-$ |
| $CH_3$ | $OCH_3$ | 6-$CH_3$ | | $-(CH_2)_5-$ |
| $CH_3$ | $OCH_3$ | 6-$CH_3$ | | $-(CH_2)_6-$ |
| $CH_3$ | $OCH_3$ | 6-$CH_3$ | | $-(CH_2)_7-$ |
| $CH_3$ | $OCH_3$ | 6-$CH_3$ | | $-(CH_2)_2-O-(CH_2)_2-$ |
| $CH_3$ | $OCH_3$ | 6-$CH_3$ | | $-(CH_2)_2-S-(CH_2)_2-$ |
| $CH_3$ | $OCH_3$ | 6-$CH_3$ | | $-CH_2-CHCH_3-(CH_2)_3-$ |
| $CH_3$ | $OCH_3$ | 6-$CH_3$ | | $-(CH_2)_2-CHCH_3-(CH_2)_2-$ |
| $CH_3$ | $OCH_3$ | 6-$CH_3$ | | $-(CH_2)_2-CHC_2H_5-(CH_2)_2-$ |
| $CH_3$ | $OCH_3$ | 6-$CH_3$ | | $-(CH_2)_2-CHC_3H_7-(CH_2)_2-$ |
| $CH_3$ | $OCH_3$ | 6-$CH_3$ | | $-(CH_2)_2-CHi\text{-}C_3H_7-(CH_2)_2-$ |
| $CH_3$ | $OCH_3$ | 6-$CH_3$ | | $-(CH_2)_2-CHOCH_3-(CH_2)_2-$ |
| $CH_3$ | $OCH_3$ | 6-$CH_3$ | | $-(CH_2)_2-CHOC_2H_5-(CH_2)_2-$ |
| $CH_3$ | $OCH_3$ | 6-$CH_3$ | | $-(CH_2)_2-CHOC_3H_7-(CH_2)_2-$ |
| $CH_3$ | $OCH_3$ | 6-$CH_3$ | | $-(CH_2)_2-CHi\text{-}OC_3H_7-(CH_2)_2-$ |
| $CH_3$ | $OCH_3$ | 6-$CH_3$ | | $-(CH_2)_2-C(CH_3)_2-(CH_2)_2-$ |
| $CH_3$ | $OCH_3$ | 6-$CH_3$ | | $-CH_2-(CHCH_3)_2-(CH_2)_2-$ |
| $CH_3$ | $OCH_3$ | 6-$CH_3$ | | 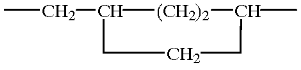 |
| $CH_3$ | $OCH_3$ | 6-$CH_3$ | | 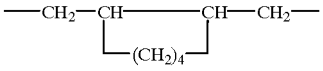 |
| $CH_3$ | $OCH_3$ | 6-$CH_3$ | | 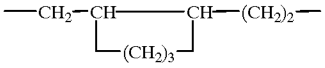 |

Specific mention may be made, in addition to the compounds specified in the Preparation Examples, of the following compounds of the formula (Ib):

TABLE 2

(Ib)

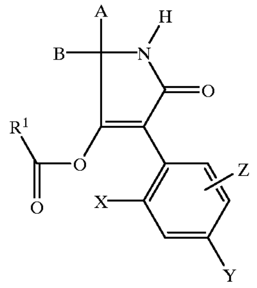

| X | Y | Z | A | B | $R^1$ |
|---|---|---|---|---|---|
| $CH_3$ | $OCH_3$ | H | $CH_3$ | H | $CH_3$ |
| $CH_3$ | $OCH_3$ | H | $C_2H_5$ | H | $CH_3$ |
| $CH_3$ | $OCH_3$ | H | $C_3H_7$ | H | $CH_3$ |
| $CH_3$ | $OCH_3$ | H | i-$C_3H_7$ | H | $CH_3$ |
| $CH_3$ | $OCH_3$ | H | $C_4H_9$ | H | $CH_3$ |
| $CH_3$ | $OCH_3$ | H | i-$C_4H_9$ | H | $CH_3$ |
| $CH_3$ | $OCH_3$ | H | s-$C_4H_9$ | H | $CH_3$ |
| $CH_3$ | $OCH_3$ | H | t-$C_4H_9$ | H | $CH_3$ |
| $CH_3$ | $OCH_3$ | H | $CH_3$ | $CH_3$ | $CH_3$ |
| $CH_3$ | $OCH_3$ | H | $C_2H_5$ | $CH_3$ | $CH_3$ |
| $CH_3$ | $OCH_3$ | H | $C_3H_7$ | $CH_3$ | $CH_3$ |
| $CH_3$ | $OCH_3$ | H | i-$C_3H_7$ | $CH_3$ | $CH_3$ |
| $CH_3$ | $OCH_3$ | H | $C_4H_9$ | $CH_3$ | $CH_3$ |
| $CH_3$ | $OCH_3$ | H | i-$C_4H_9$ | $CH_3$ | $CH_3$ |
| $CH_3$ | $OCH_3$ | H | s-$C_4H_9$ | $CH_3$ | $CH_3$ |
| $CH_3$ | $OCH_3$ | H | t-$C_4H_9$ | $CH_3$ | $CH_3$ |
| $CH_3$ | $OCH_3$ | H | $C_2H_5$ | $C_2H_5$ | $CH_3$ |
| $CH_3$ | $OCH_3$ | H | $C_3H_7$ | $C_3H_7$ | $CH_3$ |
| $CH_3$ | $OCH_3$ | H | 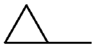 | $CH_3$ | $CH_3$ |
| $CH_3$ | $OCH_3$ | H | 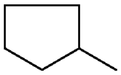 | $CH_3$ | $CH_3$ |
| $CH_3$ | $OCH_3$ | H | 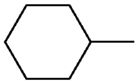 | $CH_3$ | $CH_3$ |
| $CH_3$ | H | 6-$OCH_3$ | $CH_3$ | H | $CH_3$ |
| $CH_3$ | H | 6-$OCH_3$ | $C_2H_5$ | H | $CH_3$ |
| $CH_3$ | H | 6-$OCH_3$ | $C_3H_7$ | H | $CH_3$ |
| $CH_3$ | H | 6-$OCH_3$ | i-$C_3H_7$ | H | $CH_3$ |
| $CH_3$ | H | 6-$OCH_3$ | $C_4H_9$ | H | $CH_3$ |
| $CH_3$ | H | 6-$OCH_3$ | i-$C_4H_9$ | H | $CH_3$ |
| $CH_3$ | H | 6-$OCH_3$ | s-$C_4H_9$ | H | $CH_3$ |
| $CH_3$ | H | 6-$OCH_3$ | t-$C_4H_9$ | H | $CH_3$ |
| $CH_3$ | H | 6-$OCH_3$ | $CH_3$ | $CH_3$ | $CH_3$ |
| $CH_3$ | H | 6-$OCH_3$ | $C_2H_5$ | $CH_3$ | $CH_3$ |
| $CH_3$ | H | 6-$OCH_3$ | $C_3H_7$ | $CH_3$ | $CH_3$ |
| $CH_3$ | H | 6-$OCH_3$ | i-$C_3H_7$ | $CH_3$ | $CH_3$ |
| $CH_3$ | H | 6-$OCH_3$ | $C_4H_9$ | $CH_3$ | $CH_3$ |
| $CH_3$ | H | 6-$OCH_3$ | i-$C_4H_9$ | $CH_3$ | $CH_3$ |
| $CH_3$ | H | 6-$OCH_3$ | s-$C_4H_9$ | $CH_3$ | $CH_3$ |
| $CH_3$ | H | 6-$OCH_3$ | t-$C_4H_9$ | $CH_3$ | $CH_3$ |
| $CH_3$ | H | 6-$OCH_3$ | $C_2H_5$ | $C_2H_5$ | $CH_3$ |
| $CH_3$ | H | 6-$OCH_3$ | $C_3H_7$ | $C_3H_7$ | $CH_3$ |
| $CH_3$ | H | 6-$OCH_3$ | 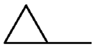 | $CH_3$ | $CH_3$ |
| $CH_3$ | H | 6-$OCH_3$ | 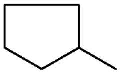 | $CH_3$ | $CH_3$ |

TABLE 2-continued (Ib)

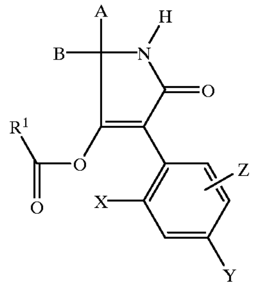

| X | Y | Z | A | B | $R^1$ |
|---|---|---|---|---|---|
| $CH_3$ | H | 6-$OCH_3$ | 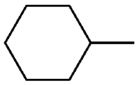 | $CH_3$ | $CH_3$ |
| $CH_3$ | $CH_3$ | 6-$OCH_3$ | $CH_3$ | H | $CH_3$ |
| $CH_3$ | $CH_3$ | 6-$OCH_3$ | $C_2H_5$ | H | $CH_3$ |
| $CH_3$ | $CH_3$ | 6-$OCH_3$ | $C_3H_7$ | H | $CH_3$ |
| $CH_3$ | $CH_3$ | 6-$OCH_3$ | i-$C_3H_7$ | H | $CH_3$ |
| $CH_3$ | $CH_3$ | 6-$OCH_3$ | $C_4H_9$ | H | $CH_3$ |
| $CH_3$ | $CH_3$ | 6-$OCH_3$ | i-$C_4H_9$ | H | $CH_3$ |
| $CH_3$ | $CH_3$ | 6-$OCH_3$ | s-$C_4H_9$ | H | $CH_3$ |
| $CH_3$ | $CH_3$ | 6-$OCH_3$ | t-$C_4H_9$ | H | $CH_3$ |
| $CH_3$ | $CH_3$ | 6-$OCH_3$ | $CH_3$ | $CH_3$ | $CH_3$ |
| $CH_3$ | $CH_3$ | 6-$OCH_3$ | $C_2H_5$ | $CH_3$ | $CH_3$ |
| $CH_3$ | $CH_3$ | 6-$OCH_3$ | $C_3H_7$ | $CH_3$ | $CH_3$ |
| $CH_3$ | $CH_3$ | 6-$OCH_3$ | i-$C_3H_7$ | $CH_3$ | $CH_3$ |
| $CH_3$ | $CH_3$ | 6-$OCH_3$ | $C_4H_9$ | $CH_3$ | $CH_3$ |
| $CH_3$ | $CH_3$ | 6-$OCH_3$ | i-$C_4H_9$ | $CH_3$ | $CH_3$ |
| $CH_3$ | $CH_3$ | 6-$OCH_3$ | s-$C_4H_9$ | $CH_3$ | $CH_3$ |
| $CH_3$ | $CH_3$ | 6-$OCH_3$ | t-$C_4H_9$ | $CH_3$ | $CH_3$ |
| $CH_3$ | $CH_3$ | 6-$OCH_3$ | $C_2H_5$ | $C_2H_5$ | $CH_3$ |
| $CH_3$ | $CH_3$ | 6-$OCH_3$ | $C_3H_7$ | $C_3H_7$ | $CH_3$ |
| $CH_3$ | $CH_3$ | 6-$OCH_3$ | 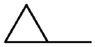 | $CH_3$ | $CH_3$ |
| $CH_3$ | $CH_3$ | 6-$OCH_3$ | 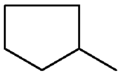 | $CH_3$ | $CH_3$ |
| $CH_3$ | $CH_3$ | 6-$OCH_3$ | 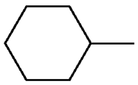 | $CH_3$ | $CH_3$ |
| $CH_3$ | $OCH_3$ | 6-$CH_3$ | $CH_3$ | H | $CH_3$ |
| $CH_3$ | $OCH_3$ | 6-$CH_3$ | $C_2H_5$ | H | $CH_3$ |
| $CH_3$ | $OCH_3$ | 6-$CH_3$ | $C_3H_7$ | H | $CH_3$ |
| $CH_3$ | $OCH_3$ | 6-$CH_3$ | i-$C_3H_7$ | H | $CH_3$ |
| $CH_3$ | $OCH_3$ | 6-$CH_3$ | $C_4H_9$ | H | $CH_3$ |
| $CH_3$ | $OCH_3$ | 6-$CH_3$ | i-$C_4H_9$ | H | $CH_3$ |
| $CH_3$ | $OCH_3$ | 6-$CH_3$ | s-$C_4H_9$ | H | $CH_3$ |
| $CH_3$ | $OCH_3$ | 6-$CH_3$ | t-$C_4H_9$ | H | $CH_3$ |
| $CH_3$ | $OCH_3$ | 6-$CH_3$ | $CH_3$ | $CH_3$ | $CH_3$ |
| $CH_3$ | $OCH_3$ | 6-$CH_3$ | $C_2H_5$ | $CH_3$ | $CH_3$ |
| $CH_3$ | $OCH_3$ | 6-$CH_3$ | $C_3H_7$ | $CH_3$ | $CH_3$ |
| $CH_3$ | $OCH_3$ | 6-$CH_3$ | i-$C_3H_7$ | $CH_3$ | $CH_3$ |
| $CH_3$ | $OCH_3$ | 6-$CH_3$ | $C_4H_9$ | $CH_3$ | $CH_3$ |
| $CH_3$ | $OCH_3$ | 6-$CH_3$ | i-$C_4H_9$ | $CH_3$ | $CH_3$ |
| $CH_3$ | $OCH_3$ | 6-$CH_3$ | s-$C_4H_9$ | $CH_3$ | $CH_3$ |
| $CH_3$ | $OCH_3$ | 6-$CH_3$ | t-$C_4H_9$ | $CH_3$ | $CH_3$ |
| $CH_3$ | $OCH_3$ | 6-$CH_3$ | $C_2H_5$ | $C_2H_5$ | $CH_3$ |
| $CH_3$ | $OCH_3$ | 6-$CH_3$ | $C_3H_7$ | $C_3H_7$ | $CH_3$ |
| $CH_3$ | $OCH_3$ | 6-$CH_3$ | 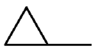 | $CH_3$ | $CH_3$ |

TABLE 2-continued (Ib)

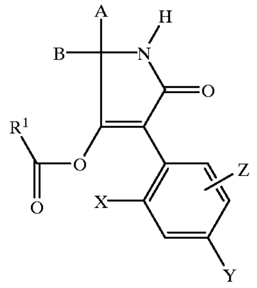

| X | Y | Z | A | B | $R^1$ |
|---|---|---|---|---|---|
| $CH_3$ | $OCH_3$ | 6-$CH_3$ | 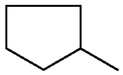 | $CH_3$ | $CH_3$ |
| $CH_3$ | $OCH_3$ | 6-$CH_3$ | 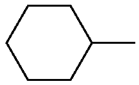 | $CH_3$ | $CH_3$ |
| $CH_3$ | $OCH_3$ | H | | $—(CH_2)_2—$ | $CH_3$ |
| $CH_3$ | $OCH_3$ | H | | $—(CH_2)_4—$ | $CH_3$ |
| $CH_3$ | $OCH_3$ | H | | $—(CH_2)_5—$ | $CH_3$ |
| $CH_3$ | $OCH_3$ | H | | $—(CH_2)_6—$ | $CH_3$ |
| $CH_3$ | $OCH_3$ | H | | $—(CH_2)_7—$ | $CH_3$ |
| $CH_3$ | $OCH_3$ | H | | $—(CH_2)_2—O—(CH_2)_2—$ | $CH_3$ |
| $CH_3$ | $OCH_3$ | H | | $—(CH_2)_2—S—(CH_2)_2—$ | $CH_3$ |
| $CH_3$ | $OCH_3$ | H | | $—CH_2—CHCH_3—(CH_2)_3—$ | $CH_3$ |
| $CH_3$ | $OCH_3$ | H | | $—(CH_2)_2—CHCH_3—(CH_2)_2—$ | $CH_3$ |
| $CH_3$ | $OCH_3$ | H | | $—(CH_2)_2—CHC_2H_5—(CH_2)_2—$ | $CH_3$ |
| $CH_3$ | $OCH_3$ | H | | $—(CH_2)_2—CHC_3H_7—(CH_2)_2—$ | $CH_3$ |
| $CH_3$ | $OCH_3$ | H | | $—(CH_2)_2—CHi\text{-}C_3H_7—(CH_2)_2—$ | $CH_3$ |
| $CH_3$ | $OCH_3$ | H | | $—(CH_2)_2—CHOCH_3—(CH_2)_2—$ | $CH_3$ |
| $CH_3$ | $OCH_3$ | H | | $—(CH_2)_2—CHOC_2H_5—(CH_2)_2—$ | $CH_3$ |
| $CH_3$ | $OCH_3$ | H | | $—(CH_2)_2—CHOC_3H_7—(CH_2)_2—$ | $CH_3$ |
| $CH_3$ | $OCH_3$ | H | | $—(CH_2)_2—CHi\text{-}OC_3H_7—(CH_2)_2—$ | $CH_3$ |
| $CH_3$ | $OCH_3$ | H | | $—(CH_2)_2—C(CH_3)_2—(CH_2)_2—$ | $CH_3$ |
| $CH_3$ | $OCH_3$ | H | | $—CH_2—(CHCH_3)_2—(CH_2)_2—$ | $CH_3$ |
| $CH_3$ | $OCH_3$ | H | | 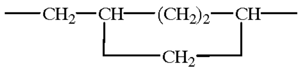 | $CH_3$ |
| $CH_3$ | $OCH_3$ | H | | 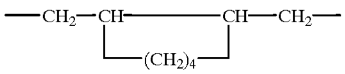 | $CH_3$ |
| $CH_3$ | $OCH_3$ | H | | 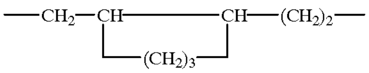 | $CH_3$ |
| $CH_3$ | H | 6-$OCH_3$ | | $—(CH_2)_2—$ | $CH_3$ |
| $CH_3$ | H | 6-$OCH_3$ | | $—(CH_2)_4—$ | $CH_3$ |
| $CH_3$ | H | 6-$OCH_3$ | | $—(CH_2)_5—$ | $CH_3$ |
| $CH_3$ | H | 6-$OCH_3$ | | $—(CH_2)_6—$ | $CH_3$ |
| $CH_3$ | H | 6-$OCH_3$ | | $—(CH_2)_7—$ | $CH_3$ |
| $CH_3$ | H | 6-$OCH_3$ | | $—(CH_2)_2—O—(CH_2)_2—$ | $CH_3$ |
| $CH_3$ | H | 6-$OCH_3$ | | $—(CH_2)_2—S—(CH_2)_2—$ | $CH_3$ |
| $CH_3$ | H | 6-$OCH_3$ | | $—CH_2—CHCH_3—(CH_2)_3—$ | $CH_3$ |
| $CH_3$ | H | 6-$OCH_3$ | | $—(CH_2)_2—CHCH_3—(CH_2)_2—$ | $CH_3$ |
| $CH_3$ | H | 6-$OCH_3$ | | $—(CH_2)_2—CHC_2H_5—(CH_2)_2—$ | $CH_3$ |
| $CH_3$ | H | 6-$OCH_3$ | | $—(CH_2)_2—CHC_3H_7—(CH_2)_2—$ | $CH_3$ |
| $CH_3$ | H | 6-$OCH_3$ | | $—(CH_2)_2—CHi\text{-}C_3H_7—(CH_2)_2—$ | $CH_3$ |
| $CH_3$ | H | 6-$OCH_3$ | | $—(CH_2)_2—CHOCH_3—(CH_2)_2—$ | $CH_3$ |
| $CH_3$ | H | 6-$OCH_3$ | | $—(CH_2)_2—CHOC_2H_5—(CH_2)_2—$ | $CH_3$ |
| $CH_3$ | H | 6-$OCH_3$ | | $—(CH_2)_2—CHOC_3H_7—(CH_2)_2—$ | $CH_3$ |
| $CH_3$ | H | 6-$OCH_3$ | | $—(CH_2)_2—CHi\text{-}OC_3H_7—(CH_2)_2—$ | $CH_3$ |

TABLE 2-continued (Ib)

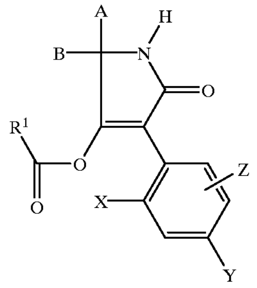

| X | Y | Z | A | B | $R^1$ |
|---|---|---|---|---|---|
| $CH_3$ | H | 6-$OCH_3$ | | $-(CH_2)_2-C(CH_3)_2-(CH_2)_2-$ | $CH_3$ |
| $CH_3$ | H | 6-$OCH_3$ | | $-CH_2-(CHCH_3)_2-(CH_2)_2-$ | $CH_3$ |
| $CH_3$ | H | 6-$OCH_3$ | | 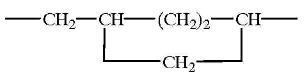 | $CH_3$ |
| $CH_3$ | H | 6-$OCH_3$ | | 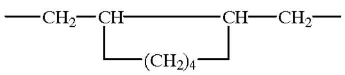 | $CH_3$ |
| $CH_3$ | H | 6-$OCH_3$ | | 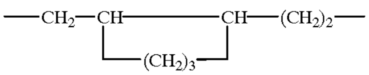 | $CH_3$ |
| $CH_3$ | $CH_3$ | 6-$OCH_3$ | | $-(CH_2)_2-$ | $CH_3$ |
| $CH_3$ | $CH_3$ | 6-$OCH_3$ | | $-(CH_2)_4-$ | $CH_3$ |
| $CH_3$ | $CH_3$ | 6-$OCH_3$ | | $-(CH_2)_5-$ | $CH_3$ |
| $CH_3$ | $CH_3$ | 6-$OCH_3$ | | $-(CH_2)_6-$ | $CH_3$ |
| $CH_3$ | $CH_3$ | 6-$OCH_3$ | | $-(CH_2)_7-$ | $CH_3$ |
| $CH_3$ | $CH_3$ | 6-$OCH_3$ | | $-(CH_2)_2-O-(CH_2)_2-$ | $CH_3$ |
| $CH_3$ | $CH_3$ | 6-$OCH_3$ | | $-(CH_2)_2-S-(CH_2)_2-$ | $CH_3$ |
| $CH_3$ | $CH_3$ | 6-$OCH_3$ | | $-CH_2-CHCH_3-(CH_2)_3-$ | $CH_3$ |
| $CH_3$ | $CH_3$ | 6-$OCH_3$ | | $-(CH_2)_2-CHCH_3-(CH_2)_2-$ | $CH_3$ |
| $CH_3$ | $CH_3$ | 6-$OCH_3$ | | $-(CH_2)_2-CHC_2H_5-(CH_2)_2-$ | $CH_3$ |
| $CH_3$ | $CH_3$ | 6-$OCH_3$ | | $-(CH_2)_2-CHC_3H_7-(CH_2)_2-$ | $CH_3$ |
| $CH_3$ | $CH_3$ | 6-$OCH_3$ | | $-(CH_2)_2-CHi\text{-}C_3H_7-(CH_2)_2-$ | $CH_3$ |
| $CH_3$ | $CH_3$ | 6-$OCH_3$ | | $-(CH_2)_2-CHOCH_3-(CH_2)_2-$ | $CH_3$ |
| $CH_3$ | $CH_3$ | 6-$OCH_3$ | | $-(CH_2)_2-CHOC_2H_5-(CH_2)_2-$ | $CH_3$ |
| $CH_3$ | $CH_3$ | 6-$OCH_3$ | | $-(CH_2)_2-CHOC_3H_7-(CH_2)_2-$ | $CH_3$ |
| $CH_3$ | $CH_3$ | 6-$OCH_3$ | | $-(CH_2)_2-CHi\text{-}OC_3H_7-(CH_2)_2-$ | $CH_3$ |
| $CH_3$ | $CH_3$ | 6-$OCH_3$ | | $-(CH_2)_2-C(CH_3)_2-(CH_2)_2-$ | $CH_3$ |
| $CH_3$ | $CH_3$ | 6-$OCH_3$ | | $-CH_2-(CHCH_3)_2-(CH_2)_2-$ | $CH_3$ |
| $CH_3$ | $CH_3$ | 6-$OCH_3$ | | 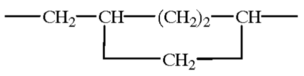 | $CH_3$ |
| $CH_3$ | $CH_3$ | 6-$OCH_3$ | | 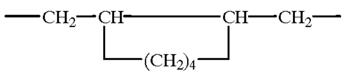 | $CH_3$ |
| $CH_3$ | $CH_3$ | 6-$OCH_3$ | | 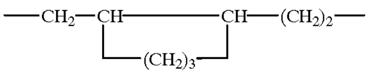 | $CH_3$ |
| $CH_3$ | $OCH_3$ | 6-$CH_3$ | | $-(CH_2)_2-$ | $CH_3$ |
| $CH_3$ | $OCH_3$ | 6-$CH_3$ | | $-(CH_2)_4-$ | $CH_3$ |
| $CH_3$ | $OCH_3$ | 6-$CH_3$ | | $-(CH_2)_5-$ | $CH_3$ |
| $CH_3$ | $OCH_3$ | 6-$CH_3$ | | $-(CH_2)_6-$ | $CH_3$ |
| $CH_3$ | $OCH_3$ | 6-$CH_3$ | | $-(CH_2)_7-$ | $CH_3$ |
| $CH_3$ | $OCH_3$ | 6-$CH_3$ | | $-(CH_2)_2-O-(CH_2)_2-$ | $CH_3$ |
| $CH_3$ | $OCH_3$ | 6-$CH_3$ | | $-(CH_2)_2-S-(CH_2)_2-$ | $CH_3$ |
| $CH_3$ | $OCH_3$ | 6-$CH_3$ | | $-CH_2-CHCH_3-(CH_2)_3-$ | $CH_3$ |
| $CH_3$ | $OCH_3$ | 6-$CH_3$ | | $-(CH_2)_2-CHCH_3-(CH_2)_2-$ | $CH_3$ |
| $CH_3$ | $OCH_3$ | 6-$CH_3$ | | $-(CH_2)_2-CHC_2H_5-(CH_2)_2-$ | $CH_3$ |
| $CH_3$ | $OCH_3$ | 6-$CH_3$ | | $-(CH_2)_2-CHC_3H_7-(CH_2)_2-$ | $CH_3$ |

TABLE 2-continued (Ib)

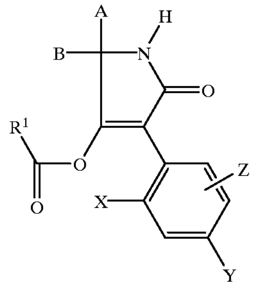

| X | Y | Z | A | B | $R^1$ |
|---|---|---|---|---|---|
| $CH_3$ | $OCH_3$ | 6-$CH_3$ | $-(CH_2)_2-CHi\text{-}C_3H_7-(CH_2)_2-$ | | $CH_3$ |
| $CH_3$ | $OCH_3$ | 6-$CH_3$ | $-(CH_2)_2-CHOCH_3-(CH_2)_2-$ | | $CH_3$ |
| $CH_3$ | $OCH_3$ | 6-$CH_3$ | $-(CH_2)_2-CHOC_2H_5-(CH_2)_2-$ | | $CH_3$ |
| $CH_3$ | $OCH_3$ | 6-$CH_3$ | $-(CH_2)_2-CHOC_3H_7-(CH_2)_2-$ | | $CH_3$ |
| $CH_3$ | $OCH_3$ | 6-$CH_3$ | $-(CH_2)_2-CHi\text{-}OC_3H_7-(CH_2)_2-$ | | $CH_3$ |
| $CH_3$ | $OCH_3$ | 6-$CH_3$ | $-(CH_2)_2-C(CH_3)_2-(CH_2)_2-$ | | $CH_3$ |
| $CH_3$ | $OCH_3$ | 6-$CH_3$ | $-CH_2-(CHCH_3)_2-(CH_2)_2-$ | | $CH_3$ |
| $CH_3$ | $OCH_3$ | 6-$CH_3$ | 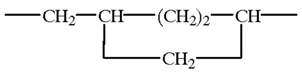 | | $CH_3$ |
| $CH_3$ | $OCH_3$ | 6-$CH_3$ | 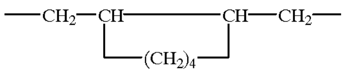 | | $CH_3$ |
| $CH_3$ | $OCH_3$ | 6-$CH_3$ | 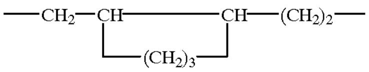 | | $CH_3$ |
| $CH_3$ | $OCH_3$ | H | $CH_3$ | H | i-$C_3H_7$ |
| $CH_3$ | $OCH_3$ | H | $C_2H_5$ | H | i-$C_3H_7$ |
| $CH_3$ | $OCH_3$ | H | $C_3H_7$ | H | i-$C_3H_7$ |
| $CH_3$ | $OCH_3$ | H | i-$C_3H_7$ | H | i-$C_3H_7$ |
| $CH_3$ | $OCH_3$ | H | $C_4H_9$ | H | i-$C_3H_7$ |
| $CH_3$ | $OCH_3$ | H | i-$C_4H_9$ | H | i-$C_3H_7$ |
| $CH_3$ | $OCH_3$ | H | s-$C_4H_9$ | H | i-$C_3H_7$ |
| $CH_3$ | $OCH_3$ | H | t-$C_4H_9$ | H | i-$C_3H_7$ |
| $CH_3$ | $OCH_3$ | H | $CH_3$ | H | i-$C_3H_7$ |
| $CH_3$ | $OCH_3$ | H | $C_2H_5$ | $CH_3$ | i-$C_3H_7$ |
| $CH_3$ | $OCH_3$ | H | $C_3H_7$ | $CH_3$ | i-$C_3H_7$ |
| $CH_3$ | $OCH_3$ | H | i-$C_3H_7$ | $CH_3$ | i-$C_3H_7$ |
| $CH_3$ | $OCH_3$ | H | $C_4H_9$ | $CH_3$ | i-$C_3H_7$ |
| $CH_3$ | $OCH_3$ | H | i-$C_4H_9$ | $CH_3$ | i-$C_3H_7$ |
| $CH_3$ | $OCH_3$ | H | s-$C_4H_9$ | $CH_3$ | i-$C_3H_7$ |
| $CH_3$ | $OCH_3$ | H | t-$C_4H_9$ | $CH_3$ | i-$C_3H_7$ |
| $CH_3$ | $OCH_3$ | H | $C_2H_5$ | $C_2H_5$ | i-$C_3H_7$ |
| $CH_3$ | $OCH_3$ | H | $C_3H_7$ | $C_3H_7$ | i-$C_3H_7$ |
| $CH_3$ | $OCH_3$ | H | 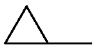 | $CH_3$ | i-$C_3H_7$ |
| $CH_3$ | $OCH_3$ | H | 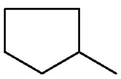 | $CH_3$ | i-$C_3H_7$ |
| $CH_3$ | $OCH_3$ | H | 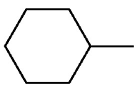 | $CH_3$ | i-$C_3H_7$ |
| $CH_3$ | H | 6-$OCH_3$ | $CH_3$ | H | i-$C_3H_7$ |
| $CH_3$ | H | 6-$OCH_3$ | $C_2H_5$ | H | i-$C_3H_7$ |
| $CH_3$ | H | 6-$OCH_3$ | $C_3H_7$ | H | i-$C_3H_7$ |
| $CH_3$ | H | 6-$OCH_3$ | i-$C_3H_7$ | H | i-$C_3H_7$ |
| $CH_3$ | H | 6-$OCH_3$ | $C_4H_9$ | H | i-$C_3H_7$ |
| $CH_3$ | H | 6-$OCH_3$ | i-$C_4H_9$ | H | i-$C_3H_7$ |

TABLE 2-continued (Ib)

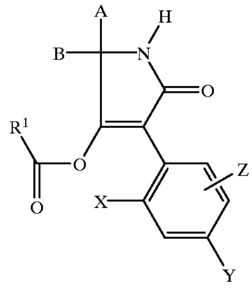

| X | Y | Z | A | B | $R^1$ |
|---|---|---|---|---|---|
| $CH_3$ | H | 6-$OCH_3$ | s-$C_4H_9$ | H | i-$C_3H_7$ |
| $CH_3$ | H | 6-$OCH_3$ | t-$C_4H_9$ | H | i-$C_3H_7$ |
| $CH_3$ | H | 6-$OCH_3$ | $CH_3$ | $CH_3$ | i-$C_3H_7$ |
| $CH_3$ | H | 6-$OCH_3$ | $C_2H_5$ | $CH_3$ | i-$C_3H_7$ |
| $CH_3$ | H | 6-$OCH_3$ | $C_3H_7$ | $CH_3$ | i-$C_3H_7$ |
| $CH_3$ | H | 6-$OCH_3$ | i-$C_3H_7$ | $CH_3$ | i-$C_3H_7$ |
| $CH_3$ | H | 6-$OCH_3$ | $C_4H_9$ | $CH_3$ | i-$C_3H_7$ |
| $CH_3$ | H | 6-$OCH_3$ | i-$C_4H_9$ | $CH_3$ | i-$C_3H_7$ |
| $CH_3$ | H | 6-$OCH_3$ | s-$C_4H_9$ | $CH_3$ | i-$C_3H_7$ |
| $CH_3$ | H | 6-$OCH_3$ | t-$C_4H_9$ | $CH_3$ | i-$C_3H_7$ |
| $CH_3$ | H | 6-$OCH_3$ | $C_2H_5$ | $C_2H_5$ | i-$C_3H_7$ |
| $CH_3$ | H | 6-$OCH_3$ | $C_3H_7$ | $C_3H_7$ | i-$C_3H_7$ |
| $CH_3$ | H | 6-$OCH_3$ | 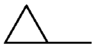 | $CH_3$ | i-$C_3H_7$ |
| $CH_3$ | H | 6-$OCH_3$ | 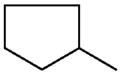 | $CH_3$ | i-$C_3H_7$ |
| $CH_3$ | H | 6-$OCH_3$ | 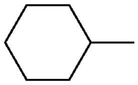 | $CH_3$ | i-$C_3H_7$ |
| $CH_3$ | $CH_3$ | 6-$OCH_3$ | $CH_3$ | H | i-$C_3H_7$ |
| $CH_3$ | $CH_3$ | 6-$OCH_3$ | $C_2H_5$ | H | i-$C_3H_7$ |
| $CH_3$ | $CH_3$ | 6-$OCH_3$ | $C_3H_7$ | H | i-$C_3H_7$ |
| $CH_3$ | $CH_3$ | 6-$OCH_3$ | i-$C_3H_7$ | H | i-$C_3H_7$ |
| $CH_3$ | $CH_3$ | 6-$OCH_3$ | $C_4H_9$ | H | i-$C_3H_7$ |
| $CH_3$ | $CH_3$ | 6-$OCH_3$ | i-$C_4H_9$ | H | i-$C_3H_7$ |
| $CH_3$ | $CH_3$ | 6-$OCH_3$ | s-$C_4H_9$ | H | i-$C_3H_7$ |
| $CH_3$ | $CH_3$ | 6-$OCH_3$ | t-$C_4H_9$ | H | i-$C_3H_7$ |
| $CH_3$ | $CH_3$ | 6-$OCH_3$ | $CH_3$ | $CH_3$ | i-$C_3H_7$ |
| $CH_3$ | $CH_3$ | 6-$OCH_3$ | $C_2H_5$ | $CH_3$ | i-$C_3H_7$ |
| $CH_3$ | $CH_3$ | 6-$OCH_3$ | $C_3H_7$ | $CH_3$ | i-$C_3H_7$ |
| $CH_3$ | $CH_3$ | 6-$OCH_3$ | i-$C_3H_7$ | $CH_3$ | i-$C_3H_7$ |
| $CH_3$ | $CH_3$ | 6-$OCH_3$ | $C_4H_9$ | $CH_3$ | i-$C_3H_7$ |
| $CH_3$ | $CH_3$ | 6-$OCH_3$ | i-$C_4H_9$ | $CH_3$ | i-$C_3H_7$ |
| $CH_3$ | $CH_3$ | 6-$OCH_3$ | s-$C_4H_9$ | $CH_3$ | i-$C_3H_7$ |
| $CH_3$ | $CH_3$ | 6-$OCH_3$ | t-$C_4H_9$ | $CH_3$ | i-$C_3H_7$ |
| $CH_3$ | $CH_3$ | 6-$OCH_3$ | $C_2H_5$ | $C_2H_5$ | i-$C_3H_7$ |
| $CH_3$ | $CH_3$ | 6-$OCH_3$ | $C_3H_7$ | $C_3H_7$ | i-$C_3H_7$ |
| $CH_3$ | $CH_3$ | 6-$OCH_3$ | 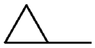 | $CH_3$ | i-$C_3H_7$ |
| $CH_3$ | $CH_3$ | 6-$OCH_3$ | 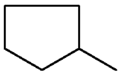 | $CH_3$ | i-$C_3H_7$ |
| $CH_3$ | $CH_3$ | 6-$OCH_3$ | 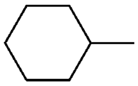 | $CH_3$ | i-$C_3H_7$ |

TABLE 2-continued (Ib)

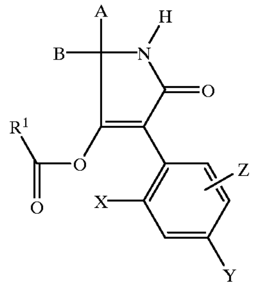

| X | Y | Z | A | B | $R^1$ |
|---|---|---|---|---|---|
| $CH_3$ | $OCH_3$ | 6-$CH_3$ | $CH_3$ | H | i-$C_3H_7$ |
| $CH_3$ | $OCH_3$ | 6-$CH_3$ | $C_2H_5$ | H | i-$C_3H_7$ |
| $CH_3$ | $OCH_3$ | 6-$CH_3$ | $C_3H_7$ | H | i-$C_3H_7$ |
| $CH_3$ | $OCH_3$ | 6-$CH_3$ | i-$C_3H_7$ | H | i-$C_3H_7$ |
| $CH_3$ | $OCH_3$ | 6-$OCH_3$ | $C_4H_9$ | H | i-$C_3H_7$ |
| $CH_3$ | $OCH_3$ | 6-$CH_3$ | i-$C_4H_9$ | H | i-$C_3H_7$ |
| $CH_3$ | $OCH_3$ | 6-$CH_3$ | s-$C_4H_9$ | H | i-$C_3H_7$ |
| $CH_3$ | $OCH_3$ | 6-$CH_3$ | t-$C_4H_9$ | H | i-$C_3H_7$ |
| $CH_3$ | $OCH_3$ | 6-$CH_3$ | $CH_3$ | $CH_3$ | i-$C_3H_7$ |
| $CH_3$ | $OCH_3$ | 6-$CH_3$ | $C_2H_5$ | $CH_3$ | i-$C_3H_7$ |
| $CH_3$ | $OCH_3$ | 6-$CH_3$ | $C_3H_7$ | $CH_3$ | i-$C_3H_7$ |
| $CH_3$ | $OCH_3$ | 6-$CH_3$ | i-$C_3H_7$ | $CH_3$ | i-$C_3H_7$ |
| $CH_3$ | $OCH_3$ | 6-$CH_3$ | $C_4H_9$ | $CH_3$ | i-$C_3H_7$ |
| $CH_3$ | $OCH_3$ | 6-$CH_3$ | i-$C_4H_9$ | $CH_3$ | i-$C_3H_7$ |
| $CH_3$ | $OCH_3$ | 6-$CH_3$ | s-$C_4H_9$ | $CH_3$ | i-$C_3H_7$ |
| $CH_3$ | $OCH_3$ | 6-$CH_3$ | t-$C_4H_9$ | $CH_3$ | i-$C_3H_7$ |
| $CH_3$ | $OCH_3$ | 6-$CH_3$ | $C_2H_5$ | $C_2H_5$ | i-$C_3H_7$ |
| $CH_3$ | $OCH_3$ | 6-$CH_3$ | $C_3H_7$ | $C_3H_7$ | i-$C_3H_7$ |
| $CH_3$ | $OCH_3$ | 6-$CH_3$ | 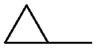 | $CH_3$ | i-$C_3H_7$ |
| $CH_3$ | $OCH_3$ | 6-$CH_3$ | 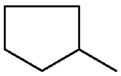 | $CH_3$ | i-$C_3H_7$ |
| $CH_3$ | $OCH_3$ | 6-$CH_3$ | 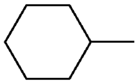 | $CH_3$ | i-$C_3H_7$ |
| $CH_3$ | $OCH_3$ | H | $-(CH_2)_2-$ | | i-$C_3H_7$ |
| $CH_3$ | $OCH_3$ | H | $-(CH_2)_4-$ | | i-$C_3H_7$ |
| $CH_3$ | $OCH_3$ | H | $-(CH_2)_5-$ | | i-$C_3H_7$ |
| $CH_3$ | $OCH_3$ | H | $-(CH_2)_6-$ | | i-$C_3H_7$ |
| $CH_3$ | $OCH_3$ | H | $-(CH_2)_7-$ | | i-$C_3H_7$ |
| $CH_3$ | $OCH_3$ | H | $-(CH_2)_2-O-(CH_2)_2-$ | | i-$C_3H_7$ |
| $CH_3$ | $OCH_3$ | H | $-(CH_2)_2-S-(CH_2)_2-$ | | i-$C_3H_7$ |
| $CH_3$ | $OCH_3$ | H | $-CH_2-CHCH_3-(CH_2)_3-$ | | i-$C_3H_7$ |
| $CH_3$ | $OCH_3$ | H | $-(CH_2)_2-CHCH_3-(CH_2)_2-$ | | i-$C_3H_7$ |
| $CH_3$ | $OCH_3$ | H | $-(CH_2)_2-CHC_2H_5-(CH_2)_2-$ | | i-$C_3H_7$ |
| $CH_3$ | $OCH_3$ | H | $-(CH_2)_2-CHC_3H_7-(CH_2)_2-$ | | i-$C_3H_7$ |
| $CH_3$ | $OCH_3$ | H | $-(CH_2)_2-$CHi-$C_3H_7-(CH_2)_2-$ | | i-$C_3H_7$ |
| $CH_3$ | $OCH_3$ | H | $-(CH_2)_2-CHOCH_3-(CH_2)_2-$ | | i-$C_3H_7$ |
| $CH_3$ | $OCH_3$ | H | $-(CH_2)_2-CHOC_2H_5-(CH_2)_2-$ | | i-$C_3H_7$ |
| $CH_3$ | $OCH_3$ | H | $-(CH_2)_2-CHOC_3H_7-(CH_2)_2-$ | | i-$C_3H_7$ |
| $CH_3$ | $OCH_3$ | H | $-(CH_2)_2-$CHi-$OC_3H_7-(CH_2)_2-$ | | i-$C_3H_7$ |
| $CH_3$ | $OCH_3$ | H | $-(CH_2)_2-C(CH_3)_2-(CH_2)_2-$ | | i-$C_3H_7$ |
| $CH_3$ | $OCH_3$ | H | $-CH_2-(CHCH_3)_2-(CH_2)-$ | | i-$C_3H_7$ |
| $CH_3$ | $OCH_3$ | H | 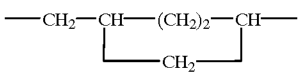 | | i-$C_3H_7$ |
| $CH_3$ | $OCH_3$ | H | 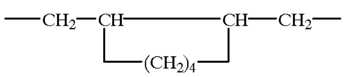 | | i-$C_3H_7$ |

TABLE 2-continued (Ib)

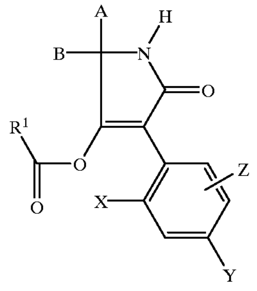

| X | Y | Z | A | B | $R^1$ |
|---|---|---|---|---|---|
| $CH_3$ | $OCH_3$ | H | | 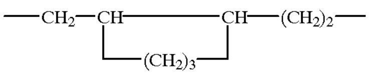 | $i\text{-}C_3H_7$ |
| $CH_3$ | H | $6\text{-}OCH_3$ | | $-(CH_2)_2-$ | $i\text{-}C_3H_7$ |
| $CH_3$ | H | $6\text{-}OCH_3$ | | $-(CH_2)_4-$ | $i\text{-}C_3H_7$ |
| $CH_3$ | H | $6\text{-}OCH_3$ | | $-(CH_2)_5-$ | $i\text{-}C_3H_7$ |
| $CH_3$ | H | $6\text{-}OCH_3$ | | $-(CH_2)_6-$ | $i\text{-}C_3H_7$ |
| $CH_3$ | H | $6\text{-}OCH_3$ | | $-(CH_2)_7-$ | $i\text{-}C_3H_7$ |
| $CH_3$ | H | $6\text{-}OCH_3$ | | $-(CH_2)_2-O-(CH_2)_2-$ | $i\text{-}C_3H_7$ |
| $CH_3$ | H | $6\text{-}OCH_3$ | | $-(CH_2)_2-S-(CH_2)_2-$ | $i\text{-}C_3H_7$ |
| $CH_3$ | H | $6\text{-}OCH_3$ | | $-CH_2-CHCH_3-(CH_2)_3-$ | $i\text{-}C_3H_7$ |
| $CH_3$ | H | $6\text{-}OCH_3$ | | $-(CH_2)_2-CHCH_3-(CH_2)_2-$ | $i\text{-}C_3H_7$ |
| $CH_3$ | H | $6\text{-}OCH_3$ | | $-(CH_2)_2-CHC_2H_5-(CH_2)_2-$ | $i\text{-}C_3H_7$ |
| $CH_3$ | H | $6\text{-}OCH_3$ | | $-(CH_2)_2-CHC_3H_7-(CH_2)_2-$ | $i\text{-}C_3H_7$ |
| $CH_3$ | H | $6\text{-}OCH_3$ | | $-(CH_2)_2-CHi\text{-}C_3H_7-(CH_2)_2-$ | $i\text{-}C_3H_7$ |
| $CH_3$ | H | $6\text{-}OCH_3$ | | $-(CH_2)_2-CHOCH_3-(CH_2)_2-$ | $i\text{-}C_3H_7$ |
| $CH_3$ | H | $6\text{-}OCH_3$ | | $-(CH_2)_2-CHOC_2H_5-(CH_2)_2-$ | $i\text{-}C_3H_7$ |
| $CH_3$ | H | $6\text{-}OCH_3$ | | $-(CH_2)_2-CHOC_3H_7-(CH_2)_2-$ | $i\text{-}C_3H_7$ |
| $CH_3$ | H | $6\text{-}OCH_3$ | | $-(CH_2)_2-CHi\text{-}OC_3H_7-(CH_2)_2-$ | $i\text{-}C_3H_7$ |
| $CH_3$ | H | $6\text{-}OCH_3$ | | $-(CH_2)_2-C(CH_3)_2-(CH_2)_2-$ | $i\text{-}C_3H_7$ |
| $CH_3$ | H | $6\text{-}OCH_3$ | | $-CH_2-(CHCH_3)_2-(CH_2)_2-$ | $i\text{-}C_3H_7$ |
| $CH_3$ | H | $6\text{-}OCH_3$ | | 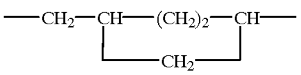 | $i\text{-}C_3H_7$ |
| $CH_3$ | H | $6\text{-}OCH_3$ | | 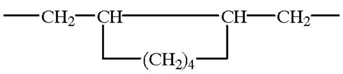 | $i\text{-}C_3H_7$ |
| $CH_3$ | H | $6\text{-}OCH_3$ | | 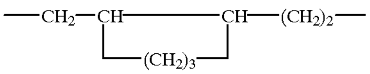 | $i\text{-}C_3H_7$ |
| $CH_3$ | H | $6\text{-}OCH_3$ | | $-(CH_2)_2-$ | $i\text{-}C_3H_7$ |
| $CH_3$ | H | $6\text{-}OCH_3$ | | $-(CH_2)_4-$ | $i\text{-}C_3H_7$ |
| $CH_3$ | H | $6\text{-}OCH_3$ | | $-(CH_2)_5-$ | $i\text{-}C_3H_7$ |
| $CH_3$ | H | $6\text{-}OCH_3$ | | $-(CH_2)_6-$ | $i\text{-}C_3H_7$ |
| $CH_3$ | H | $6\text{-}OCH_3$ | | $-(CH_2)_7-$ | $i\text{-}C_3H_7$ |
| $CH_3$ | H | $6\text{-}OCH_3$ | | $-(CH_2)_2-O-(CH_2)_2-$ | $i\text{-}C_3H_7$ |
| $CH_3$ | H | $6\text{-}OCH_3$ | | $-(CH_2)_2-S-(CH_2)_2-$ | $i\text{-}C_3H_7$ |
| $CH_3$ | H | $6\text{-}OCH_3$ | | $-CH_2-CHCH_3-(CH_2)_3-$ | $i\text{-}C_3H_7$ |
| $CH_3$ | H | $6\text{-}OCH_3$ | | $-(CH_2)_2-CHCH_3-(CH_2)_2-$ | $i\text{-}C_3H_7$ |
| $CH_3$ | H | $6\text{-}OCH_3$ | | $-(CH_2)_2-CHC_2H_5-(CH_2)_2-$ | $i\text{-}C_3H_7$ |
| $CH_3$ | H | $6\text{-}OCH_3$ | | $-(CH_2)_2-CHC_3H_7-(CH_2)_2-$ | $i\text{-}C_3H_7$ |
| $CH_3$ | H | $6\text{-}OCH_3$ | | $-(CH_2)_2-CHi\text{-}C_3H_7-(CH_2)_2-$ | $i\text{-}C_3H_7$ |
| $CH_3$ | H | $6\text{-}OCH_3$ | | $-(CH_2)_2-CHOCH_3-(CH_2)_2-$ | $i\text{-}C_3H_7$ |
| $CH_3$ | H | $6\text{-}OCH_3$ | | $-(CH_2)_2-CHOC_2H_5-(CH_2)_2-$ | $i\text{-}C_3H_7$ |
| $CH_3$ | H | $6\text{-}OCH_3$ | | $-(CH_2)_2-CHOC_3H_7-(CH_2)_2-$ | $i\text{-}C_3H_7$ |
| $CH_3$ | H | $6\text{-}OCH_3$ | | $-(CH_2)_2-CHi\text{-}OC_3H_7-(CH_2)_2-$ | $i\text{-}C_3H_7$ |
| $CH_3$ | H | $6\text{-}OCH_3$ | | $-(CH_2)_2-C(CH_3)_2-(CH_2)_2-$ | $i\text{-}C_3H_7$ |
| $CH_3$ | H | $6\text{-}OCH_3$ | | $-CH_2-(CHCH_3)_2-(CH_2)_2-$ | $i\text{-}C_3H_7$ |
| $CH_3$ | H | $6\text{-}OCH_3$ | | 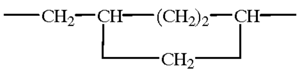 | $i\text{-}C_3H_7$ |

TABLE 2-continued (Ib)

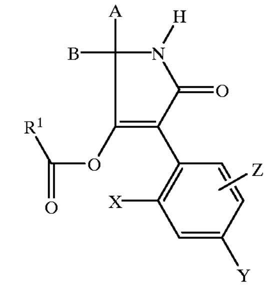

| X | Y | Z | A | B | $R^1$ |
|---|---|---|---|---|---|
| $CH_3$ | H | 6-$OCH_3$ | | 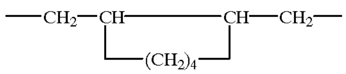 | i-$C_3H_7$ |
| $CH_3$ | H | 6-$OCH_3$ | | 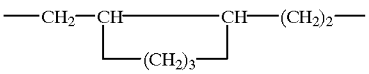 | i-$C_3H_7$ |
| $CH_3$ | $OCH_3$ | 6-$CH_3$ | | $-(CH_2)_2-$ | i-$C_3H_7$ |
| $CH_3$ | $OCH_3$ | 6-$CH_3$ | | $-(CH_2)_4-$ | i-$C_3H_7$ |
| $CH_3$ | $OCH_3$ | 6-$CH_3$ | | $-(CH_2)_5-$ | i-$C_3H_7$ |
| $CH_3$ | $OCH_3$ | 6-$CH_3$ | | $-(CH_2)_6-$ | i-$C_3H_7$ |
| $CH_3$ | $OCH_3$ | 6-$CH_3$ | | $-(CH_2)_7-$ | i-$C_3H_7$ |
| $CH_3$ | $OCH_3$ | 6-$CH_3$ | | $-(CH_2)_2-O-(CH_2)_2-$ | i-$C_3H_7$ |
| $CH_3$ | $OCH_3$ | 6-$CH_3$ | | $-(CH_2)_2-S-(CH_2)_2-$ | i-$C_3H_7$ |
| $CH_3$ | $OCH_3$ | 6-$CH_3$ | | $-CH_2-CHCH_3-(CH_2)_3-$ | i-$C_3H_7$ |
| $CH_3$ | $OCH_3$ | 6-$CH_3$ | | $-(CH_2)_2-CHCH_3-(CH_2)_2-$ | i-$C_3H_7$ |
| $CH_3$ | $OCH_3$ | 6-$CH_3$ | | $-(CH_2)_2-CHC_2H_5-(CH_2)_2-$ | i-$C_3H_7$ |
| $CH_3$ | $OCH_3$ | 6-$CH_3$ | | $-(CH_2)_2-CHC_3H_7-(CH_2)_2-$ | i-$C_3H_7$ |
| $CH_3$ | $OCH_3$ | 6-$CH_3$ | | $-(CH_2)_2-$CHi-$C_3H_7-(CH_2)_2-$ | i-$C_3H_7$ |
| $CH_3$ | $OCH_3$ | 6-$CH_3$ | | $-(CH_2)_2-CHOCH_3-(CH_2)_2-$ | i-$C_3H_7$ |
| $CH_3$ | $OCH_3$ | 6-$CH_3$ | | $-(CH_2)_2-CHOC_2H_5-(CH_2)_2-$ | i-$C_3H_7$ |
| $CH_3$ | $OCH_3$ | 6-$CH_3$ | | $-(CH_2)_2-CHOC_3H_7-(CH_2)_2$ | i-$C_3H_7$ |
| $CH_3$ | $OCH_3$ | 6-$CH_3$ | | $-(CH_2)_2-$CHi-$OC_3H_7-(CH_2)_2-$ | i-$C_3H_7$ |
| $CH_3$ | $OCH_3$ | 6-$CH_3$ | | $-(CH_2)_2-C(CH_3)_2-(CH_2)_2-$ | i-$C_3H_7$ |
| $CH_3$ | $OCH_3$ | 6-$CH_3$ | | $-CH_2-(CHCH_3)_2-(CH_2)_2-$ | i-$C_3H_7$ |
| $CH_3$ | $OCH_3$ | 6-$CH_3$ | | 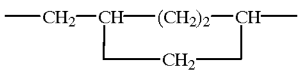 | i-$C_3H_7$ |
| $CH_3$ | $OCH_3$ | 6-$CH_3$ | | 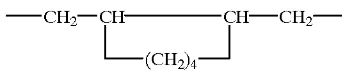 | i-$C_3H_7$ |
| $CH_3$ | $OCH_3$ | 6-$CH_3$ | | 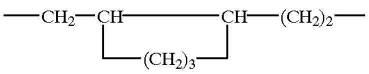 | i-$C_3H_7$ |
| $CH_3$ | $OCH_3$ | H | $CH_3$ | H | t-$C_4H_9$ |
| $CH_3$ | $OCH_3$ | H | $C_2H_5$ | H | t-$C_4H_9$ |
| $CH_3$ | $OCH_3$ | H | $C_3H_7$ | H | t-$C_4H_9$ |
| $CH_3$ | $OCH_3$ | H | i-$C_3H_7$ | H | t-$C_4H_9$ |
| $CH_3$ | $OCH_3$ | H | $C_4H_9$ | H | t-$C_4H_9$ |
| $CH_3$ | $OCH_3$ | H | i-$C_4H_9$ | H | t-$C_4H_9$ |
| $CH_3$ | $OCH_3$ | H | s-$C_4H_9$ | H | t-$C_4H_9$ |
| $CH_3$ | $OCH_3$ | H | t-$C_4H_9$ | H | t-$C_4H_9$ |
| $CH_3$ | $OCH_3$ | H | $CH_3$ | $CH_3$ | t-$C_4H_9$ |
| $CH_3$ | $OCH_3$ | H | $C_2H_5$ | $CH_3$ | t-$C_4H_9$ |
| $CH_3$ | $OCH_3$ | H | $C_3H_7$ | $CH_3$ | t-$C_4H_9$ |
| $CH_3$ | $OCH_3$ | H | i-$C_3H_7$ | $CH_3$ | t-$C_4H_9$ |
| $CH_3$ | $OCH_3$ | H | $C_4H_9$ | $CH_3$ | t-$C_4H_9$ |
| $CH_3$ | $OCH_3$ | H | i-$C_4H_9$ | $CH_3$ | t-$C_4H_9$ |
| $CH_3$ | $OCH_3$ | H | s-$C_4H_9$ | $CH_3$ | t-$C_4H_9$ |
| $CH_3$ | $OCH_3$ | H | t-$C_4H_9$ | $CH_3$ | t-$C_4H_9$ |
| $CH_3$ | $OCH_3$ | H | $C_2H_5$ | $C_2H_5$ | t-$C_4H_9$ |
| $CH_3$ | $OCH_3$ | H | $C_3H_7$ | $C_3H_7$ | t-$C_4H_9$ |

TABLE 2-continued (Ib)

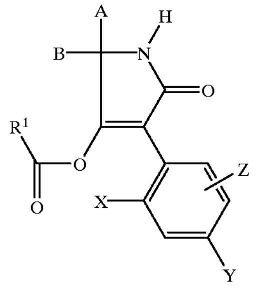

| X | Y | Z | A | B | $R^1$ |
|---|---|---|---|---|---|
| $CH_3$ | $OCH_3$ | H | 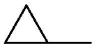 | $CH_3$ | t-$C_4H_9$ |
| $CH_3$ | $OCH_3$ | H | 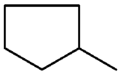 | $CH_3$ | t-$C_4H_9$ |
| $CH_3$ | $OCH_3$ | H | 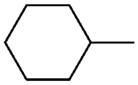 | $CH_3$ | t-$C_4H_9$ |
| $CH_3$ | H | 6-$OCH_3$ | $CH_3$ | H | t-$C_4H_9$ |
| $CH_3$ | H | 6-$OCH_3$ | $C_2H_5$ | H | t-$C_4H_9$ |
| $CH_3$ | H | 6-$OCH_3$ | $C_3H_7$ | H | t-$C_4H_9$ |
| $CH_3$ | H | 6-$OCH_3$ | i-$C_3H_7$ | H | t-$C_4H_9$ |
| $CH_3$ | H | 6-$OCH_3$ | $C_4H_9$ | H | t-$C_4H_9$ |
| $CH_3$ | H | 6-$OCH_3$ | i-$C_4H_9$ | H | t-$C_4H_9$ |
| $CH_3$ | H | 6-$OCH_3$ | s-$C_4H_9$ | H | t-$C_4H_9$ |
| $CH_3$ | H | 6-$OCH_3$ | t-$C_4H_9$ | H | t-$C_4H_9$ |
| $CH_3$ | H | 6-$OCH_3$ | $CH_3$ | $CH_3$ | t-$C_4H_9$ |
| $CH_3$ | H | 6-$OCH_3$ | $C_2H_5$ | $CH_3$ | t-$C_4H_9$ |
| $CH_3$ | H | 6-$OCH_3$ | $C_3H_7$ | $CH_3$ | t-$C_4H_9$ |
| $CH_3$ | H | 6-$OCH_3$ | i-$C_3H_7$ | $CH_3$ | t-$C_4H_9$ |
| $CH_3$ | H | 6-$OCH_3$ | $C_4H_9$ | $CH_3$ | t-$C_4H_9$ |
| $CH_3$ | H | 6-$OCH_3$ | i-$C_4H_9$ | $CH_3$ | t-$C_4H_9$ |
| $CH_3$ | H | 6-$OCH_3$ | s-$C_4H_9$ | $CH_3$ | t-$C_4H_9$ |
| $CH_3$ | H | 6-$OCH_3$ | t-$C_4H_9$ | $CH_3$ | t-$C_4H_9$ |
| $CH_3$ | H | 6-$OCH_3$ | $C_2H_5$ | $C_2H_5$ | t-$C_4H_9$ |
| $CH_3$ | H | 6-$OCH_3$ | $C_3H_7$ | $C_3H_7$ | t-$C_4H_9$ |
| $CH_3$ | H | 6-$OCH_3$ | 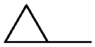 | $CH_3$ | t-$C_4H_9$ |
| $CH_3$ | H | 6-$OCH_3$ | 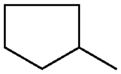 | $CH_3$ | t-$C_4H_9$ |
| $CH_3$ | H | 6-$OCH_3$ | 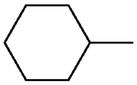 | $CH_3$ | t-$C_4H_9$ |
| $CH_3$ | $CH_3$ | 6-$OCH_3$ | $CH_3$ | H | t-$C_4H_9$ |
| $CH_3$ | $CH_3$ | 6-$OCH_3$ | $C_2H_5$ | H | t-$C_4H_9$ |
| $CH_3$ | $CH_3$ | 6-$OCH_3$ | $C_3H_7$ | H | t-$C_4H_9$ |
| $CH_3$ | $CH_3$ | 6-$OCH_3$ | i-$C_3H_7$ | H | t-$C_4H_9$ |
| $CH_3$ | $CH_3$ | 6-$OCH_3$ | $C_4H_9$ | H | t-$C_4H_9$ |
| $CH_3$ | $CH_3$ | 6-$OCH_3$ | i-$C_4H_9$ | H | t-$C_4H_9$ |
| $CH_3$ | $CH_3$ | 6-$OCH_3$ | s-$C_4H_9$ | H | t-$C_4H_9$ |
| $CH_3$ | $CH_3$ | 6-$OCH_3$ | t-$C_4H_9$ | H | t-$C_4H_9$ |
| $CH_3$ | $CH_3$ | 6-$OCH_3$ | $CH_3$ | $CH_3$ | t-$C_4H_9$ |
| $CH_3$ | $CH_3$ | 6-$OCH_3$ | $C_2H_5$ | $CH_3$ | t-$C_4H_9$ |
| $CH_3$ | $CH_3$ | 6-$OCH_3$ | $C_3H_7$ | $CH_3$ | t-$C_4H_9$ |
| $CH_3$ | $CH_3$ | 6-$OCH_3$ | i-$C_3H_7$ | $CH_3$ | t-$C_4H_9$ |

TABLE 2-continued (Ib)

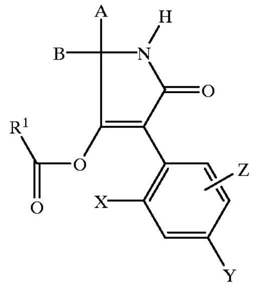

| X | Y | Z | A | B | $R^1$ |
|---|---|---|---|---|---|
| $CH_3$ | $CH_3$ | 6-$OCH_3$ | $C_4H_9$ | $CH_3$ | t-$C_4H_9$ |
| $CH_3$ | $CH_3$ | 6-$OCH_3$ | i-$C_4H_9$ | $CH_3$ | t-$C_4H_9$ |
| $CH_3$ | $CH_3$ | 6-$OCH_3$ | s-$C_4H_9$ | $CH_3$ | t-$C_4H_9$ |
| $CH_3$ | $CH_3$ | 6-$OCH_3$ | t-$C_4H_9$ | $CH_3$ | t-$C_4H_9$ |
| $CH_3$ | $CH_3$ | 6-$OCH_3$ | $C_2H_5$ | $C_2H_5$ | t-$C_4H_9$ |
| $CH_3$ | $CH_3$ | 6-$OCH_3$ | $C_3H_7$ | $C_3H_7$ | t-$C_4H_9$ |
| $CH_3$ | $CH_3$ | 6-$OCH_3$ | 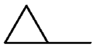 | $CH_3$ | t-$C_4H_9$ |
| $CH_3$ | $CH_3$ | 6-$OCH_3$ | 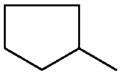 | $CH_3$ | t-$C_4H_9$ |
| $CH_3$ | $CH_3$ | 6-$OCH_3$ | 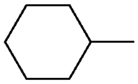 | $CH_3$ | t-$C_4H_9$ |
| $CH_3$ | $OCH_3$ | 6-$CH_3$ | $CH_3$ | H | t-$C_4H_9$ |
| $CH_3$ | $OCH_3$ | 6-$CH_3$ | $C_2H_5$ | H | t-$C_4H_9$ |
| $CH_3$ | $OCH_3$ | 6-$CH_3$ | $C_3H_7$ | H | t-$C_4H_9$ |
| $CH_3$ | $OCH_3$ | 6-$CH_3$ | i-$C_3H_7$ | H | t-$C_4H_9$ |
| $CH_3$ | $OCH_3$ | 6-$CH_3$ | $C_4H_9$ | H | t-$C_4H_9$ |
| $CH_3$ | $OCH_3$ | 6-$CH_3$ | i-$C_4H_9$ | H | t-$C_4H_9$ |
| $CH_3$ | $OCH_3$ | 6-$CH_3$ | s-$C_4H_9$ | H | t-$C_4H_9$ |
| $CH_3$ | $OCH_3$ | 6-$CH_3$ | t-$C_4H_9$ | H | t-$C_4H_9$ |
| $CH_3$ | $OCH_3$ | 6-$CH_3$ | $CH_3$ | $CH_3$ | t-$C_4H_9$ |
| $CH_3$ | $OCH_3$ | 6-$CH_3$ | $C_2H_5$ | $CH_3$ | t-$C_4H_9$ |
| $CH_3$ | $OCH_3$ | 6-$CH_3$ | $C_3H_7$ | $CH_3$ | t-$C_4H_9$ |
| $CH_3$ | $OCH_3$ | 6-$CH_3$ | i-$C_3H_7$ | $CH_3$ | t-$C_4H_9$ |
| $CH_3$ | $OCH_3$ | 6-$CH_3$ | $C_4H_9$ | $CH_3$ | t-$C_4H_9$ |
| $CH_3$ | $OCH_3$ | 6-$CH_3$ | i-$C_4H_9$ | $CH_3$ | t-$C_4H_9$ |
| $CH_3$ | $OCH_3$ | 6-$CH_3$ | s-$C_4H_9$ | $CH_3$ | t-$C_4H_9$ |
| $CH_3$ | $OCH_3$ | 6-$CH_3$ | t-$C_4H_9$ | $CH_3$ | t-$C_4H_9$ |
| $CH_3$ | $OCH_3$ | 6-$CH_3$ | $C_2H_5$ | $C_2H_5$ | t-$C_4H_9$ |
| $CH_3$ | $OCH_3$ | 6-$CH_3$ | $C_3H_7$ | $C_3H_7$ | t-$C_4H_9$ |
| $CH_3$ | $OCH_3$ | 6-$CH_3$ | 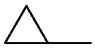 | $CH_3$ | t-$C_4H_9$ |
| $CH_3$ | $OCH_3$ | 6-$CH_3$ | 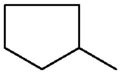 | $CH_3$ | t-$C_4H_9$ |
| $CH_3$ | $OCH_3$ | 6-$CH_3$ | 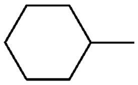 | $CH_3$ | t-$C_4H_9$ |
| $CH_3$ | $OCH_3$ | H | $-(CH_2)_2-$ | | t-$C_4H_9$ |
| $CH_3$ | $OCH_3$ | H | $-(CH_2)_4-$ | | t-$C_4H_9$ |
| $CH_3$ | $OCH_3$ | H | $-(CH_2)_5-$ | | t-$C_4H_9$ |
| $CH_3$ | $OCH_3$ | H | $-(CH_2)_6-$ | | t-$C_4H_9$ |
| $CH_3$ | $OCH_3$ | H | $-(CH_2)_7-$ | | t-$C_4H_9$ |
| $CH_3$ | $OCH_3$ | H | $-(CH_2)_2-O-(CH_2)_2-$ | | t-$C_4H_9$ |

TABLE 2-continued (Ib)

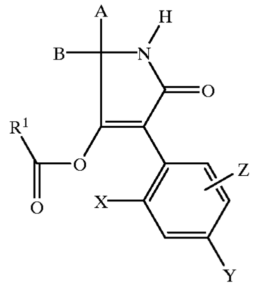

| X | Y | Z | A | B | $R^1$ |
|---|---|---|---|---|---|
| $CH_3$ | $OCH_3$ | H | | $-(CH_2)_2-S-(CH_2)_2-$ | t-$C_4H_9$ |
| $CH_3$ | $OCH_3$ | H | | $-CH_2-CHCH_3-(CH_2)_3-$ | t-$C_4H_9$ |
| $CH_3$ | $OCH_3$ | H | | $-(CH_2)_2-CHCH_3-(CH_2)_2-$ | t-$C_4H_9$ |
| $CH_3$ | $OCH_3$ | H | | $-(CH_2)_2-CHC_2H_5-(CH_2)_2-$ | t-$C_4H_9$ |
| $CH_3$ | $OCH_3$ | H | | $-(CH_2)_2-CHC_3H_7-(CH_2)_2-$ | t-$C_4H_9$ |
| $CH_3$ | $OCH_3$ | H | | $-(CH_2)_2-CHi\text{-}C_3H_7-(CH_2)_2-$ | t-$C_4H_9$ |
| $CH_3$ | $OCH_3$ | H | | $-(CH_2)_2-CHOCH_3-(CH_2)_2-$ | t-$C_4H_9$ |
| $CH_3$ | $OCH_3$ | H | | $-(CH_2)_2-CHOC_2H_5-(CH_2)_2-$ | t-$C_4H_9$ |
| $CH_3$ | $OCH_3$ | H | | $-(CH_2)_2-CHOC_3H_7-(CH_2)_2-$ | t-$C_4H_9$ |
| $CH_3$ | $OCH_3$ | H | | $-(CH_2)_2-CHi\text{-}OC_3H_7-(CH_2)_2-$ | t-$C_4H_9$ |
| $CH_3$ | $OCH_3$ | H | | $-(CH_2)_2-C(CH_3)_2-(CH_2)_2-$ | t-$C_4H_9$ |
| $CH_3$ | $OCH_3$ | H | | $-CH_2-(CHCH_3)_2-(CH_2)_2$ | t-$C_4H_9$ |
| $CH_3$ | $OCH_3$ | H | | 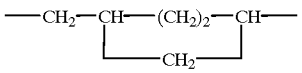 | t-$C_4H_9$ |
| $CH_3$ | $OCH_3$ | H | | 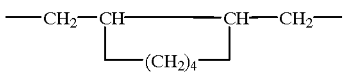 | t-$C_4H_9$ |
| $CH_3$ | $OCH_3$ | H | | 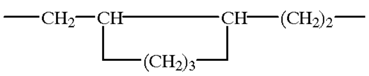 | t-$C_4H_9$ |
| $CH_3$ | H | 6-$OCH_3$ | | $-(CH_2)_2-$ | t-$C_4H_9$ |
| $CH_3$ | H | 6-$OCH_3$ | | $-(CH_2)_4-$ | t-$C_4H_9$ |
| $CH_3$ | H | 6-$OCH_3$ | | $-(CH_2)_5-$ | t-$C_4H_9$ |
| $CH_3$ | H | 6-$OCH_3$ | | $-(CH_2)_6-$ | t-$C_4H_9$ |
| $CH_3$ | H | 6-$OCH_3$ | | $-(CH_2)_7-$ | t-$C_4H_9$ |
| $CH_3$ | H | 6-$OCH_3$ | | $-(CH_2)_2-O-(CH_2)_2-$ | t-$C_4H_9$ |
| $CH_3$ | H | 6-$OCH_3$ | | $-(CH_2)_2-S-(CH_2)_2-$ | t-$C_4H_9$ |
| $CH_3$ | H | 6-$OCH_3$ | | $-CH_2-CHCH_3-(CH_2)_3-$ | t-$C_4H_9$ |
| $CH_3$ | H | 6-$OCH_3$ | | $-(CH_2)_2-CHCH_3-(CH_2)_2-$ | t-$C_4H_9$ |
| $CH_3$ | H | 6-$OCH_3$ | | $-(CH_2)_2-CHC_2H_5-(CH_2)_2-$ | t-$C_4H_9$ |
| $CH_3$ | H | 6-$OCH_3$ | | $-(CH_2)_2-CHC_3H_7-(CH_2)_2-$ | t-$C_4H_9$ |
| $CH_3$ | H | 6-$OCH_3$ | | $-(CH_2)_2-CHi\text{-}C_3H_7-(CH_2)_2-$ | t-$C_4H_9$ |
| $CH_3$ | H | 6-$OCH_3$ | | $-(CH_2)_2-CHOCH_3-(CH_2)_2-$ | t-$C_4H_9$ |
| $CH_3$ | H | 6-$OCH_3$ | | $-(CH_2)_2-CHOC_2H_5-(CH_2)_2-$ | t-$C_4H_9$ |
| $CH_3$ | H | 6-$OCH_3$ | | $-(CH_2)_2-CHOC_3H_7-(CH_2)_2-$ | t-$C_4H_9$ |
| $CH_3$ | H | 6-$OCH_3$ | | $-(CH_2)_2-CHi\text{-}OC_3H_7-(CH_2)_2-$ | t-$C_4H_9$ |
| $CH_3$ | H | 6-$OCH_3$ | | $-(CH_2)_2-C(CH_3)_2-(CH_2)_2-$ | t-$C_4H_9$ |
| $CH_3$ | H | 6-$OCH_3$ | | $-CH_2-(CHCH_3)_2-(CH_2)_2-$ | t-$C_4H_9$ |
| $CH_3$ | H | 6-$OCH_3$ | | 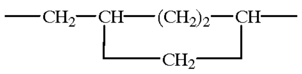 | t-$C_4H_9$ |
| $CH_3$ | H | 6-$OCH_3$ | | 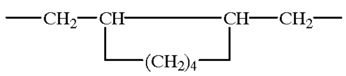 | t-$C_4H_9$ |
| $CH_3$ | H | 6-$OCH_3$ | | 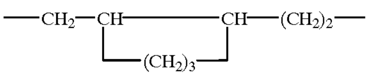 | t-$C_4H_9$ |
| $CH_3$ | $CH_3$ | 6-$OCH_3$ | | $-(CH_2)_2-$ | t-$C_4H_9$ |

TABLE 2-continued (Ib)

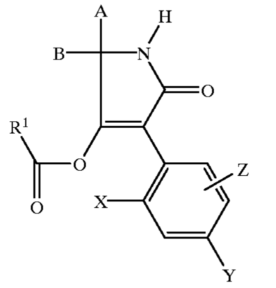

| X | Y | Z | A | B | $R^1$ |
|---|---|---|---|---|---|
| $CH_3$ | $CH_3$ | 6-$OCH_3$ | | $—(CH_2)_4—$ | t-$C_4H_9$ |
| $CH_3$ | $CH_3$ | 6-$OCH_3$ | | $—(CH_2)_5—$ | t-$C_4H_9$ |
| $CH_3$ | $CH_3$ | 6-$OCH_3$ | | $—(CH_2)_6—$ | t-$C_4H_9$ |
| $CH_3$ | $CH_3$ | 6-$OCH_3$ | | $—(CH_2)_7—$ | t-$C_4H_9$ |
| $CH_3$ | $CH_3$ | 6-$OCH_3$ | | $—(CH_2)—O—(CH_2)_2—$ | t-$C_4H_9$ |
| $CH_3$ | $CH_3$ | 6-$OCH_3$ | | $—(CH_2)_2—S—(CH_2)_2—$ | t-$C_4H_9$ |
| $CH_3$ | $CH_3$ | 6-$OCH_3$ | | $—CH_2—CHCH_3—(CH_2)_3—$ | t-$C_4H_9$ |
| $CH_3$ | $CH_3$ | 6-$OCH_3$ | | $—(CH_2)_2—CHCH_3—(CH_2)_2—$ | t-$C_4H_9$ |
| $CH_3$ | $CH_3$ | 6-$OCH_3$ | | $—(CH_2)_2—CHC_2H_5—(CH_2)_2—$ | t-$C_4H_9$ |
| $CH_3$ | $CH_3$ | 6-$OCH_3$ | | $—(CH_2)_2—CHC_3H_7—(CH_2)_2—$ | t-$C_4H_9$ |
| $CH_3$ | $CH_3$ | 6-$OCH_3$ | | $—(CH_2)_2—CHi\text{-}C_3H_7—(CH_2)_2—$ | t-$C_4H_9$ |
| $CH_3$ | $CH_3$ | 6-$OCH_3$ | | $—(CH_2)_2—CHOCH_3—(CH_2)_2—$ | t-$C_4H_9$ |
| $CH_3$ | $CH_3$ | 6-$OCH_3$ | | $—(CH_2)_2—CHOC_2H_5—(CH_2)_2—$ | t-$C_4H_9$ |
| $CH_3$ | $CH_3$ | 6-$OCH_3$ | | $—(CH_2)_2—CHOC_3H_7—(CH_2)_2—$ | t-$C_4H_9$ |
| $CH_3$ | $CH_3$ | 6-$OCH_3$ | | $—(CH_2)_2—CHi\text{-}OC_3H_7—(CH_2)_2—$ | t-$C_4H_9$ |
| $CH_3$ | $CH_3$ | 6-$OCH_3$ | | $—(CH_2)_2—C(CH_3)_2—(CH_2)_2—$ | t-$C_4H_9$ |
| $CH_3$ | $CH_3$ | 6-$OCH_3$ | | $—CH_2—(CHCH_3)_2—(CH_2)_2—$ | t-$C_4H_9$ |
| $CH_3$ | $CH_3$ | 6-$OCH_3$ | | 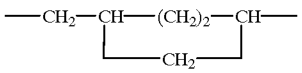 | t-$C_4H_9$ |
| $CH_3$ | $CH_3$ | 6-$OCH_3$ | | 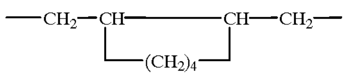 | t-$C_4H_9$ |
| $CH_3$ | $CH_3$ | 6-$OCH_3$ | | 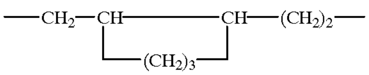 | t-$C_4H_9$ |
| $CH_3$ | $OCH_3$ | 6-$CH_3$ | | $—(CH_2)_2—$ | t-$C_4H_9$ |
| $CH_3$ | $OCH_3$ | 6-$CH_3$ | | $—(CH_2)_4—$ | t-$C_4H_9$ |
| $CH_3$ | $OCH_3$ | 6-$CH_3$ | | $—(CH_2)_5—$ | t-$C_4H_9$ |
| $CH_3$ | $OCH_3$ | 6-$CH_3$ | | $—(CH_2)_6—$ | t-$C_4H_9$ |
| $CH_3$ | $OCH_3$ | 6-$CH_3$ | | $—(CH_2)_7—$ | t-$C_4H_9$ |
| $CH_3$ | $OCH_3$ | 6-$CH_3$ | | $—(CH_2)_2—O—(CH_2)_2—$ | t-$C_4H_9$ |
| $CH_3$ | $OCH_3$ | 6-$CH_3$ | | $—(CH_2)_2—S—(CH_2)_2—$ | t-$C_4H_9$ |
| $CH_3$ | $OCH_3$ | 6-$CH_3$ | | $—CH_2—CHCH_3—(CH_2)_3—$ | t-$C_4H_9$ |
| $CH_3$ | $OCH_3$ | 6-$CH_3$ | | $—(CH_2)_2—CHCH_3—(CH_2)_2—$ | t-$C_4H_9$ |
| $CH_3$ | $OCH_3$ | 6-$CH_3$ | | $—(CH_2)_2—CHC_2H_5—(CH_2)_2—$ | t-$C_4H_9$ |
| $CH_3$ | $OCH_3$ | 6-$CH_3$ | | $—(CH_2)_2—CHC_3H_7—(CH_2)_2—$ | t-$C_4H_9$ |
| $CH_3$ | $OCH_3$ | 6-$CH_3$ | | $—(CH_2)_2—CHi\text{-}C_3H_7—(CH_2)_2—$ | t-$C_4H_9$ |
| $CH_3$ | $OCH_3$ | 6-$CH_3$ | | $—(CH_2)_2—CHOCH_3—(CH_2)_2—$ | t-$C_4H_9$ |
| $CH_3$ | $OCH_3$ | 6-$CH_3$ | | $—(CH_2)_2—CHOC_2H_5—(CH_2)_2—$ | t-$C_4H_9$ |
| $CH_3$ | $OCH_3$ | 6-$CH_3$ | | $—(CH_2)_2—CHOC_3H_7—(CH_2)_2—$ | t-$C_4H_9$ |
| $CH_3$ | $OCH_3$ | 6-$CH_3$ | | $—(CH_2)_2—CHi\text{-}OC_3H_7—(CH_2)_2—$ | t-$C_4H_9$ |
| $CH_3$ | $OCH_3$ | 6-$CH_3$ | | $—(CH_2)_2—C(CH_3)_2—(CH_2)_2—$ | t-$C_4H_9$ |
| $CH_3$ | $OCH_3$ | 6-$CH_3$ | | $—CH_2—(CHCH_3)_2—(CH_2)_2$ | t-$C_4H_9$ |
| $CH_3$ | $OCH_3$ | 6-$CH_3$ | | 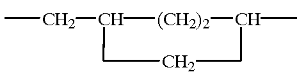 | t-$C_4H_9$ |
| $CH_3$ | $OCH_3$ | 6-$CH_3$ | | 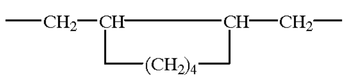 | t-$C_4H_9$ |

TABLE 2-continued (Ib)

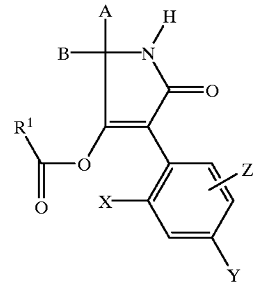

| X | Y | Z | A | B | $R^1$ |
|---|---|---|---|---|---|
| $CH_3$ | $OCH_3$ | 6-$CH_3$ | 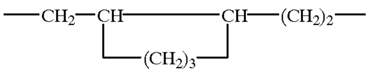 | | t-$C_4H_9$ |

Specific mention may be made, in addition to the compounds specified in the Preparation Examples, of the following compounds of the formula (Ic):

TABLE 3

(Ic)

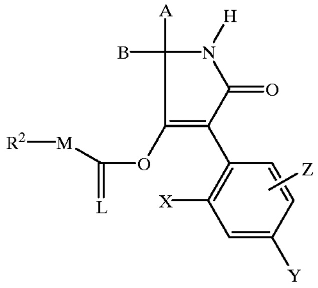

| X | Y | Z | A | B | L | M | $R^2$ |
|---|---|---|---|---|---|---|---|
| $CH_3$ | $OCH_3$ | H | $CH_3$ | H | O | O | $C_2H_5$ |
| $CH_3$ | $OCH_3$ | H | $C_2H_5$ | H | O | O | $C_2H_5$ |
| $CH_3$ | $OCH_3$ | H | $C_3H_7$ | H | O | O | $C_2H_5$ |
| $CH_3$ | $OCH_3$ | H | i-$C_3H_7$ | H | O | O | $C_2H_5$ |
| $CH_3$ | $OCH_3$ | H | $C_4H_9$ | H | O | O | $C_2H_5$ |
| $CH_3$ | $OCH_3$ | H | i-$C_4H_9$ | H | O | O | $C_2H_5$ |
| $CH_3$ | $OCH_3$ | H | s-$C_4H_9$ | H | O | O | $C_2H_5$ |
| $CH_3$ | $OCH_3$ | H | t-$C_4H_9$ | H | O | O | $C_2H_5$ |
| $CH_3$ | $OCH_3$ | H | $CH_3$ | $CH_3$ | O | O | $C_2H_5$ |
| $CH_3$ | $OCH_3$ | H | $C_2H_5$ | $CH_3$ | O | O | $C_2H_5$ |
| $CH_3$ | $OCH_3$ | H | $C_3H_7$ | $CH_3$ | O | O | $C_2H_5$ |
| $CH_3$ | $OCH_3$ | H | i-$C_3H_7$ | $CH_3$ | O | O | $C_2H_5$ |
| $CH_3$ | $OCH_3$ | H | $C_4H_9$ | $CH_3$ | O | O | $C_2H_5$ |
| $CH_3$ | $OCH_3$ | H | i-$C_4H_9$ | $CH_3$ | O | O | $C_2H_5$ |
| $CH_3$ | $OCH_3$ | H | s-$C_4H_9$ | $CH_3$ | O | O | $C_2H_5$ |
| $CH_3$ | $OCH_3$ | H | t-$C_4H_9$ | $CH_3$ | O | O | $C_2H_5$ |
| $CH_3$ | $OCH_3$ | H | $C_2H_5$ | $C_2H_5$ | O | O | $C_2H_5$ |
| $CH_3$ | $OCH_3$ | H | $C_3H_7$ | $C_3H_7$ | O | O | $C_2H_5$ |
| $CH_3$ | $OCH_3$ | H | 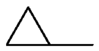 | $CH_3$ | O | O | $C_2H_5$ |
| $CH_3$ | $OCH_3$ | H | 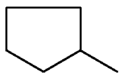 | $CH_3$ | O | O | $C_2H_5$ |

TABLE 3-continued

| | | | | | | | |
|---|---|---|---|---|---|---|---|
| $CH_3$ | $OCH_3$ | H | 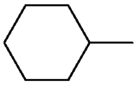 | $CH_3$ | O | O | $C_2H_5$ |
| $CH_3$ | H | 6-$OCH_3$ | $CH_3$ | H | O | O | $C_2H_5$ |
| $CH_3$ | H | 6-$OCH_3$ | $C_2H_5$ | H | O | O | $C_2H_5$ |
| $CH_3$ | H | 6-$OCH_3$ | $C_3H_7$ | H | O | O | $C_2H_5$ |
| $CH_3$ | H | 6-$OCH_3$ | i-$C_3H_7$ | H | O | O | $C_2H_5$ |
| $CH_3$ | H | 6-$OCH_3$ | $C_4H_9$ | H | O | O | $C_2H_5$ |
| $CH_3$ | H | 6-$OCH_3$ | i-$C_4H_9$ | H | O | O | $C_2H_5$ |
| $CH_3$ | H | 6-$OCH_3$ | s-$C_4H_9$ | H | O | O | $C_2H_5$ |
| $CH_3$ | H | 6-$OCH_3$ | t-$C_4H_9$ | H | O | O | $C_2H_5$ |
| $CH_3$ | H | 6-$OCH_3$ | $CH_3$ | $CH_3$ | O | O | $C_2H_5$ |
| $CH_3$ | H | 6-$OCH_3$ | $C_2H_5$ | $CH_3$ | O | O | $C_2H_5$ |
| $CH_3$ | H | 6-$OCH_3$ | $C_3H_7$ | $CH_3$ | O | O | $C_2H_5$ |
| $CH_3$ | H | 6-$OCH_3$ | i-$C_3H_7$ | $CH_3$ | O | O | $C_2H_5$ |
| $CH_3$ | H | 6-$OCH_3$ | $C_4H_9$ | $CH_3$ | O | O | $C_2H_5$ |
| $CH_3$ | H | 6-$OCH_3$ | i-$C_4H_9$ | $CH_3$ | O | O | $C_2H_5$ |
| $CH_3$ | H | 6-$OCH_3$ | s-$C_4H_9$ | $CH_3$ | O | O | $C_2H_5$ |
| $CH_3$ | H | 6-$OCH_3$ | t-$C_4H_9$ | $CH_3$ | O | O | $C_2H_5$ |
| $CH_3$ | H | 6-$OCH_3$ | $C_2H_5$ | $C_2H_5$ | O | O | $C_2H_5$ |
| $CH_3$ | H | 6-$OCH_3$ | $C_3H_7$ | $C_3H_7$ | O | O | $C_2H_5$ |
| $CH_3$ | H | 6-$OCH_3$ | 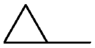 | $CH_3$ | O | O | $C_2H_5$ |
| $CH_3$ | H | 6-$OCH_3$ | 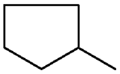 | $CH_3$ | O | O | $C_2H_5$ |
| $CH_3$ | H | 6-$OCH_3$ | 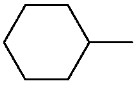 | $CH_3$ | O | O | $C_2H_5$ |
| $CH_3$ | $CH_3$ | 6-$OCH_3$ | $CH_3$ | H | O | O | $C_2H_5$ |
| $CH_3$ | $CH_3$ | 6-$OCH_3$ | $C_2H_5$ | H | O | O | $C_2H_5$ |
| $CH_3$ | $CH_3$ | 6-$OCH_3$ | $C_3H_7$ | H | O | O | $C_2H_5$ |
| $CH_3$ | $CH_3$ | 6-$OCH_3$ | i-$C_3H_7$ | H | O | O | $C_2H_5$ |
| $CH_3$ | $CH_3$ | 6-$OCH_3$ | $C_4H_9$ | H | O | O | $C_2H_5$ |
| $CH_3$ | $CH_3$ | 6-$OCH_3$ | i-$C_4H_9$ | H | O | O | $C_2H_5$ |
| $CH_3$ | $CH_3$ | 6-$OCH_3$ | s-$C_4H_9$ | H | O | O | $C_2H_5$ |
| $CH_3$ | $CH_3$ | 6-$OCH_3$ | t-$C_4H_9$ | H | O | O | $C_2H_5$ |
| $CH_3$ | $CH_3$ | 6-$OCH_3$ | $CH_3$ | $CH_3$ | O | O | $C_2H_5$ |
| $CH_3$ | $CH_3$ | 6-$OCH_3$ | $C_2H_5$ | $CH_3$ | O | O | $C_2H_5$ |
| $CH_3$ | $CH_3$ | 6-$OCH_3$ | $C_3H_7$ | $CH_3$ | O | O | $C_2H_5$ |
| $CH_3$ | $CH_3$ | 6-$OCH_3$ | i-$C_3H_7$ | $CH_3$ | O | O | $C_2H_5$ |
| $CH_3$ | $CH_3$ | 6-$OCH_3$ | $C_4H_9$ | $CH_3$ | O | O | $C_2H_5$ |
| $CH_3$ | $CH_3$ | 6-$OCH_3$ | i-$C_4H_9$ | $CH_3$ | O | O | $C_2H_5$ |
| $CH_3$ | $CH_3$ | 6-$OCH_3$ | s-$C_4H_9$ | $CH_3$ | O | O | $C_2H_5$ |
| $CH_3$ | $CH_3$ | 6-$OCH_3$ | t-$C_4H_9$ | $CH_3$ | O | O | $C_2H_5$ |
| $CH_3$ | $CH_3$ | 6-$OCH_3$ | $C_2H_5$ | $C_2H_5$ | O | O | $C_2H_5$ |
| $CH_3$ | $CH_3$ | 6-$OCH_3$ | $C_3H_7$ | $C_3H_7$ | O | O | $C_2H_5$ |
| $CH_3$ | $CH_3$ | 6-$OCH_3$ | 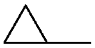 | $CH_3$ | O | O | $C_2H_5$ |
| $CH_3$ | $CH_3$ | 6-$OCH_3$ | 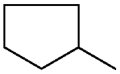 | $CH_3$ | O | O | $C_2H_5$ |
| $CH_3$ | $CH_3$ | 6-$OCH_3$ | 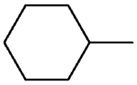 | $CH_3$ | O | O | $C_2H_5$ |
| $CH_3$ | $OCH_3$ | 6-$CH_3$ | $CH_3$ | H | O | O | $C_2H_5$ |
| $CH_3$ | $OCH_3$ | 6-$CH_3$ | $C_2H_5$ | H | O | O | $C_2H_5$ |
| $CH_3$ | $OCH_3$ | 6-$CH_3$ | $C_3H_7$ | H | O | O | $C_2H_5$ |
| $CH_3$ | $OCH_3$ | 6-$CH_3$ | i-$C_3H_7$ | H | O | O | $C_2H_5$ |
| $CH_3$ | $OCH_3$ | 6-$CH_3$ | $C_4H_9$ | H | O | O | $C_2H_5$ |
| $CH_3$ | $OCH_3$ | 6-$CH_3$ | i-$C_4H_9$ | H | O | O | $C_2H_5$ |

TABLE 3-continued

| | | | | | | | |
|---|---|---|---|---|---|---|---|
| $CH_3$ | $OCH_3$ | 6-$CH_3$ | s-$C_4H_9$ | H | O | O | $C_2H_5$ |
| $CH_3$ | $OCH_3$ | 6-$CH_3$ | t-$C_4H_9$ | H | O | O | $C_2H_5$ |
| $CH_3$ | $OCH_3$ | 6-$CH_3$ | $CH_3$ | $CH_3$ | O | O | $C_2H_5$ |
| $CH_3$ | $OCH_3$ | 6-$CH_3$ | $C_2H_5$ | $CH_3$ | O | O | $C_2H_5$ |
| $CH_3$ | $OCH_3$ | 6-$CH_3$ | $C_3H_7$ | $CH_3$ | O | O | $C_2H_5$ |
| $CH_3$ | $OCH_3$ | 6-$CH_3$ | i-$C_3H_7$ | $CH_3$ | O | O | $C_2H_5$ |
| $CH_3$ | $OCH_3$ | 6-$CH_3$ | $C_4H_9$ | $CH_3$ | O | O | $C_2H_5$ |
| $CH_3$ | $OCH_3$ | 6-$CH_3$ | i-$C_4H_9$ | $CH_3$ | O | O | $C_2H_5$ |
| $CH_3$ | $OCH_3$ | 6-$CH_3$ | s-$C_4H_9$ | $CH_3$ | O | O | $C_2H_5$ |
| $CH_3$ | $OCH_3$ | 6-$CH_3$ | t-$C_4H_9$ | $CH_3$ | O | O | $C_2H_5$ |
| $CH_3$ | $OCH_3$ | 6-$CH_3$ | $C_2H_5$ | $C_2H_5$ | O | O | $C_2H_5$ |
| $CH_3$ | $OCH_3$ | 6-$CH_3$ | $C_3H_7$ | $C_3H_7$ | O | O | $C_2H_5$ |
| $CH_3$ | $OCH_3$ | 6-$CH_3$ | 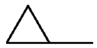 | $CH_3$ | O | O | $C_2H_5$ |
| $CH_3$ | $OCH_3$ | 6-$CH_3$ | 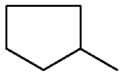 | $CH_3$ | O | O | $C_2H_5$ |
| $CH_3$ | $OCH_3$ | 6-$CH_3$ | 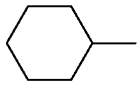 | $CH_3$ | O | O | $C_2H_5$ |

| X | Y | Z | A | B | L | M | $R^2$ |
|---|---|---|---|---|---|---|---|
| $CH_3$ | $OCH_3$ | H | | $-(CH_2)_2-$ | O | O | $C_2H_5$ |
| $CH_3$ | $OCH_3$ | H | | $-(CH_2)_4-$ | O | O | $C_2H_5$ |
| $CH_3$ | $OCH_3$ | H | | $-(CH_2)_5-$ | O | O | $C_2H_5$ |
| $CH_3$ | $OCH_3$ | H | | $-(CH_2)_6-$ | O | O | $C_2H_5$ |
| $CH_3$ | $OCH_3$ | H | | $-(CH_2)_7-$ | O | O | $C_2H_5$ |
| $CH_3$ | $OCH_3$ | H | | $-(CH_2)_2-O-(CH_2)_2-$ | O | O | $C_2H_5$ |
| $CH_3$ | $OCH_3$ | H | | $-(CH_2)_2-S-(CH_2)_2-$ | O | O | $C_2H_5$ |
| $CH_3$ | $OCH_3$ | H | | $-CH_2-CHCH_3-(CH_2)_3-$ | O | O | $C_2H_5$ |
| $CH_3$ | $OCH_3$ | H | | $-(CH_2)_2-CHCH_3-(CH_2)_2-$ | O | O | $C_2H_5$ |
| $CH_3$ | $OCH_3$ | H | | $-(CH_2)_2-CHC_2H_5-(CH_2)_2-$ | O | O | $C_2H_5$ |
| $CH_3$ | $OCH_3$ | H | | $-(CH_2)_2-CHC_3H_7-(CH_2)_2-$ | O | O | $C_2H_5$ |
| $CH_3$ | $OCH_3$ | H | | $-(CH_2)_2-$CHi-$C_3H_7-(CH_2)_2-$ | O | O | $C_2H_5$ |
| $CH_3$ | $OCH_3$ | H | | $-(CH_2)_2-CHOCH_3-(CH_2)_2-$ | O | O | $C_2H_5$ |
| $CH_3$ | $OCH_3$ | H | | $-(CH_2)_2-CHOC_2H_5-(CH_2)_2-$ | O | O | $C_2H_5$ |
| $CH_3$ | $OCH_3$ | H | | $-(CH_2)_2-CHOC_3H_7-(CH_2)_2-$ | O | O | $C_2H_5$ |
| $CH_3$ | $OCH_3$ | H | | $-(CH_2)_2-$CHi-$OC_3H_7-(CH_2)_2-$ | O | O | $C_2H_5$ |
| $CH_3$ | $OCH_3$ | H | | $-(CH_2)_2-C(CH_3)_2-(CH_2)_2-$ | O | O | $C_2H_5$ |
| $CH_3$ | $OCH_3$ | H | | $-CH_2-(CHCH_3)_2-(CH_2)_2-$ | O | O | $C_2H_5$ |
| $CH_3$ | $OCH_3$ | H | | 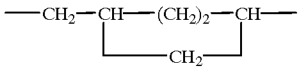 | O | O | $C_2H_5$ |
| $CH_3$ | $OCH_3$ | H | | 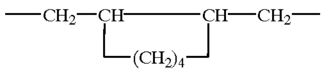 | O | O | $C_2H_5$ |
| $CH_3$ | $OCH_3$ | H | | 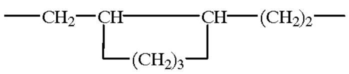 | O | O | $C_2H_5$ |
| $CH_3$ | H | 6-$OCH_3$ | | $-(CH_2)_2-$ | O | O | $C_2H_5$ |
| $CH_3$ | H | 6-$OCH_3$ | | $-(CH_2)_4-$ | O | O | $C_2H_5$ |
| $CH_3$ | H | 6-$OCH_3$ | | $-(CH_2)_5-$ | O | O | $C_2H_5$ |
| $CH_3$ | H | 6-$OCH_3$ | | $-(CH_2)_6-$ | O | O | $C_2H_5$ |
| $CH_3$ | H | 6-$OCH_3$ | | $-(CH_2)_7-$ | O | O | $C_2H_5$ |
| $CH_3$ | H | 6-$OCH_3$ | | $-(CH_2)_2-O-(CH_2)_2-$ | O | O | $C_2H_5$ |
| $CH_3$ | H | 6-$OCH_3$ | | $-(CH_2)_2-S-(CH_2)_2-$ | O | O | $C_2H_5$ |
| $CH_3$ | H | 6-$OCH_3$ | | $-CH_2-CHCH_3-(CH_2)_3-$ | O | O | $C_2H_5$ |
| $CH_3$ | H | 6-$OCH_3$ | | $-(CH_2)_2-CHCH_3-(CH_2)_2-$ | O | O | $C_2H_5$ |
| $CH_3$ | H | 6-$OCH_3$ | | $-(CH_2)_2-CHC_2H_5-(CH_2)_2-$ | O | O | $C_2H_5$ |
| $CH_3$ | H | 6-$OCH_3$ | | $-(CH_2)_2-CHC_3H_7-(CH_2)_2-$ | O | O | $C_2H_5$ |
| $CH_3$ | H | 6-$OCH_3$ | | $-(CH_2)_2-$CHi-$C_3H_7-(CH_2)_2-$ | O | O | $C_2H_5$ |
| $CH_3$ | H | 6-$OCH_3$ | | $-(CH_2)_2-CHOCH_3-(CH_2)_2-$ | O | O | $C_2H_5$ |
| $CH_3$ | H | 6-$OCH_3$ | | $-(CH_2)_2-CHOC_2H_5-(CH_2)_2-$ | O | O | $C_2H_5$ |
| $CH_3$ | H | 6-$OCH_3$ | | $-(CH_2)_2-CHOC_3H_7-(CH_2)_2-$ | O | O | $C_2H_5$ |
| $CH_3$ | H | 6-$OCH_3$ | | $-(CH_2)_2-$CHi-$OC_3H_7-(CH_2)_2-$ | O | O | $C_2H_5$ |

TABLE 3-continued

| | | | | | | |
|---|---|---|---|---|---|---|
| $CH_3$ | H | 6-$OCH_3$ | $-(CH_2)_2-C(CH_3)_2-(CH_2)_2-$ | O | O | $C_2H_5$ |
| $CH_3$ | H | 6-$OCH_3$ | $-CH_2-(CHCH_3)_2-(CH_2)_2-$ | O | O | $C_2H_5$ |
| $CH_3$ | H | 6-$OCH_3$ | 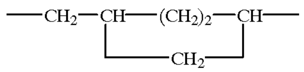 | O | O | $C_2H_5$ |
| $CH_3$ | H | 6-$OCH_3$ | 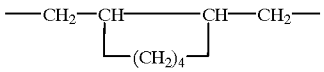 | O | O | $C_2H_5$ |
| $CH_3$ | H | 6-$OCH_3$ | 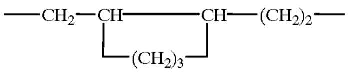 | O | O | $C_2H_5$ |
| $CH_3$ | $CH_3$ | 6-$OCH_3$ | $-(CH_2)_2-$ | O | O | $C_2H_5$ |
| $CH_3$ | $CH_3$ | 6-$OCH_3$ | $-(CH_2)_4-$ | O | O | $C_2H_5$ |
| $CH_3$ | $CH_3$ | 6-$OCH_3$ | $-(CH_2)_5-$ | O | O | $C_2H_5$ |
| $CH_3$ | $CH_3$ | 6-$OCH_3$ | $-(CH_2)_6-$ | O | O | $C_2H_5$ |
| $CH_3$ | $CH_3$ | 6-$OCH_3$ | $-(CH_2)_7-$ | O | O | $C_2H_5$ |
| $CH_3$ | $CH_3$ | 6-$OCH_3$ | $-(CH_2)_2-O-(CH_2)_2-$ | O | O | $C_2H_5$ |
| $CH_3$ | $CH_3$ | 6-$OCH_3$ | $-(CH_2)_2-S-(CH_2)_2-$ | O | O | $C_2H_5$ |
| $CH_3$ | $CH_3$ | 6-$OCH_3$ | $-CH_2-CHCH_3-(CH_2)_3-$ | O | O | $C_2H_5$ |
| $CH_3$ | $CH_3$ | 6-$OCH_3$ | $-(CH_2)_2-CHCH_3-(CH_2)_2-$ | O | O | $C_2H_5$ |
| $CH_3$ | $CH_3$ | 6-$OCH_3$ | $-(CH_2)_2-CHC_2H_5-(CH_2)_2-$ | O | O | $C_2H_5$ |
| $CH_3$ | $CH_3$ | 6-$OCH_3$ | $-(CH_2)_2-CHC_3H_7-(CH_2)_2-$ | O | O | $C_2H_5$ |
| $CH_3$ | $CH_3$ | 6-$OCH_3$ | $-(CH_2)_2-CHi\text{-}C_3H_7-(CH_2)_2-$ | O | O | $C_2H_5$ |
| $CH_3$ | $CH_3$ | 6-$OCH_3$ | $-(CH_2)_2-CHOCH_3-(CH_2)_2-$ | O | O | $C_2H_5$ |
| $CH_3$ | $CH_3$ | 6-$OCH_3$ | $-(CH_2)_2-CHOC_2H_5-(CH_2)_2-$ | O | O | $C_2H_5$ |
| $CH_3$ | $CH_3$ | 6-$OCH_3$ | $-(CH_2)_2-CHOC_3H_7-(CH_2)_2-$ | O | O | $C_2H_5$ |
| $CH_3$ | $CH_3$ | 6-$OCH_3$ | $-(CH_2)_2-CHi\text{-}OC_3H_7-(CH_2)_2-$ | O | O | $C_2H_5$ |
| $CH_3$ | $CH_3$ | 6-$OCH_3$ | $-(CH_2)_2-C(CH_3)_2-(CH_2)_2-$ | O | O | $C_2H_5$ |
| $CH_3$ | $CH_3$ | 6-$OCH_3$ | $-CH_2-(CHCH_3)_2-(CH_2)_2-$ | O | O | $C_2H_5$ |
| $CH_3$ | $CH_3$ | 6-$OCH_3$ | 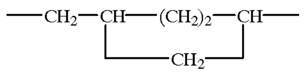 | O | O | $C_2H_5$ |
| $CH_3$ | $CH_3$ | 6-$OCH_3$ | 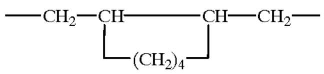 | O | O | $C_2H_5$ |
| $CH_3$ | $CH_3$ | 6-$OCH_3$ | 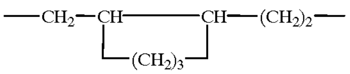 | O | O | $C_2H_5$ |
| $CH_3$ | $OCH_3$ | 6-$CH_3$ | $-(CH_2)_2-$ | O | O | $C_2H_5$ |
| $CH_3$ | $OCH_3$ | 6-$CH_3$ | $-(CH_2)_4-$ | O | O | $C_2H_5$ |
| $CH_3$ | $OCH_3$ | 6-$CH_3$ | $-(CH_2)_5-$ | O | O | $C_2H_5$ |
| $CH_3$ | $OCH_3$ | 6-$CH_3$ | $-(CH_2)_6-$ | O | O | $C_2H_5$ |
| $CH_3$ | $OCH_3$ | 6-$CH_3$ | $-(CH_2)_7-$ | O | O | $C_2H_5$ |
| $CH_3$ | $OCH_3$ | 6-$CH_3$ | $-(CH_2)_2-O-(CH_2)_2-$ | O | O | $C_2H_5$ |
| $CH_3$ | $OCH_3$ | 6-$CH_3$ | $-(CH_2)_2-S-(CH_2)_2-$ | O | O | $C_2H_5$ |
| $CH_3$ | $OCH_3$ | 6-$CH_3$ | $-CH_2-CHCH_3-(CH_2)_3-$ | O | O | $C_2H_5$ |
| $CH_3$ | $OCH_3$ | 6-$CH_3$ | $-(CH_2)_2-CHCH_3-(CH_2)_2-$ | O | O | $C_2H_5$ |
| $CH_3$ | $OCH_3$ | 6-$CH_3$ | $-(CH_2)_2-CHC_2H_5-(CH_2)_2-$ | O | O | $C_2H_5$ |
| $CH_3$ | $OCH_3$ | 6-$CH_3$ | $-(CH_2)_2-CHC_3H_7-(CH_2)_2-$ | O | O | $C_2H_5$ |
| $CH_3$ | $OCH_3$ | 6-$CH_3$ | $-(CH_2)_2-CHi\text{-}C_3H_7-(CH_2)_2-$ | O | O | $C_2H_5$ |
| $CH_3$ | $OCH_3$ | 6-$CH_3$ | $-(CH_2)_2-CHOCH_3-(CH_2)_2-$ | O | O | $C_2H_5$ |
| $CH_3$ | $OCH_3$ | 6-$CH_3$ | $-(CH_2)_2-CHOC_2H_5-(CH_2)_2-$ | O | O | $C_2H_5$ |
| $CH_3$ | $OCH_3$ | 6-$CH_3$ | $-(CH_2)_2-CHOC_3H_7-(CH_2)_2-$ | O | O | $C_2H_5$ |
| $CH_3$ | $OCH_3$ | 6-$CH_3$ | $-(CH_2)_2-CHi\text{-}OC_3H_7-(CH_2)_2-$ | O | O | $C_2H_5$ |
| $CH_3$ | $OCH_3$ | 6-$CH_3$ | $-(CH_2)_2-C(CH_3)_2-(CH_2)_2-$ | O | O | $C_2H_5$ |
| $CH_3$ | $OCH_3$ | 6-$CH_3$ | $-CH_2-(CHCH_3)_2-(CH_2)_2-$ | O | O | $C_2H_5$ |
| $CH_3$ | $OCH_3$ | 6-$CH_3$ | 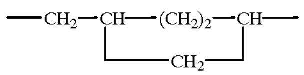 | O | O | $C_2H_5$ |
| $CH_3$ | $OCH_3$ | 6-$CH_3$ | 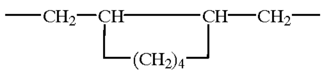 | O | O | $C_2H_5$ |

TABLE 3-continued

| | | | | | | | |
|---|---|---|---|---|---|---|---|
| $CH_3$ | $OCH_3$ | 6-$CH_3$ | 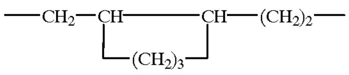 | | O | O | $C_2H_5$ |

| X | Y | Z | A | B | L | M | $R^2$ |
|---|---|---|---|---|---|---|---|
| $CH_3$ | $OCH_3$ | H | $CH_3$ | H | O | O | i-$C_3H_7$ |
| $CH_3$ | $OCH_3$ | H | $C_2H_5$ | H | O | O | i-$C_3H_7$ |
| $CH_3$ | $OCH_3$ | H | $C_3H_7$ | H | O | O | i-$C_3H_7$ |
| $CH_3$ | $OCH_3$ | H | i-$C_3H_7$ | H | O | O | i-$C_3H_7$ |
| $CH_3$ | $OCH_3$ | H | $C_4H_9$ | H | O | O | i-$C_3H_7$ |
| $CH_3$ | $OCH_3$ | H | i-$C_4H_9$ | H | O | O | i-$C_3H_7$ |
| $CH_3$ | $OCH_3$ | H | s-$C_4H_9$ | H | O | O | i-$C_3H_7$ |
| $CH_3$ | $OCH_3$ | H | t-$C_4H_9$ | H | O | O | i-$C_3H_7$ |
| $CH_3$ | $OCH_3$ | H | $CH_3$ | $CH_3$ | O | O | i-$C_3H_7$ |
| $CH_3$ | $OCH_3$ | H | $C_2H_5$ | $CH_3$ | O | O | i-$C_3H_7$ |
| $CH_3$ | $OCH_3$ | H | $C_3H_7$ | $CH_3$ | O | O | i-$C_3H_7$ |
| $CH_3$ | $OCH_3$ | H | i-$C_3H_7$ | $CH_3$ | O | O | i-$C_3H_7$ |
| $CH_3$ | $OCH_3$ | H | $C_4H_9$ | $CH_3$ | O | O | i-$C_3H_7$ |
| $CH_3$ | $OCH_3$ | H | i-$C_4H_9$ | $CH_3$ | O | O | i-$C_3H_7$ |
| $CH_3$ | $OCH_3$ | H | s-$C_4H_9$ | $CH_3$ | O | O | i-$C_3H_7$ |
| $CH_3$ | $OCH_3$ | H | t-$C_4H_9$ | $CH_3$ | O | O | i-$C_3H_7$ |
| $CH_3$ | $OCH_3$ | H | $C_2H_5$ | $C_2H_5$ | O | O | i-$C_3H_7$ |
| $CH_3$ | $OCH_3$ | H | $C_3H_7$ | $C_3H_7$ | O | O | i-$C_3H_7$ |
| $CH_3$ | $OCH_3$ | H | 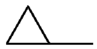 | $CH_3$ | O | O | i-$C_3H_7$ |
| $CH_3$ | $OCH_3$ | H | 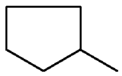 | $CH_3$ | O | O | i-$C_3H_7$ |
| $CH_3$ | $OCH_3$ | H | 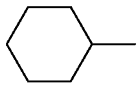 | $CH_3$ | O | O | i-$C_3H_7$ |
| $CH_3$ | H | 6-$OCH_3$ | $CH_3$ | H | O | O | i-$C_3H_7$ |
| $CH_3$ | H | 6-$OCH_3$ | $C_2H_5$ | H | O | O | i-$C_3H_7$ |
| $CH_3$ | H | 6-$OCH_3$ | $C_3H_7$ | H | O | O | i-$C_3H_7$ |
| $CH_3$ | H | 6-$OCH_3$ | i-$C_3H_7$ | H | O | O | i-$C_3H_7$ |
| $CH_3$ | H | 6-$OCH_3$ | $C_4H_9$ | H | O | O | i-$C_3H_7$ |
| $CH_3$ | H | 6-$OCH_3$ | i-$C_4H_9$ | H | O | O | i-$C_3H_7$ |
| $CH_3$ | H | 6-$OCH_3$ | s-$C_4H_9$ | H | O | O | i-$C_3H_7$ |
| $CH_3$ | H | 6-$OCH_3$ | t-$C_4H_9$ | H | O | O | i-$C_3H_7$ |
| $CH_3$ | H | 6-$OCH_3$ | $CH_3$ | $CH_3$ | O | O | i-$C_3H_7$ |
| $CH_3$ | H | 6-$OCH_3$ | $C_2H_5$ | $CH_3$ | O | O | i-$C_3H_7$ |
| $CH_3$ | H | 6-$OCH_3$ | $C_3H_7$ | $CH_3$ | O | O | i-$C_3H_7$ |
| $CH_3$ | H | 6-$OCH_3$ | i-$C_3H_7$ | $CH_3$ | O | O | i-$C_3H_7$ |
| $CH_3$ | H | 6-$OCH_3$ | $C_4H_9$ | $CH_3$ | O | O | i-$C_3H_7$ |
| $CH_3$ | H | 6-$OCH_3$ | i-$C_4H_9$ | $CH_3$ | O | O | i-$C_3H_7$ |
| $CH_3$ | H | 6-$OCH_3$ | s-$C_4H_9$ | $CH_3$ | O | O | i-$C_3H_7$ |
| $CH_3$ | H | 6-$OCH_3$ | t-$C_4H_9$ | $CH_3$ | O | O | i-$C_3H_7$ |
| $CH_3$ | H | 6-$OCH_3$ | $C_2H_5$ | $C_2H_5$ | O | O | i-$C_3H_7$ |
| $CH_3$ | H | 6-$OCH_3$ | $C_3H_7$ | $C_3H_7$ | O | O | i-$C_3H_7$ |
| $CH_3$ | H | 6-$OCH_3$ | 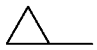 | $CH_3$ | O | O | i-$C_3H_7$ |
| $CH_3$ | H | 6-$OCH_3$ | 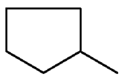 | $CH_3$ | O | O | i-$C_3H_7$ |
| $CH_3$ | H | 6-$OCH_3$ | 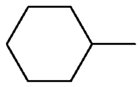 | $CH_3$ | O | O | i-$C_3H_7$ |
| $CH_3$ | $CH_3$ | 6-$OCH_3$ | $CH_3$ | H | O | O | i-$C_3H_7$ |
| $CH_3$ | $CH_3$ | 6-$OCH_3$ | $C_2H_5$ | H | O | O | i-$C_3H_7$ |
| $CH_3$ | $CH_3$ | 6-$OCH_3$ | $C_3H_7$ | H | O | O | i-$C_3H_7$ |
| $CH_3$ | $CH_3$ | 6-$OCH_3$ | i-$C_3H_7$ | H | O | O | i-$C_3H_7$ |
| $CH_3$ | $CH_3$ | 6-$OCH_3$ | $C_4H_9$ | H | O | O | i-$C_3H_7$ |

TABLE 3-continued

| | | | | | | | |
|---|---|---|---|---|---|---|---|
| $CH_3$ | $CH_3$ | 6-$OCH_3$ | i-$C_4H_9$ | H | O | O | i-$C_3H_7$ |
| $CH_3$ | $CH_3$ | 6-$OCH_3$ | s-$C_4H_9$ | H | O | O | i-$C_3H_7$ |
| $CH_3$ | $CH_3$ | 6-$OCH_3$ | t-$C_4H_9$ | H | O | O | i-$C_3H_7$ |
| $CH_3$ | $CH_3$ | 6-$OCH_3$ | $CH_3$ | $CH_3$ | O | O | i-$C_3H_7$ |
| $CH_3$ | $CH_3$ | 6-$OCH_3$ | $C_2H_5$ | $CH_3$ | O | O | i-$C_3H_7$ |
| $CH_3$ | $CH_3$ | 6-$OCH_3$ | $C_3H_7$ | $CH_3$ | O | O | i-$C_3H_7$ |
| $CH_3$ | $CH_3$ | 6-$OCH_3$ | i-$C_3H_7$ | $CH_3$ | O | O | i-$C_3H_7$ |
| $CH_3$ | $CH_3$ | 6-$OCH_3$ | $C_4H_9$ | $CH_3$ | O | O | i-$C_3H_7$ |
| $CH_3$ | $CH_3$ | 6-$OCH_3$ | i-$C_4H_9$ | $CH_3$ | O | O | i-$C_3H_7$ |
| $CH_3$ | $CH_3$ | 6-$OCH_3$ | s-$C_4H_9$ | $CH_3$ | O | O | i-$C_3H_7$ |
| $CH_3$ | $CH_3$ | 6-$OCH_3$ | t-$C_4H_9$ | $CH_3$ | O | O | i-$C_3H_7$ |
| $CH_3$ | $CH_3$ | 6-$OCH_3$ | $C_2H_5$ | $C_2H_5$ | O | O | i-$C_3H_7$ |
| $CH_3$ | $CH_3$ | 6-$OCH_3$ | $C_3H_7$ | $C_3H_7$ | O | O | i-$C_3H_7$ |
| $CH_3$ | $CH_3$ | 6-$OCH_3$ | 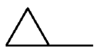 | $CH_3$ | O | O | i-$C_3H_7$ |
| $CH_3$ | $CH_3$ | 6-$OCH_3$ | 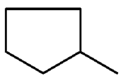 | $CH_3$ | O | O | i-$C_3H_7$ |
| $CH_3$ | $CH_3$ | 6-$OCH_3$ | 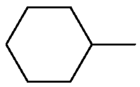 | $CH_3$ | O | O | i-$C_3H_7$ |
| $CH_3$ | $OCH_3$ | 6-$CH_3$ | $CH_3$ | H | O | O | i-$C_3H_7$ |
| $CH_3$ | $OCH_3$ | 6-$CH_3$ | $C_2H_5$ | H | O | O | i-$C_3H_7$ |
| $CH_3$ | $OCH_3$ | 6-$CH_3$ | $C_3H_7$ | H | O | O | i-$C_3H_7$ |
| $CH_3$ | $OCH_3$ | 6-$CH_3$ | i-$C_3H_7$ | H | O | O | i-$C_3H_7$ |
| $CH_3$ | $OCH_3$ | 6-$CH_3$ | $C_4H_9$ | H | O | O | i-$C_3H_7$ |
| $CH_3$ | $OCH_3$ | 6-$CH_3$ | i-$C_4H_9$ | H | O | O | i-$C_3H_7$ |
| $CH_3$ | $OCH_3$ | 6-$CH_3$ | s-$C_4H_9$ | H | O | O | i-$C_3H_7$ |
| $CH_3$ | $OCH_3$ | 6-$CH_3$ | t-$C_4H_9$ | H | O | O | i-$C_3H_7$ |
| $CH_3$ | $OCH_3$ | 6-$CH_3$ | $CH_3$ | $CH_3$ | O | O | i-$C_3H_7$ |
| $CH_3$ | $OCH_3$ | 6-$CH_3$ | $C_2H_5$ | $CH_3$ | O | O | i-$C_3H_7$ |
| $CH_3$ | $OCH_3$ | 6-$CH_3$ | $C_3H_7$ | $CH_3$ | O | O | i-$C_3H_7$ |
| $CH_3$ | $OCH_3$ | 6-$CH_3$ | i-$C_3H_7$ | $CH_3$ | O | O | i-$C_3H_7$ |
| $CH_3$ | $OCH_3$ | 6-$CH_3$ | $C_4H_9$ | $CH_3$ | O | O | i-$C_3H_7$ |
| $CH_3$ | $OCH_3$ | 6-$CH_3$ | i-$C_4H_9$ | $CH_3$ | O | O | i-$C_3H_7$ |
| $CH_3$ | $OCH_3$ | 6-$CH_3$ | s-$C_4H_9$ | $CH_3$ | O | O | i-$C_3H_7$ |
| $CH_3$ | $OCH_3$ | 6-$CH_3$ | t-$C_4H_9$ | $CH_3$ | O | O | i-$C_3H_7$ |
| $CH_3$ | $OCH_3$ | 6-$CH_3$ | $C_2H_5$ | $C_2H_5$ | O | O | i-$C_3H_7$ |
| $CH_3$ | $OCH_3$ | 6-$CH_3$ | $C_3H_7$ | $C_3H_7$ | O | O | i-$C_3H_7$ |
| $CH_3$ | $OCH_3$ | 6-$CH_3$ | 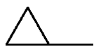 | $CH_3$ | O | O | i-$C_3H_7$ |
| $CH_3$ | $OCH_3$ | 6-$CH_3$ | 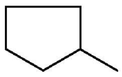 | $CH_3$ | O | O | i-$C_3H_7$ |
| $CH_3$ | $OCH_3$ | 6-$CH_3$ | 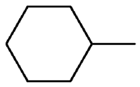 | $CH_3$ | O | O | i-$C_3H_7$ |

| X | Y | Z | A | B | L | M | $R^2$ |
|---|---|---|---|---|---|---|---|
| $CH_3$ | $OCH_3$ | H | | $-(CH_2)_2-$ | O | O | i-$C_3H_7$ |
| $CH_3$ | $OCH_3$ | H | | $-(CH_2)_4-$ | O | O | i-$C_3H_7$ |
| $CH_3$ | $OCH_3$ | H | | $-(CH_2)_5-$ | O | O | i-$C_3H_7$ |
| $CH_3$ | $OCH_3$ | H | | $-(CH_2)_6-$ | O | O | i-$C_3H_7$ |
| $CH_3$ | $OCH_3$ | H | | $-(CH_2)_7-$ | O | O | i-$C_3H_7$ |
| $CH_3$ | $OCH_3$ | H | | $-(CH_2)_2-O-(CH_2)_2-$ | O | O | i-$C_3H_7$ |
| $CH_3$ | $OCH_3$ | H | | $-(CH_2)_2-S-(CH_2)_2-$ | O | O | i-$C_3H_7$ |
| $CH_3$ | $OCH_3$ | H | | $-CH_2-CHCH_3-(CH_2)_3-$ | O | O | i-$C_3H_7$ |
| $CH_3$ | $OCH_3$ | H | | $-(CH_2)_2-CHCH_3-(CH_2)_2-$ | O | O | i-$C_3H_7$ |
| $CH_3$ | $OCH_3$ | H | | $-(CH_2)_2-CHC_2H_5-(CH_2)_2-$ | O | O | i-$C_3H_7$ |
| $CH_3$ | $OCH_3$ | H | | $-(CH_2)_2-CHC_3H_7-(CH_2)_2-$ | O | O | i-$C_3H_7$ |
| $CH_3$ | $OCH_3$ | H | | $-(CH_2)_2-CHi\text{-}C_3H_7-(CH_2)_2-$ | O | O | i-$C_3H_7$ |
| $CH_3$ | $OCH_3$ | H | | $-(CH_2)_2-CHOCH_3-(CH_2)_2-$ | O | O | i-$C_3H_7$ |
| $CH_3$ | $OCH_3$ | H | | $-(CH_2)_2-CHOC_2H_5-(CH_2)_2-$ | O | O | i-$C_3H_7$ |
| $CH_3$ | $OCH_3$ | H | | $-(CH_2)_2-CHOC_3H_7-(CH_2)_2-$ | O | O | i-$C_3H_7$ |

TABLE 3-continued

| | | | | | | |
|---|---|---|---|---|---|---|
| $CH_3$ | $OCH_3$ | H | $—(CH_2)_2—CHi\text{-}OC_3H_7—(CH_2)_2—$ | O | O | $i\text{-}C_3H_7$ |
| $CH_3$ | $OCH_3$ | H | $—(CH_2)_2—C(CH_3)_2—(CH_2)_2—$ | O | O | $i\text{-}C_3H_7$ |
| $CH_3$ | $OCH_3$ | H | $—CH_2—(CHCH_3)_2—(CH_2)_2—$ | O | O | $i\text{-}C_3H_7$ |
| $CH_3$ | $OCH_3$ | H | 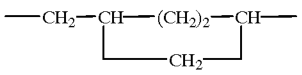 | O | O | $i\text{-}C_3H_7$ |
| $CH_3$ | $OCH_3$ | H | 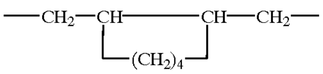 | O | O | $i\text{-}C_3H_7$ |
| $CH_3$ | $OCH_3$ | H | 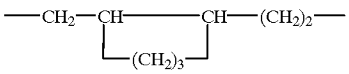 | O | O | $i\text{-}C_3H_7$ |
| $CH_3$ | H | $6\text{-}OCH_3$ | $—(CH_2)_2—$ | O | O | $i\text{-}C_3H_7$ |
| $CH_3$ | H | $6\text{-}OCH_3$ | $—(CH_2)_4—$ | O | O | $i\text{-}C_3H_7$ |
| $CH_3$ | H | $6\text{-}OCH_3$ | $—(CH_2)_5—$ | O | O | $i\text{-}C_3H_7$ |
| $CH_3$ | H | $6\text{-}OCH_3$ | $—(CH_2)_6—$ | O | O | $i\text{-}C_3H_7$ |
| $CH_3$ | H | $6\text{-}OCH_3$ | $—(CH_2)_7—$ | O | O | $i\text{-}C_3H_7$ |
| $CH_3$ | H | $6\text{-}OCH_3$ | $—(CH_2)_2—O—(CH_2)_2—$ | O | O | $i\text{-}C_3H_7$ |
| $CH_3$ | H | $6\text{-}OCH_3$ | $—(CH_2)_2—S—(CH_2)_2—$ | O | O | $i\text{-}C_3H_7$ |
| $CH_3$ | H | $6\text{-}OCH_3$ | $—CH_2—CHCH_3—(CH_2)_3—$ | O | O | $i\text{-}C_3H_7$ |
| $CH_3$ | H | $6\text{-}OCH_3$ | $—(CH_2)_2—CHCH_3—(CH_2)_2—$ | O | O | $i\text{-}C_3H_7$ |
| $CH_3$ | H | $6\text{-}OCH_3$ | $—(CH_2)_2—CHC_2H_5—(CH_2)_2—$ | O | O | $i\text{-}C_3H_7$ |
| $CH_3$ | H | $6\text{-}OCH_3$ | $—(CH_2)_2—CHC_3H_7—(CH_2)_2—$ | O | O | $i\text{-}C_3H_7$ |
| $CH_3$ | H | $6\text{-}OCH_3$ | $—(CH_2)_2—CHi\text{-}C_3H_7—(CH_2)_2—$ | O | O | $i\text{-}C_3H_7$ |
| $CH_3$ | H | $6\text{-}OCH_3$ | $—(CH_2)_2—CHOCH_3—(CH_2)_2—$ | O | O | $i\text{-}C_3H_7$ |
| $CH_3$ | H | $6\text{-}OCH_3$ | $—(CH_2)_2—CHOC_2H_5—(CH_2)_2—$ | O | O | $i\text{-}C_3H_7$ |
| $CH_3$ | H | $6\text{-}OCH_3$ | $—(CH_2)_2—CHOC_3H_7—(CH_2)_2—$ | O | O | $i\text{-}C_3H_7$ |
| $CH_3$ | H | $6\text{-}OCH_3$ | $—(CH_2)_2—CHi\text{-}OC_3H_7—(CH_2)_2—$ | O | O | $i\text{-}C_3H_7$ |
| $CH_3$ | H | $6\text{-}OCH_3$ | $—(CH_2)_2—C(CH_3)_2—(CH_2)_2—$ | O | O | $i\text{-}C_3H_7$ |
| $CH_3$ | H | $6\text{-}OCH_3$ | $—CH_2—(CHCH_3)_2—(CH_2)_2—$ | O | O | $i\text{-}C_3H_7$ |
| $CH_3$ | H | $6\text{-}OCH_3$ | 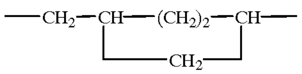 | O | O | $i\text{-}C_3H_7$ |
| $CH_3$ | H | $6\text{-}OCH_3$ | 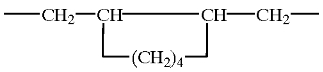 | O | O | $i\text{-}C_3H_7$ |
| $CH_3$ | H | $6\text{-}OCH_3$ | 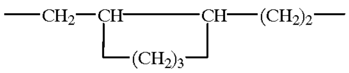 | O | O | $i\text{-}C_3H_7$ |
| $CH_3$ | $CH_3$ | $6\text{-}OCH_3$ | $—(CH_2)_2—$ | O | O | $i\text{-}C_3H_7$ |
| $CH_3$ | $CH_3$ | $6\text{-}OCH_3$ | $—(CH_2)_4—$ | O | O | $i\text{-}C_3H_7$ |
| $CH_3$ | $CH_3$ | $6\text{-}OCH_3$ | $—(CH_2)_5—$ | O | O | $i\text{-}C_3H_7$ |
| $CH_3$ | $CH_3$ | $6\text{-}OCH_3$ | $—(CH_2)_6—$ | O | O | $i\text{-}C_3H_7$ |
| $CH_3$ | $CH_3$ | $6\text{-}OCH_3$ | $—(CH_2)_7—$ | O | O | $i\text{-}C_3H_7$ |
| $CH_3$ | $CH_3$ | $6\text{-}OCH_3$ | $—(CH_2)_2—O—(CH_2)_2—$ | O | O | $i\text{-}C_3H_7$ |
| $CH_3$ | $CH_3$ | $6\text{-}OCH_3$ | $—(CH_2)_2—S—(CH_2)_2—$ | O | O | $i\text{-}C_3H_7$ |
| $CH_3$ | $CH_3$ | $6\text{-}OCH_3$ | $—CH_2—CHCH_3—(CH_2)_3—$ | O | O | $i\text{-}C_3H_7$ |
| $CH_3$ | $CH_3$ | $6\text{-}OCH_3$ | $—(CH_2)_2—CHCH_3—(CH_2)_2—$ | O | O | $i\text{-}C_3H_7$ |
| $CH_3$ | $CH_3$ | $6\text{-}OCH_3$ | $—(CH_2)_2—CHC_2H_5—(CH_2)_2—$ | O | O | $i\text{-}C_3H_7$ |
| $CH_3$ | $CH_3$ | $6\text{-}OCH_3$ | $—(CH_2)_2—CHC_3H_7—(CH_2)_2—$ | O | O | $i\text{-}C_3H_7$ |
| $CH_3$ | $CH_3$ | $6\text{-}OCH_3$ | $—(CH_2)_2—CHi\text{-}C_3H_7—(CH_2)_2—$ | O | O | $i\text{-}C_3H_7$ |
| $CH_3$ | $CH_3$ | $6\text{-}OCH_3$ | $—(CH_2)_2—CHOCH_3—(CH_2)_2—$ | O | O | $i\text{-}C_3H_7$ |
| $CH_3$ | $CH_3$ | $6\text{-}OCH_3$ | $—(CH_2)_2—CHOC_2H_5—(CH_2)_2—$ | O | O | $i\text{-}C_3H_7$ |
| $CH_3$ | $CH_3$ | $6\text{-}OCH_3$ | $—(CH_2)_2—CHOC_3H_7—(CH_2)_2—$ | O | O | $i\text{-}C_3H_7$ |
| $CH_3$ | $CH_3$ | $6\text{-}OCH_3$ | $—(CH_2)_2—CHi\text{-}OC_3H_7—(CH_2)_2—$ | O | O | $i\text{-}C_3H_7$ |
| $CH_3$ | $CH_3$ | $6\text{-}OCH_3$ | $—(CH_2)_2—C(CH_3)_2—(CH_2)_2—$ | O | O | $i\text{-}C_3H_7$ |
| $CH_3$ | $CH_3$ | $6\text{-}OCH_3$ | $—CH_2—(CHCH_3)_2—(CH_2)_2—$ | O | O | $i\text{-}C_3H_7$ |
| $CH_3$ | $CH_3$ | $6\text{-}OCH_3$ | 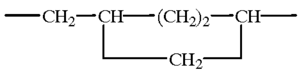 | O | O | $i\text{-}C_3H_7$ |
| $CH_3$ | $CH_3$ | $6\text{-}OCH_3$ | 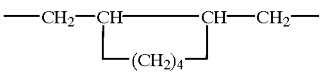 | O | O | $i\text{-}C_3H_7$ |

TABLE 3-continued

| | | | | | | |
|---|---|---|---|---|---|---|
| $CH_3$ | $CH_3$ | 6-$OCH_3$ | 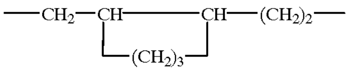 | O | O | i-$C_3H_7$ |
| $CH_3$ | $OCH_3$ | 6-$CH_3$ | $-(CH_2)_2-$ | O | O | i-$C_3H_7$ |
| $CH_3$ | $OCH_3$ | 6-$CH_3$ | $-(CH_2)_4-$ | O | O | i-$C_3H_7$ |
| $CH_3$ | $OCH_3$ | 6-$CH_3$ | $-(CH_2)_5-$ | O | O | i-$C_3H_7$ |
| $CH_3$ | $OCH_3$ | 6-$CH_3$ | $-(CH_2)_6-$ | O | O | i-$C_3H_7$ |
| $CH_3$ | $OCH_3$ | 6-$CH_3$ | $-(CH_2)_7-$ | O | O | i-$C_3H_7$ |
| $CH_3$ | $OCH_3$ | 6-$CH_3$ | $-(CH_2)_2-O-(CH_2)_2-$ | O | O | i-$C_3H_7$ |
| $CH_3$ | $OCH_3$ | 6-$CH_3$ | $-(CH_2)_2-S-(CH_2)_2-$ | O | O | i-$C_3H_7$ |
| $CH_3$ | $OCH_3$ | 6-$CH_3$ | $-CH_2-CHCH_3-(CH_2)_3-$ | O | O | i-$C_3H_7$ |
| $CH_3$ | $OCH_3$ | 6-$CH_3$ | $-(CH_2)_2-CHCH_3-(CH_2)_2-$ | O | O | i-$C_3H_7$ |
| $CH_3$ | $OCH_3$ | 6-$CH_3$ | $-(CH_2)_2-CHC_2H_5-(CH_2)_2-$ | O | O | i-$C_3H_7$ |
| $CH_3$ | $OCH_3$ | 6-$CH_3$ | $-(CH_2)_2-CHC_3H_7-(CH_2)_2-$ | O | O | i-$C_3H_7$ |
| $CH_3$ | $OCH_3$ | 6-$CH_3$ | $-(CH_2)_2-CHi\text{-}C_3H_7-(CH_2)_2-$ | O | O | i-$C_3H_7$ |
| $CH_3$ | $OCH_3$ | 6-$CH_3$ | $-(CH_2)_2-CHOCH_3-(CH_2)_2-$ | O | O | i-$C_3H_7$ |
| $CH_3$ | $OCH_3$ | 6-$CH_3$ | $-(CH_2)_2-CHOC_2H_5-(CH_2)_2-$ | O | O | i-$C_3H_7$ |
| $CH_3$ | $OCH_3$ | 6-$CH_3$ | $-(CH_2)_2-CHOC_3H_7-(CH_2)_2-$ | O | O | i-$C_3H_7$ |
| $CH_3$ | $OCH_3$ | 6-$CH_3$ | $-(CH_2)_2-CHi\text{-}OC_3H_7-(CH_2)_2-$ | O | O | i-$C_3H_7$ |
| $CH_3$ | $OCH_3$ | 6-$CH_3$ | $-(CH_2)_2-C(CH_3)_2-(CH_2)_2-$ | O | O | i-$C_3H_7$ |
| $CH_3$ | $OCH_3$ | 6-$CH_3$ | $-CH_2-(CHCH_3)_2-(CH_2)_2-$ | O | O | i-$C_3H_7$ |
| $CH_3$ | $OCH_3$ | 6-$CH_3$ | 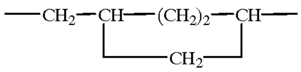 | O | O | i-$C_3H_7$ |
| $CH_3$ | $OCH_3$ | 6-$CH_3$ | 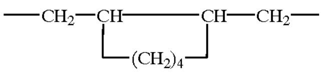 | O | O | i-$C_3H_7$ |
| $CH_3$ | $OCH_3$ | 6-$CH_3$ | 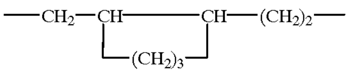 | O | O | i-$C_3H_7$ |

| X | Y | Z | A | B | L | M | $R^2$ |
|---|---|---|---|---|---|---|---|
| $CH_3$ | $OCH_3$ | H | $CH_3$ | H | O | S | i-$C_3H_7$ |
| $CH_3$ | $OCH_3$ | H | $C_2H_5$ | H | O | S | i-$C_3H_7$ |
| $CH_3$ | $OCH_3$ | H | $C_3H_7$ | H | O | S | i-$C_3H_7$ |
| $CH_3$ | $OCH_3$ | H | i-$C_3H_7$ | H | O | S | i-$C_3H_7$ |
| $CH_3$ | $OCH_3$ | H | $C_4H_9$ | H | O | S | i-$C_3H_7$ |
| $CH_3$ | $OCH_3$ | H | i-$C_4H_9$ | H | O | S | i-$C_3H_7$ |
| $CH_3$ | $OCH_3$ | H | s-$C_4H_9$ | H | O | S | i-$C_3H_7$ |
| $CH_3$ | $OCH_3$ | H | t-$C_4H_9$ | H | O | S | i-$C_3H_7$ |
| $CH_3$ | $OCH_3$ | H | $CH_3$ | $CH_3$ | O | S | i-$C_3H_7$ |
| $CH_3$ | $OCH_3$ | H | $C_2H_5$ | $CH_3$ | O | S | i-$C_3H_7$ |
| $CH_3$ | $OCH_3$ | H | $C_3H_7$ | $CH_3$ | O | S | i-$C_3H_7$ |
| $CH_3$ | $OCH_3$ | H | i-$C_3H_7$ | $CH_3$ | O | S | i-$C_3H_7$ |
| $CH_3$ | $OCH_3$ | H | $C_4H_9$ | $CH_3$ | O | S | i-$C_3H_7$ |
| $CH_3$ | $OCH_3$ | H | i-$C_4H_9$ | $CH_3$ | O | S | i-$C_3H_7$ |
| $CH_3$ | $OCH_3$ | H | s-$C_4H_9$ | $CH_3$ | O | S | i-$C_3H_7$ |
| $CH_3$ | $OCH_3$ | H | t-$C_4H_9$ | $CH_3$ | O | S | i-$C_3H_7$ |
| $CH_3$ | $OCH_3$ | H | $C_2H_5$ | $C_2H_5$ | O | S | i-$C_3H_7$ |
| $CH_3$ | $OCH_3$ | H | $C_3H_7$ | $C_3H_7$ | O | S | i-$C_3H_7$ |
| $CH_3$ | $OCH_3$ | H | 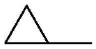 | $CH_3$ | O | S | i-$C_3H_7$ |
| $CH_3$ | $OCH_3$ | H | 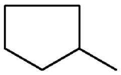 | $CH_3$ | O | S | i-$C_3H_7$ |
| $CH_3$ | $OCH_3$ | H | 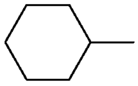 | $CH_3$ | O | S | i-$C_3H_7$ |
| $CH_3$ | H | 6-$OCH_3$ | $CH_3$ | H | O | S | i-$C_3H_7$ |
| $CH_3$ | H | 6-$OCH_3$ | $C_2H_5$ | H | O | S | i-$C_3H_7$ |
| $CH_3$ | H | 6-$OCH_3$ | $C_3H_7$ | H | O | S | i-$C_3H_7$ |
| $CH_3$ | H | 6-$OCH_3$ | i-$C_3H_7$ | H | O | S | i-$C_3H_7$ |
| $CH_3$ | H | 6-$OCH_3$ | $C_4H_9$ | H | O | S | i-$C_3H_7$ |
| $CH_3$ | H | 6-$OCH_3$ | i-$C_4H_9$ | H | O | S | i-$C_3H_7$ |

TABLE 3-continued

| | | | | | | | |
|---|---|---|---|---|---|---|---|
| $CH_3$ | H | 6-$OCH_3$ | s-$C_4H_9$ | H | O | S | i-$C_3H_7$ |
| $CH_3$ | H | 6-$OCH_3$ | t-$C_4H_9$ | H | O | S | i-$C_3H_7$ |
| $CH_3$ | H | 6-$OCH_3$ | $CH_3$ | $CH_3$ | O | S | i-$C_3H_7$ |
| $CH_3$ | H | 6-$OCH_3$ | $C_2H_5$ | $CH_3$ | O | S | i-$C_3H_7$ |
| $CH_3$ | H | 6-$OCH_3$ | $C_3H_7$ | $CH_3$ | O | S | i-$C_3H_7$ |
| $CH_3$ | H | 6-$OCH_3$ | i-$C_3H_7$ | $CH_3$ | O | S | i-$C_3H_7$ |
| $CH_3$ | H | 6-$OCH_3$ | $C_4H_9$ | $CH_3$ | O | S | i-$C_3H_7$ |
| $CH_3$ | H | 6-$OCH_3$ | i-$C_4H_9$ | $CH_3$ | O | S | i-$C_3H_7$ |
| $CH_3$ | H | 6-$OCH_3$ | s-$C_4H_9$ | $CH_3$ | O | S | i-$C_3H_7$ |
| $CH_3$ | H | 6-$OCH_3$ | t-$C_4H_9$ | $CH_3$ | O | S | i-$C_3H_7$ |
| $CH_3$ | H | 6-$OCH_3$ | $C_2H_5$ | $C_2H_5$ | O | S | i-$C_3H_7$ |
| $CH_3$ | H | 6-$OCH_3$ | $C_3H_7$ | $C_3H_7$ | O | S | i-$C_3H_7$ |
| $CH_3$ | H | 6-$OCH_3$ | 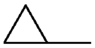 | $CH_3$ | O | S | i-$C_3H_7$ |
| $CH_3$ | H | 6-$OCH_3$ | 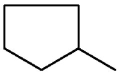 | $CH_3$ | O | S | i-$C_3H_7$ |
| $CH_3$ | H | 6-$OCH_3$ | 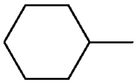 | $CH_3$ | O | S | i-$C_3H_7$ |
| $CH_3$ | $CH_3$ | 6-$OCH_3$ | $CH_3$ | H | O | S | i-$C_3H_7$ |
| $CH_3$ | $CH_3$ | 6-$OCH_3$ | $C_2H_5$ | H | O | S | i-$C_3H_7$ |
| $CH_3$ | $CH_3$ | 6-$OCH_3$ | $C_3H_7$ | H | O | S | i-$C_3H_7$ |
| $CH_3$ | $CH_3$ | 6-$OCH_3$ | i-$C_3H_7$ | H | O | S | i-$C_3H_7$ |
| $CH_3$ | $CH_3$ | 6-$OCH_3$ | $C_4H_9$ | H | O | S | i-$C_3H_7$ |
| $CH_3$ | $CH_3$ | 6-$OCH_3$ | i-$C_4H_9$ | H | O | S | i-$C_3H_7$ |
| $CH_3$ | $CH_3$ | 6-$OCH_3$ | s-$C_4H_9$ | H | O | S | i-$C_3H_7$ |
| $CH_3$ | $CH_3$ | 6-$OCH_3$ | t-$C_4H_9$ | H | O | S | i-$C_3H_7$ |
| $CH_3$ | $CH_3$ | 6-$OCH_3$ | $CH_3$ | $CH_3$ | O | S | i-$C_3H_7$ |
| $CH_3$ | $CH_3$ | 6-$OCH_3$ | $C_2H_5$ | $CH_3$ | O | S | i-$C_3H_7$ |
| $CH_3$ | $CH_3$ | 6-$OCH_3$ | $C_3H_7$ | $CH_3$ | O | S | i-$C_3H_7$ |
| $CH_3$ | $CH_3$ | 6-$OCH_3$ | i-$C_3H_7$ | $CH_3$ | O | S | i-$C_3H_7$ |
| $CH_3$ | $CH_3$ | 6-$OCH_3$ | $C_4H_9$ | $CH_3$ | O | S | i-$C_3H_7$ |
| $CH_3$ | $CH_3$ | 6-$OCH_3$ | i-$C_4H_9$ | $CH_3$ | O | S | i-$C_3H_7$ |
| $CH_3$ | $CH_3$ | 6-$OCH_3$ | s-$C_4H_9$ | $CH_3$ | O | S | i-$C_3H_7$ |
| $CH_3$ | $CH_3$ | 6-$OCH_3$ | t-$C_4H_9$ | $CH_3$ | O | S | i-$C_3H_7$ |
| $CH_3$ | $CH_3$ | 6-$OCH_3$ | $C_2H_5$ | $C_2H_5$ | O | S | i-$C_3H_7$ |
| $CH_3$ | $CH_3$ | 6-$OCH_3$ | $C_3H_7$ | $C_3H_7$ | O | S | i-$C_3H_7$ |
| $CH_3$ | $CH_3$ | 6-$OCH_3$ | 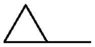 | $CH_3$ | O | S | i-$C_3H_7$ |
| $CH_3$ | $CH_3$ | 6-$OCH_3$ | 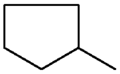 | $CH_3$ | O | S | i-$C_3H_7$ |
| $CH_3$ | $CH_3$ | 6-$OCH_3$ | 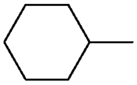 | $CH_3$ | O | S | i-$C_3H_7$ |
| $CH_3$ | $OCH_3$ | 6-$CH_3$ | $CH_3$ | H | O | S | i-$C_3H_7$ |
| $CH_3$ | $OCH_3$ | 6-$CH_3$ | $C_2H_5$ | H | O | S | i-$C_3H_7$ |
| $CH_3$ | $OCH_3$ | 6-$CH_3$ | $C_3H_7$ | H | O | S | i-$C_3H_7$ |
| $CH_3$ | $OCH_3$ | 6-$CH_3$ | i-$C_3H_7$ | H | O | S | i-$C_3H_7$ |
| $CH_3$ | $OCH_3$ | 6-$CH_3$ | $C_4H_9$ | H | O | S | i-$C_3H_7$ |
| $CH_3$ | $OCH_3$ | 6-$CH_3$ | i-$C_4H_9$ | H | O | S | i-$C_3H_7$ |
| $CH_3$ | $OCH_3$ | 6-$CH_3$ | s-$C_4H_9$ | H | O | S | i-$C_3H_7$ |
| $CH_3$ | $OCH_3$ | 6-$CH_3$ | t-$C_4H_9$ | H | O | S | i-$C_3H_7$ |
| $CH_3$ | $OCH_3$ | 6-$CH_3$ | $CH_3$ | $CH_3$ | O | S | i-$C_3H_7$ |
| $CH_3$ | $OCH_3$ | 6-$CH_3$ | $C_2H_5$ | $CH_3$ | O | S | i-$C_3H_7$ |
| $CH_3$ | $OCH_3$ | 6-$CH_3$ | $C_3H_7$ | $CH_3$ | O | S | i-$C_3H_7$ |
| $CH_3$ | $OCH_3$ | 6-$CH_3$ | i-$C_3H_7$ | $CH_3$ | O | S | i-$C_3H_7$ |
| $CH_3$ | $OCH_3$ | 6-$CH_3$ | $C_4H_9$ | $CH_3$ | O | S | i-$C_3H_7$ |
| $CH_3$ | $OCH_3$ | 6-$CH_3$ | i-$C_4H_9$ | $CH_3$ | O | S | i-$C_3H_7$ |
| $CH_3$ | $OCH_3$ | 6-$CH_3$ | s-$C_4H_9$ | $CH_3$ | O | S | i-$C_3H_7$ |
| $CH_3$ | $OCH_3$ | 6-$CH_3$ | t-$C_4H_9$ | $CH_3$ | O | S | i-$C_3H_7$ |
| $CH_3$ | $OCH_3$ | 6-$CH_3$ | $C_2H_5$ | $C_2H_5$ | O | S | i-$C_3H_7$ |
| $CH_3$ | $OCH_3$ | 6-$CH_3$ | $C_3H_7$ | $C_3H_7$ | O | S | i-$C_3H_7$ |

TABLE 3-continued

| | | | | | | | |
|---|---|---|---|---|---|---|---|
| $CH_3$ | $OCH_3$ | 6-$CH_3$ | 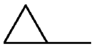 | $CH_3$ | O | S | i-$C_3H_7$ |
| $CH_3$ | $OCH_3$ | 6-$CH_3$ | 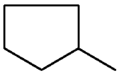 | $CH_3$ | O | S | i-$C_3H_7$ |
| $CH_3$ | $OCH_3$ | 6-$CH_3$ | 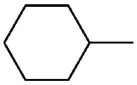 | $CH_3$ | O | S | i-$C_3H_7$ |

| X | Y | Z | A | B | L | M | $R^2$ |
|---|---|---|---|---|---|---|---|
| $CH_3$ | $OCH_3$ | H | | $-(CH_2)_2-$ | O | S | i-$C_3H_7$ |
| $CH_3$ | $OCH_3$ | H | | $-(CH_2)_4-$ | O | S | i-$C_3H_7$ |
| $CH_3$ | $OCH_3$ | H | | $-(CH_2)_5-$ | O | S | i-$C_3H_7$ |
| $CH_3$ | $OCH_3$ | H | | $-(CH_2)_6-$ | O | S | i-$C_3H_7$ |
| $CH_3$ | $OCH_3$ | H | | $-(CH_2)_7-$ | O | S | i-$C_3H_7$ |
| $CH_3$ | $OCH_3$ | H | | $-(CH_2)_2-O-(CH_2)_2-$ | O | S | i-$C_3H_7$ |
| $CH_3$ | $OCH_3$ | H | | $-(CH_2)_2-S-(CH_2)_2-$ | O | S | i-$C_3H_7$ |
| $CH_3$ | $OCH_3$ | H | | $-CH_2-CHCH_3-(CH_2)_3-$ | O | S | i-$C_3H_7$ |
| $CH_3$ | $OCH_3$ | H | | $-(CH_2)_2-CHCH_3-(CH_2)_2-$ | O | S | i-$C_3H_7$ |
| $CH_3$ | $OCH_3$ | H | | $-(CH_2)_2-CHC_2H_5-(CH_2)_2-$ | O | S | i-$C_3H_7$ |
| $CH_3$ | $OCH_3$ | H | | $-(CH_2)_2-CHC_3H_7-(CH_2)_2-$ | O | S | i-$C_3H_7$ |
| $CH_3$ | $OCH_3$ | H | | $-(CH_2)_2-CHi\text{-}C_3H_7-(CH_2)_2-$ | O | S | i-$C_3H_7$ |
| $CH_3$ | $OCH_3$ | H | | $-(CH_2)_2-CHOCH_3-(CH_2)_2-$ | O | S | i-$C_3H_7$ |
| $CH_3$ | $OCH_3$ | H | | $-(CH_2)_2-CHOC_2H_5-(CH_2)_2-$ | O | S | i-$C_3H_7$ |
| $CH_3$ | $OCH_3$ | H | | $-(CH_2)_2-CHOC_3H_7-(CH_2)_2-$ | O | S | i-$C_3H_7$ |
| $CH_3$ | $OCH_3$ | H | | $-(CH_2)_2-CHi\text{-}OC_3H_7-(CH_2)_2-$ | O | S | i-$C_3H_7$ |
| $CH_3$ | $OCH_3$ | H | | $-(CH_2)_2-C(CH_3)_2-(CH_2)_2-$ | O | S | i-$C_3H_7$ |
| $CH_3$ | $OCH_3$ | H | | $-CH_2-(CHCH_3)_2-(CH_2)_2-$ | O | S | i-$C_3H_7$ |
| $CH_3$ | $OCH_3$ | H | | 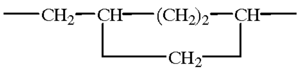 | O | S | i-$C_3H_7$ |
| $CH_3$ | $OCH_3$ | H | | 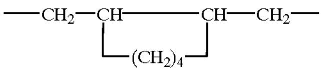 | O | S | i-$C_3H_7$ |
| $CH_3$ | $OCH_3$ | H | | 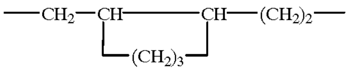 | O | S | i-$C_3H_7$ |
| $CH_3$ | H | 6-$OCH_3$ | | $-(CH_2)_2-$ | O | S | i-$C_3H_7$ |
| $CH_3$ | H | 6-$OCH_3$ | | $-(CH_2)_4-$ | O | S | i-$C_3H_7$ |
| $CH_3$ | H | 6-$OCH_3$ | | $-(CH_2)_5-$ | O | S | i-$C_3H_7$ |
| $CH_3$ | H | 6-$OCH_3$ | | $-(CH_2)_6-$ | O | S | i-$C_3H_7$ |
| $CH_3$ | H | 6-$OCH_3$ | | $-(CH_2)_7-$ | O | S | i-$C_3H_7$ |
| $CH_3$ | H | 6-$OCH_3$ | | $-(CH_2)_2-O-(CH_2)_2-$ | O | S | i-$C_3H_7$ |
| $CH_3$ | H | 6-$OCH_3$ | | $-(CH_2)_2-S-(CH_2)_2-$ | O | S | i-$C_3H_7$ |
| $CH_3$ | H | 6-$OCH_3$ | | $-CH_2-CHCH_3-(CH_2)_3-$ | O | S | i-$C_3H_7$ |
| $CH_3$ | H | 6-$OCH_3$ | | $-(CH_2)_2-CHCH_3-(CH_2)_2-$ | O | S | i-$C_3H_7$ |
| $CH_3$ | H | 6-$OCH_3$ | | $-(CH_2)_2-CHC_2H_5-(CH_2)_2-$ | O | S | i-$C_3H_7$ |
| $CH_3$ | H | 6-$OCH_3$ | | $-(CH_2)_2-CHC_3H_7-(CH_2)_2-$ | O | S | i-$C_3H_7$ |
| $CH_3$ | H | 6-$OCH_3$ | | $-(CH_2)_2-CHi\text{-}C_3H_7-(CH_2)_2-$ | O | S | i-$C_3H_7$ |
| $CH_3$ | H | 6-$OCH_3$ | | $-(CH_2)_2-CHOCH_3-(CH_2)_2-$ | O | S | i-$C_3H_7$ |
| $CH_3$ | H | 6-$OCH_3$ | | $-(CH_2)_2-CHOC_2H_5-(CH_2)_2-$ | O | S | i-$C_3H_7$ |
| $CH_3$ | H | 6-$OCH_3$ | | $-(CH_2)_2-CHOC_3H_7-(CH_2)_2-$ | O | S | i-$C_3H_7$ |
| $CH_3$ | H | 6-$OCH_3$ | | $-(CH_2)_2-CHi\text{-}OC_3H_7-(CH_2)_2-$ | O | S | i-$C_3H_7$ |
| $CH_3$ | H | 6-$OCH_3$ | | $-(CH_2)_2-C(CH_3)_2-(CH_2)_2-$ | O | S | i-$C_3H_7$ |
| $CH_3$ | H | 6-$OCH_3$ | | $-CH_2-(CHCH_3)_2-(CH_2)_2-$ | O | S | i-$C_3H_7$ |
| $CH_3$ | H | 6-$OCH_3$ | | 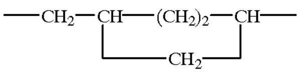 | O | S | i-$C_3H_7$ |
| $CH_3$ | H | 6-$OCH_3$ | | 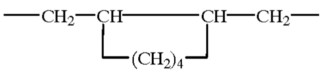 | O | S | i-$C_3H_7$ |

TABLE 3-continued

| | | | | | | |
|---|---|---|---|---|---|---|
| $CH_3$ | H | 6-$OCH_3$ | 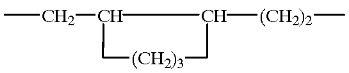 | O | S | i-$C_3H_7$ |
| $CH_3$ | $CH_3$ | 6-$OCH_3$ | $—(CH_2)_2—$ | O | S | i-$C_3H_7$ |
| $CH_3$ | $CH_3$ | 6-$OCH_3$ | $—(CH_2)_4—$ | O | S | i-$C_3H_7$ |
| $CH_3$ | $CH_3$ | 6-$OCH_3$ | $—(CH_2)_5—$ | O | S | i-$C_3H_7$ |
| $CH_3$ | $CH_3$ | 6-$OCH_3$ | $—(CH_2)_6—$ | O | S | i-$C_3H_7$ |
| $CH_3$ | $CH_3$ | 6-$OCH_3$ | $—(CH_2)_7—$ | O | S | i-$C_3H_7$ |
| $CH_3$ | $CH_3$ | 6-$OCH_3$ | $—(CH_2)_2—O—(CH_2)_2—$ | O | S | i-$C_3H_7$ |
| $CH_3$ | $CH_3$ | 6-$OCH_3$ | $—(CH_2)_2—S—(CH_2)_2—$ | O | S | i-$C_3H_7$ |
| $CH_3$ | $CH_3$ | 6-$OCH_3$ | $—CH_2—CHCH_3—(CH_2)_3—$ | O | S | i-$C_3H_7$ |
| $CH_3$ | $CH_3$ | 6-$OCH_3$ | $—(CH_2)_2—CHCH_3—(CH_2)_2—$ | O | S | i-$C_3H_7$ |
| $CH_3$ | $CH_3$ | 6-$OCH_3$ | $—(CH_2)_2—CHC_2H_5—(CH_2)_2—$ | O | S | i-$C_3H_7$ |
| $CH_3$ | $CH_3$ | 6-$OCH_3$ | $—(CH_2)_2—CHC_3H_7—(CH_2)_2—$ | O | S | i-$C_3H_7$ |
| $CH_3$ | $CH_3$ | 6-$OCH_3$ | $—(CH_2)_2—CHi\text{-}C_3H_7—(CH_2)_2—$ | O | S | i-$C_3H_7$ |
| $CH_3$ | $CH_3$ | 6-$OCH_3$ | $—(CH_2)_2—CHOCH_3—(CH_2)_2—$ | O | S | i-$C_3H_7$ |
| $CH_3$ | $CH_3$ | 6-$OCH_3$ | $—(CH_2)_2—CHOC_2H_5—(CH_2)_2—$ | O | S | i-$C_3H_7$ |
| $CH_3$ | $CH_3$ | 6-$OCH_3$ | $—(CH_2)_2—CHOC_3H_7—(CH_2)_2—$ | O | S | i-$C_3H_7$ |
| $CH_3$ | $CH_3$ | 6-$OCH_3$ | $—(CH_2)_2—CHi\text{-}OC_3H_7—(CH_2)_2—$ | O | S | i-$C_3H_7$ |
| $CH_3$ | $CH_3$ | 6-$OCH_3$ | $—(CH_2)_2—C(CH_3)_2—(CH_2)_2—$ | O | S | i-$C_3H_7$ |
| $CH_3$ | $CH_3$ | 6-$OCH_3$ | $—CH_2—(CHCH_3)_2—(CH_2)_2—$ | O | S | i-$C_3H_7$ |
| $CH_3$ | $CH_3$ | 6-$OCH_3$ | 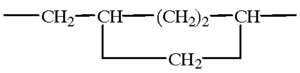 | O | S | i-$C_3H_7$ |
| $CH_3$ | $CH_3$ | 6-$OCH_3$ | 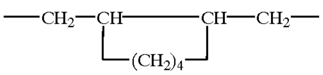 | O | S | i-$C_3H_7$ |
| $CH_3$ | $CH_3$ | 6-$OCH_3$ | 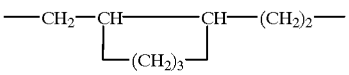 | O | S | i-$C_3H_7$ |
| $CH_3$ | $OCH_3$ | 6-$CH_3$ | $—(CH_2)_2—$ | O | S | i-$C_3H_7$ |
| $CH_3$ | $OCH_3$ | 6-$CH_3$ | $—(CH_2)_4—$ | O | S | i-$C_3H_7$ |
| $CH_3$ | $OCH_3$ | 6-$CH_3$ | $—(CH_2)_5—$ | O | S | i-$C_3H_7$ |
| $CH_3$ | $OCH_3$ | 6-$CH_3$ | $—(CH_2)_6—$ | O | S | i-$C_3H_7$ |
| $CH_3$ | $OCH_3$ | 6-$CH_3$ | $—(CH_2)_7—$ | O | S | i-$C_3H_7$ |
| $CH_3$ | $OCH_3$ | 6-$CH_3$ | $—(CH_2)_2—O—(CH_2)_2—$ | O | S | i-$C_3H_7$ |
| $CH_3$ | $OCH_3$ | 6-$CH_3$ | $—(CH_2)_2—S—(CH_2)_2—$ | O | S | i-$C_3H_7$ |
| $CH_3$ | $OCH_3$ | 6-$CH_3$ | $—CH_2—CHCH_3—(CH_2)_3—$ | O | S | i-$C_3H_7$ |
| $CH_3$ | $OCH_3$ | 6-$CH_3$ | $—(CH_2)_2—CHCH_3—(CH_2)_2—$ | O | S | i-$C_3H_7$ |
| $CH_3$ | $OCH_3$ | 6-$CH_3$ | $—(CH_2)_2—CHC_2H_5—(CH_2)_2—$ | O | S | i-$C_3H_7$ |
| $CH_3$ | $OCH_3$ | 6-$CH_3$ | $—(CH_2)_2—CHC_3H_7—(CH_2)_2—$ | O | S | i-$C_3H_7$ |
| $CH_3$ | $OCH_3$ | 6-$CH_3$ | $—(CH_2)_2—CHi\text{-}C_3H_7—(CH_2)_2—$ | O | S | i-$C_3H_7$ |
| $CH_3$ | $OCH_3$ | 6-$CH_3$ | $—(CH_2)_2—CHOCH_3—(CH_2)_2—$ | O | S | i-$C_3H_7$ |
| $CH_3$ | $OCH_3$ | 6-$CH_3$ | $—(CH_2)_2—CHOC_2H_5—(CH_2)_2—$ | O | S | i-$C_3H_7$ |
| $CH_3$ | $OCH_3$ | 6-$CH_3$ | $—(CH_2)_2—CHOC_3H_7—(CH_2)_2—$ | O | S | i-$C_3H_7$ |
| $CH_3$ | $OCH_3$ | 6-$CH_3$ | $—(CH_2)_2—CHi\text{-}OC_3H_7—(CH_2)_2—$ | O | S | i-$C_3H_7$ |
| $CH_3$ | $OCH_3$ | 6-$CH_3$ | $—(CH_2)_2—C(CH_3)_2—(CH_2)_2—$ | O | S | i-$C_3H_7$ |
| $CH_3$ | $OCH_3$ | 6-$CH_3$ | $—CH_2—(CHCH_3)_2—(CH_2)_2—$ | O | S | i-$C_3H_7$ |
| $CH_3$ | $OCH_3$ | 6-$CH_3$ | 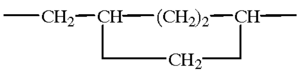 | O | S | i-$C_3H_7$ |
| $CH_3$ | $OCH_3$ | 6-$CH_3$ | 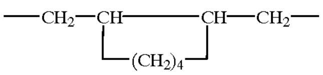 | O | S | i-$C_3H_7$ |
| $CH_3$ | $OCH_3$ | 6-$CH_3$ | 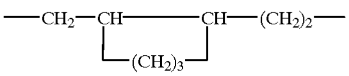 | O | S | i-$C_3H_7$ |

| X | Y | Z | A | B | L | M | $R^2$ |
|---|---|---|---|---|---|---|---|
| $CH_3$ | $OCH_3$ | H | $CH_3$ | H | O | O | s-$C_4H_9$ |
| $CH_3$ | $OCH_3$ | H | $C_2H_5$ | H | O | O | s-$C_4H_9$ |
| $CH_3$ | $OCH_3$ | H | $C_3H_7$ | H | O | O | s-$C_4H_9$ |
| $CH_3$ | $OCH_3$ | H | i-$C_3H_7$ | H | O | O | s-$C_4H_9$ |
| $CH_3$ | $OCH_3$ | H | $C_4H_9$ | H | O | O | s-$C_4H_9$ |
| $CH_3$ | $OCH_3$ | H | i-$C_4H_9$ | H | O | O | s-$C_4H_9$ |

TABLE 3-continued

| | | | | | | | |
|---|---|---|---|---|---|---|---|
| $CH_3$ | $OCH_3$ | H | s-$C_4H_9$ | H | O | O | s-$C_4H_9$ |
| $CH_3$ | $OCH_3$ | H | t-$C_4H_9$ | H | O | O | s-$C_4H_9$ |
| $CH_3$ | $OCH_3$ | H | $CH_3$ | $CH_3$ | O | O | s-$C_4H_9$ |
| $CH_3$ | $OCH_3$ | H | $C_2H_5$ | $CH_3$ | O | O | s-$C_4H_9$ |
| $CH_3$ | $OCH_3$ | H | $C_3H_7$ | $CH_3$ | O | O | s-$C_4H_9$ |
| $CH_3$ | $OCH_3$ | H | i-$C_3H_7$ | $CH_3$ | O | O | s-$C_4H_9$ |
| $CH_3$ | $OCH_3$ | H | $C_4H_9$ | $CH_3$ | O | O | s-$C_4H_9$ |
| $CH_3$ | $OCH_3$ | H | i-$C_4H_9$ | $CH_3$ | O | O | s-$C_4H_9$ |
| $CH_3$ | $OCH_3$ | H | s-$C_4H_9$ | $CH_3$ | O | O | s-$C_4H_9$ |
| $CH_3$ | $OCH_3$ | H | t-$C_4H_9$ | $CH_3$ | O | O | s-$C_4H_9$ |
| $CH_3$ | $OCH_3$ | H | $C_2H_5$ | $C_2H_5$ | O | O | s-$C_4H_9$ |
| $CH_3$ | $OCH_3$ | H | $C_3H_7$ | $C_3H_7$ | O | O | s-$C_4H_9$ |
| $CH_3$ | $OCH_3$ | H | 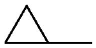 | $CH_3$ | O | O | s-$C_4H_9$ |
| $CH_3$ | $OCH_3$ | H | 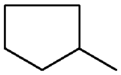 | $CH_3$ | O | O | s-$C_4H_9$ |
| $CH_3$ | $OCH_3$ | H | 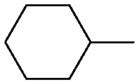 | $CH_3$ | O | O | s-$C_4H_9$ |
| $CH_3$ | H | 6-$OCH_3$ | $CH_3$ | H | O | O | s-$C_4H_9$ |
| $CH_3$ | H | 6-$OCH_3$ | $C_2H_5$ | H | O | O | s-$C_4H_9$ |
| $CH_3$ | H | 6-$OCH_3$ | $C_3H_7$ | H | O | O | s-$C_4H_9$ |
| $CH_3$ | H | 6-$OCH_3$ | i-$C_3H_7$ | H | O | O | s-$C_4H_9$ |
| $CH_3$ | H | 6-$OCH_3$ | $C_4H_9$ | H | O | O | s-$C_4H_9$ |
| $CH_3$ | H | 6-$OCH_3$ | i-$C_4H_9$ | H | O | O | s-$C_4H_9$ |
| $CH_3$ | H | 6-$OCH_3$ | s-$C_4H_9$ | H | O | O | s-$C_4H_9$ |
| $CH_3$ | H | 6-$OCH_3$ | t-$C_4H_9$ | H | O | O | s-$C_4H_9$ |
| $CH_3$ | H | 6-$OCH_3$ | $CH_3$ | $CH_3$ | O | O | s-$C_4H_9$ |
| $CH_3$ | H | 6-$OCH_3$ | $C_2H_5$ | $CH_3$ | O | O | s-$C_4H_9$ |
| $CH_3$ | H | 6-$OCH_3$ | $C_3H_7$ | $CH_3$ | O | O | s-$C_4H_9$ |
| $CH_3$ | H | 6-$OCH_3$ | i-$C_3H_7$ | $CH_3$ | O | O | s-$C_4H_9$ |
| $CH_3$ | H | 6-$OCH_3$ | $C_4H_9$ | $CH_3$ | O | O | s-$C_4H_9$ |
| $CH_3$ | H | 6-$OCH_3$ | i-$C_4H_9$ | $CH_3$ | O | O | s-$C_4H_9$ |
| $CH_3$ | H | 6-$OCH_3$ | s-$C_4H_9$ | $CH_3$ | O | O | s-$C_4H_9$ |
| $CH_3$ | H | 6-$OCH_3$ | t-$C_4H_9$ | $CH_3$ | O | O | s-$C_4H_9$ |
| $CH_3$ | H | 6-$OCH_3$ | $C_2H_5$ | $C_2H_5$ | O | O | s-$C_4H_9$ |
| $CH_3$ | H | 6-$OCH_3$ | $C_3H_7$ | $C_3H_7$ | O | O | s-$C_4H_9$ |
| $CH_3$ | H | 6-$OCH_3$ | 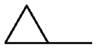 | $CH_3$ | O | O | s-$C_4H_9$ |
| $CH_3$ | H | 6-$OCH_3$ | 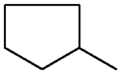 | $CH_3$ | O | O | s-$C_4H_9$ |
| $CH_3$ | H | 6-$OCH_3$ | 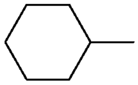 | $CH_3$ | O | O | s-$C_4H_9$ |
| $CH_3$ | $CH_3$ | 6-$OCH_3$ | $CH_3$ | H | O | O | s-$C_4H_9$ |
| $CH_3$ | $CH_3$ | 6-$OCH_3$ | $C_2H_5$ | H | O | O | s-$C_4H_9$ |
| $CH_3$ | $CH_3$ | 6-$OCH_3$ | $C_3H_7$ | H | O | O | s-$C_4H_9$ |
| $CH_3$ | $CH_3$ | 6-$OCH_3$ | i-$C_3H_7$ | H | O | O | s-$C_4H_9$ |
| $CH_3$ | $CH_3$ | 6-$OCH_3$ | $C_4H_9$ | H | O | O | s-$C_4H_9$ |
| $CH_3$ | $CH_3$ | 6-$OCH_3$ | i-$C_4H_9$ | H | O | O | s-$C_4H_9$ |
| $CH_3$ | $CH_3$ | 6-$OCH_3$ | s-$C_4H_9$ | H | O | O | s-$C_4H_9$ |
| $CH_3$ | $CH_3$ | 6-$OCH_3$ | t-$C_4H_9$ | H | O | O | s-$C_4H_9$ |
| $CH_3$ | $CH_3$ | 6-$OCH_3$ | $CH_3$ | $CH_3$ | O | O | s-$C_4H_9$ |
| $CH_3$ | $CH_3$ | 6-$OCH_3$ | $C_2H_5$ | $CH_3$ | O | O | s-$C_4H_9$ |
| $CH_3$ | $CH_3$ | 6-$OCH_3$ | $C_3H_7$ | $CH_3$ | O | O | s-$C_4H_9$ |
| $CH_3$ | $CH_3$ | 6-$OCH_3$ | i-$C_3H_7$ | $CH_3$ | O | O | s-$C_4H_9$ |
| $CH_3$ | $CH_3$ | 6-$OCH_3$ | $C_4H_9$ | $CH_3$ | O | O | s-$C_4H_9$ |
| $CH_3$ | $CH_3$ | 6-$OCH_3$ | i-$C_4H_9$ | $CH_3$ | O | O | s-$C_4H_9$ |
| $CH_3$ | $CH_3$ | 6-$OCH_3$ | s-$C_4H_9$ | $CH_3$ | O | O | s-$C_4H_9$ |
| $CH_3$ | $CH_3$ | 6-$OCH_3$ | t-$C_4H_9$ | $CH_3$ | O | O | s-$C_4H_9$ |
| $CH_3$ | $CH_3$ | 6-$OCH_3$ | $C_2H_5$ | $C_2H_5$ | O | O | s-$C_4H_9$ |
| $CH_3$ | $CH_3$ | 6-$OCH_3$ | $C_3H_7$ | $C_3H_7$ | O | O | s-$C_4H_9$ |

TABLE 3-continued

| | | | | | | | |
|---|---|---|---|---|---|---|---|
| $CH_3$ | $CH_3$ | 6-$OCH_3$ | 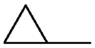 | $CH_3$ | O | O | s-$C_4H_9$ |
| $CH_3$ | $CH_3$ | 6-$OCH_3$ | 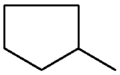 | $CH_3$ | O | O | s-$C_4H_9$ |
| $CH_3$ | $CH_3$ | 6-$OCH_3$ | 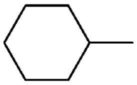 | $CH_3$ | O | O | s-$C_4H_9$ |
| $CH_3$ | $OCH_3$ | 6-$CH_3$ | $CH_3$ | H | O | O | s-$C_4H_9$ |
| $CH_3$ | $OCH_3$ | 6-$CH_3$ | $C_2H_5$ | H | O | O | s-$C_4H_9$ |
| $CH_3$ | $OCH_3$ | 6-$CH_3$ | $C_3H_7$ | H | O | O | s-$C_4H_9$ |
| $CH_3$ | $OCH_3$ | 6-$CH_3$ | i-$C_3H_7$ | H | O | O | s-$C_4H_9$ |
| $CH_3$ | $OCH_3$ | 6-$CH_3$ | $C_4H_9$ | H | O | O | s-$C_4H_9$ |
| $CH_3$ | $OCH_3$ | 6-$CH_3$ | i-$C_4H_9$ | H | O | O | s-$C_4H_9$ |
| $CH_3$ | $OCH_3$ | 6-$CH_3$ | s-$C_4H_9$ | H | O | O | s-$C_4H_9$ |
| $CH_3$ | $OCH_3$ | 6-$CH_3$ | t-$C_4H_9$ | H | O | O | s-$C_4H_9$ |
| $CH_3$ | $OCH_3$ | 6-$CH_3$ | $CH_3$ | $CH_3$ | O | O | s-$C_4H_9$ |
| $CH_3$ | $OCH_3$ | 6-$CH_3$ | $C_2H_5$ | $CH_3$ | O | O | s-$C_4H_9$ |
| $CH_3$ | $OCH_3$ | 6-$CH_3$ | $C_3H_7$ | $CH_3$ | O | O | s-$C_4H_9$ |
| $CH_3$ | $OCH_3$ | 6-$CH_3$ | i-$C_3H_7$ | $CH_3$ | O | O | s-$C_4H_9$ |
| $CH_3$ | $OCH_3$ | 6-$CH_3$ | $C_4H_9$ | $CH_3$ | O | O | s-$C_4H_9$ |
| $CH_3$ | $OCH_3$ | 6-$CH_3$ | i-$C_4H_9$ | $CH_3$ | O | O | s-$C_4H_9$ |
| $CH_3$ | $OCH_3$ | 6-$CH_3$ | s-$C_4H_9$ | $CH_3$ | O | O | s-$C_4H_9$ |
| $CH_3$ | $OCH_3$ | 6-$CH_3$ | t-$C_4H_9$ | $CH_3$ | O | O | s-$C_4H_9$ |
| $CH_3$ | $OCH_3$ | 6-$CH_3$ | $C_2H_5$ | $C_2H_5$ | O | O | s-$C_4H_9$ |
| $CH_3$ | $OCH_3$ | 6-$CH_3$ | $C_3H_7$ | $C_3H_7$ | O | O | s-$C_4H_9$ |
| $CH_3$ | $OCH_3$ | 6-$CH_3$ | 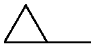 | $CH_3$ | O | O | s-$C_4H_9$ |
| $CH_3$ | $OCH_3$ | 6-$CH_3$ | 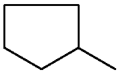 | $CH_3$ | O | O | s-$C_4H_9$ |
| $CH_3$ | $OCH_3$ | 6-$CH_3$ | 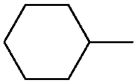 | $CH_3$ | O | O | s-$C_4H_9$ |

| X | Y | Z | A | B | L | M | $R^2$ |
|---|---|---|---|---|---|---|---|
| $CH_3$ | $OCH_3$ | H | | $-(CH_2)_2-$ | O | O | s-$C_4H_9$ |
| $CH_3$ | $OCH_3$ | H | | $-(CH_2)_4-$ | O | O | s-$C_4H_9$ |
| $CH_3$ | $OCH_3$ | H | | $-(CH_2)_5-$ | O | O | s-$C_4H_9$ |
| $CH_3$ | $OCH_3$ | H | | $-(CH_2)_6-$ | O | O | s-$C_4H_9$ |
| $CH_3$ | $OCH_3$ | H | | $-(CH_2)_7-$ | O | O | s-$C_4H_9$ |
| $CH_3$ | $OCH_3$ | H | | $-(CH_2)_2-O-(CH_2)_2-$ | O | O | s-$C_4H_9$ |
| $CH_3$ | $OCH_3$ | H | | $-(CH_2)_2-S-(CH_2)_2-$ | O | O | s-$C_4H_9$ |
| $CH_3$ | $OCH_3$ | H | | $-CH_2-CHCH_3-(CH_2)_3-$ | O | O | s-$C_4H_9$ |
| $CH_3$ | $OCH_3$ | H | | $-(CH_2)_2-CHCH_3-(CH_2)_2-$ | O | O | s-$C_4H_9$ |
| $CH_3$ | $OCH_3$ | H | | $-(CH_2)_2-CHC_2H_5-(CH_2)_2-$ | O | O | s-$C_4H_9$ |
| $CH_3$ | $OCH_3$ | H | | $-(CH_2)_2-CHC_3H_7-(CH_2)_2-$ | O | O | s-$C_4H_9$ |
| $CH_3$ | $OCH_3$ | H | | $-(CH_2)_2-CHi\text{-}C_3H_7-(CH_2)_2-$ | O | O | s-$C_4H_9$ |
| $CH_3$ | $OCH_3$ | H | | $-(CH_2)_2-CHOCH_3-(CH_2)_2-$ | O | O | s-$C_4H_9$ |
| $CH_3$ | $OCH_3$ | H | | $-(CH_2)_2-CHOC_2H_5-(CH_2)_2-$ | O | O | s-$C_4H_9$ |
| $CH_3$ | $OCH_3$ | H | | $-(CH_2)_2-CHOC_3H_7-(CH_2)_2-$ | O | O | s-$C_4H_9$ |
| $CH_3$ | $OCH_3$ | H | | $-(CH_2)_2-CHi\text{-}OC_3H_7-(CH_2)_2-$ | O | O | s-$C_4H_9$ |
| $CH_3$ | $OCH_3$ | H | | $-(CH_2)_2-C(CH_3)_2-(CH_2)_2-$ | O | O | s-$C_4H_9$ |
| $CH_3$ | $OCH_3$ | H | | $-CH_2-(CHCH_3)_2-(CH_2)_2-$ | O | O | s-$C_4H_9$ |
| $CH_3$ | $OCH_3$ | H | | 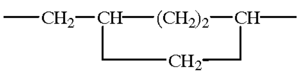 | O | O | s-$C_4H_9$ |
| $CH_3$ | $OCH_3$ | H | | 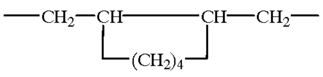 | O | O | s-$C_4H_9$ |

TABLE 3-continued

| | | | | | | |
|---|---|---|---|---|---|---|
| $CH_3$ | $OCH_3$ | H | 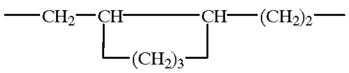 | O | O | s-$C_4H_9$ |
| $CH_3$ | H | 6-$OCH_3$ | $-(CH_2)_2-$ | O | O | s-$C_4H_9$ |
| $CH_3$ | H | 6-$OCH_3$ | $-(CH_2)_4-$ | O | O | s-$C_4H_9$ |
| $CH_3$ | H | 6-$OCH_3$ | $-(CH_2)_5-$ | O | O | s-$C_4H_9$ |
| $CH_3$ | H | 6-$OCH_3$ | $-(CH_2)_6-$ | O | O | s-$C_4H_9$ |
| $CH_3$ | H | 6-$OCH_3$ | $-(CH_2)_7-$ | O | O | s-$C_4H_9$ |
| $CH_3$ | H | 6-$OCH_3$ | $-(CH_2)_2-O-(CH_2)_2-$ | O | O | s-$C_4H_9$ |
| $CH_3$ | H | 6-$OCH_3$ | $-(CH_2)_2-S-(CH_2)_2-$ | O | O | s-$C_4H_9$ |
| $CH_3$ | H | 6-$OCH_3$ | $-CH_2-CHCH_3-(CH_2)_3-$ | O | O | s-$C_4H_9$ |
| $CH_3$ | H | 6-$OCH_3$ | $-(CH_2)_2-CHCH_3-(CH_2)_2-$ | O | O | s-$C_4H_9$ |
| $CH_3$ | H | 6-$OCH_3$ | $-(CH_2)_2-CHC_2H_5-(CH_2)_2-$ | O | O | s-$C_4H_9$ |
| $CH_3$ | H | 6-$OCH_3$ | $-(CH_2)_2-CHC_3H_7-(CH_2)_2-$ | O | O | s-$C_4H_9$ |
| $CH_3$ | H | 6-$OCH_3$ | $-(CH_2)_2-CHi\text{-}C_3H_7-(CH_2)_2-$ | O | O | s-$C_4H_9$ |
| $CH_3$ | H | 6-$OCH_3$ | $-(CH_2)_2-CHOCH_3-(CH_2)_2-$ | O | O | s-$C_4H_9$ |
| $CH_3$ | H | 6-$OCH_3$ | $-(CH_2)_2-CHOC_2H_5-(CH_2)_2-$ | O | O | s-$C_4H_9$ |
| $CH_3$ | H | 6-$OCH_3$ | $-(CH_2)_2-CHOC_3H_7-(CH_2)_2-$ | O | O | s-$C_4H_9$ |
| $CH_3$ | H | 6-$OCH_3$ | $-(CH_2)_2-CHi\text{-}OC_3H_7-(CH_2)_2-$ | O | O | s-$C_4H_9$ |
| $CH_3$ | H | 6-$OCH_3$ | $-(CH_2)_2-C(CH_3)_2-(CH_2)_2-$ | O | O | s-$C_4H_9$ |
| $CH_3$ | H | 6-$OCH_3$ | $-CH_2-(CHCH_3)_2-(CH_2)_2-$ | O | O | s-$C_4H_9$ |
| $CH_3$ | H | 6-$OCH_3$ | 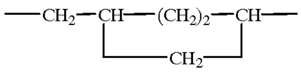 | O | O | s-$C_4H_9$ |
| $CH_3$ | H | 6-$OCH_3$ | 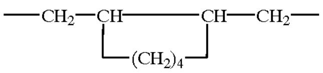 | O | O | s-$C_4H_9$ |
| $CH_3$ | H | 6-$OCH_3$ | 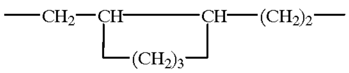 | O | O | s-$C_4H_9$ |
| $CH_3$ | $CH_3$ | 6-$OCH_3$ | $-(CH_2)_2-$ | O | O | s-$C_4H_9$ |
| $CH_3$ | $CH_3$ | 6-$OCH_3$ | $-(CH_2)_4-$ | O | O | s-$C_4H_9$ |
| $CH_3$ | $CH_3$ | 6-$OCH_3$ | $-(CH_2)_5-$ | O | O | s-$C_4H_9$ |
| $CH_3$ | $CH_3$ | 6-$OCH_3$ | $-(CH_2)_6-$ | O | O | s-$C_4H_9$ |
| $CH_3$ | $CH_3$ | 6-$OCH_3$ | $-(CH_2)_7-$ | O | O | s-$C_4H_9$ |
| $CH_3$ | $CH_3$ | 6-$OCH_3$ | $-(CH_2)_2-O-(CH_2)_2-$ | O | O | s-$C_4H_9$ |
| $CH_3$ | $CH_3$ | 6-$OCH_3$ | $-(CH_2)_2-S-(CH_2)_2-$ | O | O | s-$C_4H_9$ |
| $CH_3$ | $CH_3$ | 6-$OCH_3$ | $-CH_2-CHCH_3-(CH_2)_3-$ | O | O | s-$C_4H_9$ |
| $CH_3$ | $CH_3$ | 6-$OCH_3$ | $-(CH_2)_2-CHCH_3-(CH_2)_2-$ | O | O | s-$C_4H_9$ |
| $CH_3$ | $CH_3$ | 6-$OCH_3$ | $-(CH_2)_2-CHC_2H_5-(CH_2)_2-$ | O | O | s-$C_4H_9$ |
| $CH_3$ | $CH_3$ | 6-$OCH_3$ | $-(CH_2)_2-CHC_3H_7-(CH_2)_2-$ | O | O | s-$C_4H_9$ |
| $CH_3$ | $CH_3$ | 6-$OCH_3$ | $-(CH_2)_2-CHi\text{-}C_3H_7-(CH_2)_2-$ | O | O | s-$C_4H_9$ |
| $CH_3$ | $CH_3$ | 6-$OCH_3$ | $-(CH_2)_2-CHOCH_3-(CH_2)_2-$ | O | O | s-$C_4H_9$ |
| $CH_3$ | $CH_3$ | 6-$OCH_3$ | $-(CH_2)_2-CHOC_2H_5-(CH_2)_2-$ | O | O | s-$C_4H_9$ |
| $CH_3$ | $CH_3$ | 6-$OCH_3$ | $-(CH_2)_2-CHOC_3H_7-(CH_2)_2-$ | O | O | s-$C_4H_9$ |
| $CH_3$ | $CH_3$ | 6-$OCH_3$ | $-(CH_2)_2-CHi\text{-}OC_3H_7-(CH_2)_2-$ | O | O | s-$C_4H_9$ |
| $CH_3$ | $CH_3$ | 6-$OCH_3$ | $-(CH_2)_2-C(CH_3)_2-(CH_2)_2-$ | O | O | s-$C_4H_9$ |
| $CH_3$ | $CH_3$ | 6-$OCH_3$ | $-CH_2-(CHCH_3)_2-(CH_2)_2-$ | O | O | s-$C_4H_9$ |
| $CH_3$ | $CH_3$ | 6-$OCH_3$ | 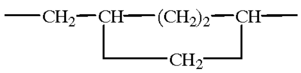 | O | O | s-$C_4H_9$ |
| $CH_3$ | $CH_3$ | 6-$OCH_3$ | 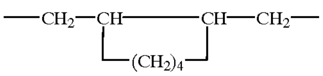 | O | O | s-$C_4H_9$ |
| $CH_3$ | $CH_3$ | 6-$OCH_3$ | 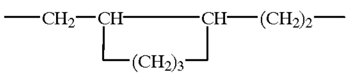 | O | O | s-$C_4H_9$ |
| $CH_3$ | $OCH_3$ | 6-$CH_3$ | $-(CH_2)_2-$ | O | O | s-$C_4H_9$ |
| $CH_3$ | $OCH_3$ | 6-$CH_3$ | $-(CH_2)_4-$ | O | O | s-$C_4H_9$ |
| $CH_3$ | $OCH_3$ | 6-$CH_3$ | $-(CH_2)_5-$ | O | O | s-$C_4H_9$ |
| $CH_3$ | $OCH_3$ | 6-$CH_3$ | $-(CH_2)_6-$ | O | O | s-$C_4H_9$ |
| $CH_3$ | $OCH_3$ | 6-$CH_3$ | $-(CH_2)_7-$ | O | O | s-$C_4H_9$ |
| $CH_3$ | $OCH_3$ | 6-$CH_3$ | $-(CH_2)_2-O-(CH_2)_2-$ | O | O | s-$C_4H_9$ |
| $CH_3$ | $OCH_3$ | 6-$CH_3$ | $-(CH_2)_2-S-(CH_2)_2-$ | O | O | s-$C_4H_9$ |
| $CH_3$ | $OCH_3$ | 6-$CH_3$ | $-CH_2-CHCH_3-(CH_2)_3-$ | O | O | s-$C_4H_9$ |

TABLE 3-continued

| | | | | | | |
|---|---|---|---|---|---|---|
| $CH_3$ | $OCH_3$ | 6-$CH_3$ | $-(CH_2)_2-CHCH_3-(CH_2)_2-$ | O | O | s-$C_4H_9$ |
| $CH_3$ | $OCH_3$ | 6-$CH_3$ | $-(CH_2)_2-CHC_2H_5-(CH_2)_2-$ | O | O | s-$C_4H_9$ |
| $CH_3$ | $OCH_3$ | 6-$CH_3$ | $-(CH_2)_2-CHC_3H_7-(CH_2)_2-$ | O | O | s-$C_4H_9$ |
| $CH_3$ | $OCH_3$ | 6-$CH_3$ | $-(CH_2)_2-CHi\text{-}C_3H_7-(CH_2)_2-$ | O | O | s-$C_4H_9$ |
| $CH_3$ | $OCH_3$ | 6-$CH_3$ | $-(CH_2)_2-CHOCH_3-(CH_2)_2-$ | O | O | s-$C_4H_9$ |
| $CH_3$ | $OCH_3$ | 6-$CH_3$ | $-(CH_2)_2-CHOC_2H_5-(CH_2)_2-$ | O | O | s-$C_4H_9$ |
| $CH_3$ | $OCH_3$ | 6-$CH_3$ | $-(CH_2)_2-CHOC_3H_7-(CH_2)_2-$ | O | O | s-$C_4H_9$ |
| $CH_3$ | $OCH_3$ | 6-$CH_3$ | $-(CH_2)_2-CHi\text{-}OC_3H_7-(CH_2)_2-$ | O | O | s-$C_4H_9$ |
| $CH_3$ | $OCH_3$ | 6-$CH_3$ | $-(CH_2)_2-C(CH_3)_2-(CH_2)_2-$ | O | O | s-$C_4H_9$ |
| $CH_3$ | $OCH_3$ | 6-$CH_3$ | $-CH_2-(CHCH_3)_2-(CH_2)_2-$ | O | O | s-$C_4H_9$ |
| $CH_3$ | $OCH_3$ | 6-$CH_3$ | 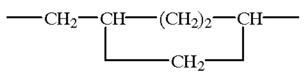 | O | O | s-$C_4H_9$ |
| $CH_3$ | $OCH_3$ | 6-$CH_3$ | 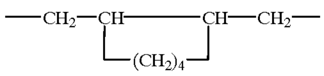 | O | O | s-$C_4H_9$ |
| $CH_3$ | $OCH_3$ | 6-$CH_3$ | 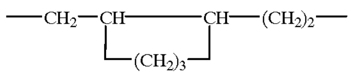 | O | O | s-$C_4H_9$ |

Specific mention may be made, in addition to the compounds specified in the Preparation Examples, of the following compounds of the formula (Id):

TABLE 4

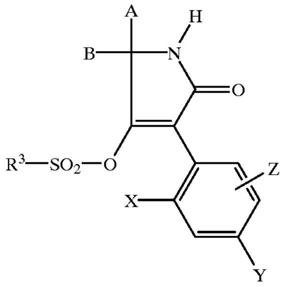

(Id)

| | Y | Z | A | B | $R^3$ |
|---|---|---|---|---|---|
| $CH_3$ | $OCH_3$ | H | $CH_3$ | H | $CH_3$ |
| $CH_3$ | $OCH_3$ | H | $C_2H_5$ | H | $CH_3$ |
| $CH_3$ | $OCH_3$ | H | $C_3H_7$ | H | $CH_3$ |
| $CH_3$ | $OCH_3$ | H | i-$C_3H_7$ | H | $CH_3$ |
| $CH_3$ | $OCH_3$ | H | $C_4H_9$ | H | $CH_3$ |
| $CH_3$ | $OCH_3$ | H | i-$C_4H_9$ | H | $CH_3$ |
| $CH_3$ | $OCH_3$ | H | s-$C_4H_9$ | H | $CH_3$ |
| $CH_3$ | $OCH_3$ | H | t-$C_4H_9$ | H | $CH_3$ |
| $CH_3$ | $OCH_3$ | H | $CH_3$ | $CH_3$ | $CH_3$ |
| $CH_3$ | $OCH_3$ | H | $C_2H_5$ | $CH_3$ | $CH_3$ |
| $CH_3$ | $OCH_3$ | H | $C_3H_7$ | $CH_3$ | $CH_3$ |
| $CH_3$ | $OCH_3$ | H | i-$C_3H_7$ | $CH_3$ | $CH_3$ |
| $CH_3$ | $OCH_3$ | H | $C_4H_9$ | $CH_3$ | $CH_3$ |
| $CH_3$ | $OCH_3$ | H | i-$C_4H_9$ | $CH_3$ | $CH_3$ |
| $CH_3$ | $OCH_3$ | H | s-$C_4H_9$ | $CH_3$ | $CH_3$ |
| $CH_3$ | $OCH_3$ | H | t-$C_4H_9$ | $CH_3$ | $CH_3$ |
| $CH_3$ | $OCH_3$ | H | $C_2H_5$ | $C_2H_5$ | $CH_3$ |
| $CH_3$ | $OCH_3$ | H | $C_3H_7$ | $C_3H_7$ | $CH_3$ |
| $CH_3$ | $OCH_3$ | H | 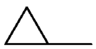 | $CH_3$ | $CH_3$ |
| $CH_3$ | $OCH_3$ | H | 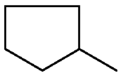 | $CH_3$ | $CH_3$ |

TABLE 4-continued (Id)

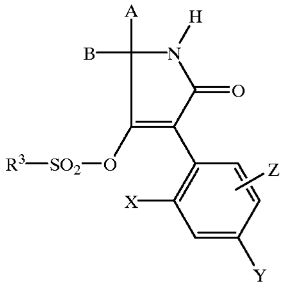

| | Y | Z | A | B | $R^3$ |
|---|---|---|---|---|---|
| $CH_3$ | $OCH_3$ | H | 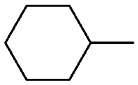 | $CH_3$ | $CH_3$ |
| $CH_3$ | $CH_3$ | 6-$OCH_3$ | $CH_3$ | H | $CH_3$ |
| $CH_3$ | $CH_3$ | 6-$OCH_3$ | $C_2H_5$ | H | $CH_3$ |
| $CH_3$ | $CH_3$ | 6-$OCH_3$ | $C_3H_7$ | H | $CH_3$ |
| $CH_3$ | $CH_3$ | 6-$OCH_3$ | i-$C_3H_7$ | H | $CH_3$ |
| $CH_3$ | $CH_3$ | 6-$OCH_3$ | $C_4H_9$ | H | $CH_3$ |
| $CH_3$ | $CH_3$ | 6-$OCH_3$ | i-$C_4H_9$ | H | $CH_3$ |
| $CH_3$ | $CH_3$ | 6-$OCH_3$ | s-$C_4H_9$ | H | $CH_3$ |
| $CH_3$ | $CH_3$ | 6-$OCH_3$ | t-$C_4H_9$ | H | $CH_3$ |
| $CH_3$ | $CH_3$ | 6-$OCH_3$ | $CH_3$ | $CH_3$ | $CH_3$ |
| $CH_3$ | $CH_3$ | 6-$OCH_3$ | $C_2H_5$ | $CH_3$ | $CH_3$ |
| $CH_3$ | $CH_3$ | 6-$OCH_3$ | $C_3H_7$ | $CH_3$ | $CH_3$ |
| $CH_3$ | $CH_3$ | 6-$OCH_3$ | i-$C_3H_7$ | $CH_3$ | $CH_3$ |
| $CH_3$ | $CH_3$ | 6-$OCH_3$ | $C_4H_9$ | $CH_3$ | $CH_3$ |
| $CH_3$ | $CH_3$ | 6-$OCH_3$ | i-$C_4H_9$ | $CH_3$ | $CH_3$ |
| $CH_3$ | $CH_3$ | 6-$OCH_3$ | s-$C_4H_9$ | $CH_3$ | $CH_3$ |
| $CH_3$ | $CH_3$ | 6-$OCH_3$ | t-$C_4H_9$ | $CH_3$ | $CH_3$ |
| $CH_3$ | $CH_3$ | 6-$OCH_3$ | $C_2H_5$ | $C_2H_5$ | $CH_3$ |
| $CH_3$ | $CH_3$ | 6-$OCH_3$ | $C_3H_7$ | $C_3H_7$ | $CH_3$ |
| $CH_3$ | $CH_3$ | 6-$OCH_3$ | 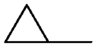 | $CH_3$ | $CH_3$ |
| $CH_3$ | $CH_3$ | 6-$OCH_3$ | 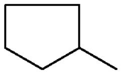 | $CH_3$ | $CH_3$ |
| $CH_3$ | $CH_3$ | 6-$OCH_3$ | 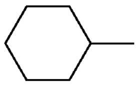 | $CH_3$ | $CH_3$ |
| $CH_3$ | $OCH_3$ | 6-$CH_3$ | $CH_3$ | H | $CH_3$ |
| $CH_3$ | $OCH_3$ | 6-$CH_3$ | $C_2H_5$ | H | $CH_3$ |
| $CH_3$ | $OCH_3$ | 6-$CH_3$ | $C_3H_7$ | H | $CH_3$ |
| $CH_3$ | $OCH_3$ | 6-$CH_3$ | i-$C_3H_7$ | H | $CH_3$ |
| $CH_3$ | $OCH_3$ | 6-$CH_3$ | $C_4H_9$ | H | $CH_3$ |
| $CH_3$ | $OCH_3$ | 6-$CH_3$ | i-$C_4H_9$ | H | $CH_3$ |
| $CH_3$ | $OCH_3$ | 6-$CH_3$ | s-$C_4H_9$ | H | $CH_3$ |
| $CH_3$ | $OCH_3$ | 6-$CH_3$ | t-$C_4H_9$ | H | $CH_3$ |
| $CH_3$ | $OCH_3$ | 6-$CH_3$ | $CH_3$ | $CH_3$ | $CH_3$ |
| $CH_3$ | $OCH_3$ | 6-$CH_3$ | $C_2H_5$ | $CH_3$ | $CH_3$ |
| $CH_3$ | $OCH_3$ | 6-$CH_3$ | $C_3H_7$ | $CH_3$ | $CH_3$ |
| $CH_3$ | $OCH_3$ | 6-$CH_3$ | i-$C_3H_7$ | $CH_3$ | $CH_3$ |
| $CH_3$ | $OCH_3$ | 6-$CH_3$ | $C_4H_9$ | $CH_3$ | $CH_3$ |
| $CH_3$ | $OCH_3$ | 6-$CH_3$ | i-$C_4H_9$ | $CH_3$ | $CH_3$ |
| $CH_3$ | $OCH_3$ | 6-$CH_3$ | s-$C_4H_9$ | $CH_3$ | $CH_3$ |
| $CH_3$ | $OCH_3$ | 6-$CH_3$ | t-$C_4H_9$ | $CH_3$ | $CH_3$ |
| $CH_3$ | $OCH_3$ | 6-$CH_3$ | $C_2H_5$ | $C_2H_5$ | $CH_3$ |
| $CH_3$ | $OCH_3$ | 6-$CH_3$ | $C_3H_7$ | $C_3H_7$ | $CH_3$ |
| $CH_3$ | $OCH_3$ | 6-$CH_3$ | 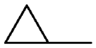 | $CH_3$ | $CH_3$ |

TABLE 4-continued (Id)

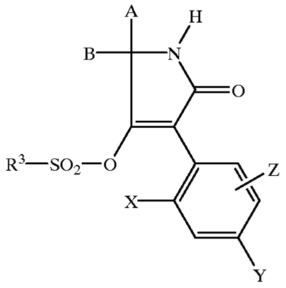

| | Y | Z | A | B | $R^3$ |
|---|---|---|---|---|---|
| $CH_3$ | $OCH_3$ | 6-$CH_3$ | 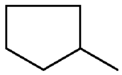 | $CH_3$ | $CH_3$ |
| $CH_3$ | $OCH_3$ | 6-$CH_3$ | 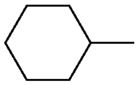 | $CH_3$ | $CH_3$ |
| $CH_3$ | $OCH_3$ | H | $-(CH_2)_2-$ | | $CH_3$ |
| $CH_3$ | $OCH_3$ | H | $-(CH_2)_4-$ | | $CH_3$ |
| $CH_3$ | $OCH_3$ | H | $-(CH_2)_5-$ | | $CH_3$ |
| $CH_3$ | $OCH_3$ | H | $-(CH_2)_6-$ | | $CH_3$ |
| $CH_3$ | $OCH_3$ | H | $-(CH_2)_7-$ | | $CH_3$ |
| $CH_3$ | $OCH_3$ | H | $-(CH_2)_2-O-(CH_2)_2-$ | | $CH_3$ |
| $CH_3$ | $OCH_3$ | H | $-(CH_2)_2-S-(CH_2)_2-$ | | $CH_3$ |
| $CH_3$ | $OCH_3$ | H | $-CH_2-CHCH_3-(CH_2)_3-$ | | $CH_3$ |
| $CH_3$ | $OCH_3$ | H | $-(CH_2)_2-CHCH_3-(CH_2)_2-$ | | $CH_3$ |
| $CH_3$ | $OCH_3$ | H | $-(CH_2)_2-CHC_2H_5-(CH_2)_2-$ | | $CH_3$ |
| $CH_3$ | $OCH_3$ | H | $-(CH_2)_2-CHC_3H_7-(CH_2)_2-$ | | |
| $CH_3$ | $OCH_3$ | H | $-(CH_2)_2-CHi-C_3H_7-(CH_2)_2-$ | | $CH_3$ |
| $CH_3$ | $OCH_3$ | H | $-(CH_2)_2-CHOCH_3-(CH_2)_2-$ | | $CH_3$ |
| $CH_3$ | $OCH_3$ | H | $-(CH_2)_2-CHOC_2H_5-(CH_2)_2-$ | | |
| $CH_3$ | $OCH_3$ | H | $-(CH_2)_2-CHOC_3H_7-(CH_2)_2-$ | | $CH_3$ |
| $CH_3$ | $OCH_3$ | H | $-(CH_2)_2-CHi-OC_3H_7-(CH_2)_2-$ | | $CH_3$ |
| $CH_3$ | $OCH_3$ | H | $-(CH_2)_2-C(CH_3)_2-(CH_2)_2-$ | | $CH_3$ |
| $CH_3$ | $OCH_3$ | H | $-CH_2-(CHCH_3)_2-(CH_2)_2-$ | | $CH_3$ |
| $CH_3$ | $OCH_3$ | H | 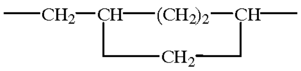 | | $CH_3$ |
| $CH_3$ | $OCH_3$ | H | 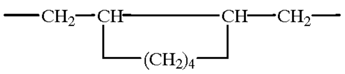 | | $CH_3$ |
| $CH_3$ | $OCH_3$ | H | 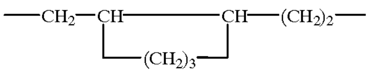 | | $CH_3$ |
| $CH_3$ | $CH_3$ | 6-$OCH_3$ | $-(CH_2)_2-$ | | $CH_3$ |
| $CH_3$ | $CH_3$ | 6-$OCH_3$ | $-(CH_2)_4-$ | | $CH_3$ |
| $CH_3$ | $CH_3$ | 6-$OCH_3$ | $-(CH_2)_5-$ | | $CH_3$ |
| $CH_3$ | $CH_3$ | 6-$OCH_3$ | $-(CH_2)_6-$ | | $CH_3$ |
| $CH_3$ | $CH_3$ | 6-$OCH_3$ | $-(CH_2)_7-$ | | $CH_3$ |
| $CH_3$ | $CH_3$ | 6-$OCH_3$ | $-(CH_2)_2-O-(CH_2)_2-$ | | $CH_3$ |
| $CH_3$ | $CH_3$ | 6-$OCH_3$ | $-(CH_2)_2-S-(CH_2)_2-$ | | $CH_3$ |
| $CH_3$ | $CH_3$ | 6-$OCH_3$ | $-CH_2-CHCH_3-(CH_2)_3-$ | | $CH_3$ |
| $CH_3$ | $CH_3$ | 6-$OCH_3$ | $-(CH_2)_2-CHCH_3-(CH_2)_2-$ | | $CH_3$ |
| $CH_3$ | $CH_3$ | 6-$OCH_3$ | $-(CH_2)_2-CHC_2H_5-(CH_2)_2-$ | | $CH_3$ |
| $CH_3$ | $CH_3$ | 6-$OCH_3$ | $-(CH_2)_2-CHC_3H_7-(CH_2)_2-$ | | $CH_3$ |
| $CH_3$ | $CH_3$ | 6-$OCH_3$ | $-(CH_2)_2-CHi-C_3H_7-(CH_2)_2-$ | | $CH_3$ |
| $CH_3$ | $CH_3$ | 6-$OCH_3$ | $-(CH_2)_2-CHOCH_3-(CH_2)_2-$ | | $CH_3$ |
| $CH_3$ | $CH_3$ | 6-$OCH_3$ | $-(CH_2)_2-CHOC_2H_5-(CH_2)_2-$ | | $CH_3$ |
| $CH_3$ | $CH_3$ | 6-$OCH_3$ | $-(CH_2)_2-CHOC_3H_7-(CH_2)_2-$ | | $CH_3$ |
| $CH_3$ | $CH_3$ | 6-$OCH_3$ | $-(CH_2)_2-CHi-OC_3H_7-(CH_2)_2-$ | | $CH_3$ |

TABLE 4-continued (Id)

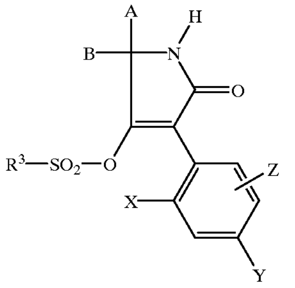

| | Y | Z | A B | R$^3$ |
|---|---|---|---|---|
| $CH_3$ | $CH_3$ | 6-$OCH_3$ | $-(CH_2)_2-C(CH_3)_2-(CH_2)_2-$ | $CH_3$ |
| $CH_3$ | $CH_3$ | 6-$OCH_3$ | $-CH_2-(CHCH_3)_2-(CH_2)_2-$ | $CH_3$ |
| $CH_3$ | $CH_3$ | 6-$OCH_3$ | 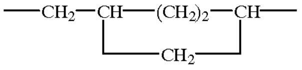 | $CH_3$ |
| $CH_3$ | $CH_3$ | 6-$OCH_3$ | 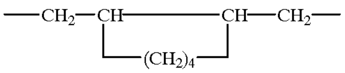 | $CH_3$ |
| $CH_3$ | $CH_3$ | 6-$OCH_3$ | 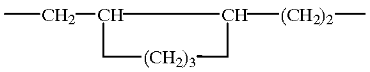 | $CH_3$ |
| $CH_3$ | $OCH_3$ | 6-$CH_3$ | $-(CH_2)_2-$ | $CH_3$ |
| $CH_3$ | $OCH_3$ | 6-$CH_3$ | $-(CH_2)_4-$ | $CH_3$ |
| $CH_3$ | $OCH_3$ | 6-$CH_3$ | $-(CH_2)_5-$ | $CH_3$ |
| $CH_3$ | $OCH_3$ | 6-$CH_3$ | $-(CH_2)_6-$ | $CH_3$ |
| $CH_3$ | $OCH_3$ | 6-$CH_3$ | $-(CH_2)_7-$ | $CH_3$ |
| $CH_3$ | $OCH_3$ | 6-$CH_3$ | $-(CH_2)_2-O-(CH_2)_2-$ | $CH_3$ |
| $CH_3$ | $OCH_3$ | 6-$CH_3$ | $-(CH_2)_2-S-(CH_2)_2-$ | $CH_3$ |
| $CH_3$ | $OCH_3$ | 6-$CH_3$ | $-CH_2-CHCH_3-(CH_2)_3-$ | $CH_3$ |
| $CH_3$ | $OCH_3$ | 6-$CH_3$ | $-(CH_2)_2-CHCH_3-(CH_2)_2-$ | $CH_3$ |
| $CH_3$ | $OCH_3$ | 6-$CH_3$ | $-(CH_2)_2-CHC_2H_5-(CH_2)_2-$ | $CH_2$ |
| $CH_3$ | $OCH_3$ | 6-$CH_3$ | $-(CH_2)_2-CHC_3H_7-(CH_2)_2-$ | $CH_3$ |
| $CH_3$ | $OCH_3$ | 6-$CH_3$ | $-(CH_2)_2-CHi\text{-}C_3H_7-(CH_2)_2-$ | $CH_3$ |
| $CH_3$ | $OCH_3$ | 6-$CH_3$ | $-(CH_2)_2-CHOCH_3-(CH_2)_2-$ | $CH_3$ |
| $CH_3$ | $OCH_3$ | 6-$CH_3$ | $-(CH_2)_2-CHOC_2H_5-(CH_2)_2-$ | $CH_3$ |
| $CH_3$ | $OCH_3$ | 6-$CH_3$ | $-(CH_2)_2-CHOC_3H_7-(CH_2)_2-$ | $CH_3$ |
| $CH_3$ | $OCH_3$ | 6-$CH_3$ | $-(CH_2)_2-CHi\text{-}OC_3H_7-(CH_2)_2-$ | $CH_3$ |
| $CH_3$ | $OCH_3$ | 6-$CH_3$ | $-(CH_2)_2-C(CH_3)_2-(CH_2)_2-$ | $CH_3$ |
| $CH_3$ | $OCH_3$ | 6-$CH_3$ | $-CH_2-(CHCH_3)_2-(CH_2)_2-$ | |
| $CH_3$ | $OCH_3$ | 6-$CH_3$ | 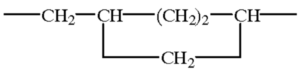 | $CH_3$ |
| $CH_3$ | $OCH_3$ | 6-$CH_3$ | 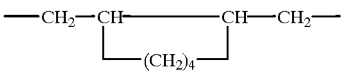 | $CH_3$ |
| $CH_3$ | $OCH_3$ | 6-$CH_3$ | 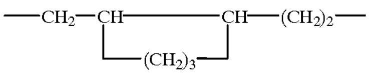 | $CH_3$ |

Specific mention may be made, in addition to the compounds specified in the Preparation Examples, of the following compounds of the formula (Ie):

TABLE 5

(Ie)

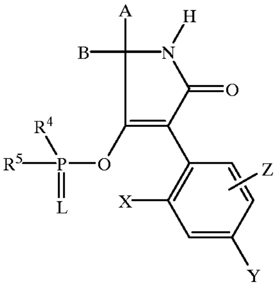

| X | Y | Z | A | B | L | $R^4$ | $R^5$ |
|---|---|---|---|---|---|---|---|
| $CH_3$ | $OCH_3$ | H | $CH_3$ | H | S | $CH_3$ | i-$C_3H_7$—S— |
| $CH_3$ | $OCH_3$ | H | $C_2H_5$ | H | S | $CH_3$ | i-$C_3H_7$—S— |
| $CH_3$ | $OCH_3$ | H | $C_3H_7$ | H | S | $CH_3$ | i-$C_3H_7$—S— |
| $CH_3$ | $OCH_3$ | H | i-$C_3H_7$ | H | S | $CH_3$ | i-$C_3H_7$—S— |
| $CH_3$ | $OCH_3$ | H | $C_4H_9$ | H | S | $CH_3$ | i-$C_3H_7$—S— |
| $CH_3$ | $OCH_3$ | H | i-$C_4H_9$ | H | S | $CH_3$ | i-$C_3H_7$—S— |
| $CH_3$ | $OCH_3$ | H | s-$C_4H_9$ | H | S | $CH_3$ | i-$C_3H_7$—S— |
| $CH_3$ | $OCH_3$ | H | t-$C_4H_9$ | H | S | $CH_3$ | i-$C_3H_7$—S— |
| $CH_3$ | $OCH_3$ | H | $CH_3$ | $CH_3$ | S | $CH_3$ | i-$C_3H_7$—S— |
| $CH_3$ | $OCH_3$ | H | $C_2H_5$ | $CH_3$ | S | $CH_3$ | i-$C_3H_7$—S— |
| $CH_3$ | $OCH_3$ | H | $C_3H_7$ | $CH_3$ | S | $CH_3$ | i-$C_3H_7$—S— |
| $CH_3$ | $OCH_3$ | H | i-$C_3H_7$ | $CH_3$ | S | $CH_3$ | i-$C_3H_7$—S— |
| $CH_3$ | $OCH_3$ | H | $C_4H_9$ | $CH_3$ | S | $CH_3$ | i-$C_3H_7$—S— |
| $CH_3$ | $OCH_3$ | H | i-$C_4H_9$ | $CH_3$ | S | $CH_3$ | i-$C_3H_7$—S— |
| $CH_3$ | $OCH_3$ | H | s-$C_4H_9$ | $CH_3$ | S | $CH_3$ | i-$C_3H_7$—S— |
| $CH_3$ | $OCH_3$ | H | t-$C_4H_9$ | $CH_3$ | S | $CH_3$ | i-$C_3H_7$—S— |
| $CH_3$ | $OCH_3$ | H | $C_2H_5$ | $C_2H_5$ | S | $CH_3$ | i-$C_3H_7$—S— |
| $CH_3$ | $OCH_3$ | H | $C_3H_7$ | $C_3H_7$ | S | $CH_3$ | i-$C_3H_7$—S— |
| $CH_3$ | $OCH_3$ | H | 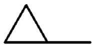 | $CH_3$ | S | $CH_3$ | i-$C_3H_7$—S— |
| $CH_3$ | $OCH_3$ | H | 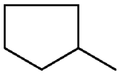 | $CH_3$ | S | $CH_3$ | i-$C_3H_7$—S— |
| $CH_3$ | $OCH_3$ | H | 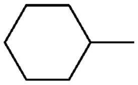 | $CH_3$ | S | $CH_3$ | i-$C_3H_7$—S— |
| $CH_3$ | $CH_3$ | 6-$OCH_3$ | $CH_3$ | H | S | $CH_3$ | i-$C_3H_7$—S— |
| $CH_3$ | $CH_3$ | 6-$OCH_3$ | $C_2H_5$ | H | S | $CH_3$ | i-$C_3H_7$—S— |
| $CH_3$ | $CH_3$ | 6-$OCH_3$ | $C_3H_7$ | H | S | $CH_3$ | i-$C_3H_7$—S— |
| $CH_3$ | $CH_3$ | 6-$OCH_3$ | i-$C_3H_7$ | H | S | $CH_3$ | i-$C_3H_7$—S— |
| $CH_3$ | $CH_3$ | 6-$OCH_3$ | $C_4H_9$ | H | S | $CH_3$ | i-$C_3H_7$—S— |
| $CH_3$ | $CH_3$ | 6-$OCH_3$ | i-$C_4H_9$ | H | S | $CH_3$ | i-$C_3H_7$—S— |
| $CH_3$ | $CH_3$ | 6-$OCH_3$ | s-$C_4H_9$ | H | S | $CH_3$ | i-$C_3H_7$—S— |
| $CH_3$ | $CH_3$ | 6-$OCH_3$ | t-$C_4H_9$ | H | S | $CH_3$ | i-$C_3H_7$—S— |
| $CH_3$ | $CH_3$ | 6-$OCH_3$ | $CH_3$ | $CH_3$ | S | $CH_3$ | i-$C_3H_7$—S— |
| $CH_3$ | $CH_3$ | 6-$OCH_3$ | $C_2H_5$ | $CH_3$ | S | $CH_3$ | i-$C_3H_7$—S— |
| $CH_3$ | $CH_3$ | 6-$OCH_3$ | $C_3H_7$ | $CH_3$ | S | $CH_3$ | i-$C_3H_7$—S— |
| $CH_3$ | $CH_3$ | 6-$OCH_3$ | i-$C_3H_7$ | $CH_3$ | S | $CH_3$ | i-$C_3H_7$—S— |
| $CH_3$ | $CH_3$ | 6-$OCH_3$ | $C_4H_9$ | $CH_3$ | S | $CH_3$ | i-$C_3H_7$—S— |
| $CH_3$ | $CH_3$ | 6-$OCH_3$ | i-$C_4H_9$ | $CH_3$ | S | $CH_3$ | i-$C_3H_7$—S— |
| $CH_3$ | $CH_3$ | 6-$OCH_3$ | s-$C_4H_9$ | $CH_3$ | S | $CH_3$ | i-$C_3H_7$—S— |
| $CH_3$ | $CH_3$ | 6-$OCH_3$ | t-$C_4H_9$ | $CH_3$ | S | $CH_3$ | i-$C_3H_7$—S— |
| $CH_3$ | $CH_3$ | 6-$OCH_3$ | $C_2H_5$ | $C_2H_5$ | S | $CH_3$ | i-$C_3H_7$—S— |
| $CH_3$ | $CH_3$ | 6-$OCH_3$ | $C_3H_7$ | $C_3H_7$ | S | $CH_3$ | i-$C_3H_7$—S— |
| $CH_3$ | $CH_3$ | 6-$OCH_3$ | 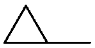 | $CH_3$ | S | $CH_3$ | i-$C_3H_7$—S— |
| $CH_3$ | $CH_3$ | 6-$OCH_3$ | 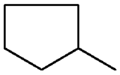 | $CH_3$ | S | $CH_3$ | i-$C_3H_7$—S— |

TABLE 5-continued (Ie)

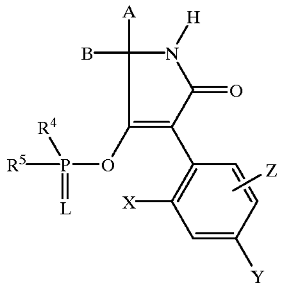

| X | Y | Z | A | B | L | $R^4$ | $R^5$ |
|---|---|---|---|---|---|---|---|
| $CH_3$ | $CH_3$ | 6-$OCH_3$ | 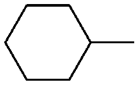 | $CH_3$ | S | $CH_3$ | i-$C_3H_7$—S— |
| $CH_3$ | $OCH_3$ | 6-$CH_3$ | $CH_3$ | H | S | $CH_3$ | i-$C_3H_7$—S— |
| $CH_3$ | $OCH_3$ | 6-$CH_3$ | $C_2H_5$ | H | S | $CH_3$ | i-$C_3H_7$—S— |
| $CH_3$ | $OCH_3$ | 6-$CH_3$ | $C_3H_7$ | H | S | $CH_3$ | i-$C_3H_7$—S— |
| $CH_3$ | $OCH_3$ | 6-$CH_3$ | i-$C_3H_7$ | H | S | $CH_3$ | i-$C_3H_7$—S— |
| $CH_3$ | $OCH_3$ | 6-$CH_3$ | $C_4H_9$ | H | S | $CH_3$ | i-$C_3H_7$—S— |
| $CH_3$ | $OCH_3$ | 6-$CH_3$ | i-$C_4H_9$ | H | S | $CH_3$ | i-$C_3H_7$—S— |
| $CH_3$ | $OCH_3$ | 6-$CH_3$ | s-$C_4H_9$ | H | S | $CH_3$ | i-$C_3H_7$—S— |
| $CH_3$ | $OCH_3$ | 6-$CH_3$ | t-$C_4H_9$ | H | S | $CH_3$ | i-$C_3H_7$—S— |
| $CH_3$ | $OCH_3$ | 6-$CH_3$ | $CH_3$ | $CH_3$ | S | $CH_3$ | i-$C_3H_7$—S— |
| $CH_3$ | $OCH_3$ | 6-$CH_3$ | $C_2H_5$ | $CH_3$ | S | $CH_3$ | i-$C_3H_7$—S— |
| $CH_3$ | $OCH_3$ | 6-$CH_3$ | $C_3H_7$ | $CH_3$ | S | $CH_3$ | i-$C_3H_7$—S— |
| $CH_3$ | $OCH_3$ | 6-$CH_3$ | i-$C_3H_7$ | $CH_3$ | S | $CH_3$ | i-$C_3H_7$—S— |
| $CH_3$ | $OCH_3$ | 6-$CH_3$ | $C_4H_9$ | $CH_3$ | S | $CH_3$ | i-$C_3H_7$—S— |
| $CH_3$ | $OCH_3$ | 6-$CH_3$ | i-$C_4H_9$ | $CH_3$ | S | $CH_3$ | i-$C_3H_7$—S— |
| $CH_3$ | $OCH_3$ | 6-$CH_3$ | s-$C_4H_9$ | $CH_3$ | S | $CH_3$ | i-$C_3H_7$—S— |
| $CH_3$ | $OCH_3$ | 6-$CH_3$ | t-$C_4H_9$ | $CH_3$ | S | $CH_3$ | i-$C_3H_7$—S— |
| $CH_3$ | $OCH_3$ | 6-$CH_3$ | $C_2H_5$ | $C_2H_5$ | S | $CH_3$ | i-$C_3H_7$—S— |
| $CH_3$ | $OCH_3$ | 6-$CH_3$ | $C_3H_7$ | $C_3H_7$ | S | $CH_3$ | i-$C_3H_7$—S— |
| $CH_3$ | $OCH_3$ | 6-$CH_3$ | 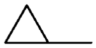 | $CH_3$ | S | $CH_3$ | i-$C_3H_7$—S— |
| $CH_3$ | $OCH_3$ | 6-$CH_3$ | 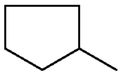 | $CH_3$ | S | $CH_3$ | i-$C_3H_7$—S— |
| $CH_3$ | $OCH_3$ | 6-$CH_3$ | 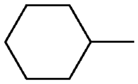 | $CH_3$ | S | $CH_3$ | i-$C_3H_7$—S— |
| $CH_3$ | $OCH_3$ | H | $-(CH_2)_2-$ | | S | $CH_3$ | i-$C_3H_7$—S— |
| $CH_3$ | $OCH_3$ | H | $-(CH_2)_4-$ | | S | $CH_3$ | i-$C_3H_7$—S— |
| $CH_3$ | $OCH_3$ | H | $-(CH_2)_5-$ | | S | $CH_3$ | i-$C_3H_7$—S— |
| $CH_3$ | $OCH_3$ | H | $-(CH_2)_6-$ | | S | $CH_3$ | i-$C_3H_7$—S— |
| $CH_3$ | $OCH_3$ | H | $-(CH_2)_7-$ | | S | $CH_3$ | i-$C_3H_7$—S— |
| $CH_3$ | $OCH_3$ | H | $-(CH_2)_2-O-(CH_2)_2-$ | | S | $CH_3$ | i-$C_3H_7$—S— |
| $CH_3$ | $OCH_3$ | H | $-(CH_2)_2-S-(CH_2)_2-$ | | S | $CH_3$ | i-$C_3H_7$—S— |
| $CH_3$ | $OCH_3$ | H | $-CH_2-CHCH_3-(CH_2)_3-$ | | S | $CH_3$ | i-$C_3H_7$—S— |
| $CH_3$ | $OCH_3$ | H | $-(CH_2)_2-CHCH_3-(CH_2)_2-$ | | S | $CH_3$ | i-$C_3H_7$—S— |
| $CH_3$ | $OCH_3$ | H | $-(CH_2)_2-CHC_2H_5-(CH_2)_2-$ | | S | $CH_3$ | i-$C_3H_7$—S— |
| $CH_3$ | $OCH_3$ | H | $-(CH_2)_2-CHC_3H_7-(CH_2)_2-$ | | S | $CH_3$ | i-$C_3H_7$—S— |
| $CH_3$ | $OCH_3$ | H | $-(CH_2)_2-$CHi-$C_3H_7-(CH_2)_2-$ | | S | $CH_3$ | i-$C_3H_7$—S— |
| $CH_3$ | $OCH_3$ | H | $-(CH_2)_2-CHOCH_3-(CH_2)_2-$ | | S | $CH_3$ | i-$C_3H_7$—S— |
| $CH_3$ | $OCH_3$ | H | $-(CH_2)_2-CHOC_2H_5-(CH_2)_2-$ | | S | $CH_3$ | i-$C_3H_7$—S— |
| $CH_3$ | $OCH_3$ | H | $-(CH_2)_2-CHOC_3H_7-(CH_2)_2-$ | | S | $CH_3$ | i-$C_3H_7$—S— |
| $CH_3$ | $OCH_3$ | H | $-(CH_2)_2-$CHi-$OC_3H_7-(CH_2)_2-$ | | S | $CH_3$ | i-$C_3H_7$—S— |
| $CH_3$ | $OCH_3$ | H | $-(CH_2)_2-C(CH_3)_2-(CH_2)_2-$ | | S | $CH_3$ | i-$C_3H_7$—S— |
| $CH_3$ | $OCH_3$ | H | $-CH_2-(CHCH_3)_2-(CH_2)_2-$ | | S | $CH_3$ | i-$C_3H_7$—S— |
| $CH_3$ | $OCH_3$ | H | 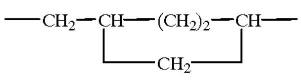 | | S | $CH_3$ | i-$C_3H_7$—S— |

TABLE 5-continued (Ie)

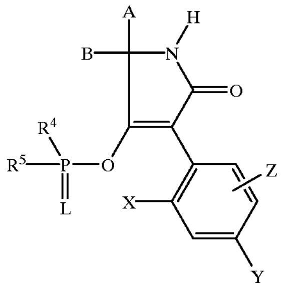

| X | Y | Z | A | B | L | $R^4$ | $R^5$ |
|---|---|---|---|---|---|---|---|
| $CH_3$ | $OCH_3$ | H | 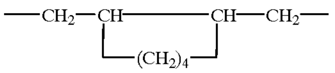 | | S | $CH_3$ | $i\text{-}C_3H_7$—S— |
| $CH_3$ | $OCH_3$ | H | 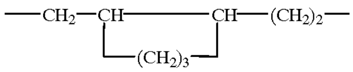 | | S | $CH_3$ | $i\text{-}C_3H_7$—S— |
| $CH_3$ | $CH_3$ | 6-$OCH_3$ | —$(CH_2)_2$— | | S | $CH_3$ | $i\text{-}C_3H_7$—S— |
| $CH_3$ | $CH_3$ | 6-$OCH_3$ | —$(CH_2)_4$— | | S | $CH_3$ | $i\text{-}C_3H_7$—S— |
| $CH_3$ | $CH_3$ | 6-$OCH_3$ | —$(CH_2)_5$— | | S | $CH_3$ | $i\text{-}C_3H_7$—S— |
| $CH_3$ | $CH_3$ | 6-$OCH_3$ | —$(CH_2)_6$— | | S | $CH_3$ | $i\text{-}C_3H_7$—S— |
| $CH_3$ | $CH_3$ | 6-$OCH_3$ | —$(CH_2)_7$— | | S | $CH_3$ | $i\text{-}C_3H_7$—S— |
| $CH_3$ | $CH_3$ | 6-$OCH_3$ | —$(CH_2)_2$—O—$(CH_2)_2$— | | S | $CH_3$ | $i\text{-}C_3H_7$—S— |
| $CH_3$ | $CH_3$ | 6-$OCH_3$ | —$(CH_2)_2$—S—$(CH_2)_2$— | | S | $CH_3$ | $i\text{-}C_3H_7$—S— |
| $CH_3$ | $CH_3$ | 6-$OCH_3$ | —$CH_2$—$CHCH_3$—$(CH_2)_3$— | | S | $CH_3$ | $i\text{-}C_3H_7$—S— |
| $CH_3$ | $CH_3$ | 6-$OCH_3$ | —$(CH_2)_2$—$CHCH_3$—$(CH_2)_2$— | | S | $CH_3$ | $i\text{-}C_3H_7$—S— |
| $CH_3$ | $CH_3$ | 6-$OCH_3$ | —$(CH_2)_2$—$CHC_2H_5$—$(CH_2)_2$— | | S | $CH_3$ | $i\text{-}C_3H_7$—S— |
| $CH_3$ | $CH_3$ | 6-$OCH_3$ | —$(CH_2)_2$—$CHC_3H_7$—$(CH_2)_2$— | | S | $CH_3$ | $i\text{-}C_3H_7$—S— |
| $CH_3$ | $CH_3$ | 6-$OCH_3$ | —$(CH_2)_2$—$CHi\text{-}C_3H_7$—$(CH_2)_2$— | | S | $CH_3$ | $i\text{-}C_3H_7$—S— |
| $CH_3$ | $CH_3$ | 6-$OCH_3$ | —$(CH_2)_2$—$CHOCH_3$—$(CH_2)_2$— | | S | $CH_3$ | $i\text{-}C_3H_7$—S— |
| $CH_3$ | $CH_3$ | 6-$OCH_3$ | —$(CH_2)_2$—$CHOC_2H_5$—$(CH_2)_2$— | | S | $CH_3$ | $i\text{-}C_3H_7$—S— |
| $CH_3$ | $CH_3$ | 6-$OCH_3$ | —$(CH_2)_2$—$CHOC_3H_7$—$(CH_2)_2$— | | S | $CH_3$ | $i\text{-}C_3H_7$—S— |
| $CH_3$ | $CH_3$ | 6-$OCH_3$ | —$(CH_2)_2$—$CHi\text{-}OC_3H_7$—$(CH_2)_2$— | | S | $CH_3$ | $i\text{-}C_3H_7$—S— |
| $CH_3$ | $CH_3$ | 6-$OCH_3$ | —$(CH_2)_2$—$C(CH_3)_2$—$(CH_2)_2$— | | S | $CH_3$ | $i\text{-}C_3H_7$—S— |
| $CH_3$ | $CH_3$ | 6-$OCH_3$ | —$CH_2$—$(CHCH_3)_2$—$(CH_2)_2$— | | S | $CH_3$ | $i\text{-}C_3H_7$—S— |
| $CH_3$ | $CH_3$ | 6-$OCH_3$ | 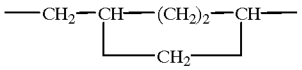 | | S | $CH_3$ | $i\text{-}C_3H_7$—S— |
| $CH_3$ | $CH_3$ | 6-$OCH_3$ | 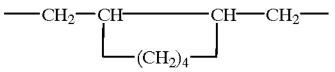 | | S | $CH_3$ | $i\text{-}C_3H_7$—S— |
| $CH_3$ | $CH_3$ | 6-$OCH_3$ | 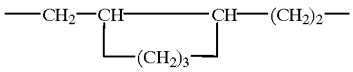 | | S | $CH_3$ | $i\text{-}C_3H_7$—S— |
| $CH_3$ | $OCH_3$ | 6-$CH_3$ | —$(CH_2)_2$— | | S | $CH_3$ | $i\text{-}C_3H_7$—S— |
| $CH_3$ | $OCH_3$ | 6-$CH_3$ | —$(CH_2)_4$— | | S | $CH_3$ | $i\text{-}C_3H_7$—S— |
| $CH_3$ | $OCH_3$ | 6-$CH_3$ | —$(CH_2)_5$— | | S | $CH_3$ | $i\text{-}C_3H_7$—S— |
| $CH_3$ | $OCH_3$ | 6-$CH_3$ | —$(CH_2)_6$— | | S | $CH_3$ | $i\text{-}C_3H_7$—S— |
| $CH_3$ | $OCH_3$ | 6-$CH_3$ | —$(CH_2)_7$— | | S | $CH_3$ | $i\text{-}C_3H_7$—S— |
| $CH_3$ | $OCH_3$ | 6-$CH_3$ | —$(CH_2)_2$—O—$(CH_2)_2$— | | S | $CH_3$ | $i\text{-}C_3H_7$—S— |
| $CH_3$ | $OCH_3$ | 6-$CH_3$ | —$(CH_2)_2$—S—$(CH_2)_2$— | | S | $CH_3$ | $i\text{-}C_3H_7$—S— |
| $CH_3$ | $OCH_3$ | 6-$CH_3$ | —$CH_2$—$CHCH_3$—$(CH_2)_3$— | | S | $CH_3$ | $i\text{-}C_3H_7$—S— |
| $CH_3$ | $OCH_3$ | 6-$CH_3$ | —$(CH_2)_2$—$CHCH_3$—$(CH_2)_2$— | | S | $CH_3$ | $i\text{-}C_3H_7$—S— |
| $CH_3$ | $OCH_3$ | 6-$CH_3$ | —$(CH_2)_2$—$CHC_2H_5$—$(CH_2)_2$— | | S | $CH_3$ | $i\text{-}C_3H_7$—S— |
| $CH_3$ | $OCH_3$ | 6-$CH_3$ | —$(CH_2)_2$—$CHC_3H_7$—$(CH_2)_2$— | | S | $CH_3$ | $i\text{-}C_3H_7$—S— |
| $CH_3$ | $OCH_3$ | 6-$CH_3$ | —$(CH_2)_2$—$CHi\text{-}C_3H_7$—$(CH_2)_2$— | | S | $CH_3$ | $i\text{-}C_3H_7$—S— |
| $CH_3$ | $OCH_3$ | 6-$CH_3$ | —$(CH_2)_2$—$CHOCH_3$—$(CH_2)_2$— | | S | $CH_3$ | $i\text{-}C_3H_7$—S— |
| $CH_3$ | $OCH_3$ | 6-$CH_3$ | —$(CH_2)_2$—$CHOC_2H_5$—$(CH_2)_2$— | | S | $CH_3$ | $i\text{-}C_3H_7$—S— |
| $CH_3$ | $OCH_3$ | 6-$CH_3$ | —$(CH_2)_2$—$CHOC_3H_7$—$(CH_2)_2$— | | S | $CH_3$ | $i\text{-}C_3H_7$—S— |
| $CH_3$ | $OCH_3$ | 6-$CH_3$ | —$(CH_2)_2$—$CHi\text{-}OC_3H_7$—$(CH_2)_2$— | | S | $CH_3$ | $i\text{-}C_3H_7$—S— |
| $CH_3$ | $OCH_3$ | 6-$CH_3$ | —$(CH_2)_2$—$C(CH_3)_2$—$(CH_2)_2$— | | S | $CH_3$ | $i\text{-}C_3H_7$—S— |
| $CH_3$ | $OCH_3$ | 6-$CH_3$ | —$CH_2$—$(CHCH_3)_2$—$(CH_2)_2$— | | S | $CH_3$ | $i\text{-}C_3H_7$—S— |

TABLE 5-continued (Ie)

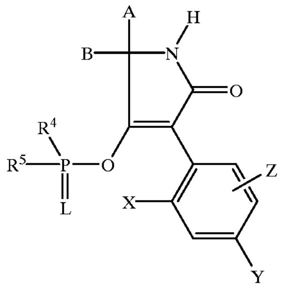

| X | Y | Z | A | B | L | $R^4$ | $R^5$ |
|---|---|---|---|---|---|---|---|
| $CH_3$ | $OCH_3$ | 6-$CH_3$ | 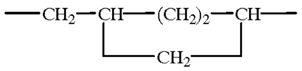 | | S | $CH_3$ | i-$C_3H_7$—S— |
| $CH_3$ | $OCH_3$ | 6-$CH_3$ | 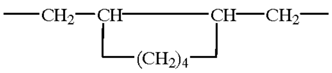 | | S | $CH_3$ | i-$C_3H_7$—S— |
| $CH_3$ | $OCH_3$ | 6-$CH_3$ | 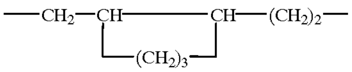 | | S | $CH_3$ | i-$C_3H_7$—S— |
| $CH_3$ | $OCH_3$ | H | $CH_3$ | H | S | $C_2H_5$ | i-$C_3H_7$—S— |
| $CH_3$ | $OCH_3$ | H | $C_2H_5$ | H | S | $C_2H_5$ | i-$C_3H_7$—S— |
| $CH_3$ | $OCH_3$ | H | $C_3H_7$ | H | S | $C_2H_5$ | i-$C_3H_7$—S— |
| $CH_3$ | $OCH_3$ | H | i-$C_3H_7$ | H | S | $C_2H_5$ | i-$C_3H_7$—S— |
| $CH_3$ | $OCH_3$ | H | $C_4H_9$ | H | S | $C_2H_5$ | i-$C_3H_7$—S— |
| $CH_3$ | $OCH_3$ | H | i-$C_4H_9$ | H | S | $C_2H_5$ | i-$C_3H_7$—S— |
| $CH_3$ | $OCH_3$ | H | s-$C_4H_9$ | H | S | $C_2H_5$ | i-$C_3H_7$—S— |
| $CH_3$ | $OCH_3$ | H | t-$C_4H_9$ | H | S | $C_2H_5$ | i-$C_3H_7$—S— |
| $CH_3$ | $OCH_3$ | H | $CH_3$ | $CH_3$ | S | $C_2H_5$ | i-$C_3H_7$—S— |
| $CH_3$ | $OCH_3$ | H | $C_2H_5$ | $CH_3$ | S | $C_2H_5$ | i-$C_3H_7$—S— |
| $CH_3$ | $OCH_3$ | H | $C_3H_7$ | $CH_3$ | S | $C_2H_5$ | i-$C_3H_7$—S— |
| $CH_3$ | $OCH_3$ | H | i-$C_3H_7$ | $CH_3$ | S | $C_2H_5$ | i-$C_3H_7$—S— |
| $CH_3$ | $OCH_3$ | H | $C_4H_9$ | $CH_3$ | S | $C_2H_5$ | i-$C_3H_7$—S— |
| $CH_3$ | $OCH_3$ | H | i-$C_4H_9$ | $CH_3$ | S | $C_2H_5$ | i-$C_3H_7$—S— |
| $CH_3$ | $OCH_3$ | H | s-$C_4H_9$ | $CH_3$ | S | $C_2H_5$ | i-$C_3H_7$—S— |
| $CH_3$ | $OCH_3$ | H | t-$C_4H_9$ | $CH_3$ | S | $C_2H_5$ | i-$C_3H_7$—S— |
| $CH_3$ | $OCH_3$ | H | $C_2H_5$ | $C_2H_5$ | S | $C_2H_5$ | i-$C_3H_7$—S— |
| $CH_3$ | $OCH_3$ | H | $C_3H_7$ | $C_3H_7$ | S | $C_2H_5$ | i-$C_3H_7$—S— |
| $CH_3$ | $OCH_3$ | H | 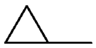 | $CH_3$ | S | $C_2H_5$ | i-$C_3H_7$—S— |
| $CH_3$ | $OCH_3$ | H | 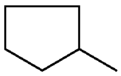 | $CH_3$ | S | $C_2H_5$ | i-$C_3H_7$—S— |
| $CH_3$ | $OCH_3$ | H | 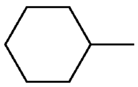 | $CH_3$ | S | $C_2H_5$ | i-$C_3H_7$—S— |
| $CH_3$ | $CH_3$ | 6-$OCH_3$ | $CH_3$ | H | S | $C_2H_5$ | i-$C_3H_7$—S— |
| $CH_3$ | $CH_3$ | 6-$OCH_3$ | $C_2H_5$ | H | S | $C_2H_5$ | i-$C_3H_7$—S— |
| $CH_3$ | $CH_3$ | 6-$OCH_3$ | $C_3H_7$ | H | S | $C_2H_5$ | i-$C_3H_7$—S— |
| $CH_3$ | $CH_3$ | 6-$OCH_3$ | i-$C_3H_7$ | H | S | $C_2H_5$ | i-$C_3H_7$—S— |
| $CH_3$ | $CH_3$ | 6-$OCH_3$ | $C_4H_9$ | H | S | $C_2H_5$ | i-$C_3H_7$—S— |
| $CH_3$ | $CH_3$ | 6-$OCH_3$ | i-$C_4H_9$ | H | S | $C_2H_5$ | i-$C_3H_7$—S— |
| $CH_3$ | $CH_3$ | 6-$OCH_3$ | s-$C_4H_9$ | H | S | $C_2H_5$ | i-$C_3H_7$—S— |
| $CH_3$ | $CH_3$ | 6-$OCH_3$ | t-$C_4H_9$ | H | S | $C_2H_5$ | i-$C_3H_7$—S— |
| $CH_3$ | $CH_3$ | 6-$OCH_3$ | $CH_3$ | $CH_3$ | S | $C_2H_5$ | i-$C_3H_7$—S— |
| $CH_3$ | $CH_3$ | 6-$OCH_3$ | $C_2H_5$ | $CH_3$ | S | $C_2H_5$ | i-$C_3H_7$—S— |
| $CH_3$ | $CH_3$ | 6-$OCH_3$ | $C_3H_7$ | $CH_3$ | S | $C_2H_5$ | i-$C_3H_7$—S— |
| $CH_3$ | $CH_3$ | 6-$OCH_3$ | i-$C_3H_7$ | $CH_3$ | S | $C_2H_5$ | i-$C_3H_7$—S— |
| $CH_3$ | $CH_3$ | 6-$OCH_3$ | $C_4H_9$ | $CH_3$ | S | $C_2H_5$ | i-$C_3H_7$—S— |
| $CH_3$ | $CH_3$ | 6-$OCH_3$ | i-$C_4H_9$ | $CH_3$ | S | $C_2H_5$ | i-$C_3H_7$—S— |
| $CH_3$ | $CH_3$ | 6-$OCH_3$ | s-$C_4H_9$ | $CH_3$ | S | $C_2H_5$ | i-$C_3H_7$—S— |
| $CH_3$ | $CH_3$ | 6-$OCH_3$ | t-$C_4H_9$ | $CH_3$ | S | $C_2H_5$ | i-$C_3H_7$—S— |

TABLE 5-continued (Ie)

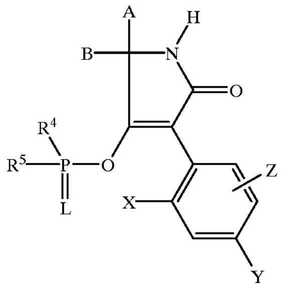

| X | Y | Z | A | B | L | $R^4$ | $R^5$ |
|---|---|---|---|---|---|---|---|
| $CH_3$ | $CH_3$ | 6-$OCH_3$ | $C_2H_5$ | $C_2H_5$ | S | $C_2H_5$ | i-$C_3H_7$—S— |
| $CH_3$ | $CH_3$ | 6-$OCH_3$ | $C_3H_7$ | $C_3H_7$ | S | $C_2H_5$ | i-$C_3H_7$—S— |
| $CH_3$ | $CH_3$ | 6-$OCH_3$ | 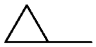 | $CH_3$ | S | $C_2H_5$ | i-$C_3H_7$—S— |
| $CH_3$ | $CH_3$ | 6-$OCH_3$ | 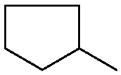 | $CH_3$ | S | $C_2H_5$ | i-$C_3H_7$—S— |
| $CH_3$ | $CH_3$ | 6-$OCH_3$ | 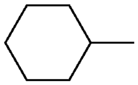 | $CH_3$ | S | $C_2H_5$ | i-$C_3H_7$—S— |
| $CH_3$ | $OCH_3$ | 6-$CH_3$ | $CH_3$ | H | S | $C_2H_5$ | i-$C_3H_7$—S— |
| $CH_3$ | $OCH_3$ | 6-$CH_3$ | $C_2H_5$ | H | S | $C_2H_5$ | i-$C_3H_7$—S— |
| $CH_3$ | $OCH_3$ | 6-$CH_3$ | $C_3H_7$ | H | S | $C_2H_5$ | i-$C_3H_7$—S— |
| $CH_3$ | $OCH_3$ | 6-$CH_3$ | i-$C_3H_7$ | H | S | $C_2H_5$ | i-$C_3H_7$—S— |
| $CH_3$ | $OCH_3$ | 6-$CH_3$ | $C_4H_9$ | H | S | $C_2H_5$ | i-$C_3H_7$—S— |
| $CH_3$ | $OCH_3$ | 6-$CH_3$ | i-$C_4H_9$ | H | S | $C_2H_5$ | i-$C_3H_7$—S— |
| $CH_3$ | $OCH_3$ | 6-$CH_3$ | s-$C_4H_9$ | H | S | $C_2H_5$ | i-$C_3H_7$—S— |
| $CH_3$ | $OCH_3$ | 6-$CH_3$ | t-$C_4H_9$ | H | S | $C_2H_5$ | i-$C_3H_7$—S— |
| $CH_3$ | $OCH_3$ | 6-$CH_3$ | $CH_3$ | $CH_3$ | S | $C_2H_5$ | i-$C_3H_7$—S— |
| $CH_3$ | $OCH_3$ | 6-$CH_3$ | $C_2H_5$ | $CH_3$ | S | $C_2H_5$ | i-$C_3H_7$—S— |
| $CH_3$ | $OCH_3$ | 6-$CH_3$ | $C_3H_7$ | $CH_3$ | S | $C_2H_5$ | i-$C_3H_7$—S— |
| $CH_3$ | $OCH_3$ | 6-$CH_3$ | i-$C_3H_7$ | $CH_3$ | S | $C_2H_5$ | i-$C_3H_7$—S— |
| $CH_3$ | $OCH_3$ | 6-$CH_3$ | $C_4H_9$ | $CH_3$ | S | $C_2H_5$ | i-$C_3H_7$—S— |
| $CH_3$ | $OCH_3$ | 6-$CH_3$ | i-$C_4H_9$ | $CH_3$ | S | $C_2H_5$ | i-$C_3H_7$—S— |
| $CH_3$ | $OCH_3$ | 6-$CH_3$ | s-$C_4H_9$ | $CH_3$ | S | $C_2H_5$ | i-$C_3H_7$—S— |
| $CH_3$ | $OCH_3$ | 6-$CH_3$ | t-$C_4H_9$ | $CH_3$ | S | $C_2H_5$ | i-$C_3H_7$—S— |
| $CH_3$ | $OCH_3$ | 6-$CH_3$ | $C_2H_5$ | $C_2H_5$ | S | $C_2H_5$ | i-$C_3H_7$—S— |
| $CH_3$ | $OCH_3$ | 6-$CH_3$ | $C_3H_7$ | $C_3H_7$ | S | $C_2H_5$ | i-$C_3H_7$—S— |
| $CH_3$ | $OCH_3$ | 6-$CH_3$ | 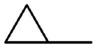 | $CH_3$ | S | $C_2H_5$ | i-$C_3H_7$—S— |
| $CH_3$ | $OCH_3$ | 6-$CH_3$ | 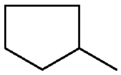 | $CH_3$ | S | $CH_3$ | i-$C_3H_7$—S— |
| $CH_3$ | $OCH_3$ | 6-$CH_3$ | 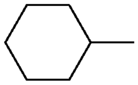 | $CH_3$ | S | $CH_3$ | i-$C_3H_7$—S— |
| $CH_3$ | $OCH_3$ | H | $—(CH_2)_2—$ | | S | $C_2H_5$ | i-$C_3H_7$—S— |
| $CH_3$ | $OCH_3$ | H | $—(CH_2)_4—$ | | S | $C_2H_5$ | i-$C_3H_7$—S— |
| $CH_3$ | $OCH_3$ | H | $—(CH_2)_5—$ | | S | $C_2H_5$ | i-$C_3H_7$—S— |
| $CH_3$ | $OCH_3$ | H | $—(CH_2)_6—$ | | S | $C_2H_5$ | i-$C_3H_7$—S— |
| $CH_3$ | $OCH_3$ | H | $—(CH_2)_7—$ | | S | $C_2H_5$ | i-$C_3H_7$—S— |
| $CH_3$ | $OCH_3$ | H | $—(CH_2)_2—O—(CH_2)_2—$ | | S | $C_2H_5$ | i-$C_3H_7$—S— |
| $CH_3$ | $OCH_3$ | H | $—(CH_2)_2—S—(CH_2)_2—$ | | S | $C_2H_5$ | i-$C_3H_7$—S— |
| $CH_3$ | $OCH_3$ | H | $—CH_2—CHCH_3—(CH_2)_3—$ | | S | $C_2H_5$ | i-$C_3H_7$—S— |
| $CH_3$ | $OCH_3$ | H | $—(CH_2)_2—CHCH_3—(CH_2)_2—$ | | S | $C_2H_5$ | i-$C_3H_7$—S— |
| $CH_3$ | $OCH_3$ | H | $—(CH_2)_2—CHC_2H_5—(CH_2)_2—$ | | S | $C_2H_5$ | i-$C_3H_7$—S— |
| $CH_3$ | $OCH_3$ | H | $—(CH_2)_2—CHC_3H_7—(CH_2)_2—$ | | S | $C_2H_5$ | i-$C_3H_7$—S— |
| $CH_3$ | $OCH_3$ | H | $—(CH_2)_2—CHi\text{-}C_3H_7—(CH_2)_2—$ | | S | $C_2H_5$ | i-$C_3H_7$—S— |

TABLE 5-continued (Ie)

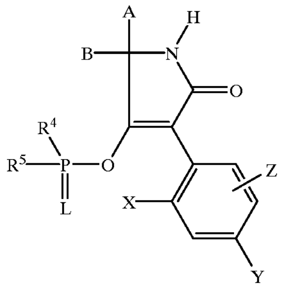

| X | Y | Z | A | B | L | $R^4$ | $R^5$ |
|---|---|---|---|---|---|---|---|
| $CH_3$ | $OCH_3$ | H | $—(CH_2)_2—CHOCH_3—(CH_2)_2—$ | | S | $C_2H_5$ | $i\text{-}C_3H_7—S—$ |
| $CH_3$ | $OCH_3$ | H | $—(CH_2)_2—CHOC_2H_5—(CH_2)_2—$ | | S | $C_2H_5$ | $i\text{-}C_3H_7—S—$ |
| $CH_3$ | $OCH_3$ | H | $—(CH_2)_2—CHOC_3H_7—(CH_2)_2—$ | | S | $C_2H_5$ | $i\text{-}C_3H_7—S—$ |
| $CH_3$ | $OCH_3$ | H | $—(CH_2)_2—CHi\text{-}OC_3H_7—(CH_2)_2—$ | | S | $C_2H_5$ | $i\text{-}C_3H_7—S—$ |
| $CH_3$ | $OCH_3$ | H | $—(CH_2)_2—C(CH_3)_2—(CH_2)_2—$ | | S | $C_2H_5$ | $i\text{-}C_3H_7—S—$ |
| $CH_3$ | $OCH_3$ | H | $—CH_2—(CHCH_3)_2—(CH_2)_2—$ | | S | $C_2H_5$ | $i\text{-}C_3H_7—S—$ |
| $CH_3$ | $OCH_3$ | H | 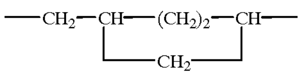 | | S | $C_2H_5$ | $i\text{-}C_3H_7—S—$ |
| $CH_3$ | $OCH_3$ | H | 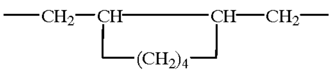 | | S | $C_2H_5$ | $i\text{-}C_3H_7—S—$ |
| $CH_3$ | $OCH_3$ | H | 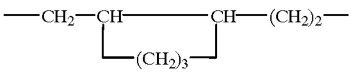 | | S | $C_2H_5$ | $i\text{-}C_3H_7—S—$ |
| $CH_3$ | $CH_3$ | 6-$OCH_3$ | $—(CH_2)_2—$ | | S | $C_2H_5$ | $i\text{-}C_3H_7—S—$ |
| $CH_3$ | $CH_3$ | 6-$OCH_3$ | $—(CH_2)_4—$ | | S | $C_2H_5$ | $i\text{-}C_3H_7—S—$ |
| $CH_3$ | $CH_3$ | 6-$OCH_3$ | $—(CH_2)_5—$ | | S | $C_2H_5$ | $i\text{-}C_3H_7—S—$ |
| $CH_3$ | $CH_3$ | 6-$OCH_3$ | $—(CH_2)_6—$ | | S | $C_2H_5$ | $i\text{-}C_3H_7—S—$ |
| $CH_3$ | $CH_3$ | 6-$OCH_3$ | $—(CH_2)_7—$ | | S | $C_2H_5$ | $i\text{-}C_3H_7—S—$ |
| $CH_3$ | $CH_3$ | 6-$OCH_3$ | $—(CH_2)_2—O—(CH_2)_2—$ | | S | $C_2H_5$ | $i\text{-}C_3H_7—S—$ |
| $CH_3$ | $CH_3$ | 6-$OCH_3$ | $—(CH_2)_2—S—(CH_2)_2—$ | | S | $C_2H_5$ | $i\text{-}C_3H_7—S—$ |
| $CH_3$ | $CH_3$ | 6-$OCH_3$ | $—CH_2—CHCH_3—(CH_2)_3—$ | | S | $C_2H_5$ | $i\text{-}C_3H_7—S—$ |
| $CH_3$ | $CH_3$ | 6-$OCH_3$ | $—(CH_2)_2—CHCH_3—(CH_2)_2—$ | | S | $C_2H_5$ | $i\text{-}C_3H_7—S—$ |
| $CH_3$ | $CH_3$ | 6-$OCH_3$ | $—(CH_2)_2—CHC_2H_5—(CH_2)_2—$ | | S | $C_2H_5$ | $i\text{-}C_3H_7—S—$ |
| $CH_3$ | $CH_3$ | 6-$OCH_3$ | $—(CH_2)_2—CHC_3H_7—(CH_2)_2—$ | | S | $C_2H_5$ | $i\text{-}C_3H_7—S—$ |
| $CH_3$ | $CH_3$ | 6-$OCH_3$ | $—(CH_2)_2—CHi\text{-}C_3H_7—(CH_2)_2—$ | | S | $C_2H_5$ | $i\text{-}C_3H_7—S—$ |
| $CH_3$ | $CH_3$ | 6-$OCH_3$ | $—(CH_2)_2—CHOCH_3—(CH_2)_2—$ | | S | $C_2H_5$ | $i\text{-}C_3H_7—S—$ |
| $CH_3$ | $CH_3$ | 6-$OCH_3$ | $—(CH_2)_2—CHOC_2H_5—(CH_2)_2—$ | | S | $C_2H_5$ | $i\text{-}C_3H_7—S—$ |
| $CH_3$ | $CH_3$ | 6-$OCH_3$ | $—(CH_2)_2—CHOC_3H_7—(CH_2)_2—$ | | S | $C_2H_5$ | $i\text{-}C_3H_7—S—$ |
| $CH_3$ | $CH_3$ | 6-$OCH_3$ | $—(CH_2)_2—CHi\text{-}OC_3H_7—(CH_2)_2—$ | | S | $C_2H_5$ | $i\text{-}C_3H_7—S—$ |
| $CH_3$ | $CH_3$ | 6-$OCH_3$ | $—(CH_2)_2—C(CH_3)_2—(CH_2)_2—$ | | S | $C_2H_5$ | $i\text{-}C_3H_7—S—$ |
| $CH_3$ | $CH_3$ | 6-$OCH_3$ | $—CH_2—(CHCH_3)_2—(CH_2)_2—$ | | S | $C_2H_5$ | $i\text{-}C_3H_7—S—$ |
| $CH_3$ | $CH_3$ | 6-$OCH_3$ | 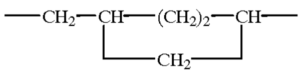 | | S | $C_2H_5$ | $i\text{-}C_3H_7—S—$ |
| $CH_3$ | $CH_3$ | 6-$OCH_3$ | 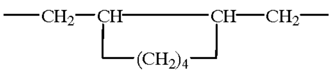 | | S | $C_2H_5$ | $i\text{-}C_3H_7—S—$ |
| $CH_3$ | $CH_3$ | 6-$OCH_3$ | 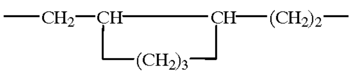 | | S | $C_2H_5$ | $i\text{-}C_3H_7—S—$ |
| $CH_3$ | $OCH_3$ | 6-$CH_3$ | $—(CH_2)_2—$ | | S | $C_2H_5$ | $i\text{-}C_3H_7—S—$ |
| $CH_3$ | $OCH_3$ | 6-$CH_3$ | $—(CH_2)_4—$ | | S | $C_2H_5$ | $i\text{-}C_3H_7—S—$ |
| $CH_3$ | $OCH_3$ | 6-$CH_3$ | $—(CH_2)_5—$ | | S | $C_2H_5$ | $i\text{-}C_3H_7—S—$ |
| $CH_3$ | $OCH_3$ | 6-$CH_3$ | $—(CH_2)_6—$ | | S | $C_2H_5$ | $i\text{-}C_3H_7—S—$ |
| $CH_3$ | $OCH_3$ | 6-$CH_3$ | $—(CH_2)_7—$ | | S | $C_2H_5$ | $i\text{-}C_3H_7—S—$ |
| $CH_3$ | $OCH_3$ | 6-$CH_3$ | $—(CH_2)_2—O—(CH_2)_2—$ | | S | $C_2H_5$ | $i\text{-}C_3H_7—S—$ |
| $CH_3$ | $OCH_3$ | 6-$CH_3$ | $—(CH_2)_2—S—(CH_2)_2—$ | | S | $C_2H_5$ | $i\text{-}C_3H_7—S—$ |
| $CH_3$ | $OCH_3$ | 6-$CH_3$ | $—CH_2—CHCH_3—(CH_2)_3—$ | | S | $C_2H_5$ | $i\text{-}C_3H_7—S—$ |

TABLE 5-continued (Ie)

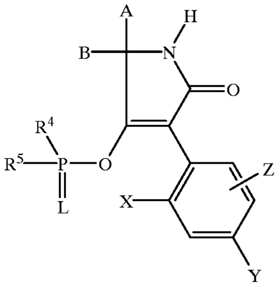

| X | Y | Z | A | B | L | $R^4$ | $R^5$ |
|---|---|---|---|---|---|---|---|
| $CH_3$ | $OCH_3$ | 6-$CH_3$ | $—(CH_2)_2—CHCH_3—(CH_2)_2—$ | | S | $C_2H_5$ | $i\text{-}C_3H_7—S—$ |
| $CH_3$ | $OCH_3$ | 6-$CH_3$ | $—(CH_2)_2—CHC_2H_5—(CH_2)_2—$ | | S | $C_2H_5$ | $i\text{-}C_3H_7—S—$ |
| $CH_3$ | $OCH_3$ | 6-$CH_3$ | $—(CH_2)_2—CHC_3H_7—(CH_2)_2—$ | | S | $C_2H_5$ | $i\text{-}C_3H_7—S—$ |
| $CH_3$ | $OCH_3$ | 6-$CH_3$ | $—(CH_2)_2—CHi\text{-}C_3H_7—(CH_2)_2—$ | | S | $C_2H_5$ | $i\text{-}C_3H_7—S—$ |
| $CH_3$ | $OCH_3$ | 6-$CH_3$ | $—(CH_2)_2—CHOCH_3—(CH_2)_2—$ | | S | $C_2H_5$ | $i\text{-}C_3H_7—S—$ |
| $CH_3$ | $OCH_3$ | 6-$CH_3$ | $—(CH_2)_2—CHOC_2H_5—(CH_2)_2—$ | | S | $C_2H_5$ | $i\text{-}C_3H_7—S—$ |
| $CH_3$ | $OCH_3$ | 6-$CH_3$ | $—(CH_2)_2—CHOC_3H_7—(CH_2)_2—$ | | S | $C_2H_5$ | $i\text{-}C_3H_7—S—$ |
| $CH_3$ | $OCH_3$ | 6-$CH_3$ | $—(CH_2)_2—CHi\text{-}OC_3H_7—(CH_2)_2—$ | | S | $C_2H_5$ | $i\text{-}C_3H_7—S—$ |
| $CH_3$ | $OCH_3$ | 6-$CH_3$ | $—(CH_2)_2—C(CH_3)_2—(CH_2)_2—$ | | S | $C_2H_5$ | $i\text{-}C_3H_7—S—$ |
| $CH_3$ | $OCH_3$ | 6-$CH_3$ | $—CH_2—(CHCH_3)_2—(CH_2)_2—$ | | S | $C_2H_5$ | $i\text{-}C_3H_7—S—$ |
| $CH_3$ | $OCH_3$ | 6-$CH_3$ | 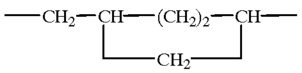 | | S | $C_2H_5$ | $i\text{-}C_3H_7—S—$ |
| $CH_3$ | $OCH_3$ | 6-$CH_3$ | 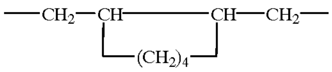 | | S | $C_2H_5$ | $i\text{-}C_3H_7—S—$ |
| $CH_3$ | $OCH_3$ | 6-$CH_3$ | 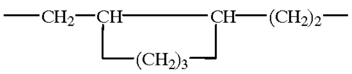 | | S | $C_2H_5$ | $i\text{-}C_3H_7—S—$ |
| $CH_3$ | $OCH_3$ | H | $CH_3$ | H | O | $CH_3$ | $i\text{-}C_3H_7—S—$ |
| $CH_3$ | $OCH_3$ | H | $C_2H_5$ | H | O | $CH_3$ | $i\text{-}C_3H_7—S—$ |
| $CH_3$ | $OCH_3$ | H | $C_3H_7$ | H | O | $CH_3$ | $i\text{-}C_3H_7—S—$ |
| $CH_3$ | $OCH_3$ | H | $i\text{-}C_3H_7$ | H | O | $CH_3$ | $i\text{-}C_3H_7—S—$ |
| $CH_3$ | $OCH_3$ | H | $C_4H_9$ | H | O | $CH_3$ | $i\text{-}C_3H_7—S—$ |
| $CH_3$ | $OCH_3$ | H | $i\text{-}C_4H_9$ | H | O | $CH_3$ | $i\text{-}C_3H_7—S—$ |
| $CH_3$ | $OCH_3$ | H | $s\text{-}C_4H_9$ | H | O | $CH_3$ | $i\text{-}C_3H_7—S—$ |
| $CH_3$ | $OCH_3$ | H | $t\text{-}C_4H_9$ | H | O | $CH_3$ | $i\text{-}C_3H_7—S—$ |
| $CH_3$ | $OCH_3$ | H | $CH_3$ | $CH_3$ | O | $CH_3$ | $i\text{-}C_3H_7—S—$ |
| $CH_3$ | $OCH_3$ | H | $C_2H_5$ | $CH_3$ | O | $CH_3$ | $i\text{-}C_3H_7—S—$ |
| $CH_3$ | $OCH_3$ | H | $C_3H_7$ | $CH_3$ | O | $CH_3$ | $i\text{-}C_3H_7—S—$ |
| $CH_3$ | $OCH_3$ | H | $i\text{-}C_3H_7$ | $CH_3$ | O | $CH_3$ | $i\text{-}C_3H_7—S—$ |
| $CH_3$ | $OCH_3$ | H | $C_4H_9$ | $CH_3$ | O | $CH_3$ | $i\text{-}C_3H_7—S—$ |
| $CH_3$ | $OCH_3$ | H | $i\text{-}C_4H_9$ | $CH_3$ | O | $CH_3$ | $i\text{-}C_3H_7—S—$ |
| $CH_3$ | $OCH_3$ | H | $s\text{-}C_4H_9$ | $CH_3$ | O | $CH_3$ | $i\text{-}C_3H_7—S—$ |
| $CH_3$ | $OCH_3$ | H | $t\text{-}C_4H_9$ | $CH_3$ | O | $CH_3$ | $i\text{-}C_3H_7—S—$ |
| $CH_3$ | $OCH_3$ | H | $C_2H_5$ | $C_2H_5$ | O | $CH_3$ | $i\text{-}C_3H_7—S—$ |
| $CH_3$ | $OCH_3$ | H | $C_3H_7$ | $C_3H_7$ | O | $CH_3$ | $i\text{-}C_3H_7—S—$ |
| $CH_3$ | $OCH_3$ | H | 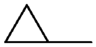 | $CH_3$ | O | $CH_3$ | $i\text{-}C_3H_7—S—$ |
| $CH_3$ | $OCH_3$ | H | 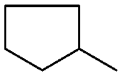 | $CH_3$ | O | $CH_3$ | $i\text{-}C_3H_7—S—$ |
| $CH_3$ | $OCH_3$ | H | 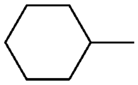 | $CH_3$ | O | $CH_3$ | $i\text{-}C_3H_7—S—$ |
| $CH_3$ | $CH_3$ | 6-$OCH_3$ | $CH_3$ | H | O | $CH_3$ | $i\text{-}C_3H_7—S—$ |
| $CH_3$ | $CH_3$ | 6-$OCH_3$ | $C_2H_5$ | H | O | $CH_3$ | $i\text{-}C_3H_7—S—$ |
| $CH_3$ | $CH_3$ | 6-$OCH_3$ | $C_3H_7$ | H | O | $CH_3$ | $i\text{-}C_3H_7—S—$ |
| $CH_3$ | $CH_3$ | 6-$OCH_3$ | $i\text{-}C_3H_7$ | H | O | $CH_3$ | $i\text{-}C_3H_7—S—$ |
| $CH_3$ | $CH_3$ | 6-$OCH_3$ | $C_4H_9$ | H | O | $CH_3$ | $i\text{-}C_3H_7—S—$ |

TABLE 5-continued (Ie)

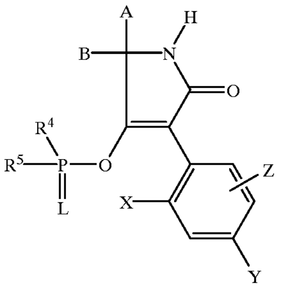

| X | Y | Z | A | B | L | $R^4$ | $R^5$ |
|---|---|---|---|---|---|---|---|
| $CH_3$ | $CH_3$ | 6-$OCH_3$ | i-$C_4H_9$ | H | O | $CH_3$ | i-$C_3H_7$—S— |
| $CH_3$ | $CH_3$ | 6-$OCH_3$ | s-$C_4H_9$ | H | O | $CH_3$ | i-$C_3H_7$—S— |
| $CH_3$ | $CH_3$ | 6-$OCH_3$ | t-$C_4H_9$ | H | O | $CH_3$ | i-$C_3H_7$—S— |
| $CH_3$ | $CH_3$ | 6-$OCH_3$ | $CH_3$ | $CH_3$ | O | $CH_3$ | i-$C_3H_7$—S— |
| $CH_3$ | $CH_3$ | 6-$OCH_3$ | $C_2H_5$ | $CH_3$ | O | $CH_3$ | i-$C_3H_7$—S— |
| $CH_3$ | $CH_3$ | 6-$OCH_3$ | $C_3H_7$ | $CH_3$ | O | $CH_3$ | i-$C_3H_7$—S— |
| $CH_3$ | $CH_3$ | 6-$OCH_3$ | i-$C_3H_7$ | $CH_3$ | O | $CH_3$ | i-$C_3H_7$—S— |
| $CH_3$ | $CH_3$ | 6-$OCH_3$ | $C_4H_9$ | $CH_3$ | O | $CH_3$ | i-$C_3H_7$—S— |
| $CH_3$ | $CH_3$ | 6-$OCH_3$ | i-$C_4H_9$ | $CH_3$ | O | $CH_3$ | i-$C_3H_7$—S— |
| $CH_3$ | $CH_3$ | 6-$OCH_3$ | s-$C_4H_9$ | $CH_3$ | O | $CH_3$ | i-$C_3H_7$—S— |
| $CH_3$ | $CH_3$ | 6-$OCH_3$ | t-$C_4H_9$ | $CH_3$ | O | $CH_3$ | i-$C_3H_7$—S— |
| $CH_3$ | $CH_3$ | 6-$OCH_3$ | $C_2H_5$ | $C_2H_5$ | O | $CH_3$ | i-$C_3H_7$—S— |
| $CH_3$ | $CH_3$ | 6-$OCH_3$ | $C_3H_7$ | $C_3H_7$ | O | $CH_3$ | i-$C_3H_7$—S— |
| $CH_3$ | $CH_3$ | 6-$OCH_3$ | 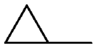 | $CH_3$ | O | $CH_3$ | i-$C_3H_7$—S— |
| $CH_3$ | $CH_3$ | 6-$OCH_3$ | 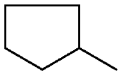 | $CH_3$ | O | $CH_3$ | i-$C_3H_7$—S— |
| $CH_3$ | $CH_3$ | 6-$OCH_3$ | 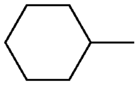 | $CH_3$ | O | $CH_3$ | i-$C_3H_7$—S— |
| $CH_3$ | $OCH_3$ | 6-$CH_3$ | $CH_3$ | H | O | $CH_3$ | i-$C_3H_7$—S— |
| $CH_3$ | $OCH_3$ | 6-$CH_3$ | $C_2H_5$ | H | O | $CH_3$ | i-$C_3H_7$—S— |
| $CH_3$ | $OCH_3$ | 6-$CH_3$ | $C_3H_7$ | H | O | $CH_3$ | i-$C_3H_7$—S— |
| $CH_3$ | $OCH_3$ | 6-$CH_3$ | i-$C_3H_7$ | H | O | $CH_3$ | i-$C_3H_7$—S— |
| $CH_3$ | $OCH_3$ | 6-$CH_3$ | $C_4H_9$ | H | O | $CH_3$ | i-$C_3H_7$—S— |
| $CH_3$ | $OCH_3$ | 6-$CH_3$ | i-$C_4H_9$ | H | O | $CH_3$ | i-$C_3H_7$—S— |
| $CH_3$ | $OCH_3$ | 6-$CH_3$ | s-$C_4H_9$ | H | O | $CH_3$ | i-$C_3H_7$—S— |
| $CH_3$ | $OCH_3$ | 6-$CH_3$ | t-$C_4H_9$ | H | O | $CH_3$ | i-$C_3H_7$—S— |
| $CH_3$ | $OCH_3$ | 6-$CH_3$ | $CH_3$ | $CH_3$ | O | $CH_3$ | i-$C_3H_7$—S— |
| $CH_3$ | $OCH_3$ | 6-$CH_3$ | $C_2H_5$ | $CH_3$ | O | $CH_3$ | i-$C_3H_7$—S— |
| $CH_3$ | $OCH_3$ | 6-$CH_3$ | $C_3H_7$ | $CH_3$ | O | $CH_3$ | i-$C_3H_7$—S— |
| $CH_3$ | $OCH_3$ | 6-$CH_3$ | i-$C_3H_7$ | $CH_3$ | O | $CH_3$ | i-$C_3H_7$—S— |
| $CH_3$ | $OCH_3$ | 6-$CH_3$ | $C_4H_9$ | $CH_3$ | O | $CH_3$ | i-$C_3H_7$—S— |
| $CH_3$ | $OCH_3$ | 6-$CH_3$ | i-$C_4H_9$ | $CH_3$ | O | $CH_3$ | i-$C_3H_7$—S— |
| $CH_3$ | $OCH_3$ | 6-$CH_3$ | s-$C_4H_9$ | $CH_3$ | O | $CH_3$ | i-$C_3H_7$—S— |
| $CH_3$ | $OCH_3$ | 6-$CH_3$ | t-$C_4H_9$ | $CH_3$ | O | $CH_3$ | i-$C_3H_7$—S— |
| $CH_3$ | $OCH_3$ | 6-$CH_3$ | $C_2H_5$ | $C_2H_5$ | O | $CH_3$ | i-$C_3H_7$—S— |
| $CH_3$ | $OCH_3$ | 6-$CH_3$ | $C_3H_7$ | $C_3H_7$ | O | $CH_3$ | i-$C_3H_7$—S— |
| $CH_3$ | $OCH_3$ | 6-$CH_3$ | 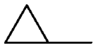 | $CH_3$ | O | $CH_3$ | i-$C_3H_7$—S— |
| $CH_3$ | $OCH_3$ | 6-$CH_3$ | 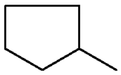 | $CH_3$ | O | $CH_3$ | i-$C_3H_7$—S— |
| $CH_3$ | $OCH_3$ | 6-$CH_3$ | 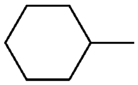 | $CH_3$ | O | $CH_3$ | i-$C_3H_7$—S— |
| $CH_3$ | $OCH_3$ | H | $-(CH_2)_2-$ | | O | $CH_3$ | i-$C_3H_7$—S— |

TABLE 5-continued (Ie)

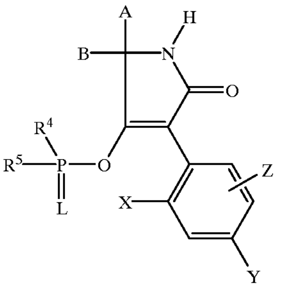

| X | Y | Z | A B | L | $R^4$ | $R^5$ |
|---|---|---|---|---|---|---|
| $CH_3$ | $OCH_3$ | H | $—(CH_2)_4—$ | O | $CH_3$ | $i\text{-}C_3H_7—S—$ |
| $CH_3$ | $OCH_3$ | H | $—(CH_2)_5—$ | O | $CH_3$ | $i\text{-}C_3H_7—S—$ |
| $CH_3$ | $OCH_3$ | H | $—(CH_2)_6—$ | O | $CH_3$ | $i\text{-}C_3H_7—S—$ |
| $CH_3$ | $OCH_3$ | H | $—(CH_2)_7—$ | O | $CH_3$ | $i\text{-}C_3H_7—S—$ |
| $CH_3$ | $OCH_3$ | H | $—(CH_2)_2—O—(CH_2)_2—$ | O | $CH_3$ | $i\text{-}C_3H_7—S—$ |
| $CH_3$ | $OCH_3$ | H | $—(CH_2)_2—S—(CH_2)_2—$ | O | $CH_3$ | $i\text{-}C_3H_7—S—$ |
| $CH_3$ | $OCH_3$ | H | $—CH_2—CHCH_3—(CH_2)_3—$ | O | $CH_3$ | $i\text{-}C_3H_7—S—$ |
| $CH_3$ | $OCH_3$ | H | $—(CH_2)_2—CHCH_3—(CH_2)_2—$ | O | $CH_3$ | $i\text{-}C_3H_7—S—$ |
| $CH_3$ | $OCH_3$ | H | $—(CH_2)_2—CHC_2H_5—(CH_2)_2—$ | O | $CH_3$ | $i\text{-}C_3H_7—S—$ |
| $CH_3$ | $OCH_3$ | H | $—(CH_2)_2—CHC_3H_7—(CH_2)_2—$ | O | $CH_3$ | $i\text{-}C_3H_7—S—$ |
| $CH_3$ | $OCH_3$ | H | $—(CH_2)_2—CHi\text{-}C_3H_7—(CH_2)_2—$ | O | $CH_3$ | $i\text{-}C_3H_7—S—$ |
| $CH_3$ | $OCH_3$ | H | $—(CH_2)_2—CHOCH_3—(CH_2)_2—$ | O | $CH_3$ | $i\text{-}C_3H_7—S—$ |
| $CH_3$ | $OCH_3$ | H | $—(CH_2)_2—CHOC_2H_5—(CH_2)_2—$ | O | $CH_3$ | $i\text{-}C_3H_7—S—$ |
| $CH_3$ | $OCH_3$ | H | $—(CH_2)_2—CHOC_3H_7—(CH_2)_2—$ | O | $CH_3$ | $i\text{-}C_3H_7—S—$ |
| $CH_3$ | $OCH_3$ | H | $—(CH_2)_2—CHi\text{-}OC_3H_7—(CH_2)_2—$ | O | $CH_3$ | $i\text{-}C_3H_7—S—$ |
| $CH_3$ | $OCH_3$ | H | $—(CH_2)_2—C(CH_3)_2—(CH_2)_2—$ | O | $CH_3$ | $i\text{-}C_3H_7—S—$ |
| $CH_3$ | $OCH_3$ | H | $—CH_2—(CHCH_3)_2—(CH_2)_2—$ | O | $CH_3$ | $i\text{-}C_3H_7—S—$ |
| $CH_3$ | $OCH_3$ | H | 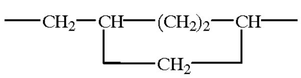 | O | $CH_3$ | $i\text{-}C_3H_7—S—$ |
| $CH_3$ | $OCH_3$ | H | 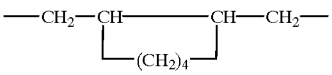 | O | $CH_3$ | $i\text{-}C_3H_7—S—$ |
| $CH_3$ | $OCH_3$ | H | 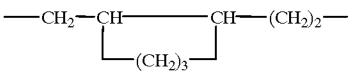 | O | $CH_3$ | $i\text{-}C_3H_7—S—$ |
| $CH_3$ | $CH_3$ | $6\text{-}OCH_3$ | $—(CH_2)_2—$ | O | $CH_3$ | $i\text{-}C_3H_7—S—$ |
| $CH_3$ | $CH_3$ | $6\text{-}OCH_3$ | $—(CH_2)_4—$ | O | $CH_3$ | $i\text{-}C_3H_7—S—$ |
| $CH_3$ | $CH_3$ | $6\text{-}OCH_3$ | $—(CH_2)_5—$ | O | $CH_3$ | $i\text{-}C_3H_7—S—$ |
| $CH_3$ | $CH_3$ | $6\text{-}OCH_3$ | $—(CH_2)_6—$ | O | $CH_3$ | $i\text{-}C_3H_7—S—$ |
| $CH_3$ | $CH_3$ | $6\text{-}OCH_3$ | $—(CH_2)_7—$ | O | $CH_3$ | $i\text{-}C_3H_7—S—$ |
| $CH_3$ | $CH_3$ | $6\text{-}OCH_3$ | $—(CH_2)_2—O—(CH_2)_2—$ | O | $CH_3$ | $i\text{-}C_3H_7—S—$ |
| $CH_3$ | $CH_3$ | $6\text{-}OCH_3$ | $—(CH_2)_2—S—(CH_2)_2—$ | O | $CH_3$ | $i\text{-}C_3H_7—S—$ |
| $CH_3$ | $CH_3$ | $6\text{-}OCH_3$ | $—CH_2—CHCH_3—(CH_2)_3—$ | O | $CH_3$ | $i\text{-}C_3H_7—S—$ |
| $CH_3$ | $CH_3$ | $6\text{-}OCH_3$ | $—(CH_2)_2—CHCH_3—(CH_2)_2—$ | O | $CH_3$ | $i\text{-}C_3H_7—S—$ |
| $CH_3$ | $CH_3$ | $6\text{-}OCH_3$ | $—(CH_2)_2—CHC_2H_5—(CH_2)_2—$ | O | $CH_3$ | $i\text{-}C_3H_7—S—$ |
| $CH_3$ | $CH_3$ | $6\text{-}OCH_3$ | $—(CH_2)_2—CHC_3H_7—(CH_2)_2—$ | O | $CH_3$ | $i\text{-}C_3H_7—S—$ |
| $CH_3$ | $CH_3$ | $6\text{-}OCH_3$ | $—(CH_2)_2—CHi\text{-}C_3H_7—(CH_2)_2—$ | O | $CH_3$ | $i\text{-}C_3H_7—S—$ |
| $CH_3$ | $CH_3$ | $6\text{-}OCH_3$ | $—(CH_2)_2—CHOCH_3—(CH_2)_2—$ | O | $CH_3$ | $i\text{-}C_3H_7—S—$ |
| $CH_3$ | $CH_3$ | $6\text{-}OCH_3$ | $—(CH_2)_2—CHOC_2H_5—(CH_2)_2—$ | O | $CH_3$ | $i\text{-}C_3H_7—S—$ |
| $CH_3$ | $CH_3$ | $6\text{-}OCH_3$ | $—(CH_2)_2—CHOC_3H_7—(CH_2)_2—$ | O | $CH_3$ | $i\text{-}C_3H_7—S—$ |
| $CH_3$ | $CH_3$ | $6\text{-}OCH_3$ | $—(CH_2)_2—CHi\text{-}OC_3H_7—(CH_2)_2—$ | O | $CH_3$ | $i\text{-}C_3H_7—S—$ |
| $CH_3$ | $CH_3$ | $6\text{-}OCH_3$ | $—(CH_2)_2—C(CH_3)_2—(CH_2)_2—$ | O | $CH_3$ | $i\text{-}C_3H_7—S—$ |
| $CH_3$ | $CH_3$ | $6\text{-}OCH_3$ | $—CH_2—(CHCH_3)_2—(CH_2)_2—$ | O | $CH_3$ | $i\text{-}C_3H_7—S—$ |
| $CH_3$ | $CH_3$ | $6\text{-}OCH_3$ | 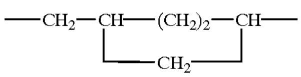 | O | $CH_3$ | $i\text{-}C_3H_7—S—$ |
| $CH_3$ | $CH_3$ | $6\text{-}OCH_3$ | 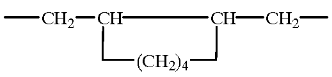 | O | $CH_3$ | $i\text{-}C_3H_7—S—$ |

TABLE 5-continued (Ie)

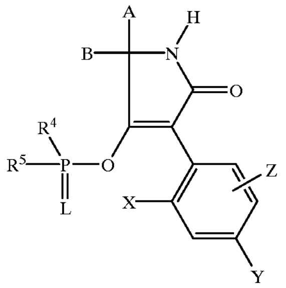

| X | Y | Z | A | B | L | $R^4$ | $R^5$ |
|---|---|---|---|---|---|---|---|
| $CH_3$ | $CH_3$ | 6-$OCH_3$ | 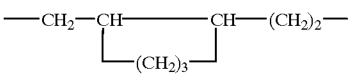 | | O | $CH_3$ | i-$C_3H_7$—S— |
| $CH_3$ | $OCH_3$ | 6-$CH_3$ | —$(CH_2)_2$— | | O | $CH_3$ | i-$C_3H_7$—S— |
| $CH_3$ | $OCH_3$ | 6-$CH_3$ | —$(CH_2)_4$— | | O | $CH_3$ | i-$C_3H_7$—S— |
| $CH_3$ | $OCH_3$ | 6-$CH_3$ | —$(CH_2)_5$— | | O | $CH_3$ | i-$C_3H_7$—S— |
| $CH_3$ | $OCH_3$ | 6-$CH_3$ | —$(CH_2)_6$— | | O | $CH_3$ | i-$C_3H_7$—S— |
| $CH_3$ | $OCH_3$ | 6-$CH_3$ | —$(CH_2)_7$— | | O | $CH_3$ | i-$C_3H_7$—S— |
| $CH_3$ | $OCH_3$ | 6-$CH_3$ | —$(CH_2)_2$—O—$(CH_2)_2$— | | O | $CH_3$ | i-$C_3H_7$—S— |
| $CH_3$ | $OCH_3$ | 6-$CH_3$ | —$(CH_2)_2$—S—$(CH_2)_2$— | | O | $CH_3$ | i-$C_3H_7$—S— |
| $CH_3$ | $OCH_3$ | 6-$CH_3$ | —$CH_2$—$CHCH_3$—$(CH_2)_3$— | | O | $CH_3$ | i-$C_3H_7$—S— |
| $CH_3$ | $OCH_3$ | 6-$CH_3$ | —$(CH_2)_2$—$CHCH_3$—$(CH_2)_2$— | | O | $CH_3$ | i-$C_3H_7$—S— |
| $CH_3$ | $OCH_3$ | 6-$CH_3$ | —$(CH_2)_2$—$CHC_2H_5$—$(CH_2)_2$— | | O | $CH_3$ | i-$C_3H_7$—S— |
| $CH_3$ | $OCH_3$ | 6-$CH_3$ | —$(CH_2)_2$—$CHC_3H_7$—$(CH_2)_2$— | | O | $CH_3$ | i-$C_3H_7$—S— |
| $CH_3$ | $OCH_3$ | 6-$CH_3$ | —$(CH_2)_2$—CHi-$C_3H_7$—$(CH_2)_2$— | | O | $CH_3$ | i-$C_3H_7$—S— |
| $CH_3$ | $OCH_3$ | 6-$CH_3$ | —$(CH_2)_2$—$CHOCH_3$—$(CH_2)_2$— | | O | $CH_3$ | i-$C_3H_7$—S— |
| $CH_3$ | $OCH_3$ | 6-$CH_3$ | —$(CH_2)_2$—$CHOC_2H_5$—$(CH_2)_2$— | | O | $CH_3$ | i-$C_3H_7$—S— |
| $CH_3$ | $OCH_3$ | 6-$CH_3$ | —$(CH_2)_2$—$CHOC_3H_7$—$(CH_2)_2$— | | O | $CH_3$ | i-$C_3H_7$—S— |
| $CH_3$ | $OCH_3$ | 6-$CH_3$ | —$(CH_2)_2$—CHi-$OC_3H_7$—$(CH_2)_2$— | | O | $CH_3$ | i-$C_3H_7$—S— |
| $CH_3$ | $OCH_3$ | 6-$CH_3$ | —$(CH_2)_2$—$C(CH_3)_2$—$(CH_2)_2$— | | O | $CH_3$ | i-$C_3H_7$—S— |
| $CH_3$ | $OCH_3$ | 6-$CH_3$ | —$CH_2$—$(CHCH_3)_2$—$(CH_2)_2$— | | O | $CH_3$ | i-$C_3H_7$—S— |
| $CH_3$ | $OCH_3$ | 6-$CH_3$ | 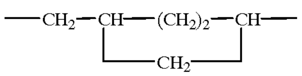 | | O | $CH_3$ | i-$C_3H_7$—S— |
| $CH_3$ | $OCH_3$ | 6-$CH_3$ | 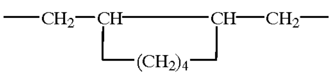 | | O | $CH_3$ | i-$C_3H_7$—S— |
| $CH_3$ | $OCH_3$ | 6-$CH_3$ | 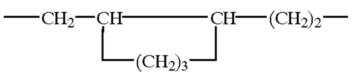 | | O | $CH_3$ | i-$C_3H_7$—S— |
| $CH_3$ | $OCH_3$ | H | $CH_3$ | H | O | $C_2H_5$ | i-$C_3H_7$—S— |
| $CH_3$ | $OCH_3$ | H | $C_2H_5$ | H | O | $C_2H_5$ | i-$C_3H_7$—S— |
| $CH_3$ | $OCH_3$ | H | $C_3H_7$ | H | O | $C_2H_5$ | i-$C_3H_7$—S— |
| $CH_3$ | $OCH_3$ | H | i-$C_3H_7$ | H | O | $C_2H_5$ | i-$C_3H_7$—S— |
| $CH_3$ | $OCH_3$ | H | $C_4H_9$ | H | O | $C_2H_5$ | i-$C_3H_7$—S— |
| $CH_3$ | $OCH_3$ | H | i-$C_4H_9$ | H | O | $C_2H_5$ | i-$C_3H_7$—S— |
| $CH_3$ | $OCH_3$ | H | s-$C_4H_9$ | H | O | $C_2H_5$ | i-$C_3H_7$—S— |
| $CH_3$ | $OCH_3$ | H | t-$C_4H_9$ | H | O | $C_2H_5$ | i-$C_3H_7$—S— |
| $CH_3$ | $OCH_3$ | H | $CH_3$ | $CH_3$ | O | $C_2H_5$ | i-$C_3H_7$—S— |
| $CH_3$ | $OCH_3$ | H | $C_2H_5$ | $CH_3$ | O | $C_2H_5$ | i-$C_3H_7$—S— |
| $CH_3$ | $OCH_3$ | H | $C_3H_7$ | $CH_3$ | O | $C_2H_5$ | i-$C_3H_7$—S— |
| $CH_3$ | $OCH_3$ | H | i-$C_3H_7$ | $CH_3$ | O | $C_2H_5$ | i-$C_3H_7$—S— |
| $CH_3$ | $OCH_3$ | H | $C_4H_9$ | $CH_3$ | O | $C_2H_5$ | i-$C_3H_7$—S— |
| $CH_3$ | $OCH_3$ | H | i-$C_4H_9$ | $CH_3$ | O | $C_2H_5$ | i-$C_3H_7$—S— |
| $CH_3$ | $OCH_3$ | H | s-$C_4H_9$ | $CH_3$ | O | $C_2H_5$ | i-$C_3H_7$—S— |
| $CH_3$ | $OCH_3$ | H | t-$C_4H_9$ | $CH_3$ | O | $C_2H_5$ | i-$C_3H_7$—S— |
| $CH_3$ | $OCH_3$ | H | $C_2H_5$ | $C_2H_5$ | O | $C_2H_5$ | i-$C_3H_7$—S— |
| $CH_3$ | $OCH_3$ | H | $C_3H_7$ | $C_3H_7$ | O | $C_2H_5$ | i-$C_3H_7$—S— |
| $CH_3$ | $OCH_3$ | H | 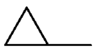 | $CH_3$ | O | $C_2H_5$ | i-$C_3H_7$—S— |

TABLE 5-continued (Ie)

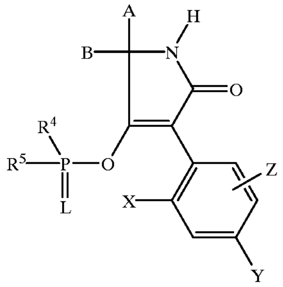

| X | Y | Z | A | B | L | $R^4$ | $R^5$ |
|---|---|---|---|---|---|---|---|
| $CH_3$ | $OCH_3$ | H | 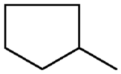 | $CH_3$ | O | $C_2H_5$ | $i-C_3H_7$—S— |
| $CH_3$ | $OCH_3$ | H | 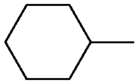 | $CH_3$ | O | $C_2H_5$ | $i-C_3H_7$—S— |
| $CH_3$ | $CH_3$ | $6-OCH_3$ | $CH_3$ | H | O | $C_2H_5$ | $i-C_3H_7$—S— |
| $CH_3$ | $CH_3$ | $6-OCH_3$ | $C_2H_5$ | H | O | $C_2H_5$ | $i-C_3H_7$—S— |
| $CH_3$ | $CH_3$ | $6-OCH_3$ | $C_3H_7$ | H | O | $C_2H_5$ | $i-C_3H_7$—S— |
| $CH_3$ | $CH_3$ | $6-OCH_3$ | $i-C_3H_7$ | H | O | $C_2H_5$ | $i-C_3H_7$—S— |
| $CH_3$ | $CH_3$ | $6-OCH_3$ | $C_4H_9$ | H | O | $C_2H_5$ | $i-C_3H_7$—S— |
| $CH_3$ | $CH_3$ | $6-OCH_3$ | $i-C_4H_9$ | H | O | $C_2H_5$ | $i-C_3H_7$—S— |
| $CH_3$ | $CH_3$ | $6-OCH_3$ | $s-C_4H_9$ | H | O | $C_2H_5$ | $i-C_3H_7$—S— |
| $CH_3$ | $CH_3$ | $6-OCH_3$ | $t-C_4H_9$ | H | O | $C_2H_5$ | $i-C_3H_7$—S— |
| $CH_3$ | $CH_3$ | $6-OCH_3$ | $CH_3$ | $CH_3$ | O | $C_2H_5$ | $i-C_3H_7$—S— |
| $CH_3$ | $CH_3$ | $6-OCH_3$ | $C_2H_5$ | $CH_3$ | O | $C_2H_5$ | $i-C_3H_7$—S— |
| $CH_3$ | $CH_3$ | $6-OCH_3$ | $C_3H_7$ | $CH_3$ | O | $C_2H_5$ | $i-C_3H_7$—S— |
| $CH_3$ | $CH_3$ | $6-OCH_3$ | $i-C_3H_7$ | $CH_3$ | O | $C_2H_5$ | $i-C_3H_7$—S— |
| $CH_3$ | $CH_3$ | $6-OCH_3$ | $C_4H_9$ | $CH_3$ | O | $C_2H_5$ | $i-C_3H_7$—S— |
| $CH_3$ | $CH_3$ | $6-OCH_3$ | $i-C_4H_9$ | $CH_3$ | O | $C_2H_5$ | $i-C_3H_7$—S— |
| $CH_3$ | $CH_3$ | $6-OCH_3$ | $s-C_4H_9$ | $CH_3$ | O | $C_2H_5$ | $i-C_3H_7$—S— |
| $CH_3$ | $CH_3$ | $6-OCH_3$ | $t-C_4H_9$ | $CH_3$ | O | $C_2H_5$ | $i-C_3H_7$—S— |
| $CH_3$ | $CH_3$ | $6-OCH_3$ | $C_2H_5$ | $C_2H_5$ | O | $C_2H_5$ | $i-C_3H_7$—S— |
| $CH_3$ | $CH_3$ | $6-OCH_3$ | $C_3H_7$ | $C_3H_7$ | O | $C_2H_5$ | $i-C_3H_7$—S— |
| $CH_3$ | $CH_3$ | $6-OCH_3$ | 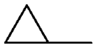 | $CH_3$ | O | $C_2H_5$ | $i-C_3H_7$—S— |
| $CH_3$ | $CH_3$ | $6-OCH_3$ | 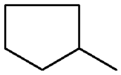 | $CH_3$ | O | $C_2H_5$ | $i-C_3H_7$—S— |
| $CH_3$ | $CH_3$ | $6-OCH_3$ | 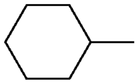 | $CH_3$ | O | $C_2H_5$ | $i-C_3H_7$—S— |
| $CH_3$ | $OCH_3$ | $6-CH_3$ | $CH_3$ | H | O | $C_2H_5$ | $i-C_3H_7$—S— |
| $CH_3$ | $OCH_3$ | $6-CH_3$ | $C_2H_5$ | H | O | $C_2H_5$ | $i-C_3H_7$—S— |
| $CH_3$ | $OCH_3$ | $6-CH_3$ | $C_3H_7$ | H | O | $C_2H_5$ | $i-C_3H_7$—S— |
| $CH_3$ | $OCH_3$ | $6-CH_3$ | $i-C_3H_7$ | H | O | $C_2H_5$ | $i-C_3H_7$—S— |
| $CH_3$ | $OCH_3$ | $6-CH_3$ | $C_4H_9$ | H | O | $C_2H_5$ | $i-C_3H_7$—S— |
| $CH_3$ | $OCH_3$ | $6-CH_3$ | $i-C_4H_9$ | H | O | $C_2H_5$ | $i-C_3H_7$—S— |
| $CH_3$ | $OCH_3$ | $6-CH_3$ | $s-C_4H_9$ | H | O | $C_2H_5$ | $i-C_3H_7$—S— |
| $CH_3$ | $OCH_3$ | $6-CH_3$ | $t-C_4H_9$ | H | O | $C_2H_5$ | $i-C_3H_7$—S— |
| $CH_3$ | $OCH_3$ | $6-CH_3$ | $CH_3$ | $CH_3$ | O | $C_2H_5$ | $i-C_3H_7$—S— |
| $CH_3$ | $OCH_3$ | $6-CH_3$ | $C_2H_5$ | $CH_3$ | O | $C_2H_5$ | $i-C_3H_7$—S— |
| $CH_3$ | $OCH_3$ | $6-CH_3$ | $C_3H_7$ | $CH_3$ | O | $C_2H_5$ | $i-C_3H_7$—S— |
| $CH_3$ | $OCH_3$ | $6-CH_3$ | $i-C_3H_7$ | $CH_3$ | O | $C_2H_5$ | $i-C_3H_7$—S— |
| $CH_3$ | $OCH_3$ | $6-CH_3$ | $C_4H_9$ | $CH_3$ | O | $C_2H_5$ | $i-C_3H_7$—S— |
| $CH_3$ | $OCH_3$ | $6-CH_3$ | $i-C_4H_9$ | $CH_3$ | O | $C_2H_5$ | $i-C_3H_7$—S— |
| $CH_3$ | $OCH_3$ | $6-CH_3$ | $s-C_4H_9$ | $CH_3$ | O | $C_2H_5$ | $i-C_3H_7$—S— |
| $CH_3$ | $OCH_3$ | $6-CH_3$ | $t-C_4H_9$ | $CH_3$ | O | $C_2H_5$ | $i-C_3H_7$—S— |
| $CH_3$ | $OCH_3$ | $6-CH_3$ | $C_2H_5$ | $C_2H_5$ | O | $C_2H_5$ | $i-C_3H_7$—S— |
| $CH_3$ | $OCH_3$ | $6-CH_3$ | $C_3H_7$ | $C_3H_7$ | O | $C_2H_5$ | $i-C_3H_7$—S— |

TABLE 5-continued (Ie)

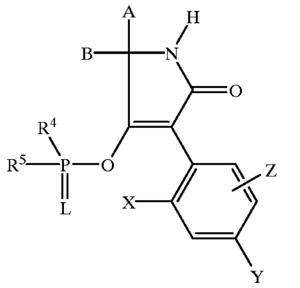

| X | Y | Z | A | B | L | $R^4$ | $R^5$ |
|---|---|---|---|---|---|---|---|
| $CH_3$ | $OCH_3$ | 6-$CH_3$ | 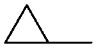 | $CH_3$ | O | $C_2H_5$ | i-$C_3H_7$—S— |
| $CH_3$ | $OCH_3$ | 6-$CH_3$ | 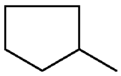 | $CH_3$ | O | $C_2H_5$ | i-$C_3H_7$—S— |
| $CH_3$ | $OCH_3$ | 6-$CH_3$ | 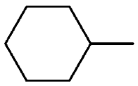 | $CH_3$ | O | $C_2H_5$ | i-$C_3H_7$—S— |
| $CH_3$ | $OCH_3$ | H | —$(CH_2)_2$— | | O | $C_2H_5$ | i-$C_3H_7$—S— |
| $CH_3$ | $OCH_3$ | H | —$(CH_2)_4$— | | O | $C_2H_5$ | i-$C_3H_7$—S— |
| $CH_3$ | $OCH_3$ | H | —$(CH_2)_5$— | | O | $C_2H_5$ | i-$C_3H_7$—S— |
| $CH_3$ | $OCH_3$ | H | —$(CH_2)_6$— | | O | $C_2H_5$ | i-$C_3H_7$—S— |
| $CH_3$ | $OCH_3$ | H | —$(CH_2)_7$— | | O | $C_2H_5$ | i-$C_3H_7$—S— |
| $CH_3$ | $OCH_3$ | H | —$(CH_2)_2$—O—$(CH_2)_2$— | | O | $C_2H_5$ | i-$C_3H_7$—S— |
| $CH_3$ | $OCH_3$ | H | —$(CH_2)_2$—S—$(CH_2)_2$— | | O | $C_2H_5$ | i-$C_3H_7$—S— |
| $CH_3$ | $OCH_3$ | H | —$CH_2$—$CHCH_3$—$(CH_2)_3$— | | O | $C_2H_5$ | i-$C_3H_7$—S— |
| $CH_3$ | $OCH_3$ | H | —$(CH_2)_2$—$CHCH_3$—$(CH_2)_2$— | | O | $C_2H_5$ | i-$C_3H_7$—S— |
| $CH_3$ | $OCH_3$ | H | —$(CH_2)_2$—$CHC_2H_5$—$(CH_2)_2$— | | O | $C_2H_5$ | i-$C_3H_7$—S— |
| $CH_3$ | $OCH_3$ | H | —$(CH_2)_2$—$CHC_3H_7$—$(CH_2)_2$— | | O | $C_2H_5$ | i-$C_3H_7$—S— |
| $CH_3$ | $OCH_3$ | H | —$(CH_2)_2$—CHi-$C_3H_7$—$(CH_2)_2$— | | O | $C_2H_5$ | i-$C_3H_7$—S— |
| $CH_3$ | $OCH_3$ | H | —$(CH_2)_2$—$CHOCH_3$—$(CH_2)_2$— | | O | $C_2H_5$ | i-$C_3H_7$—S— |
| $CH_3$ | $OCH_3$ | H | —$(CH_2)_2$—$CHOC_2H_5$—$(CH_2)_2$— | | O | $C_2H_5$ | i-$C_3H_7$—S— |
| $CH_3$ | $OCH_3$ | H | —$(CH_2)_2$—$CHOC_3H_7$—$(CH_2)_2$— | | O | $C_2H_5$ | i-$C_3H_7$—S— |
| $CH_3$ | $OCH_3$ | H | —$(CH_2)_2$—CHi-$OC_3H_7$—$(CH_2)_2$— | | O | $C_2H_5$ | i-$C_3H_7$—S— |
| $CH_3$ | $OCH_3$ | H | —$(CH_2)_2$—$C(CH_3)_2$—$(CH_2)_2$— | | O | $C_2H_5$ | i-$C_3H_7$—S— |
| $CH_3$ | $OCH_3$ | H | —$CH_2$—$(CHCH_3)_2$—$(CH_2)_2$— | | O | $C_2H_5$ | i-$C_3H_7$—S— |
| $CH_3$ | $OCH_3$ | H | 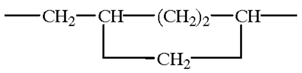 | | O | $C_2H_5$ | i-$C_3H_7$—S— |
| $CH_3$ | $OCH_3$ | H | 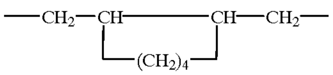 | | O | $C_2H_5$ | i-$C_3H_7$—S— |
| $CH_3$ | $OCH_3$ | H | 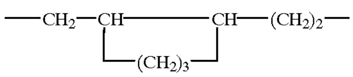 | | O | $C_2H_5$ | i-$C_3H_7$—S— |
| $CH_3$ | $CH_3$ | 6-$OCH_3$ | —$(CH_2)_2$— | | O | $C_2H_5$ | i-$C_3H_7$—S— |
| $CH_3$ | $CH_3$ | 6-$OCH_3$ | —$(CH_2)_4$— | | O | $C_2H_5$ | i-$C_3H_7$—S— |
| $CH_3$ | $CH_3$ | 6-$OCH_3$ | —$(CH_2)_5$— | | O | $C_2H_5$ | i-$C_3H_7$—S— |
| $CH_3$ | $CH_3$ | 6-$OCH_3$ | —$(CH_2)_6$— | | O | $C_2H_5$ | i-$C_3H_7$—S— |
| $CH_3$ | $CH_3$ | 6-$OCH_3$ | —$(CH_2)_7$— | | O | $C_2H_5$ | i-$C_3H_7$—S— |
| $CH_3$ | $CH_3$ | 6-$OCH_3$ | —$(CH_2)_2$—O—$(CH_2)_2$— | | O | $C_2H_5$ | i-$C_3H_7$—S— |
| $CH_3$ | $CH_3$ | 6-$OCH_3$ | —$(CH_2)_2$—S—$(CH_2)_2$— | | O | $C_2H_5$ | i-$C_3H_7$—S— |
| $CH_3$ | $CH_3$ | 6-$OCH_3$ | —$CH_2$—$CHCH_3$—$(CH_2)_3$— | | O | $C_2H_5$ | i-$C_3H_7$—S— |
| $CH_3$ | $CH_3$ | 6-$OCH_3$ | —$(CH_2)_2$—$CHCH_3$—$(CH_2)_2$— | | O | $C_2H_5$ | i-$C_3H_7$—S— |
| $CH_3$ | $CH_3$ | 6-$OCH_3$ | —$(CH_2)_2$—$CHC_2H_5$—$(CH_2)_2$— | | O | $C_2H_5$ | i-$C_3H_7$—S— |
| $CH_3$ | $CH_3$ | 6-$OCH_3$ | —$(CH_2)_2$—$CHC_3H_7$—$(CH_2)_2$— | | O | $C_2H_5$ | i-$C_3H_7$—S— |
| $CH_3$ | $CH_3$ | 6-$OCH_3$ | —$(CH_2)_2$—CHi-$C_3H_7$—$(CH_2)_2$— | | O | $C_2H_5$ | i-$C_3H_7$—S— |
| $CH_3$ | $CH_3$ | 6-$OCH_3$ | —$(CH_2)_2$—$CHOCH_3$—$(CH_2)_2$— | | O | $C_2H_5$ | i-$C_3H_7$—S— |
| $CH_3$ | $CH_3$ | 6-$OCH_3$ | —$(CH_2)_2$—$CHOC_2H_5$—$(CH_2)_2$— | | O | $C_2H_5$ | i-$C_3H_7$—S— |
| $CH_3$ | $CH_3$ | 6-$OCH_3$ | —$(CH_2)_2$—$CHOC_3H_7$—$(CH_2)_2$— | | O | $C_2H_5$ | i-$C_3H_7$—S— |

TABLE 5-continued (Ie)

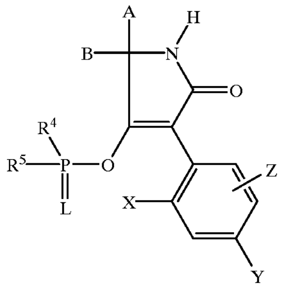

| X | Y | Z | A B | L | R4 | R5 |
|---|---|---|---|---|---|---|
| $CH_3$ | $CH_3$ | 6-$OCH_3$ | $-(CH_2)_2-CH$i-$OC_3H_7-(CH_2)_2-$ | O | $C_2H_5$ | i-$C_3H_7-S-$ |
| $CH_3$ | $CH_3$ | 6-$OCH_3$ | $-(CH_2)_2-C(CH_3)_2-(CH_2)_2-$ | O | $C_2H_5$ | i-$C_3H_7-S-$ |
| $CH_3$ | $CH_3$ | 6-$OCH_3$ | $-CH_2-(CHCH_3)_2-(CH_2)_2-$ | O | $C_2H_5$ | i-$C_3H_7-S-$ |
| $CH_3$ | $CH_3$ | 6-$OCH_3$ | 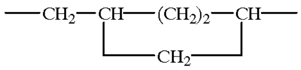 | O | $C_2H_5$ | i-$C_3H_7-S-$ |
| $CH_3$ | $CH_3$ | 6-$OCH_3$ | 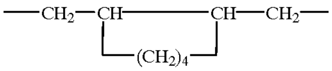 | O | $C_2H_5$ | i-$C_3H_7-S-$ |
| $CH_3$ | $CH_3$ | 6-$OCH_3$ | 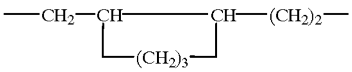 | O | $C_2H_5$ | i-$C_3H_7-S-$ |
| $CH_3$ | $OCH_3$ | 6-$CH_3$ | $-(CH_2)_2-$ | O | $C_2H_5$ | i-$C_3H_7-S-$ |
| $CH_3$ | $OCH_3$ | 6-$CH_3$ | $-(CH_2)_4-$ | O | $C_2H_5$ | i-$C_3H_7-S-$ |
| $CH_3$ | $OCH_3$ | 6-$CH_3$ | $-(CH_2)_5-$ | O | $C_2H_5$ | i-$C_3H_7-S-$ |
| $CH_3$ | $OCH_3$ | 6-$CH_3$ | $-(CH_2)_6-$ | O | $C_2H_5$ | i-$C_3H_7-S-$ |
| $CH_3$ | $OCH_3$ | 6-$CH_3$ | $-(CH_2)_7-$ | O | $C_2H_5$ | i-$C_3H_7-S-$ |
| $CH_3$ | $OCH_3$ | 6-$CH_3$ | $-(CH_2)_2-O-(CH_2)_2-$ | O | $C_2H_5$ | i-$C_3H_7-S-$ |
| $CH_3$ | $OCH_3$ | 6-$CH_3$ | $-(CH_2)_2-S-(CH_2)_2-$ | O | $C_2H_5$ | i-$C_3H_7-S-$ |
| $CH_3$ | $OCH_3$ | 6-$CH_3$ | $-CH_2-CHCH_3-(CH_2)_3-$ | O | $C_2H_5$ | i-$C_3H_7-S-$ |
| $CH_3$ | $OCH_3$ | 6-$CH_3$ | $-(CH_2)_2-CHCH_3-(CH_2)_2-$ | O | $C_2H_5$ | i-$C_3H_7-S-$ |
| $CH_3$ | $OCH_3$ | 6-$CH_3$ | $-(CH_2)_2-CHC_2H_5-(CH_2)_2-$ | O | $C_2H_5$ | i-$C_3H_7-S-$ |
| $CH_3$ | $OCH_3$ | 6-$CH_3$ | $-(CH_2)_2-CHC_3H_7-(CH_2)_2-$ | O | $C_2H_5$ | i-$C_3H_7-S-$ |
| $CH_3$ | $OCH_3$ | 6-$CH_3$ | $-(CH_2)_2-CH$i-$C_3H_7-(CH_2)_2-$ | O | $C_2H_5$ | i-$C_3H_7-S-$ |
| $CH_3$ | $OCH_3$ | 6-$CH_3$ | $-(CH_2)_2-CHOCH_3-(CH_2)_2-$ | O | $C_2H_5$ | i-$C_3H_7-S-$ |
| $CH_3$ | $OCH_3$ | 6-$CH_3$ | $-(CH_2)_2-CHOC_2H_5-(CH_2)_2-$ | O | $C_2H_5$ | i-$C_3H_7-S-$ |
| $CH_3$ | $OCH_3$ | 6-$CH_3$ | $-(CH_2)_2-CHOC_3H_7-(CH_2)_2-$ | O | $C_2H_5$ | i-$C_3H_7-S-$ |
| $CH_3$ | $OCH_3$ | 6-$CH_3$ | $-(CH_2)_2-CH$i-$OC_3H_7-(CH_2)_2-$ | O | $C_2H_5$ | i-$C_3H_7-S-$ |
| $CH_3$ | $OCH_3$ | 6-$CH_3$ | $-(CH_2)_2-C(CH_3)_2-(CH_2)_2-$ | O | $C_2H_5$ | i-$C_3H_7-S-$ |
| $CH_3$ | $OCH_3$ | 6-$CH_3$ | $-CH_2-(CHCH_3)_2-(CH_2)_2-$ | O | $C_2H_5$ | i-$C_3H_7-S-$ |
| $CH_3$ | $OCH_3$ | 6-$CH_3$ | 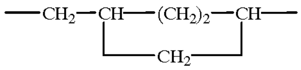 | O | $C_2H_5$ | i-$C_3H_7-S-$ |
| $CH_3$ | $OCH_3$ | 6-$CH_3$ | 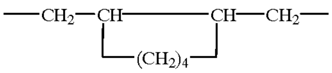 | O | $C_2H_5$ | i-$C_3H_7-S-$ |
| $CH_3$ | $OCH_3$ | 6-$CH_3$ | 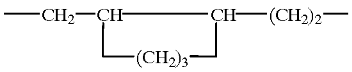 | O | $C_2H_5$ | i-$C_3H_7-S-$ |

Specific mention may be made, in addition to the compounds specified in the Preparation Examples, of the following compounds of the formula (If-a):

TABLE 6a (If-a)

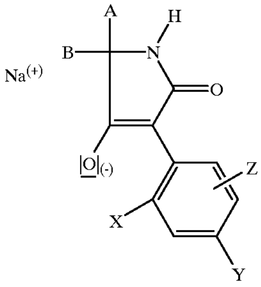

| X | Y | Z | A | B |
|---|---|---|---|---|
| $CH_3$ | $OCH_3$ | H | $CH_3$ | H |
| $CH_3$ | $OCH_3$ | H | $C_2H_5$ | H |
| $CH_3$ | $OCH_3$ | H | $C_3H_7$ | H |
| $CH_3$ | $OCH_3$ | H | i-$C_3H_7$ | H |
| $CH_3$ | $OCH_3$ | H | $C_4H_9$ | H |
| $CH_3$ | $OCH_3$ | H | i-$C_4H_9$ | H |
| $CH_3$ | $OCH_3$ | H | s-$C_4H_9$ | H |
| $CH_3$ | $OCH_3$ | H | t-$C_4H_9$ | H |
| $CH_3$ | $OCH_3$ | H | $CH_3$ | $CH_3$ |
| $CH_3$ | $OCH_3$ | H | $C_2H_5$ | $CH_3$ |
| $CH_3$ | $OCH_3$ | H | $C_3H_7$ | $CH_3$ |
| $CH_3$ | $OCH_3$ | H | i-$C_3H_7$ | $CH_3$ |
| $CH_3$ | $OCH_3$ | H | $C_4H_9$ | $CH_3$ |
| $CH_3$ | $OCH_3$ | H | i-$C_4H_9$ | $CH_3$ |
| $CH_3$ | $OCH_3$ | H | s-$C_4H_9$ | $CH_3$ |
| $CH_3$ | $OCH_3$ | H | t-$C_4H_9$ | $CH_3$ |
| $CH_3$ | $OCH_3$ | H | $C_2H_5$ | $C_2H_5$ |
| $CH_3$ | $OCH_3$ | H | $C_3H_7$ | $C_3H_7$ |
| $CH_3$ | $OCH_3$ | H | 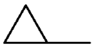 | $CH_3$ |
| $CH_3$ | $OCH_3$ | H | 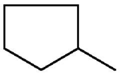 | $CH_3$ |
| $CH_3$ | $OCH_3$ | H | 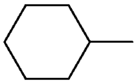 | $CH_3$ |
| $CH_3$ | $CH_3$ | 6-$OCH_3$ | $CH_3$ | H |
| $CH_3$ | $CH_3$ | 6-$OCH_3$ | $C_2H_5$ | H |
| $CH_3$ | $CH_3$ | 6-$OCH_3$ | $C_3H_7$ | H |
| $CH_3$ | $CH_3$ | 6-$OCH_3$ | i-$C_3H_7$ | H |
| $CH_3$ | $CH_3$ | 6-$OCH_3$ | $C_4H_9$ | H |
| $CH_3$ | $CH_3$ | 6-$OCH_3$ | i-$C_4H_9$ | H |
| $CH_3$ | $CH_3$ | 6-$OCH_3$ | s-$C_4H_9$ | H |
| $CH_3$ | $CH_3$ | 6-$OCH_3$ | t-$C_4H_7$ | H |
| $CH_3$ | $CH_3$ | 6-$OCH_3$ | $CH_3$ | $CH_3$ |
| $CH_3$ | $CH_3$ | 6-$OCH_3$ | $C_2H_5$ | $CH_3$ |
| $CH_3$ | $CH_3$ | 6-$OCH_3$ | $C_3H_7$ | $CH_3$ |
| $CH_3$ | $CH_3$ | 6-$OCH_3$ | i-$C_3H_7$ | $CH_3$ |
| $CH_3$ | $CH_3$ | 6-$OCH_3$ | $C_4H_9$ | $CH_3$ |
| $CH_3$ | $CH_3$ | 6-$OCH_3$ | i-$C_4H_9$ | |
| $CH_3$ | $CH_3$ | 6-$OCH_3$ | s-$C_4H_9$ | $CH_3$ |
| $CH_3$ | $CH_3$ | 6-$OCH_3$ | t-$C_4H_9$ | $CH_3$ |
| $CH_3$ | $CH_3$ | 6-$OCH_3$ | $C_2H_5$ | $C_2H_5$ |
| $CH_3$ | $CH_3$ | 6-$OCH_3$ | $C_3H_7$ | $C_3H_7$ |
| $CH_3$ | $CH_3$ | 6-$OCH_3$ | 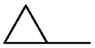 | $CH_3$ |
| $CH_3$ | $CH_3$ | 6-$OCH_3$ | 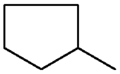 | $CH_3$ |

TABLE 6a-continued (If-a)

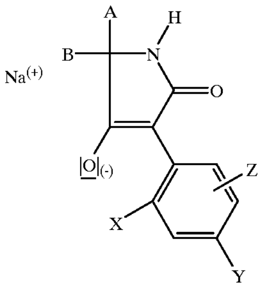

| X | Y | Z | A | B |
|---|---|---|---|---|
| $CH_3$ | $CH_3$ | 6-$OCH_3$ | 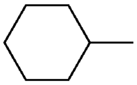 | $CH_3$ |
| $CH_3$ | $OCH_3$ | 6-$CH_3$ | $CH_3$ | H |
| $CH_3$ | $OCH_3$ | 6-$CH_3$ | $C_2H_5$ | H |
| $CH_3$ | $OCH_3$ | 6-$CH_3$ | $C_3H_7$ | H |
| $CH_3$ | $OCH_3$ | 6-$CH_3$ | i-$C_3H_7$ | H |
| $CH_3$ | $OCH_3$ | 6-$CH_3$ | $C_4H_9$ | H |
| $CH_3$ | $OCH_3$ | 6-$CH_3$ | i-$C_4H_9$ | H |
| $CH_3$ | $OCH_3$ | 6-$CH_3$ | s-$C_4H_9$ | H |
| $CH_3$ | $OCH_3$ | 6-$CH_3$ | t-$C_4H_9$ | H |
| $CH_3$ | $OCH_3$ | 6-$CH_3$ | $CH_3$ | $CH_3$ |
| $CH_3$ | $OCH_3$ | 6-$CH_3$ | $C_2H_5$ | $CH_3$ |
| $CH_3$ | $OCH_3$ | 6-$CH_3$ | $C_3H_7$ | $CH_3$ |
| $CH_3$ | $OCH_3$ | 6-$CH_3$ | i-$C_3H_7$ | $CH_3$ |
| $CH_3$ | $OCH_3$ | 6-$CH_3$ | $C_4H_9$ | $CH_3$ |
| $CH_3$ | $OCH_3$ | 6-$CH_3$ | i-$C_4H_9$ | $CH_3$ |
| $CH_3$ | $OCH_3$ | 6-$CH_3$ | s-$C_4H_9$ | $CH_3$ |
| $CH_3$ | $OCH_3$ | 6-$CH_3$ | t-$C_4H_9$ | $CH_3$ |
| $CH_3$ | $OCH_3$ | 6-$CH_3$ | $C_2H_5$ | $C_2H_5$ |
| $CH_3$ | $OCH_3$ | 6-$CH_3$ | $C_3H_7$ | $C_3H_7$ |
| $CH_3$ | $OCH_3$ | 6-$CH_3$ | 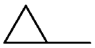 | $CH_3$ |
| $CH_3$ | $OCH_3$ | 6-$CH_3$ | 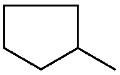 | $CH_3$ |
| $CH_3$ | $OCH_3$ | 6-$CH_3$ | 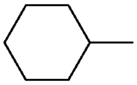 | $CH_3$ |
| $CH_3$ | $OCH_3$ | H | $-(CH_2)_2-$ | |
| $CH_3$ | $OCH_3$ | H | $-(CH_2)_4-$ | |
| $CH_3$ | $OCH_3$ | H | $-(CH_2)_5-$ | |
| $CH_3$ | $OCH_3$ | H | $-(CH_2)_6-$ | |
| $CH_3$ | $OCH_3$ | H | $-(CH_2)_7-$ | |
| $CH_3$ | $OCH_3$ | H | $-(CH_2)_2-O-(CH_2)_2-$ | |
| $CH_3$ | $OCH_3$ | H | $-(CH_2)_2-S-(CH_2)_2-$ | |
| $CH_3$ | $OCH_3$ | H | $-(CH_2)_2-CHCH_3-(CH_2)_3-$ | |
| $CH_3$ | $OCH_3$ | H | $-(CH_2)_2-CHCH_3-(CH_2)_2-$ | |
| $CH_3$ | $OCH_3$ | H | $-(CH_2)_2-CHC_2H_5-(CH_2)_2-$ | |
| $CH_3$ | $OCH_3$ | H | $-(CH_2)_2-CHC_3H_7-(CH_2)_2-$ | |
| $CH_3$ | $OCH_3$ | H | $-(CH_2)_2-CHi\text{-}C_3H_7-(CH_2)_2-$ | |
| $CH_3$ | $OCH_3$ | H | $-(CH_2)_2-CHOCH_3-(CH_2)_2-$ | |
| $CH_3$ | $OCH_3$ | H | $-(CH_2)_2-CHOC_2H_5-(CH_2)_2-$ | |
| $CH_3$ | $OCH_3$ | H | $-(CH_2)_2-CHOC_3H_7-(CH_2)_2-$ | |
| $CH_3$ | $OCH_3$ | H | $-(CH_2)_2-CHi\text{-}OC_3H_7-(CH_2)_2-$ | |
| $CH_3$ | $OCH_3$ | H | $-(CH_2)_2-C(CH_3)_2-(CH_2)_2-$ | |
| $CH_3$ | $OCH_3$ | H | $-CH_2-(CHCH_3)_2-(CH_2)_2-$ | |

TABLE 6a-continued (If-a)

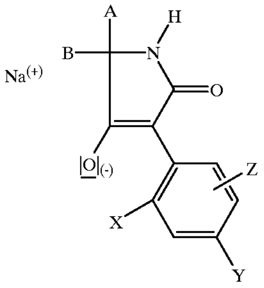

| X | Y | Z | A | B |
|---|---|---|---|---|
| $CH_3$ | $OCH_3$ | H | 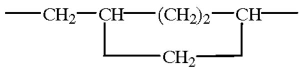 | |
| $CH_3$ | $OCH_3$ | H | 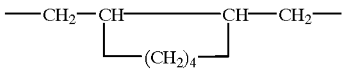 | |
| $CH_3$ | $OCH_3$ | H | 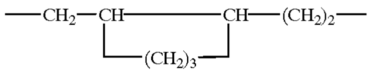 | |
| $CH_3$ | $CH_3$ | 6-$OCH_3$ | $-(CH_2)_2-$ | |
| $CH_3$ | $CH_3$ | 6-$OCH_3$ | $-(CH_2)_4-$ | |
| $CH_3$ | $CH_3$ | 6-$OCH_3$ | $-(CH_2)_5-$ | |
| $CH_3$ | $CH_3$ | 6-$OCH_3$ | $-(CH_2)_6-$ | |
| $CH_3$ | $CH_3$ | 6-$OCH_3$ | $-(CH_2)_7-$ | |
| $CH_3$ | $CH_3$ | 6-$OCH_3$ | $-(CH_2)_2-O-(CH_2)_2-$ | |
| $CH_3$ | $CH_3$ | 6-$OCH_3$ | $-(CH_2)_2-S-(CH_2)_2-$ | |
| $CH_3$ | $CH_3$ | 6-$OCH_3$ | $-CH_2-CHCH_3-(CH_2)_3-$ | |
| $CH_3$ | $CH_3$ | 6-$OCH_3$ | $-(CH_2)_2-CHCH_3-(CH_2)_2-$ | |
| $CH_3$ | $CH_3$ | 6-$OCH_3$ | $-(CH_2)_2-CHC_2H_5-(CH_2)_2-$ | |
| $CH_3$ | $CH_3$ | 6-$OCH_3$ | $-(CH_2)_2-CHC_3H_7-(CH_2)_2-$ | |
| $CH_3$ | $CH_3$ | 6-$OCH_3$ | $-(CH_2)_2-CHi\text{-}C_3H_7-(CH_2)_2-$ | |
| $CH_3$ | $CH_3$ | 6-$OCH_3$ | $-(CH_2)_2-CHOCH_3-(CH_2)_2-$ | |
| $CH_3$ | $CH_3$ | 6-$OCH_3$ | $-(CH_2)_2-CHOC_2H_5-(CH_2)_2-$ | |
| $CH_3$ | $CH_3$ | 6-$OCH_3$ | $-(CH_2)_2-CHOC_3H_7-(CH_2)_2-$ | |
| $CH_3$ | $CH_3$ | 6-$OCH_3$ | $-(CH_2)_2-CHi\text{-}OC_3H_7-(CH_2)_2-$ | |
| $CH_3$ | $CH_3$ | 6-$OCH_3$ | $-(CH_2)_2-C(CH_3)_2-(CH_2)_2-$ | |
| $CH_3$ | $CH_3$ | 6-$OCH_3$ | $-CH_2-(CHCH_3)_2-(CH_2)_2-$ | |
| $CH_3$ | $CH_3$ | 6-$OCH_3$ | 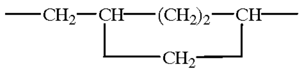 | |
| $CH_3$ | $CH_3$ | 6-$OCH_3$ | 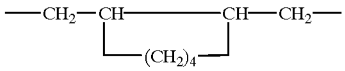 | |
| $CH_3$ | $CH_3$ | 6-$OCH_3$ | 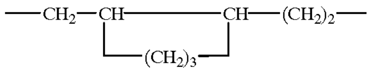 | |
| $CH_3$ | $OCH_3$ | 6-$CH_3$ | $-(CH_2)_2-$ | |
| $CH_3$ | $OCH_3$ | 6-$CH_3$ | $-(CH_2)_4-$ | |
| $CH_3$ | $OCH_3$ | 6-$CH_3$ | $-(CH_2)_5-$ | |
| $CH_3$ | $OCH_3$ | 6-$CH_3$ | $-(CH_2)_6-$ | |
| $CH_3$ | $OCH_3$ | 6-$CH_3$ | $-(CH_2)_7-$ | |
| $CH_3$ | $OCH_3$ | 6-$CH_3$ | $-(CH_2)_2-O-(CH_2)_2-$ | |
| $CH_3$ | $OCH_3$ | 6-$CH_3$ | $-(CH_2)_2-S-(CH_2)_2-$ | |
| $CH_3$ | $OCH_3$ | 6-$CH_3$ | $-CH_2-CHCH_3-(CH_2)_3-$ | |
| $CH_3$ | $OCH_3$ | 6-$CH_3$ | $-(CH_2)_2-CHCH_3-(CH_2)_2-$ | |
| $CH_3$ | $OCH_3$ | 6-$CH_3$ | $-(CH_2)_2-CHC_2H_5-(CH_2)_2-$ | |
| $CH_3$ | $OCH_3$ | 6-$CH_3$ | $-(CH_2)_2-CHC_3H_7-(CH_2)_2-$ | |
| $CH_3$ | $OCH_3$ | 6-$CH_3$ | $-(CH_2)_2-CHi\text{-}C_3H_7-(CH_2)_2-$ | |
| $CH_3$ | $OCH_3$ | 6-$CH_3$ | $-(CH_2)_2-CHOCH_3-(CH_2)_2-$ | |
| $CH_3$ | $OCH_3$ | 6-$CH_3$ | $-(CH_2)_2-CHOC_2H_5-(CH_2)_2-$ | |

TABLE 6a-continued (If-a)

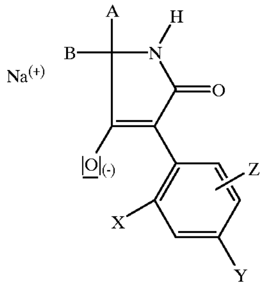

| X | Y | Z | A | B |
|---|---|---|---|---|
| $CH_3$ | $OCH_3$ | 6-$CH_3$ | $—(CH_2)_2—CHOC_3H_7—(CH_2)_2—$ | |
| $CH_3$ | $OCH_3$ | 6-$CH_3$ | $—(CH_2)_2—CHi\text{-}OC_3H_7—(CH_2)_2—$ | |
| $CH_3$ | $OCH_3$ | 6-$CH_3$ | $—(CH_2)_2—C(CH_3)_2—(CH_2)_2—$ | |
| $CH_3$ | $OCH_3$ | 6-$CH_3$ | $—CH_2—(CHCH_3)_2—(CH_2)_2—$ | |
| $CH_3$ | $OCH_3$ | 6-$CH_3$ | 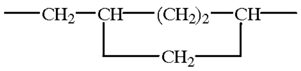 | |
| $CH_3$ | $OCH_3$ | 6-$CH_3$ | 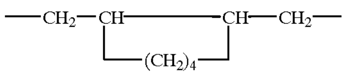 | |
| $CH_3$ | $OCH_3$ | 6-$CH_3$ | 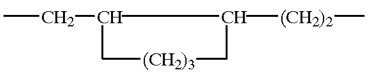 | |

Specific mention may be made, in addition to the compounds specified in the Preparation Examples, of the following compounds of the formula (If-b):

TABLE 6b (If-b)

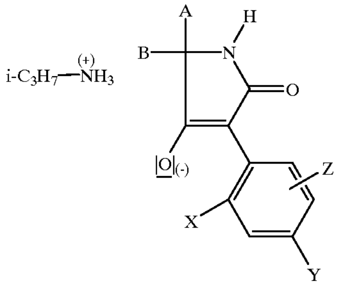

| X | Y | Z | A | B |
|---|---|---|---|---|
| $CH_3$ | $OCH_3$ | H | $CH_3$ | H |
| $CH_3$ | $OCH_3$ | H | $C_2H_5$ | H |
| $CH_3$ | $OCH_3$ | H | $C_3H_7$ | H |
| $CH_3$ | $OCH_3$ | H | i-$C_3H_7$ | H |
| $CH_3$ | $OCH_3$ | H | $C_4H_9$ | H |
| $CH_3$ | $OCH_3$ | H | i-$C_4H_9$ | H |
| $CH_3$ | $OCH_3$ | H | s-$C_4H_9$ | H |
| $CH_3$ | $OCH_3$ | H | t-$C_4H_9$ | H |
| $CH_3$ | $OCH_3$ | H | $CH_3$ | $CH_3$ |
| $CH_3$ | $OCH_3$ | H | $C_2H_5$ | $CH_3$ |
| $CH_3$ | $OCH_3$ | H | $C_3H_7$ | $CH_3$ |
| $CH_3$ | $OCH_3$ | H | i-$C_3H_7$ | $CH_3$ |
| $CH_3$ | $OCH_3$ | H | $C_4H_9$ | $CH_3$ |
| $CH_3$ | $OCH_3$ | H | i-$C_4H_9$ | $CH_3$ |
| $CH_3$ | $OCH_3$ | H | s-$C_4H_9$ | $CH_3$ |
| $CH_3$ | $OCH_3$ | H | t-$C_4H_9$ | $CH_3$ |

TABLE 6b-continued (If-b)

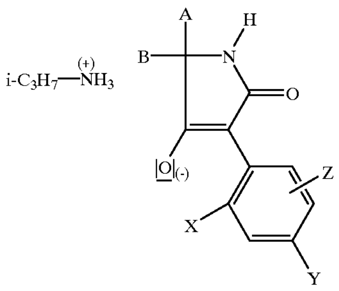

| X | Y | Z | A | B |
| --- | --- | --- | --- | --- |
| $CH_3$ | $OCH_3$ | H | $C_2H_5$ | $C_2H_5$ |
| $CH_3$ | $OCH_3$ | H | $C_3H_7$ | $C_3H_7$ |
| $CH_3$ | $OCH_3$ | H | 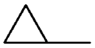 | $CH_3$ |
| $CH_3$ | $OCH_3$ | H | 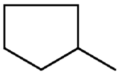 | $CH_3$ |
| $CH_3$ | $OCH_3$ | H | 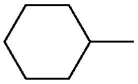 | $CH_3$ |
| $CH_3$ | $CH_3$ | 6-$OCH_3$ | $CH_3$ | H |
| $CH_3$ | $CH_3$ | 6-$OCH_3$ | $C_2H_5$ | H |
| $CH_3$ | $CH_3$ | 6-$OCH_3$ | $C_3H_7$ | H |
| $CH_3$ | $CH_3$ | 6-$OCH_3$ | i-$C_3H_7$ | H |
| $CH_3$ | $CH_3$ | 6-$OCH_3$ | $C_4H_9$ | H |
| $CH_3$ | $CH_3$ | 6-$OCH_3$ | i-$C_4H_9$ | H |
| $CH_3$ | $CH_3$ | 6-$OCH_3$ | s-$C_4H_9$ | H |
| $CH_3$ | $CH_3$ | 6-$OCH_3$ | t-$C_4H_9$ | H |
| $CH_3$ | $CH_3$ | 6-$OCH_3$ | $CH_3$ | $CH_3$ |
| $CH_3$ | $CH_3$ | 6-$OCH_3$ | $C_2H_5$ | $CH_3$ |
| $CH_3$ | $CH_3$ | 6-$OCH_3$ | $C_3H_7$ | $CH_3$ |
| $CH_3$ | $CH_3$ | 6-$OCH_3$ | i-$C_3H_7$ | $CH_3$ |
| $CH_3$ | $CH_3$ | 6-$OCH_3$ | $C_4H_9$ | $CH_3$ |
| $CH_3$ | $CH_3$ | 6-$OCH_3$ | i-$C_4H_9$ | $CH_3$ |
| $CH_3$ | $CH_3$ | 6-$OCH_3$ | s-$C_4H_9$ | $CH_3$ |
| $CH_3$ | $CH_3$ | 6-$OCH_3$ | t-$C_4H_9$ | $CH_3$ |
| $CH_3$ | $CH_3$ | 6-$OCH_3$ | $C_2H_5$ | $C_2H_5$ |
| $CH_3$ | $CH_3$ | 6-$OCH_3$ | $C_3H_7$ | $CH_7$ |
| $CH_3$ | $CH_3$ | 6-$OCH_3$ | 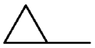 | $CH_3$ |
| $CH_3$ | $CH_3$ | 6-$OCH_3$ | 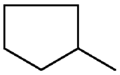 | $CH_3$ |
| $CH_3$ | $CH_3$ | 6-$OCH_3$ | 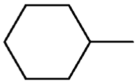 | $CH_3$ |
| $CH_3$ | $OCH_3$ | 6-$CH_3$ | $CH_3$ | H |
| $CH_3$ | $OCH_3$ | 6-$CH_3$ | $C_2H_5$ | H |
| $CH_3$ | $OCH_3$ | 6-$CH_3$ | $C_3H_7$ | H |
| $CH_3$ | $OCH_3$ | 6-$CH_3$ | i-$C_3H_7$ | H |
| $CH_3$ | $OCH_3$ | 6-$CH_3$ | $C_4H_9$ | H |
| $CH_3$ | $OCH_3$ | 6-$CH_3$ | i-$C_4H_9$ | H |
| $CH_3$ | $OCH_3$ | 6-$CH_3$ | s-$C_4H_9$ | H |
| $CH_3$ | $OCH_3$ | 6-$CH_3$ | t-$C_4H_9$ | H |
| $CH_3$ | $OCH_3$ | 6-$CH_3$ | $CH_3$ | $CH_3$ |
| $CH_3$ | $OCH_3$ | 6-$CH_3$ | $C_2H_5$ | $CH_3$ |

TABLE 6b-continued (If-b)

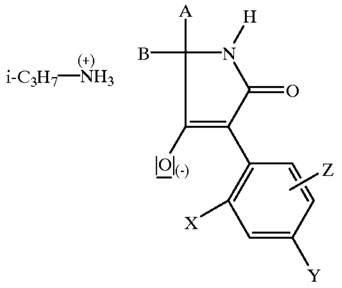

| X | Y | Z | A | B |
|---|---|---|---|---|
| $CH_3$ | $OCH_3$ | 6-$CH_3$ | $C_3H_7$ | $CH_3$ |
| $CH_3$ | $OCH_3$ | 6-$CH_3$ | i-$C_3H_7$ | $CH_3$ |
| $CH_3$ | $OCH_3$ | 6-$CH_3$ | $C_4H_9$ | $CH_3$ |
| $CH_3$ | $OCH_3$ | 6-$CH_3$ | i-$C_4H_9$ | $CH_3$ |
| $CH_3$ | $OCH_3$ | 6-$CH_3$ | s-$C_4H_9$ | $CH_3$ |
| $CH_3$ | $OCH_3$ | 6-$CH_3$ | t-$C_4H_9$ | $CH_3$ |
| $CH_3$ | $OCH_3$ | 6-$CH_3$ | $C_2H_5$ | $C_2H_5$ |
| $CH_3$ | $OCH_3$ | 6-$CH_3$ | $C_3H_7$ | $C_3H_7$ |
| $CH_3$ | $OCH_3$ | 6-$CH_3$ | 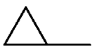 | $CH_3$ |
| $CH_3$ | $OCH_3$ | 6-$CH_3$ | 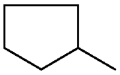 | $CH_3$ |
| $CH_3$ | $OCH_3$ | 6-$CH_3$ | 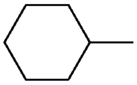 | $CH_3$ |
| $CH_3$ | $OCH_3$ | H | $—(CH_2)_2—$ | |
| $CH_3$ | $OCH_3$ | H | $—(CH_2)_4—$ | |
| $CH_3$ | $OCH_3$ | H | $—(CH_2)_5—$ | |
| $CH_3$ | $OCH_3$ | H | $—(CH_2)_6—$ | |
| $CH_3$ | $OCH_3$ | H | $—(CH_2)_7—$ | |
| $CH_3$ | $OCH_3$ | H | $—(CH_2)_2—O—(CH_2)_2—$ | |
| $CH_3$ | $OCH_3$ | H | $—(CH_2)_2—S—(CH_2)_2—$ | |
| $CH_3$ | $OCH_3$ | H | $—CH_2—CHCH_3—(CH_2)_3—$ | |
| $CH_3$ | $OCH_3$ | H | $—(CH_2)_2—CHCH_3—(CH_2)_2—$ | |
| $CH_3$ | $OCH_3$ | H | $—(CH_2)_2—CHC_2H_5—(CH_2)_2—$ | |
| $CH_3$ | $OCH_3$ | H | $—(CH_2)_2—CHC_3H_7—(CH_2)_2—$ | |
| $CH_3$ | $OCH_3$ | H | $—(CH_2)_2—CHi\text{-}C_3H_7—(CH_2)_2—$ | |
| $CH_3$ | $OCH_3$ | H | $—(CH_2)_2—CHOCH_3—(CH_2)_2—$ | |
| $CH_3$ | $OCH_3$ | H | $—(CH_2)_2—CHOC_2H_5—(CH_2)_2—$ | |
| $CH_3$ | $OCH_3$ | H | $—(CH_2)_2—CHOC_3H_7—(CH_2)_2$ | |
| $CH_3$ | $OCH_3$ | H | $—(CH_2)_2—CHi\text{-}OC_3H_7—(CH_2)_2—$ | |
| $CH_3$ | $OCH_3$ | H | $—(CH_2)_2—C(CH_3)_2—(CH_2)_2—$ | |
| $CH_3$ | $OCH_3$ | H | $—CH_2—(CHCH_3)_2—(CH_2)_2—$ | |
| $CH_3$ | $OCH_3$ | H | 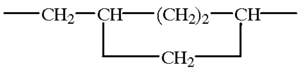 | |
| $CH_3$ | $OCH_3$ | H | 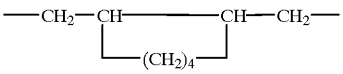 | |
| $CH_3$ | $OCH_3$ | H | 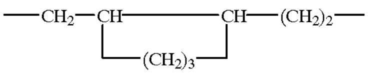 | |
| $CH_3$ | $CH_3$ | 6-$OCH_3$ | $—(CH_2)_2—$ | |
| $CH_3$ | $CH_3$ | 6-$OCH_3$ | $—(CH_2)_4—$ | |
| $CH_3$ | $CH_3$ | 6-$OCH_3$ | $—(CH_2)_5—$ | |
| $CH_3$ | $CH_3$ | 6-$OCH_3$ | $—(CH_2)_6—$ | |
| $CH_3$ | $CH_3$ | 6-$OCH_3$ | $—(CH_2)_7—$ | |

TABLE 6b-continued (If-b)

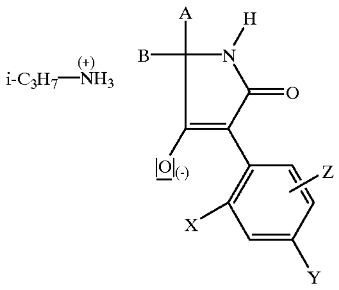

| X | Y | Z | A | B |
|---|---|---|---|---|
| $CH_3$ | $CH_3$ | 6-$OCH_3$ | | $—(CH_2)_2—O—(CH_2)_2—$ |
| $CH_3$ | $CH_3$ | 6-$OCH_3$ | | $—(CH_2)_2—S—(CH_2)_2—$ |
| $CH_3$ | $CH_3$ | 6-$OCH_3$ | | $—CH_2—CHCH_3—(CH_2)_3—$ |
| $CH_3$ | $CH_3$ | 6-$OCH_3$ | | $—(CH_2)_2—CHCH_3—(CH_2)_2—$ |
| $CH_3$ | $CH_3$ | 6-$OCH_3$ | | $—(CH_2)_2—CHC_2H_5—(CH_2)_2—$ |
| $CH_3$ | $CH_3$ | 6-$OCH_3$ | | $—(CH_2)_2—CHC_3H_7—(CH_2)_2—$ |
| $CH_3$ | $CH_3$ | 6-$OCH_3$ | | $—(CH_2)_2—CHi\text{-}C_3H_7—(CH_2)_2—$ |
| $CH_3$ | $CH_3$ | 6-$OCH_3$ | | $—(CH_2)_2—CHOCH_3—(CH_2)_2—$ |
| $CH_3$ | $CH_3$ | 6-$OCH_3$ | | $—(CH_2)_2—CHOC_2H_5—(CH_2)_2—$ |
| $CH_3$ | $CH_3$ | 6-$OCH_3$ | | $—(CH_2)_2—CHOC_3H_7—(CH_2)_2—$ |
| $CH_3$ | $CH_3$ | 6 -$OCH_3$ | | $—(CH_2)_2—CHi\text{-}OC_3H_7—(CH_2)_2—$ |
| $CH_3$ | $CH_3$ | 6-$OCH_3$ | | $—(CH_2)_2—C(CH_3)_2—(CH_2)_2—$ |
| $CH_3$ | $CH_3$ | 6-$OCH_3$ | | $—CH_2—(CHCH_3)_2—(CH_2)_2—$ |
| $CH_3$ | $CH_3$ | 6-$OCH_3$ | | 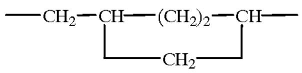 |
| $CH_3$ | $CH_3$ | 6-$OCH_3$ | | 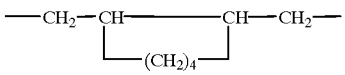 |
| $CH_3$ | $CH_3$ | 6-$OCH_3$ | | 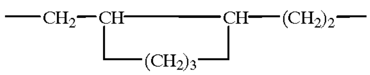 |
| $CH_3$ | $OCH_3$ | 6-$CH_3$ | | $—(CH_2)_2—$ |
| $CH_3$ | $OCH_3$ | 6-$CH_3$ | | $—(CH_2)_4—$ |
| $CH_3$ | $OCH_3$ | 6-$CH_3$ | | $—(CH_2)_5—$ |
| $CH_3$ | $OCH_3$ | 6-$CH_3$ | | $—(CH_2)_6—$ |
| $CH_3$ | $OCH_3$ | 6-$CH_3$ | | $—(CH_2)_7—$ |
| $CH_3$ | $OCH_3$ | 6-$CH_3$ | | $—(CH_2)_2—O—(CH_2)_2—$ |
| $CH_3$ | $OCH_3$ | 6-$CH_3$ | | $—(CH_2)_2—S—(CH_2)_2—$ |
| $CH_3$ | $OCH_3$ | 6-$CH_3$ | | $—CH_2—CHCH_3—(CH_2)_3—$ |
| $CH_3$ | $OCH_3$ | 6-$CH_3$ | | $—(CH_2)_2—CHCH_3—(CH_2)_2—$ |
| $CH_3$ | $OCH_3$ | 6-$CH_3$ | | $—(CH)_2—CHC_2H_5—(CH_2)_2—$ |
| $CH_3$ | $OCH_3$ | 6-$CH_3$ | | $—(CH_2)_2—CHC_3H_7—(CH_2)_2—$ |
| $CH_3$ | $OCH_3$ | 6-$CH_3$ | | $—(CH_2)_2—CHi\text{-}C_3H_7—(CH_2)_2—$ |
| $CH_3$ | $OCH_3$ | 6-$CH_3$ | | $—(CH_2)_2—CHOCH_3—(CH_2)_2—$ |
| $CH_3$ | $OCH_3$ | 6-$CH_3$ | | $—(CH_2)_2—CHOC_2H_5—(CH_2)_2—$ |
| $CH_3$ | $OCH_3$ | 6-$CH_3$ | | $—(CH_2)_2—CHOC_3H_7—(CH_2)_2—$ |
| $CH_3$ | $OCH_3$ | 6-$CH_3$ | | $—(CH_2)_2—CHi\text{-}OC_3H_7—(CH_2)_2—$ |
| $CH_3$ | $OCH_3$ | 6-$CH_3$ | | $—(CH)_2—C(CH_3)_2—(CH_2)_2—$ |
| $CH_3$ | $OCH_3$ | 6-$CH_3$ | | $—CH_2—(CHCH_3)_2—(CH_2)_2—$ |
| $CH_3$ | $OCH_3$ | 6-$CH_3$ | | 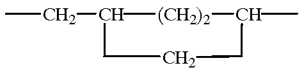 |
| $CH_3$ | $OCH_3$ | 6-$CH_3$ | | 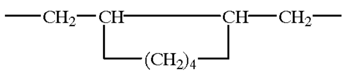 |
| $CH_3$ | $OCH_3$ | 6-$CH_3$ | | 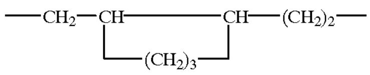 |

Specific mention may be made, in addition to the compounds specified in the Preparation Examples, of the following compounds of the formula (Ig-a):

TABLE 7a (Ig-a)

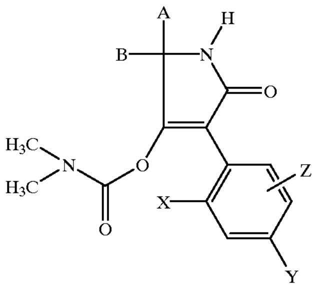

| X | Y | Z | A | B |
|---|---|---|---|---|
| $CH_3$ | $OCH_3$ | H | $CH_3$ | H |
| $CH_3$ | $OCH_3$ | H | $C_2H_5$ | H |
| $CH_3$ | $OCH_3$ | H | $C_3H_7$ | H |
| $CH_3$ | $OCH_3$ | H | i-$C_3H_7$ | H |
| $CH_3$ | $OCH_3$ | H | $C_4H_9$ | H |
| $CH_3$ | $OCH_3$ | H | i-$C_4H_9$ | H |
| $CH_3$ | $OCH_3$ | H | s-$C_4H_9$ | H |
| $CH_3$ | $OCH_3$ | H | t-$C_4H_9$ | H |
| $CH_3$ | $OCH_3$ | H | $CH_3$ | $CH_3$ |
| $CH_3$ | $OCH_3$ | H | $C_2H_5$ | $CH_3$ |
| $CH_3$ | $OCH_3$ | H | $C_3H_7$ | $CH_3$ |
| $CH_3$ | $OCH_3$ | H | i-$C_3H_7$ | $CH_3$ |
| $CH_3$ | $OCH_3$ | H | $C_4H_9$ | $CH_3$ |
| $CH_3$ | $OCH_3$ | H | i-$C_4H_9$ | $CH_3$ |
| $CH_3$ | $OCH_3$ | H | s-$C_4H_9$ | $CH_3$ |
| $CH_3$ | $OCH_3$ | H | t-$C_4H_9$ | $CH_3$ |
| $CH_3$ | $OCH_3$ | H | $C_2H_5$ | $C_2H_5$ |
| $CH_3$ | $OCH_3$ | H | $C_3H_7$ | $C_3H_7$ |
| $CH_3$ | $OCH_3$ | H | 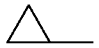 | $CH_3$ |
| $CH_3$ | $OCH_3$ | H | 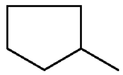 | $CH_3$ |
| $CH_3$ | $OCH_3$ | H | 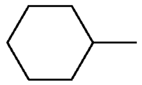 | $CH_3$ |
| $CH_3$ | $CH_3$ | 6-$OCH_3$ | $CH_3$ | H |
| $CH_3$ | $CH_3$ | 6-$OCH_3$ | $C_2H_5$ | H |
| $CH_3$ | $CH_3$ | 6-$OCH_3$ | $C_3H_7$ | H |
| $CH_3$ | $CH_3$ | 6-$OCH_3$ | i-$C_3H_7$ | H |
| $CH_3$ | $CH_3$ | 6-$OCH_3$ | $C_4H_9$ | H |
| $CH_3$ | $CH_3$ | 6-$OCH_3$ | i-$C_4H_9$ | H |
| $CH_3$ | $CH_3$ | 6-$OCH_3$ | s-$C_4H_9$ | H |
| $CH_3$ | $CH_3$ | 6-$OCH_3$ | t-$C_4H_9$ | H |
| $CH_3$ | $CH_3$ | 6-$OCH_3$ | $CH_3$ | $CH_3$ |
| $CH_3$ | $CH_3$ | 6-$OCH_3$ | $C_2H_5$ | $CH_3$ |
| $CH_3$ | $CH_3$ | 6-$OCH_3$ | $C_3H_7$ | $CH_3$ |
| $CH_3$ | $CH_3$ | 6-$OCH_3$ | i-$C_3H_7$ | $CH_3$ |
| $CH_3$ | $CH_3$ | 6-$OCH_3$ | $C_4H_9$ | $CH_3$ |
| $CH_3$ | $CH_3$ | 6-$OCH_3$ | i-$C_4H_9$ | $CH_3$ |
| $CH_3$ | $CH_3$ | 6-$OCH_3$ | s-$C_4H_9$ | $CH_3$ |
| $CH_3$ | $CH_3$ | 6-$OCH_3$ | t-$C_4H_9$ | $CH_3$ |
| $CH_3$ | $CH_3$ | 6-$OCH_3$ | $C_2H_5$ | $C_2H_5$ |
| $CH_3$ | $CH_3$ | 6-$OCH_3$ | $C_3H_7$ | $C_3H_7$ |
| $CH_3$ | $CH_3$ | 6-$OCH_3$ | 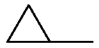 | $CH_3$ |

TABLE 7a-continued (Ig-a)

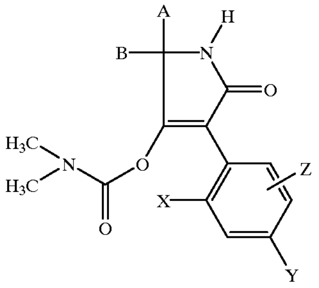

| X | Y | Z | A | B |
|---|---|---|---|---|
| $CH_3$ | $CH_3$ | 6-$OCH_3$ | 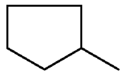 | $CH_3$ |
| $CH_3$ | $CH_3$ | 6-$OCH_3$ | 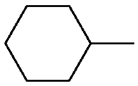 | $CH_3$ |
| $CH_3$ | $OCH_3$ | 6-$CH_3$ | $CH_3$ | H |
| $CH_3$ | $OCH_3$ | 6-$CH_3$ | $C_2H_5$ | H |
| $CH_3$ | $OCH_3$ | 6-$CH_3$ | $C_3H_7$ | H |
| $CH_3$ | $OCH_3$ | 6-$CH_3$ | i-$C_3H_7$ | H |
| $CH_3$ | $OCH_3$ | 6-$CH_3$ | $C_4H_9$ | H |
| $CH_3$ | $OCH_3$ | 6-$CH_3$ | i-$C_4H_9$ | H |
| $CH_3$ | $OCH_3$ | 6-$CH_3$ | s-$C_4H_9$ | H |
| $CH_3$ | $OCH_3$ | 6-$CH_3$ | t-$C_4H_9$ | H |
| $CH_3$ | $OCH_3$ | 6-$CH_3$ | $CH_3$ | $CH_3$ |
| $CH_3$ | $OCH_3$ | 6-$CH_3$ | $C_2H_5$ | $CH_3$ |
| $CH_3$ | $OCH_3$ | 6-$CH_3$ | $C_3H_7$ | $CH_3$ |
| $CH_3$ | $OCH_3$ | 6-$CH_3$ | i-$C_3H_7$ | $CH_3$ |
| $CH_3$ | $OCH_3$ | 6-$CH_3$ | $C_4H_9$ | $CH_3$ |
| $CH_3$ | $OCH_3$ | 6-$CH_3$ | i-$C_4H_9$ | $CH_3$ |
| $CH_3$ | $OCH_3$ | 6-$CH_3$ | s-$C_4H_9$ | $CH_3$ |
| $CH_3$ | $OCH_3$ | 6-$CH_3$ | t-$C_4H_9$ | $CH_3$ |
| $CH_3$ | $OCH_3$ | 6-$CH_3$ | $C_2H_5$ | $C_2H_5$ |
| $CH_3$ | $OCH_3$ | 6-$CH_3$ | $C_3H_7$ | $C_3H_7$ |
| $CH_3$ | $OCH_3$ | 6-$CH_3$ | 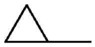 | $CH_3$ |
| $CH_3$ | $OCH_3$ | 6-$CH_3$ | 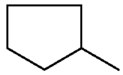 | $CH_3$ |
| $CH_3$ | $OCH_3$ | 6-$CH_3$ | 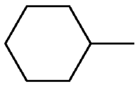 | $CH_3$ |
| $CH_3$ | $OCH_3$ | H | $-(CH_2)_2-$ | |
| $CH_3$ | $OCH_3$ | H | $-(CH_2)_4-$ | |
| $CH_3$ | $OCH_3$ | H | $-(CH_2)_5-$ | |
| $CH_3$ | $OCH_3$ | H | $-(CH_2)_6-$ | |
| $CH_3$ | $OCH_3$ | H | $-(CH_2)_7-$ | |
| $CH_3$ | $OCH_3$ | H | $-(CH_2)_2-O-(CH_2)_2-$ | |
| $CH_3$ | $OCH_3$ | H | $-(CH_2)_2-S-(CH_2)_2-$ | |
| $CH_3$ | $OCH_3$ | H | $-CH_2-CHCH_3-(CH_2)_3-$ | |
| $CH_3$ | $OCH_3$ | H | $-(CH_2)_2-CHCH_3-(CH_2)_2-$ | |
| $CH_3$ | $OCH_3$ | H | $-(CH_2)_2-CHC_2H_5-(CH_2)_2-$ | |
| $CH_3$ | $OCH_3$ | H | $-(CH_2)_2-CHC_3H_7-(CH_2)_2-$ | |
| $CH_3$ | $OCH_3$ | H | $-(CH_2)_2-CHi\text{-}C_3H_7-(CH_2)_2-$ | |
| $CH_3$ | $OCH_3$ | H | $-(CH_2)_2-CHOCH_3-(CH_2)_2-$ | |
| $CH_3$ | $OCH_3$ | H | $-(CH_2)_2-CHOC_2H_5-(CH_2)_2-$ | |
| $CH_3$ | $OCH_3$ | H | $-(CH_2)_2-CHOC_3H_7-(CH_2)_2-$ | |
| $CH_3$ | $OCH_3$ | H | $-(CH_2)_2-CHi\text{-}OC_3H_7-(CH_2)_2-$ | |
| $CH_3$ | $OCH_3$ | H | $-(CH_2)_2-C(CH_3)_2-(CH_2)_2-$ | |

TABLE 7a-continued (Ig-a)

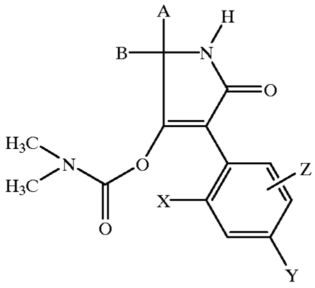

| X | Y | Z | A | B |
|---|---|---|---|---|
| $CH_3$ | $OCH_3$ | H | | $—CH_2—(CHCH_3)_2—(CH_2)_2—$ |
| $CH_3$ | $OCH_3$ | H | | 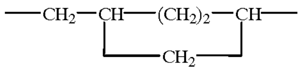 |
| $CH_3$ | $OCH_3$ | H | | 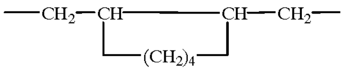 |
| $CH_3$ | $OCH_3$ | H | | 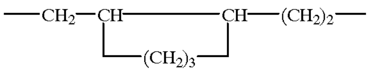 |
| $CH_3$ | $CH_3$ | 6-$OCH_3$ | | $—(CH_2)_2—$ |
| $CH_3$ | $CH_3$ | 6-$OCH_3$ | | $—(CH_2)_4—$ |
| $CH_3$ | $CH_3$ | 6-$OCH_3$ | | $—(CH_2)_5—$ |
| $CH_3$ | $CH_3$ | 6-$OCH_3$ | | $—(CH_2)_6—$ |
| $CH_3$ | $CH_3$ | 6-$OCH_3$ | | $—(CH_2)_7—$ |
| $CH_3$ | $CH_3$ | 6-$OCH_3$ | | $—(CH_2)_2—O—(CH_2)_2—$ |
| $CH_3$ | $CH_3$ | 6-$OCH_3$ | | $—(CH_2)_2—S—(CH_2)_2—$ |
| $CH_3$ | $CH_3$ | 6-$OCH_3$ | | $—CH_2—CHCH_3—(CH_2)_3—$ |
| $CH_3$ | $CH_3$ | 6-$OCH_3$ | | $—(CH_2)_2—CHCH_3—(CH_2)_2—$ |
| $CH_3$ | $CH_3$ | 6-$OCH_3$ | | $—(CH_2)_2—CHC_2H_5—(CH_2)_2—$ |
| $CH_3$ | $CH_3$ | 6-$OCH_3$ | | $—(CH_2)_2—CHC_3H_7—(CH_2)_2—$ |
| $CH_3$ | $CH_3$ | 6-$OCH_3$ | | $—(CH_2)_2—CHi\text{-}C_3H_7—(CH_2)_2—$ |
| $CH_3$ | $CH_3$ | 6-$OCH_3$ | | $—(CH_2)_2—CHOCH_3—(CH_2)_2—$ |
| $CH_3$ | $CH_3$ | 6-$OCH_3$ | | $—(CH_2)_2—CHOC_2H_5—(CH_2)_2—$ |
| $CH_3$ | $CH_3$ | 6-$OCH_3$ | | $—(CH_2)_2—CHOC_3H_7—(CH_2)_2—$ |
| $CH_3$ | $CH_3$ | 6-$OCH_3$ | | $—(CH_2)_2—CHi\text{-}OC_3H_7—(CH_2)_2—$ |
| $CH_3$ | $CH_3$ | 6-$OCH_3$ | | $—(CH_2)_2—C(CH_3)_2—(CH_2)_2—$ |
| $CH_3$ | $CH_3$ | 6-$OCH_3$ | | $—CH_2—(CHCH_3)_2—(CH_2)_2—$ |
| $CH_3$ | $CH_3$ | 6-$OCH_3$ | | 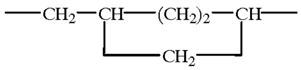 |
| $CH_3$ | $CH_3$ | 6-$OCH_3$ | | 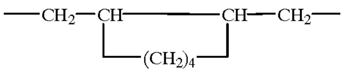 |
| $CH_3$ | $CH_3$ | 6-$OCH_3$ | | 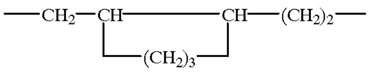 |
| $CH_3$ | $OCH_3$ | 6-$CH_3$ | | $—(CH_2)_2—$ |
| $CH_3$ | $OCH_3$ | 6-$CH_3$ | | $—(CH_2)_4—$ |
| $CH_3$ | $OCH_3$ | 6-$CH_3$ | | $—(CH_2)_5—$ |
| $CH_3$ | $OCH_3$ | 6-$CH_3$ | | $—(CH_2)_6—$ |
| $CH_3$ | $OCH_3$ | 6-$CH_3$ | | $—(CH_2)_7—$ |
| $CH_3$ | $OCH_3$ | 6-$CH_3$ | | $—(CH_2)_2—O—(CH_2)_2—$ |
| $CH_3$ | $OCH_3$ | 6-$CH_3$ | | $—(CH_2)_2—S—(CH_2)_2—$ |
| $CH_3$ | $OCH_3$ | 6-$CH_3$ | | $—CH_2—CHCH_3—(CH_2)_3—$ |
| $CH_3$ | $OCH_3$ | 6-$CH_3$ | | $—(CH_2)_2—CHCH_3—(CH_2)_2—$ |
| $CH_3$ | $OCH_3$ | 6-$CH_3$ | | $—(CH_2)_2—CHC_2H_5—(CH_2)_2—$ |
| $CH_3$ | $OCH_3$ | 6-$CH_3$ | | $—(CH_2)_2—CHC_3H_7—(CH_2)_2—$ |
| $CH_3$ | $OCH_3$ | 6-$CH_3$ | | $—(CH_2)_2—CHi\text{-}C_3H_7—(CH_2)_2—$ |

TABLE 7a-continued (Ig-a)

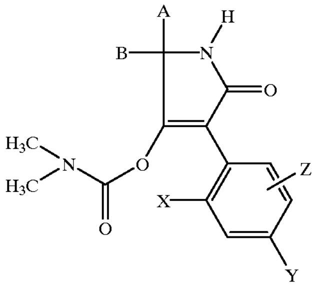

| X | Y | Z | A | B |
|---|---|---|---|---|
| $CH_3$ | $CCH_3$ | 6-$CH_3$ | $-(CH_2)_2-CHOCH_3-(CH_2)_2-$ | |
| $CH_3$ | $OCH_3$ | 6-$CH_3$ | $-(CH_2)_2-CHOC_2H_5-(CH_2)_2-$ | |
| $CH_3$ | $OCH_3$ | 6-$CH_3$ | $-(CH_2)_2-CHOC_3H_7-(CH_2)_2-$ | |
| $CH_3$ | $OCH_3$ | 6-$CH_3$ | $-(CH_2)_2-CHi\text{-}OC_3H_7-(CH_2)_2-$ | |
| $CH_3$ | $OCH_3$ | 6-$CH_3$ | $-(CH_2)_2-C(CH_3)_2-(CH_2)_2-$ | |
| $CH_3$ | $OCH_3$ | 6-$CH_3$ | $-CH_2-(CHCH_3)_2-(CH_2)_2-$ | |
| $CH_3$ | $OCH_3$ | 6-$CH_3$ | 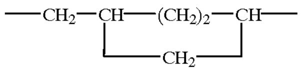 | |
| $CH_3$ | $OCH_3$ | 6-$CH_3$ | 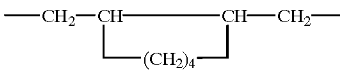 | |
| $CH_3$ | $OCH_3$ | 6-$CH_3$ | 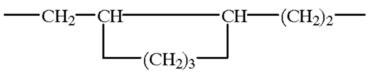 | |

Specific mention may be made, in addition to the compounds specified in the Preparation Examples, of the following compounds of the formula (Ig-b):

TABLE 7b (Ig-b)

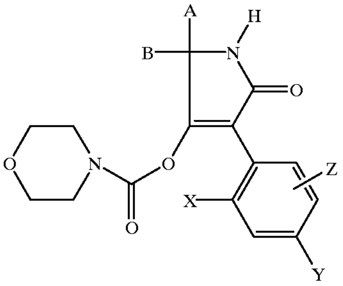

| X | Y | Z | A | B |
|---|---|---|---|---|
| $CH_3$ | $OCH_3$ | H | $CH_3$ | H |
| $CH_3$ | $OCH_3$ | H | $C_2H_5$ | H |
| $CH_3$ | $OCH_3$ | H | $C_3H_7$ | H |
| $CH_3$ | $OCH_3$ | H | i-$C_3H_7$ | H |
| $CH_3$ | $OCH_3$ | H | $C_4H_9$ | H |
| $CH_3$ | $OCH_3$ | H | i-$C_4H_9$ | H |
| $CH_3$ | $OCH_3$ | H | s-$C_4H_9$ | H |
| $CH_3$ | $OCH_3$ | H | t-$C_4H_9$ | H |
| $CH_3$ | $OCH_3$ | H | $CH_3$ | $CH_3$ |
| $CH_3$ | $OCH_3$ | H | $C_2H_5$ | $CH_3$ |
| $CH_3$ | $OCH_3$ | H | $C_3H_7$ | $CH_3$ |
| $CH_3$ | $OCH_3$ | H | i-$C_3H_7$ | $CH_3$ |
| $CH_3$ | $OCH_3$ | H | $C_4H_9$ | $CH_3$ |
| $CH_3$ | $OCH_3$ | H | i-$C_4H_9$ | $CH_3$ |

TABLE 7b-continued (Ig-b)

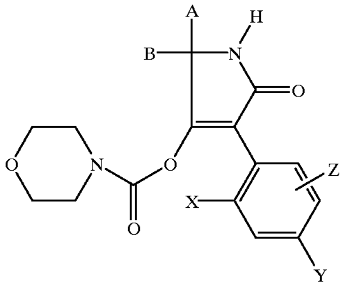

| X | Y | Z | A | B |
|---|---|---|---|---|
| $CH_3$ | $OCH_3$ | H | s-$C_4H_9$ | $CH_3$ |
| $CH_3$ | $OCH_3$ | H | t-$C_4H_9$ | $CH_3$ |
| $CH_3$ | $OCH_3$ | H | $C_2H_5$ | $C_2H_5$ |
| $CH_3$ | $OCH_3$ | H | $C_3H_7$ | $C_3H_7$ |
| $CH_3$ | $OCH_3$ | H | 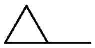 | $CH_3$ |
| $CH_3$ | $OCH_3$ | H | 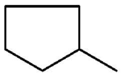 | $CH_3$ |
| $CH_3$ | $OCH_3$ | H | 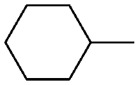 | $CH_3$ |
| $CH_3$ | $CH_3$ | 6-$OCH_3$ | $CH_3$ | H |
| $CH_3$ | $CH_3$ | 6-$OCH_3$ | $C_2H_5$ | H |
| $CH_3$ | $CH_3$ | 6-$OCH_3$ | $C_3H_7$ | H |
| $CH_3$ | $CH_3$ | 6-$OCH_3$ | i-$C_3H_7$ | H |
| $CH_3$ | $CH_3$ | 6-$OCH_3$ | $C_4H_9$ | H |
| $CH_3$ | $CH_3$ | 6-$OCH_3$ | i-$C_4H_9$ | H |
| $CH_3$ | $CH_3$ | 6-$OCH_3$ | s-$C_4H_9$ | H |
| $CH_3$ | $CH_3$ | 6-$OCH_3$ | t-$C_4H_9$ | H |
| $CH_3$ | $CH_3$ | 6-$OCH_3$ | $CH_3$ | $CH_3$ |
| $CH_3$ | $CH_3$ | 6-$OCH_3$ | $C_2H_5$ | $CH_3$ |
| $CH_3$ | $CH_3$ | 6-$OCH_3$ | $C_3H_7$ | $CH_3$ |
| $CH_3$ | $CH_3$ | 6-$OCH_3$ | i-$C_3H_7$ | $CH_3$ |
| $CH_3$ | $CH_3$ | 6-$OCH_3$ | $C_4H_9$ | $CH_3$ |
| $CH_3$ | $CH_3$ | 6-$OCH_3$ | i-$C_4H_9$ | $CH_3$ |
| $CH_3$ | $CH_3$ | 6-$OCH_3$ | s-$C_4H_9$ | $CH_3$ |
| $CH_3$ | $CH_3$ | 6-$OCH_3$ | t-$C_4H_9$ | $CH_3$ |
| $CH_3$ | $CH_3$ | 6-$OCH_3$ | $C_2H_5$ | $C_2H_5$ |
| $CH_3$ | $CH_3$ | 6-$OCH_3$ | $C_3H_7$ | $C_3H_7$ |
| $CH_3$ | $CH_3$ | 6-$OCH_3$ | 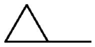 | $CH_3$ |
| $CH_3$ | $CH_3$ | 6-$OCH_3$ | 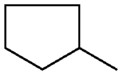 | $CH_3$ |
| $CH_3$ | $CH_3$ | 6-$OCH_3$ | 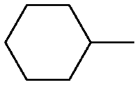 | $CH_3$ |
| $CH_3$ | $OCH_3$ | 6-$CH_3$ | $CH_3$ | H |
| $CH_3$ | $OCH_3$ | 6-$CH_3$ | $C_2H_5$ | H |
| $CH_3$ | $OCH_3$ | 6-$CH_3$ | $C_3H_7$ | H |
| $CH_3$ | $OCH_3$ | 6-$CH_3$ | i-$C_3H_7$ | H |
| $CH_3$ | $OCH_3$ | 6-$CH_3$ | $C_4H_9$ | H |
| $CH_3$ | $OCH_3$ | 6-$CH_3$ | i-$C_4H_9$ | H |
| $CH_3$ | $OCH_3$ | 6-$CH_3$ | s-$C_4H_9$ | H |
| $CH_3$ | $OCH_3$ | 6-$CH_3$ | t-$C_4H_9$ | H |

TABLE 7b-continued (Ig-b)

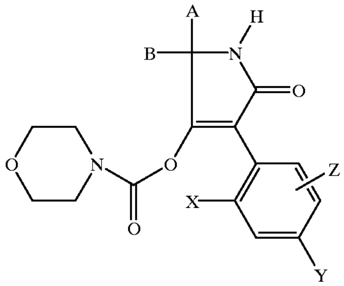

| X | Y | Z | A | B |
|---|---|---|---|---|
| $CH_3$ | $OCH_3$ | 6-$CH_3$ | $CH_3$ | $CH_3$ |
| $CH_3$ | $OCH_3$ | 6-$CH_3$ | $C_2H_5$ | $CH_3$ |
| $CH_3$ | $OCH_3$ | 6-$CH_3$ | $C_3H_7$ | $CH_3$ |
| $CH_3$ | $OCH_3$ | 6-$CH_3$ | i-$C_3H_7$ | $CH_3$ |
| $CH_3$ | $OCH_3$ | 6-$CH_3$ | $C_4H_9$ | $CH_3$ |
| $CH_3$ | $OCH_3$ | 6-$CH_3$ | i-$C_4H_9$ | $CH_3$ |
| $CH_3$ | $OCH_3$ | 6-$CH_3$ | s-$C_4H_9$ | $CH_3$ |
| $CH_3$ | $OCH_3$ | 6-$CH_3$ | t-$C_4H_9$ | $CH_3$ |
| $CH_3$ | $OCH_3$ | 6-$CH_3$ | $C_2H_5$ | $C_2H_5$ |
| $CH_3$ | $OCH_3$ | 6-$CH_3$ | $C_3H_7$ | $C_3H_7$ |
| $CH_3$ | $OCH_3$ | 6-$CH_3$ | 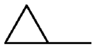 | $CH_3$ |
| $CH_3$ | $OCH_3$ | 6-$CH_3$ | 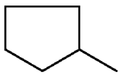 | $CH_3$ |
| $CH_3$ | $OCH_3$ | 6-$CH_3$ | 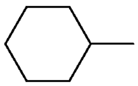 | $CH_3$ |
| $CH_3$ | $OCH_3$ | H | $-(CH_2)_2-$ | |
| $CH_3$ | $OCH_3$ | H | $-(CH_2)_4-$ | |
| $CH_3$ | $OCH_3$ | H | $-(CH_2)_5-$ | |
| $CH_3$ | $OCH_3$ | H | $-(CH_2)_6-$ | |
| $CH_3$ | $OCH_3$ | H | $-(CH_2)_7-$ | |
| $CH_3$ | $OCH_3$ | H | $-(CH_2)_2-O-(CH_2)_2-$ | |
| $CH_3$ | $OCH_3$ | H | $-(CH_2)_2-S-(CH_2)_2-$ | |
| $CH_3$ | $OCH_3$ | H | $-CH_2-CHCH_3-(CH_2)_3-$ | |
| $CH_3$ | $OCH_3$ | H | $-(CH_2)_2-CHCH_3-(CH_2)_2-$ | |
| $CH_3$ | $OCH_3$ | H | $-(CH_2)_2-CHC_2H_5-(CH_2)_2-$ | |
| $CH_3$ | $OCH_3$ | H | $-(CH_2)_2-CHC_3H_7-(CH_2)_2-$ | |
| $CH_3$ | $OCH_3$ | H | $-(CH_2)_2-CHC_3H_7-(CH_2)_2-$ | |
| $CH_3$ | $OCH_3$ | H | $-(CH_2)_2-CHOCH_3-(CH_2)_2-$ | |
| $CH_3$ | $OCH_3$ | H | $-(CH_2)_2-CHOC_2H_5-(CH_2)_2-$ | |
| $CH_3$ | $OCH_3$ | H | $-(CH_2)_2-CHOC_3H_7-(CH_2)_2-$ | |
| $CH_3$ | $OCH_3$ | H | $-(CH_2)_2-$CHi-$OC_3H_7-(CH_2)_2-$ | |
| $CH_3$ | $OCH_3$ | H | $-(CH_2)_2-C(CH_3)_2-(CH_2)_2-$ | |
| $CH_3$ | $OCH_3$ | H | $-CH_2-(CHCH_3)_2-(CH_2)_2-$ | |
| $CH_3$ | $OCH_3$ | H | 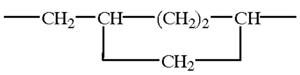 | |
| $CH_3$ | $OCH_3$ | H | 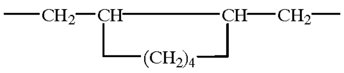 | |
| $CH_3$ | $OCH_3$ | H | 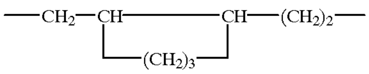 | |
| $CH_3$ | $CH_3$ | 6-$OCH_3$ | $-(CH_2)_2-$ | |
| $CH_3$ | $CH_3$ | 6-$OCH_3$ | $-(CH_2)_4-$ | |
| $CH_3$ | $CH_3$ | 6-$OCH_3$ | $-(CH_2)_5-$ | |

TABLE 7b-continued (Ig-b)

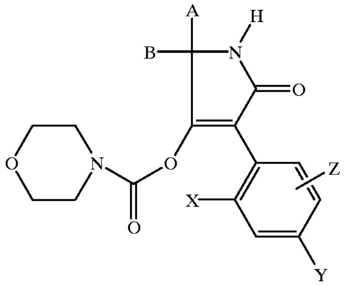

| X | Y | Z | A | B |
|---|---|---|---|---|
| $CH_3$ | $CH_3$ | 6-$OCH_3$ | | $—(CH_2)_6—$ |
| $CH_3$ | $CH_3$ | 6-$OCH_3$ | | $—(CH_2)_7—$ |
| $CH_3$ | $CH_3$ | 6-$OCH_3$ | | $—(CH_2)_2—O—(CH_2)_2—$ |
| $CH_3$ | $CH_3$ | 6-$OCH_3$ | | $—(CH_2)_2—S—(CH_2)_2—$ |
| $CH_3$ | $CH_3$ | 6-$OCH_3$ | | $—CH_2—CHCH_3—(CH_2)_3—$ |
| $CH_3$ | $CH_3$ | 6-$OCH_3$ | | $—(CH_2)_2—CHCH_3—(CH_2)_2—$ |
| $CH_3$ | $CH_3$ | 6-$OCH_3$ | | $—(CH_2)_2—CHC_2H_5—(CH_2)_2—$ |
| $CH_3$ | $CH_3$ | 6-$OCH_3$ | | $—(CH_2)_2—CHC_3H_7—(CH_2)_2—$ |
| $CH_3$ | $CH_3$ | 6-$OCH_3$ | | $—(CH_2)_2—CHi\text{-}C_3H_7—(CH_2)_2—$ |
| $CH_3$ | $CH_3$ | 6-$OCH_3$ | | $—(CH_2)_2—CHOCH_3—(CH_2)_2—$ |
| $CH_3$ | $CH_3$ | 6-$OCH_3$ | | $—(CH_2)_2—CHOC_2H_5—(CH_2)_2—$ |
| $CH_3$ | $CH_3$ | 6-$OCH_3$ | | $—(CH_2)_2—CHOC_3H_7—(CH_2)_2—$ |
| $CH_3$ | $CH_3$ | 6-$OCH_3$ | | $—(CH_2)_2—CHi\text{-}OC_3H_7—(CH_2)_2—$ |
| $CH_3$ | $CH_3$ | 6-$OCH_3$ | | $—(CH_2)_2—C(CH_3)_2—(CH_2)_2—$ |
| $CH_3$ | $CH_3$ | 6-$OCH_3$ | | $—CH_2—(CHCH_3)_2—(CH_2)_2—$ |
| $CH_3$ | $CH_3$ | 6-$OCH_3$ | | 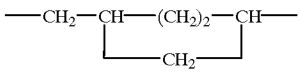 |
| $CH_3$ | $CH_3$ | 6-$OCH_3$ | | 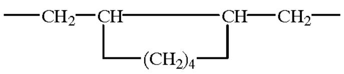 |
| $CH_3$ | $CH_3$ | 6-$OCH_3$ | | 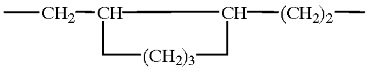 |
| $CH_3$ | $OCH_3$ | 6-$CH_3$ | | $—(CH_2)_2—$ |
| $CH_3$ | $OCH_3$ | 6-$CH_3$ | | $—(CH_2)_4—$ |
| $CH_3$ | $OCH_3$ | 6-$CH_3$ | | $—(CH_2)_5—$ |
| $CH_3$ | $OCH_3$ | 6-$CH_3$ | | $—(CH_2)_6—$ |
| $CH_3$ | $OCH_3$ | 6-$CH_3$ | | $—(CH_2)_7—$ |
| $CH_3$ | $OCH_3$ | 6-$CH_3$ | | $—(CH_2)_2—O—(CH_2)_2—$ |
| $CH_3$ | $OCH_3$ | 6-$CH_3$ | | $—(CH_2)_2—S—(CH_2)_2—$ |
| $CH_3$ | $OCH_3$ | 6-$CH_3$ | | $—CH_2—CHCH_3—(CH_2)_3—$ |
| $CH_3$ | $OCH_3$ | 6-$CH_3$ | | $—(CH_2)_2—CHCH_3—(CH_2)_2—$ |
| $CH_3$ | $OCH_3$ | 6-$CH_3$ | | $—(CH_2)_2—CHC_2H_5—(CH_2)_2—$ |
| $CH_3$ | $OCH_3$ | 6-$CH_3$ | | $—(CH_2)_2—CHC_3H_7—(CH_2)_2—$ |
| $CH_3$ | $OCH_3$ | 6-$CH_3$ | | $—(CH_2)_2—CHi\text{-}C_3H_7—(CH_2)_2—$ |
| $CH_3$ | $OCH_3$ | 6-$CH_3$ | | $—(CH_2)_2—CHOCH_3—(CH_2)_2—$ |
| $CH_3$ | $OCH_3$ | 6-$CH_3$ | | $—(CH_2)_2—CHOC_2H_5—(CH_2)_2—$ |
| $CH_3$ | $OCH_3$ | 6-$CH_3$ | | $—(CH_2)_2—CHOC_3H_7—(CH_2)_2—$ |
| $CH_3$ | $OCH_3$ | 6-$CH_3$ | | $—(CH_2)_2—CHi\text{-}OC_3H_7—(CH_2)_2—$ |
| $CH_3$ | $OCH_3$ | 6-$CH_3$ | | $—(CH_2)_2—C(CH_3)_2—(CH_2)_2—$ |
| $CH_3$ | $OCH_3$ | 6-$CH_3$ | | $—CH_2—(CHCH_3)_2—(CH_2)_2$ |
| $CH_3$ | $OCH_3$ | 6-$CH_3$ | | 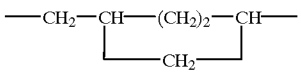 |
| $CH_3$ | $OCH_3$ | 6-$CH_3$ | | 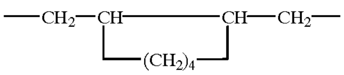 |

TABLE 7b-continued (Ig-b)

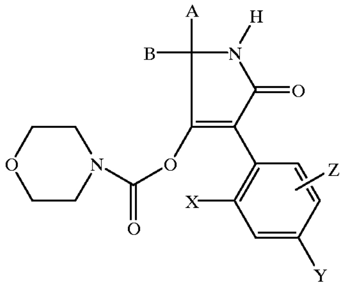

| X | Y | Z | A | B |
|---|---|---|---|---|
| $CH_3$ | $OCH_3$ | $6\text{-}CH_3$ | 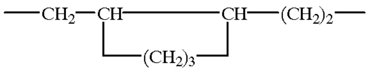 | |

Using ethyl N-(2-methyl-4-methoxyphenylacetyl)-1-amino-4-ethyl-cyclohexane-carboxylate as starting material according to process (A), the course of the process according to the invention can be represented by the following reaction scheme:

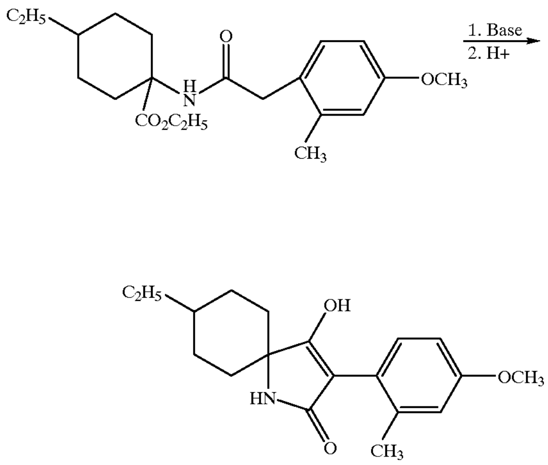

Using 3-(2-methyl-6-methoxyphenyl)-5,5-dimethyl-pyrrolidine-2,4-dione and pivaloyl chloride as starting materials according to process ($B_\alpha$), the course of the process according to the invention can be represented by the following reaction scheme:

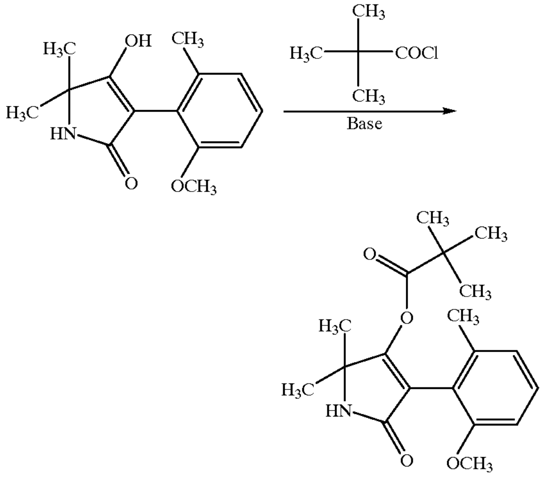

Using 3-(2,4-dimethyl-6-methoxyphenyl)-5-isopropyl-5-methyl-pyrrolidine-2,4-dione and acetic anhydride as starting compounds according to process ($B_\beta$), the course of the process according to the invention can be represented by the following reaction scheme:

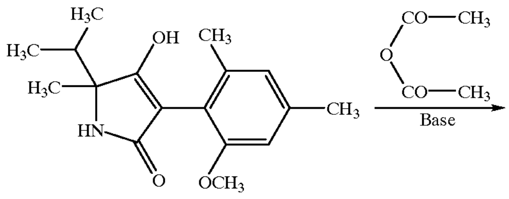

-continued

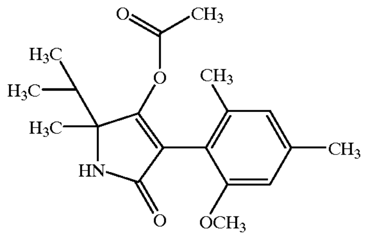

Using 3-(2-methoxy-4-methyl-phenyl)-5,5-diethyl-pyrrolidine-2,4-dione and ethoxyethyl chloroformate as starting compounds according to process (C), the course of the process according to the invention can be represented by the following reaction scheme:

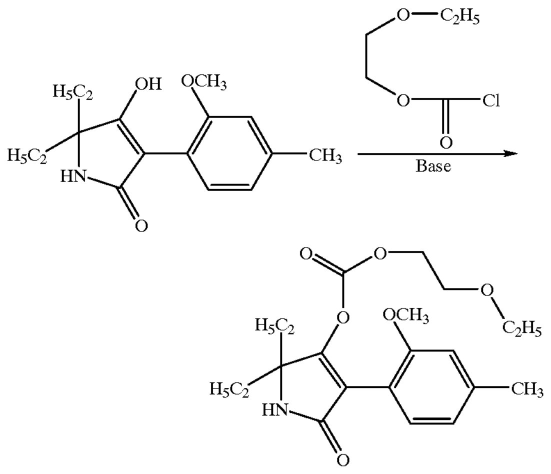

Using 3-(2,6-dimethyl-4-methoxyphenyl)-5,5-pentamethylene-pyrrolidine-2,4-dione and methyl chloromono-thioformate as starting materials according to process ($D_\alpha$), the course of the reaction can be represented as follows:

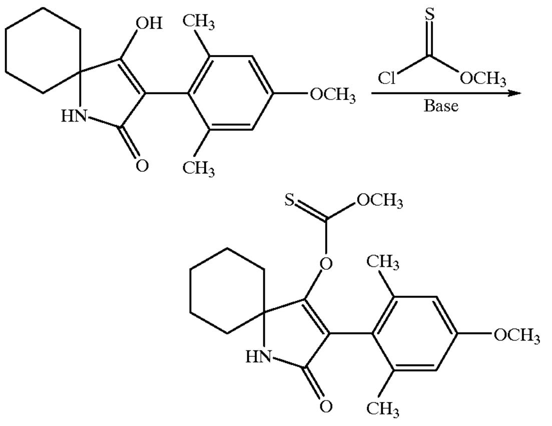

Using 3-(2-methyl-4-ethoxy-phenyl)-5,5-ethylmercapto-ethyl-pyrrolidine-2,4-dione, carbon disulfide and methyl iodide as starting components according to process ($D_\beta$), the course of the reaction can be represented as follows:

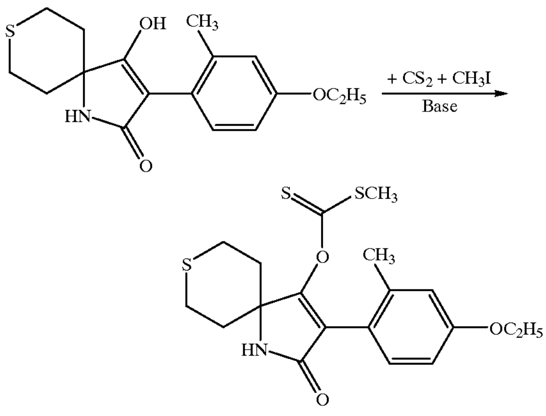

Using 3-(2-methyl-4-isopropoxy-phenyl)-5,5-(2-methyl)-pentamethylene-pyrrolidine-2,4-dione and methanesulfonyl chloride as starting materials according to process (E), the course of the reaction can be represented by the following reaction scheme:

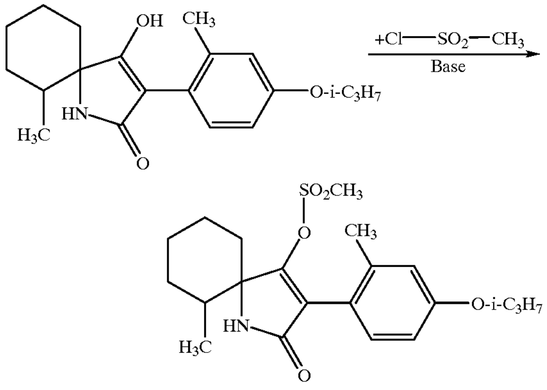

Using 3-(2-methoxy-4-methylphenyl)-5-isobutyl-5-methyl-pyrrolidine-2,4-dione and methanethio-phosphonyl chloride 2,2,2-trifluoroethyl ester as starting products according to process (F), the course of the reaction can be represented by the following reaction scheme:

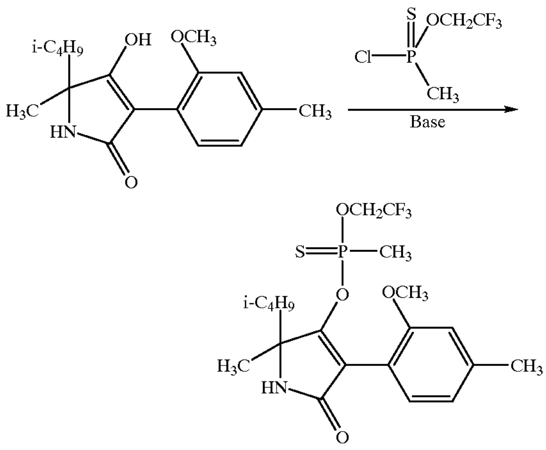

Using 3-(2-methyl-4-methoxyphenyl)-5-cyclopropyl-5-methyl-pyrrolidine-2,4-dione and NaOH as starting components according to process (G), the course of the process according to the invention can be represented by the following reaction scheme:

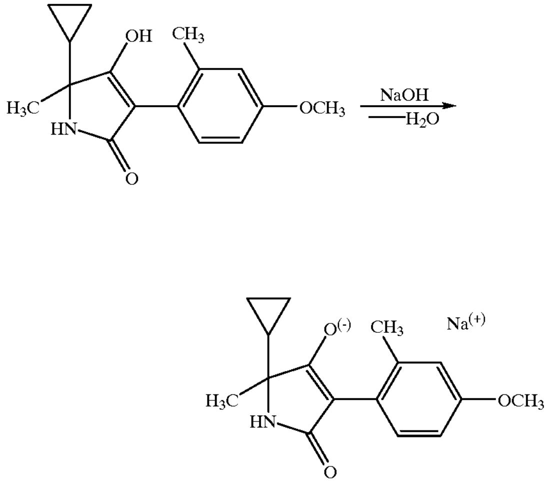

Using 3-(2-methyl-4-ethoxyphenyl)-5,5-hexamethylene-pyrrolidine-2,4-dione and ethyl isocyanate as starting materials according to process ($H_\alpha$), the course of the reaction can be represented by the following scheme:

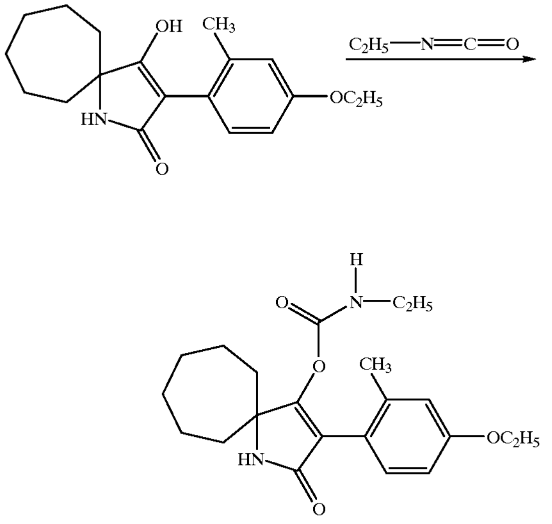

Using 3-(2-methoxy-4-methylphenyl)-5-methyl-pyrrolidine-2,4-dione and dimethylcarbamoyl chloride as starting materials according to process ($H_\beta$), the course of the reaction can be represented by the following scheme:

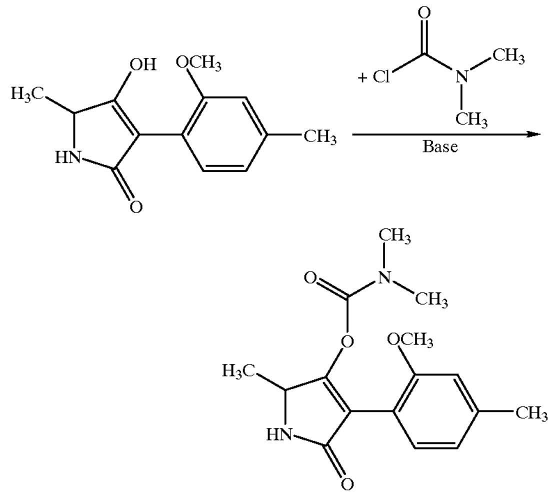

The compounds of the formula (II)

(II)

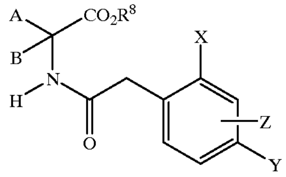

in which

A, B, X, Y, Z and $R^8$ have the meaning given above, which are required as starting materials in process (A) according to the invention, are novel.

Acyl-amino acid esters of the formula (II) are obtained, for example, if amino acid derivatives of the formula (XIV)

(XIV)

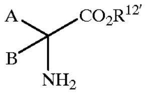

in which $R^{12'}$ represents hydrogen (XIVa) or alkyl (XIVb) and

A and B have the meaning given above are acylated with phenylacetyl halides of the formula (XV)

(XV)

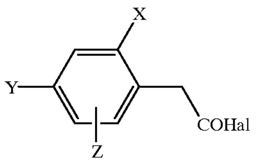

in which

X, Y and Z have the meaning given above and

Hal represents chlorine or bromine (Chem. Reviews 52, 237–416 (1953); Bhattacharya, Indian J. Chem. 6, 341–5, 1968)

or if acylamino acids of the formula (IIa)

(IIa)

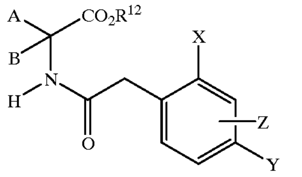

in which

A, B, X, Y and Z have the meaning given above and $R^{12}$ represents hydrogen are esterified (Chem. Ind. (London) 1568 (1968)).

If the substituents A and B form a ring, then the resulting substituted cyclic aminocarboxylic acids of the formula (XIVa) are in general obtainable by the Bucherer-Bergs reaction or by the Strecker synthesis, in each of which cases they are obtained in different isomeric forms. Thus, under the conditions of the Bucherer-Bergs reaction, the predominant isomers obtained (referred to below for simplicity as β) are those in which the radicals R and the carboxyl group are in the equatorial positions, whereas under the conditions of the Strecker synthesis the predominant isomers obtained (referred to below for simplicity as α) are those in which the amino group and the radicals R are in the equatorial positions.

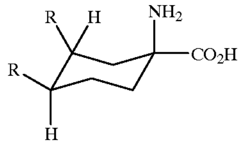

Bucherer-Bergs synthesis
(β isomer)

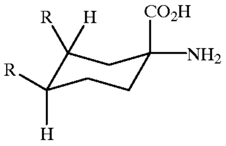

Strecker synthesis
(α isomer)

(L. Munday, J. Chem. Soc. 4372 (1961); J. T. Edward, C. Jitrangeri, Can. J. Chem. 53, 3339 (1975).

Furthermore, the starting substances used in the above process (A), of the formula (II)

(II)

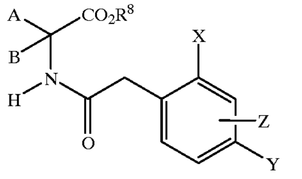

in which

A, B, X, Y, Z and $R^8$ have the meaning give above, can be prepared if aminonitriles of the formula (XVI)

(XVI)

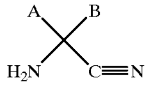

in which

A and B have the meaning given above are reacted with phenylacetyl halides of the formula (XV)

(XV)

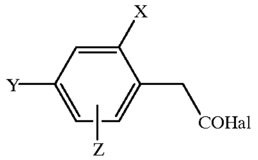

in which

X, Y and Z have the meaning given above and

Hal represents chlorine or bromine to five compounds of the formula (XVII)

(XVII)

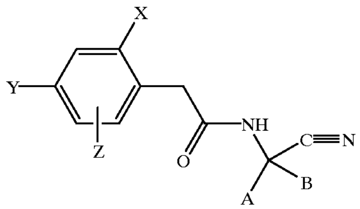

in which

A, B, X, Y and z have the meaning given above and these are subsequently subjected to alcoholysis in the presence of sulfuric acid.

The compounds of the formula (XVII) are likewise novel.

By way of example but not of limitation, and in addition to the intermediates specified in the Preparation Examples, the following compounds of the formula (II) may be mentioned:

N-(2-Methyl-4-methoxyphenylacetyl)-alanine methyl ester

N-(2-Methyl-4-methoxyphenylacetyl)-leucine methyl ester

N-(2-Methyl-4-methoxyphenylacetyl)-isoleucine methyl ester

N-(2-Methyl-4-methoxyphenylacetyl)-valine methyl ester

Methyl N-(2-methyl-4-methoxyphenylacetyl)-aminoisobutyrate

Methyl N-(2-methyl-4-methoxyphenylacetyl)-2-ethyl-2-aminobutyrate

Methyl N-(2-methyl-4-methoxyphenylacetyl)-2-methyl-2-aminovalerate

Methyl N-(2-methyl-4-methoxyphenylacetyl)-2,3-dimethyl-2-aminovalerate

Methyl N-(2-methyl-4-methoxyphenylacetyl)-1-amino-cyclopentanecarboxylate

Methyl N-(2-methyl-4-methoxyphenylacetyl)-1-amino-cyclohexanecarboxylate

Methyl N-(2-methyl-4-methoxyphenylacetyl)-1-amino-cycloheptanecarboxylate

Methyl N-(2-methyl-4-methoxyphenylacetyl)-1-amino-cyclooctanecarboxylate

N-(2,6-Dimethyl-4-methoxyphenylacetyl)-alanine methyl ester

N-(2,6-Dimethyl-4-methoxyphenylacetyl)-leucine methyl ester

N-(2,6-Dimethyl-4-methoxyphenylacetyl)-isoleucine methyl ester

N-(2,6-Dimethyl-4-methoxyphenylacetyl)-valine methyl ester

Methyl N-(2,6-dimethyl-4-methoxyphenylacetyl)-aminoisobutyrate

Methyl N-(2,6-dimethyl-4-methoxyphenylacetyl)-2-ethyl-2-aminobutyrate

Methyl N-(2,6-dimethyl-4-methoxyphenylacetyl)-2-methyl-2-aminovalerate

Methyl N-(2,6-dimethyl-4-methoxyphenylacetyl)-2,3-dimethyl-2-aminovalerate

Methyl N-(2,6-dimethyl-4-methoxyphenylacetyl)-1-aminocyclopentanecarboxylate

Methyl N-(2,6-dimethyl-4-methoxyphenylacetyl)-1-aminocyclohexanecarboxylate

Methyl N-(2,6-dimethyl-4-methoxyphenylacetyl)-1-aminocycloheptanecarboxylate

Methyl N-(2,6-dimethyl-4-methoxyphenylacetyl)-1-aminocyclooctanecarboxylate

N-(2,4-Dimethyl-6-methoxyphenylacetyl)-alanine methyl ester

N-(2,4-Dimethyl-6-methoxyphenylacetyl)-leucine methyl ester

N-(2,4-Dimethyl-6-methoxyphenylacetyl)-isoleucine methyl ester

N-(2,4-Dimethyl-6-methoxyphenylacetyl)-valine methyl ester

Methyl N-(2,4-dimethyl-6-methoxyphenylacetyl)-aminoisobutyrate

Methyl N-(2,4-dimethyl-6-methoxyphenylacetyl)-2-ethyl-2-aminobutyrate

Methyl N-(2,4-dimethyl-6-methoxyphenylacetyl)-2-methyl-2-aminovalerate

Methyl N-(2,4-dimethyl-6-methoxyphenylacetyl)-2,3-dimethyl-2-aminovalerate

Methyl N-(2,4-dimethyl-6-methoxyphenylacetyl)-1-aminocyclopentanecarboxylate

Methyl N-(2,4-dimethyl-6-methoxyphenylacetyl)-1-aminocyclohexanecarboxylate

Methyl N-(2,4-dimethyl-6-methoxyphenylacetyl)-1-aminocycloheptanecarboxylate

Methyl N-(2,4-dimethyl-6-methoxyphenylacetyl)-1-aminocyclooctanecarboxylate

Methyl N-(2-methyl-4-methoxy-phenylacetyl)-1-amino-2-methyl-cyclohexanecarboxylate Methyl N-(2-methyl-4-methoxy-phenylacetyl)-1-amino-3-methyl-cyclohexanecarboxylate Methyl N-(2-methyl-4-methoxy-phenylacetyl)-1-amino-4-methyl-cyclohexanecarboxylate Methyl N-(2-methyl-4-methoxy-phenylacetyl)-1-amino-3,4-dimethyl-cyclohexanecarboxylate Methyl N-(2-methyl-4-methoxy-phenylacetyl)-1-amino-4-ethyl-cyclohexanecarboxylate Methyl N-(2-methyl-4-methoxy-phenylacetyl)-1-amino-4-isopropyl-cyclohexanecarboxylate Methyl N-(2-methyl-4-methoxy-phenylacetyl)-1-amino-4-tert-butyl-cyclohexanecarboxylate Methyl N-(2-methyl-4-methoxy-phenylacetyl)-1-amino-4-methoxy-cyclohexanecarboxylate Methyl N-(2,4-dimethyl-6-methoxy-phenylacetyl)-1-amino-2-methyl-cyclohexanecarboxylate Methyl N-(2,4-dimethyl-6-methoxy-phenylacetyl)-1-amino-3-methyl-cyclohexanecarboxylate Methyl N-(2,4-dimethyl-6-methoxy-phenylacetyl)-1-amino-4-methyl-cyclohexanecarboxylate Methyl N-(2,4-dimethyl-6-methoxy-phenylacetyl)-1-amino-3,4-dimethyl-cyclohexanecarboxylate Methyl N-(2,4-dimethyl-6-methoxy-phenylacetyl)-1-amino-4-ethyl-cyclohexanecarboxylate Methyl N-(2,4-dimethyl-6-methoxy-phenylacetyl)-1-amino-4-isopropyl-cyclohexanecarboxylate Methyl N-(2,4-dimethyl-6-methoxy-phenylacetyl)-1-amino-4-tert-butyl-cyclohexanecarboxylate Methyl N-(2,4-dimethyl-6-methoxy-phenylacetyl)-1-amino-4-methoxy-cyclohexanecarboxylate Methyl N-(2,6-dimethyl-4-methoxy-phenylacetyl)-1-amino-2-methyl-cyclohexanecarboxylate Methyl N-(2,6-dimethyl-4-methoxy-phenylacetyl)-1-amino-3-methyl-cyclohexanecarboxylate Methyl N-(2,6-dimethyl-4-methoxy-phenylacetyl)-1-amino-4-methyl-cyclohexanecarboxylate Methyl N-(2,6-dimethyl-4-methoxy-phenylacetyl)-1-amino-3,4-dimethyl-cyclohexanecarboxylate Methyl N-(2,6-dimethyl-4-methoxy-phenylacetyl)-1-amino-4-ethyl-cyclohexanecarboxylate Methyl N-(2,6-dimethyl-4-methoxy-phenylacetyl)-1-amino-4-isopropyl-cyclohexanecarboxylate Methyl N-(2,6-dimethyl-4-methoxy-phenylacetyl)-1-amino-4-tert-butyl-cyclohexanecarboxylate Methyl N-(4-chloro-2-methoxy-phenylacetyl)-1-amino-4-methoxy-cyclohexanecarboxylate.

By way of example but not of limitation, and in addition to the intermediates specified in the Preparation Examples, the following compounds of the formula (IIa) may be mentioned:

N-(2-Methyl-4-methoxyphenylacetyl)-alanine

N-(2-Methyl-4-methoxyphenylacetyl)-leucine

N-(2-Methyl-4-methoxyphenylacetyl)-isoleucine

N-(2-Methyl-4-methoxyphenylacetyl)-valine

N-(2-Methyl-4-methoxyphenylacetyl)-aminoisobutyric acid.

N-(2-Methyl-4-methoxyphenylacetyl)-2-ethyl-2-aminobutyric acid

N-(2-Methyl-4-methoxyphenylacetyl)-2-methyl-2-aminovaleric acid

N-(2-Methyl-4-methoxyphenylacetyl)-2,3-dimethyl-2-aminovaleric acid

N-(2-Methyl-4-methoxyphenylacetyl)-1-amino-cyclopentane-carboxylic acid

N-(2-Methyl-4-methoxyphenylacetyl)-1-amino-cyclohexane-carboxylic acid

N-(2-Methyl-4-methoxyphenylacetyl)-1-amino-cycloheptane-carboxylic acid

N-(2-Methyl-4-methoxyphenylacetyl)-1-amino-cyclooctane-carboxylic acid

N-(Methyl-2-methoxyphenylacetyl)-alanine

N-(2,6-Dimethyl-4-methoxyphenylacetyl)-leucine

N-(2,6-Dimethyl-4,2-methoxyphenylacetyl)-isoleucine

N-(2,6-Dimethyl-4-methoxyphenylacetyl)-valine

N-(2,6-Dimethyl-4-methoxyphenylacetyl)-aminoisobutyric acid

N-(2,6-Dimethyl-4-methoxyphenylacetyl)-2-ethyl-2-aminobutyric acid

N-(2,6-Dimethyl-4-methoxyphenylacetyl)-2-methyl-2-aminovaleric acid

N-(2,6-Dimethyl-4-methoxyphenylacetyl)-2,3-dimethyl-2-aminovaleric acid

N-(2,6-Dimethyl-4-methoxyphenylacetyl)-1-amino-cyclopentanecarboxylic acid

N-(2,6-Dimethyl-4-methoxyphenylacetyl)-1-amino-cyclohexanecarboxylic acid

N-(2,6-Dimethyl-4-methoxyphenylacetyl)-1-amino-cycloheptanecarboxylic acid

N-(2,6-Dimethyl-4-methoxyphenylacetyl)-1-amino-cyclooctanecarboxylic acid

N-(2,4-Dimethyl-6-methoxyphenylacetyl)-alanine

N-(2,4-Dimethyl-6-methoxyphenylacetyl)-leucine

N-(2,4-Dimethyl-6-methoxyphenylacetyl)-isoleucine

N-(2,4-Dimethyl-6-methoxyphenylacetyl)-valine

N-(2,4-Dimethyl-6-methoxyphenylacetyl)-aminoisobutyric acid

N(2,4-Dimethyl-6-methoxyphenylacetyl)-2-ethyl-2-aminobutyric acid

N-(2,4-Dimethyl-6-methoxyphenylacetyl)-2-methyl-2-aminovaleric acid

N-(2,4-Dimethyl-6-methoxyphenylacetyl)-2,3-dimethyl-2-aminovaleric acid

N-(2,4-Dimethyl-6-methoxyphenylacetyl)-1-amino-cyclopentanecarboxylic acid

N-(2,4-Dimethyl-6-methoxyphenylacetyl)-1-amino-cyclohexanecarboxylic acid

N-(2,4-Dimethyl-6-methoxyphenylacetyl)-1-amino-cyclo heptanecarboxylic acid

N-(2,4-Dimethyl-6-methoxyphenylacetyl)-1-amino-cyclo octanecarboxylic acid

N-(2-Methyl-4-methoxy-phenylacetyl)-1-amino-2-methyl-cyclohexanecarboxylic acid

N-(2-Methyl-4-methoxy-phenylacetyl)-1-amino-3-methyl-cyclohexanecarboxylic acid

N-(2-Methyl-4-methoxy-phenylacetyl)-1-amino-4-methyl-cyclohexanecarboxylic acid

N-(2-Methyl-4-methoxy-phenylacetyl)-1-amino-3,4-dimethyl-cyclohexanecarboxylic acid N-(2-Methyl-4-methoxy-phenylacetyl)-1-amino-4-ethyl-cyclohexanecarboxylic acid N-(2-Methyl-4-methoxy-phenylacetyl)-1-amino-4-isopropyl-cyclohexanecarboxylic acid N-(2-Methyl-4-methoxy-phenylacetyl)-1-amino-4-tert-butyl-cyclohexanecarboxylic acid N-(2-Methyl-4-methoxy-phenylacetyl)-1-amino-4-methoxy-cyclohexanecarboxylic acid N-(2,6-Dimethyl-4-methoxy-phenylacetyl)-1-amino-2-methyl-cyclohexanecarboxylic acid N-(2,6-Dimethyl-4-methoxy-phenylacetyl)-1-amino-3-methyl-cyclohexanecarboxylic acid N-(2,6-Dimethyl-4-methoxy-phenylacetyl)-1-amino-4-methyl-cyclohexanecarboxylic acid N-(2,6-Dimethyl-4-methoxy-phenylacetyl)-1-amino-3,4-dimethyl-cyclohexanecarboxylic acid N-(2,6-Dimethyl-4-methoxy-phenylacetyl)-1-amino-4-ethyl-cyclohexanecarboxylic acid N-(2,6-Dimethyl-4-methoxy-phenylacetyl)-1-amino-4-isopropyl-cyclohexanecarboxylic acid N-(2,6-Dimethyl-4-methoxy-phenylacetyl)-1-amino-4-tert-butyl-cyclohexanecarboxylic acid N-(2,6-Dimethyl-4-methoxy-phenylacetyl)-1-amino-4-methoxy-cyclohexanecarboxylic acid N-(2,4-Dimethyl-6-methoxy-phenylacetyl)-1-amino-2-methyl-cyclohexanecarboxylic acid N-(2,4-Dimethyl-6-methoxy-phenylacetyl)-1-amino-3-methyl-cyclohexanecarboxylic acid N-(2,4-Dimethyl-6-methoxy-phenylacetyl)-1-amino-4-methyl cyclohexanecarboxylic acid N-(2,4-Dimethyl-6-methoxy-phenylacetyl)-1-amino-3,4-dimethyl-cyclohexanecarboxylic acid N-(2,4-Dimethyl-6-methoxy-phenylacetyl)-1-amino-4-ethyl-cyclohexanecarboxylic acid N-(2,4-Dimethyl-6-methoxy-phenylacetyl)-1-amino-4-iso-propyl-cyclohexanecarboxylic acid N-(2,4-Dimethyl-6-methoxy-phenylacetyl)-1-amino-4-tert-butyl-cyclohexanecarboxylic acid N-(2,4-Dimethyl-6-methoxy-phenylacetyl)-1-amino-4-methoxy-cyclohexanecarboxylic acid.

Compounds of the formula (IIa) are obtainable, for example, from the phenylacetyl halides of the formula (XV) and amino acids of the formula (XIVa) according to Schotten-Baumann (Organikum, 9th Edition, 446 (1970) VEB Deutscher Verlag der Wissenschaften, Berlin).

The phenylacetyl halides of the formula (XV)

(XV)

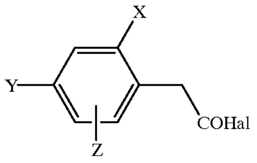

in which

X, Y and Z have the meaning given above and

Hal represents bromine or chlorine are in some instances novel. They can be prepared simply by known methods from the corresponding, known phenylacetic acids.

The compounds which are additionally required as starting substances in order to carry out the processes (B), (C), (D), (E), (F), (G) and (H) according to the invention, namely acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulfonyl chlorides of the formula (VIII), phosphorus compounds of the formula (Ix) and metal compounds or amines of the formula (X) and (XI) and isocyanates, isothiocyanates or carbamoyl chlorides of the formula (XIII) are generally known compounds of organic and/or inorganic chemistry.

Process (A) is characterized in that compounds of the formula (II) in which A, B, X, Y, Z and $R^8$ have the meaning given above are subjected to an intramolecular condensation in the presence of bases.

Diluents which can be employed in process (A) according to the invention are all inert organic solvents. Preferred possibilities for use are hydrocarbons such as toluene and xylene, and also ethers such as dibutyl ether, tetrahydrofuran, dioxane, glycol dimethyl ether and diglycol dimethyl ether, and also polar solvents such as dimethyl sulfoxide, sulfolane, dimethylformamide and N-methyl-pyrrolidone, and alcohols such as methanol, ethanol, propanol, isopropanol, butanol, isobutanol and tert-butanol.

Bases (deprotonating agents) which can be employed when carrying out process (A) according to the invention are all conventional proton acceptors. Preferred possibilities for use are alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be employed in the presence of phase transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). It is also possible to use alkali metals such as sodium or potassium. Further possibilities for use are alkali metal and alkaline earth metal amides and hydrides, such as sodium amide, sodium hydride and calcium hydride, and also alkali metal alcoholates such as sodium methylate, sodium ethylate and potassium tert-butylate.

When carrying out process (A) according to the invention the reaction temperatures can be varied within a relatively wide range. The process is in general carried out at temperatures between 0° C. and 250° C., preferably between 50° C. and 150° C.

Process (A) according to the invention is generally carried out under atmospheric pressure.

When carrying out process (A) according to the invention, about 2 mol of the deprotonating base are employed per mole of the reaction component of the formula (II). However, it is also possible to use one or the other component in a relatively large excess (up to 3 mol).

Process (Bα) is characterized in that compounds of the formula (Ia) are reacted with carboxylic halides of the formula (III).

Diluents which can be employed in process (Bα) according to the invention are all solvents which are inert towards the acid halides. Preferred possibilities for use are hydrocarbons such as benzine, benzene, toluene, xylene and tetralin, and also halogenated hydrocarbons such as methylene chloride, chloroform, carbon tetrachloride, chlorobenzene and o-dichlorobenzene, and also ketones such as acetone and methyl isopropyl ketone, and additionally ethers such as diethyl ether, tetrahydrofuran and dioxane, and furthermore carboxylic esters such as ethyl acetate, and also strongly polar solvents such as dimethyl sulfoxide and sulfolane. If the stability to hydrolysis of the acid halide permits, the reaction can also be carried out in the presence of water.

Suitable acid-binding agents in the reaction according to process ($B_\alpha$) according to the invention are all conventional acid acceptors. Preferred possibilities for use are tertiary mines such as triethylamine, pyridine, diazabicyclooctane (DABCO), diazabicycloundecene (DBU), diazabicyclononene (DBN), Hunig base and N,N-dimethylaniline, and also alkaline earth metal oxides such as magnesium oxide and calcium oxide, and also alkali metal and alkaline earth metal carbonates, such as sodium carbonate, potassium carbonate and calcium carbonate, and alkali metal hydroxides such as sodium hydroxide and potassium hydroxide.

When carrying out process (Bα) according to the invention the reaction temperatures can be varied within a relatively wide range. The process is in general carried out at temperatures between −20° C. and +150° C., preferably between 0° C. and 100° C.

When carrying out process ($B_\alpha$) according to the invention the starting materials of the formula (Ia) and the carboxylic halide of the formula (III) are generally used in approximately equivalent quantities. However, it is also possible to employ the carboxylic halide in a relatively large excess (up to 5 mol). The product is worked up by conventional methods.

Process (Bβ) is characterized in that compounds of the formula (Ia) are reacted with carboxylic anhydrides of the formula (IV).

When carboxylic anhydrides are used as reaction component: of the formula (IV) in process (Bβ) according to the invention, the diluents which may be used are preferably those diluents which are also preferably suitable when acid halides are used. In addition, a carboxylic anhydride employed in excess may also function simultaneously as diluent.

In process (Bβ) according to the invention the reaction temperatures can be varied within a relatively wide range. The process is in general carried out at temperatures between −20° C. and +150° C., preferably between 0° C. and 100° C.

When carrying out the process (Bβ) according to the invention the starting materials of the formula (Ia) and the carboxylic anhydride of the formula (IV) are generally used in approximately equivalent quantities. However, it is also possible to employ the carboxylic anhydride in a relatively large excess (up to 5 mol). The product is worked up by conventional methods.

The general procedure is one in which diluent and excess carboxylic anhydride and also the carboxylic acid formed are removed by distillation or by washing with an organic solvent or with water.

Process (C) is characterized in that compounds of the formula (Ia) are reacted with chloroformic esters or chloroformic thioesters of the formula (V).

If the corresponding chloroformic esters or chloroformic thioesters are used, then suitable acid-binding agents in the reaction according to process (C) are all conventional acid acceptors. Preferred possibilities for use are tertiary amines such as triethylamine, pyridine, DABCO, DBU, DBN, Hunig base and N,N-dimethyl-aniline, and also alkaline earth metal oxides, such as magnesium oxide and calcium oxide, and furthermore alkali metal and alkaline earth metal carbonates, such as sodium carbonate, potassium carbonate and calcium carbonate, and also alkali metal hydroxides such as sodium hydroxide and potassium hydroxide.

Diluents which can be employed in process (C) according to the invention, when using the chloroformic esters or chloroformic thioesters, are all solvents which are inert towards these compounds. Preferred possibilities for use are hydrocarbons such as benzine, benzene, toluene, xylene and tetralin, and also halogenated hydrocarbons such as methylene chloride, chloroform, carbon tetrachloride, chlorobenzene and o-dichlorobenzene, and also ketones such as acetone and methyl isopropyl ketone, and furthermore ethers such as diethyl ether, tetrahydrofuran and dioxane, and moreover carboxylic esters such as ethyl acetate, and also strongly polar solvents such as dimethyl sulfoxide and sulfolane.

When chloroformic esters and/or chloroformic thioesters are used as carboxylic acid derivatives of the formula (V), the reaction temperatures when carrying out process (C) according to the invention can be varied within a relative wide range. When the process is carried out in the presence of a diluent and of an acid-binding agent, the reaction temperature are in general between −20° C. and +100° C., preferably between 0° C. and 50° C.

Process (C) according to the invention is generally carried out under atmospheric pressure.

When carrying out process (C) according to the invention the starting materials of the formula (Ia) and the corresponding chloroformic ester and/or chloroformic thioester of the formula (v) are generally used in approximately equivalent quantities. However, it is also possible to employ one or the other component in a relatively large excess (up to 2 mol). The product is then worked up by conventional methods. The general procedure is one in which precipitated salts are removed and the reaction mixture which remains is concentrated by stripping off the diluent.

In preparation process ($D_\alpha$), about 1 mol of chloromonothioformic ester or chlorodithioformic ester of the formula (VI) is reacted per mole of starting compound of the formula (Ia), at from 0 to 120° C., preferably at from 20 to 60° C.

Suitable diluents for optional addition are all inert polar organic solvents, such as ethers, amides, sulfones and sulfoxides but also halogenoalkanes.

It preferred to employ dimethyl sulfoxide, tetrahydrofuran, dimethylformamide or methylene chloride.

If in a preferred embodiment strong deprotonating agents such as, for example, sodium hydride or potassium tert-butylate are added to prepare the enolate salt of the compound (Ia), then the further addition of acid-binding agents can be omitted.

If acid-binding agents are employed, then they are suitably conventional inorganic or organic bases, examples being sodium hydroxide, sodium carbonate, potassium carbonate, pyridine and triethylamine.

The reaction can be carried out at atmospheric pressure or under elevated pressure, preferably at atmospheric pressure. The product is worked up by conventional methods.

In preparation process ($D_\beta$) the equimolar quantity or an excess of carbon disulfide is added per mole of starting compound of the formula (Ia). In this context the process is preferably carried out at temperatures of from 0 to 50° C. and, in particular, at from 20 to 30° C.

In the process ($D_\beta$), bases which can be employed are all conventional proton acceptors. Preferred possibilities for use are alkali metal hydrides, alkali metal alcoholates, alkali metal or alkaline earth metal carbonates or hydrogen carbonates, or nitrogen bases. Examples which may be mentioned are sodium hydride, sodium methanolate, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

Diluents which can be employed in this process are all conventional solvents. Preferred possibilities for use are aromatic hydrocarbons such as benzene or toluene, alcohols such as methanol, ethanol, isopropanol or ethylene glycol, nitriles such as acetonitrile, ethers such as tetrahydrofuran or dioxane, amides such as dimethylformamide or other polar solvents such as dimethyl sulfoxide or sulfolane.

It is often expedient initially to prepare, from the compound of the formula (Ia), the corresponding salt, by addition of a deprotonating agent (for example potassium tert-butylate or sodium hydride). The compound (Ia) is reacted with carbon disulfide until the formation of the intermediate compound is concluded, for example after stirring for several hours at room temperature.

The further reaction with the alkyl halide of the formula (VII) is carried out preferably at from 0 to 70° C. and in particular at from 20 to 50° C. In this context at least the equimolar quantity of alkyl halide is employed.

The process is carried out at atmospheric pressure or under elevated pressure, preferably at atmospheric pressure.

The product is again worked up by conventional methods.

In preparation process (E) about 1 mol of sulfonyl chloride (VIII) is reacted per mole of starting compound of the formula (Ia), at from −20 to 150° C., preferably at from 20 to 70° C.

Suitable diluents which are optionally added are all inert polar organic solvents, such as ethers, amides, nitriles, sulfones and sulfoxides or halogenated hydrocarbons such as methylene chloride.

It is preferred to employ dimethyl sulfoxide, tetrahydrofuran, dimethylformamide, dimethyl sulfide or methylene chloride.

If in a preferred embodiment-the enolate salt of the compound (Ia) is prepared by adding strong deprotonating agents (for example sodium hydride or potassium tert-butylate), the further addition of acid-binding agents can be omitted.

If acid-binding agents are employed, then they are suitably conventional inorganic or organic bases, examples being sodium hydroxide, sodium carbonate, potassium carbonate, pyridine and triethylamine.

The reaction can be carried out at atmospheric pressure or under elevated pressure, preferably at atmospheric pressure. The product is worked up by conventional methods.

In preparation process (F) from 1 to 2, preferably 1 to 1.3, mol of the phosphorus compound of the formula (IX) are reacted per mole of the compound (Ia) in order to obtain compounds of the structure (Ie), reaction taking place at temperatures of between −40° C. and 150° C., preferably between −10 and 110° C.

Suitable diluents which are optionally added are all inert, polar organic solvents, such as ethers, amides, nitrites, alcohols, sulfides, sulfones, sulfoxides, etc.

It is preferred to employ acetonitrile, dimethyl sulfoxide, tetrahydrofuran, dimethylformamide or methylene chloride.

Suitable acid-binding agents which are optionally added are conventional inorganic or organic bases, such as hydroxides, carbonates or amines. Examples of these are sodium hydroxide, sodium carbonate, potassium carbonate, pyridine and triethylamine.

The reaction can be carried out at atmospheric pressure or under elevated pressure, preferably at atmospheric pressure. The product is worked up by conventional methods of organic chemistry. The purification of the ends products which are obtained is carried out preferably by crystallization, chromatographic purification or by so-called partial distillation, that is removal of the volatile fractions in vacuo.

Process (G) is characterized in that compounds of the formula (Ia) are reacted with metal compounds (X) or amines (XI).

Diluents which can be employed in the process according to the invention are preferably ethers such as tetrahydrofuran, dioxane, diethyl ether or else alcohols such as methanol, ethanol or isopropanol, but also water. Process (G) according to the invention is generally carried out under atmospheric pressure. The reaction temperatures are in general between −20° C. and 100° C., preferably between 0° C. and 50° C.

In preparation process ($H_\alpha$) about 1 mol of isocyanate of formula (XII) is reacted per mole of starting compound of the formula (Ia), at from 0 to 100° C., preferably at from 20 to 50° C.

Suitable diluents which are optionally added are all inert organic solvents, such as ethers, amides, nitriles, sulfones and sulfoxides.

Catalysts may optionally be added in order to accelerate the reaction. Catalysts which can be employed with great advantage are organotin compounds such as, for example, dibutyltin dilaurate. The reaction is preferably carried out at atmospheric pressure.

In preparation process ($H_\beta$) about 1 mol of carbamoyl chloride of the formula (XIII) is reacted per mole of starting compound of the formula (Ia), at from 0 to 150° C., preferably at from 20 to 70° C.

Suitable diluents which are optionally added are all inert polar organic solvents, such as ethers, amides, sulfones, sulfoxides or halogenated hydrocarbons.

It preferred to employ dimethyl sulfoxide, tetrahydrofuran, dimethylformamide or methylene chloride.

If in a preferred embodiment the enolate salt of the compound (Ia) is prepared by addition of strong deprotonating agents (for example sodium hydride or potassium tert-butylate), the further addition of acid-binding agents can be omitted.

If acid-binding agents are employed, then they are suitably conventional inorganic or organic bases, examples being sodium hydroxide, sodium carbonate, potassium carbonate, triethylamine or pyridine.

The reaction can be carried out at atmospheric pressure or under elevated pressure, preferably at atmospheric pressure. The product is worked up by conventional methods.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusiani, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and, *Tortrix viridana.*

From the order of the Coleoptera, for example, *Anobiumi punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaridical activity.

They can be employed with particular success for combatting phytopathogenic insects such as, for example, against the larvae of the mustard beetle (*Phaedon cochleariae*), against the larvae of the green rice leaf-hopper (*Nephotettix cincticeps*) or against the caterpillars of the cabbage moth (*Plutella maculipennis*).

The compounds according to the invention also have a fungicidal action, for example against *Venturia inaequalis.*

The active compounds according to the invention can also be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The active compounds according to the invention are very highly suited to the pre- and post-emergence, selective control of monocotyledon weeds in dicotyledon cultures. They can be employed, for example, in cotton or sugar beet with very great success for controlling gramineous harmful plants.

The active compounds can be converted into the customary formulations, such as solutions, emulsions, wettable powders, suspensions, powders, dusting agents, pastes, soluble powders, granules,. suspension emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable:

for example ammonium salts, ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polybxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations contain in general between 0.1 and 95% by weight of active compound, preferably between 0.5 and 90%.

The active compound according to the invention may be present in its usual commercial formulations and in the use forms prepared from these formulations, as a mixture with other active compounds such as insecticides, attractants, sterilants, acaricides, nematocides, fungicides, growth-regulating substances or herbicides. The insecticides include, for example, phosphates, carbamates, carboxylic esters, chlorinated hydrocarbons, phenylureas, substances produced by microorganisms, etc.

Examples of particularly advantageous components for mixture are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyano-phenoxy)-pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinan, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolypfluanid, triadipefon, triadimenol, triazoxide, trichamide, tricyclazole, tridemorph, triflpizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufyencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxy-alkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and ttifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention may furthermore be present in its commercially available formulations and in the use forms prepared from these formulations, as a mixture with synergistic agents. Synergistic agents are compounds which increase the effect of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate to the use forms.

When used against hygiene pests and pests of stored products, the active compound is distinguished by in excellent residual action on wood and clay, as well by a good stability to alkali on limed substrates.

The active compounds according to the invention are active not only against pests of plants, hygiene and stored products but also in the veterinary sector, against animal ectoparasites such as scaly ticks, argasid ticks, scab mites, trombiculid mites, flies (stinging and sucking), parasitic fly larvae, lice, hair lice, bird lice and fleas. For example, they display an outstanding activity against ticks, for example *Boophilus microplus*.

The active compounds of the formula (I) according to the invention are also suitable for controlling arthropods which infest productive animals in agriculture, for example cattle, sheep, goats, horses, pigs, donkeys, camels, buffalo, rabbits, hens, turkeys, ducks, geese, bees, other pets such as dogs, cats, cage birds, aquarium fish, and also so-called experimental animals, such as hamsters, guinea pigs, rats and mice. By controlling these arthropods the intention is to reduce fatalities and reductions in yield (for example of meat, milk, wools, skins, eggs, honey and the like), so that the use of the active compounds according to the invention enables the keeping of animals to be more economic and of greater simplicity.

The active compounds according to the invention are employed in the veterinary sector in a known manner, by enteral administration in the form of, for example, tablets, capsules, drinks, drenches, granules, pastes, boli or by means of the feed-through method, as suppositories, or by parenteral administration such as, for example, by injection (intramuscular, subcutaneous, intravenous, intraperitoneal, etc.), implants, by nasal application, by dermal application in the form, for example, of dipping or bathing, spraying, pouring on and spotting on, washing and powdering, and with the aid of shaped articles containing active compound, such as neck bands, ear tags, tail tags, limb bands, halters, marking devices and the like.

The preparation and the use of the substances according to the invention is illustrated by the following examples.

EXAMPLE (Ia-1)

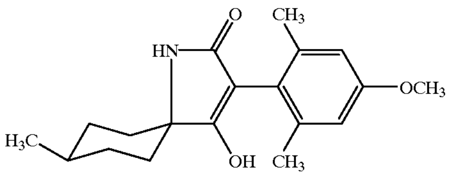

13.96 g (0.124 mol) of potassium tert-butylate are placed in 45 ml of absolute THF and, at reflux temperature, a solution of 20.4 g (0.0564 mol) of methyl N-(2,6-di-methyl-4-methoxyphenyl)acetyl-4-methyl-1-amino-cyclohexanecarboxylate in 120 ml of absolute toluene is added dropwise. Heating under reflux is continued for 1.5 h and the mixture is cooled, 180 ml of water are added, the aqueous phase is separated off and extraction takes place. again with 70 ml of water, the aqueous phases are combined, acidified with about 20 ml of concentrated hydrochloric acid at 10–20° C., and the precipitate is filtered off with suction and dried. After stirring with methyl tert-butyl (MTB) ether/n-hexane, 16.8 g (94% of theory) of the compound shown above are obtained, of melting point 169° C.

In analogy to Example Ia-1 the compounds listed in the following table are obtained:

TABLE 8

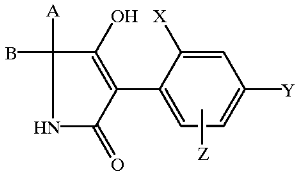

| Ex. No. | X | Y | Z | A | B | m.p. ° C. | Isomer |
|---|---|---|---|---|---|---|---|
| Ia-2 | $CH_3$ | $OCH_3$ | 6-$CH_3$ | 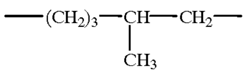 | | >220 | β |
| Ia-3 | $CH_3$ | $OCH_3$ | 6-$CH_3$ | $—(CH_2)_5—$ | | 201 | — |
| Ia-4 | $CH_3$ | $OCH_3$ | 6-$CH_3$ | i-$C_3H_7$ | $CH_3$ | i31 | — |
| Ia-5 | $CH_3$ | $OCH_3$ | 6-$CH_3$ | $—(CH_2)_2—O—(CH_2)_2$ | | 186 | — |
| Ia-6 | $CH_3$ | $CH_3$ | 6-$OCH_3$ | 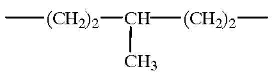 | | 212 | β |

TABLE 8-continued

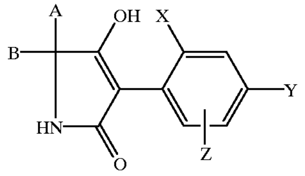

| Ex. No. | X | Y | Z | A | B | m.p. ° C. | Isomer |
|---|---|---|---|---|---|---|---|
| Ia-7 | $CH_3$ | $OCH_3$ | H | 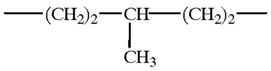 | | 170 | β |
| Ia-8 | $CH_3$ | $OCH_3$ | H | 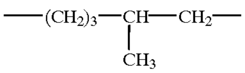 | | 174 | β |
| Ia-9 | $OCH_3$ | $CH_3$ | H | $—(CH_2)_2—CHCH_3—(CH_2)_2—$ | | 198 | β |
| Ia-10 | $OCH_3$ | $CH_3$ | H | $—(CH_2)_3—CHCH_3—CH_2—$ | | 174 | β |
| Ia-11 | $CH_3$ | H | 6-$OCH_3$ | $—(CH_2)_2—CHCH_3—(CH_2)_2—$ | | 211 | β |
| Ia-12 | $CH_3$ | $OCH_3$ | 6-$CH_3$ | $—(CH_2)_2—CHOCH_3—(CH_2)_2—$ | | 203 | β |

EXAMPLE (Ib-1)

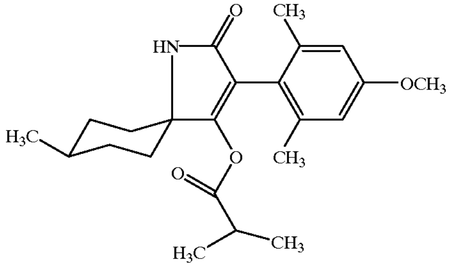

4.73 g (15 mmol) of 3-(2,6-dimethyl-4-methoxyphenyl)-5,5-(3-methyl)-pentamethylene-pyrrolidine-2,4-dione are suspended in 70 ml of absolute methylene chloride, 2.1 ml of triethylamine are added, and, at 0–10° C., 1.58 ml of isobutyryl chloride in 5 ml of absolute methylene chloride are added dropwise. Stirring is continued at room temperature with monitoring by thin-layer chromatography. After the end of the reaction the organic phase is washed with twice 100 ml of 0.5 N sodium hydroxide solution, dried over magnesium sulfate and concentrated by evaporation in vacuo. After recrystallization from MTB ether/n-hexane, 2.6 g (≙45% of theory) of the compound shown above are obtained, of melting point 218° C.

In analogy to Example Ib-1 the compounds shown in Table 9 below are obtained:

TABLE 9

(Ib)

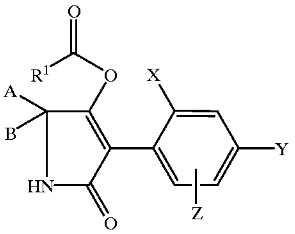

| Ex. No. | X | Y | Z | A | B | $R^1$ | m.p. ° C. | Isomer |
|---|---|---|---|---|---|---|---|---|
| Ib-2 | $CH_3$ | $OCH_3$ | 6-$CH_3$ | 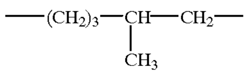 | | i-$C_3H_7$ | | b |
| Ib-3 | $CH_3$ | $OCH_3$ | 6-$CH_3$ | $—(CH_2)_5—$ | | $CH_3$ | 198 | — |
| Ib-4 | $CH_3$ | $OCH_3$ | 6-$CH_3$ | $—(CH_2)_2—O—(CH_2)_2—$ | | $CH_3$ | >220 | — |
| Ib-5 | $CH_3$ | $OCH_3$ | 6-$CH_3$ | $—(CH_2)_2—O—(CH_2)_2—$ | | i-$C_3H_7$ | >220 | — |
| Ib-6 | $CH_3$ | $OCH_3$ | 6-$CH_3$ | i-$C_3H_7$ | $CH_3$ | $CH_3$ | 179 | — |
| Ib-7 | $CH_3$ | $OCH_3$ | 6-$CH_3$ | i-$C_3H_7$ | $CH_3$ | i-$C_3H_7$ | 181 | — |

TABLE 9-continued (Ib)

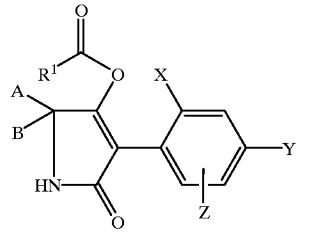

| Ex. No. | X | Y | Z | A | B | $R^1$ | m.p. ° C. | Isomer |
|---|---|---|---|---|---|---|---|---|
| Ib-8 | $CH_3$ | $CH_3$ | 6-$OCH_3$ | 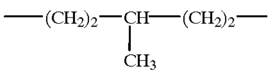 | | $CH_3$ | 164 | β |
| Ib-9 | $OCH_3$ | $CH_3$ | H | $—(CH_2)_2—CHCH_3—(CH_2)_2—$ | | $CH_3$ | 188 | β |
| Ib-10 | $OCH_3$ | $CH_3$ | H | $—(CH_2)_3—CHCH_3—CH_2—$ | | $CH_3$ | 208 | β |
| Ib-11 | $OCH_3$ | $CH_3$ | H | $—(CH_2)_3—CHCH_3—CH_2—$ | | i-$C_3H_7$ | 196 | β |
| Ib-12 | $CH_3$ | H | 6-$OCH_3$ | $—(CH_2)_2—CHCH_3—(CH_2)_2—$ | | $CH_3$ | 215 | β |
| Ib-13 | $CH_3$ | H | 6-$OCH_3$ | $—(CH_2)_2—CHCH_3—(CH_2)_2—$ | | i-$C_3H_7$ | >220 | β |
| Ib-14 | $OCH_3$ | $CH_3$ | H | $—(CH_2)_2—CHCH_3—(CH_2)_2—$ | | i-$C_3H_7$ | 193 | β |

EXAMPLE (Ic-1)

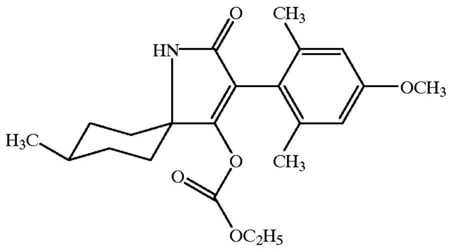

4.73 g (15 mmol) of 3-(2,6-dimethyl-4-methoxyphenyl)-5,5-(3-methyl)-pentamethylene-pyrrolidine-2,4-dione are suspended in 70 ml of absolute methylene chloride, 2.1 ml of triethylamine are added, and, at 0–10° C., 1.5 ml of ethyl chloroformate in 5 ml of absolute methylene chloride are added dropwise. Stirring is continued at room temperature with monitoring by thin-layer chromatography. After the end of the reaction the organic phase is washed with twice 100 ml of 0.5 N sodium hydroxide solution, dried over magnesium sulfate and concentrated by evaporation in vacuo. After recrystallization from MTB ether/n-hexane, 3.9 g (≙67% of theory) of the compound shown above are obtained, of melting point 202° C.

In analogy to Example Ic-1 the compounds shown in Table 10 below are obtained:

TABLE 10

(Ic)

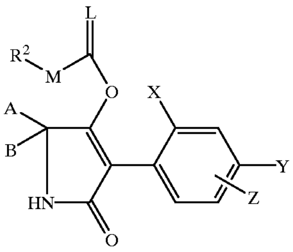

| Ex. No. | X | Y | Z | A | B | L | M | $R^2$ | m.p. ° C. | Isomer |
|---|---|---|---|---|---|---|---|---|---|---|
| Ic-2 | $CH_3$ | $OCH_3$ | 6-$CH_3$ | 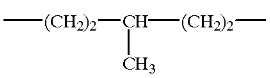 | | O | O | m-$C_4H_9$ | 172 | β |
| Ic-3 | $CH_3$ | $OCH_3$ | 6-$CH_3$ | 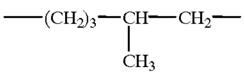 | | O | O | $C_2H_5$ | 181 | β |
| Ic-4 | $CH_3$ | $OCH_3$ | 6-$CH_3$ | $—(CH_2)_5—$ | | O | O | $C_2H_5$ | 219 | — |

TABLE 10-continued (Ic)

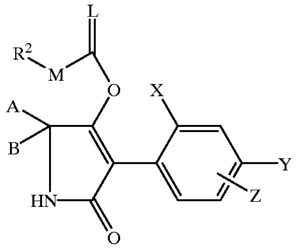

| Ex. No. | X | Y | Z | A | B | L | M | $R^2$ | m.p. ° C. | Isomer |
|---|---|---|---|---|---|---|---|---|---|---|
| Ic-5 | $CH_3$ | $OCH_3$ | 6-$CH_3$ | $-(CH_2)_5-$ | | O | O | s-$C_4H_9$ | 217 | — |
| Ic-6 | $CH_3$ | $OCH_3$ | 6-$CH_3$ | $-(CH_2)_2-O-(CH_2)_2-$ | | O | O | $C_2H_5$ | >220 | — |
| Ic-7 | $CH_3$ | $OCH_3$ | 6-$CH_3$ | $-(CH_2)_2-O-(CH_2)_2-$ | | O | O | s-$C_4H_9$ | >220 | — |
| Ic-8 | $CH_3$ | $OCH_3$ | 6-$CH_3$ | i-$C_3H_7$ | $CH_3$ | O | O | s-$C_4H_9$ | 181 | — |
| Ic-9 | $CH_3$ | $CH_3$ | 6-$OCH_3$ | $-(CH_2)_2-\underset{CH_3}{\underset{\mid}{CH}}-(CH_2)_2-$ | | O | O | $C_2H_5$ | 183 | β |
| Ic-10 | $OCH_3$ | $CH_3$ | H | $-(CH_2)_2-CHCH_3-(CH_2)_2-$ | | O | O | $C_2H_5$ | >220 | β |
| IC-11 | $CH_3$ | H | 6-$OCH_3$ | $-(CH_2)_2-CHCH_3-(CH_2)_2-$ | | O | O | $C_2H_5$ | 197 | β |
| IC-12 | $OCH_3$ | $CH_3$ | H | $-(CH_2)_3CHCH_3-CH_2-$ | | O | O | $C_2H_5$ | 158 | β |

EXAMPLE II-1

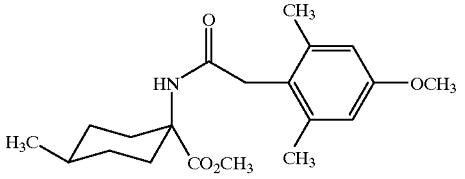

15 g (0.0773 mol) of 2,6-dimethyl-4-methoxy-phenylacetic acid are heated at a 80° C. with 11.3 ml of thionyl chloride until the evolution of gas has come to an end. Excess thionyl chloride is removed in vacuo in vacuo at 50° C. and the residue is taken up in 100 ml of absolute tetrahydrofuran. This solution is added dropwise at 0–10° C. to a suspension of 16.1 g of methyl cis-1-amino-4-methyl-cyclohexanecarboxylate and 27.1 ml of triethylamine in 200 ml of absolute tetrahydrofuran. The mixture is subsequently stirred for 1 h at room temperature, the precipitate is filtered off with suction and washed with tetrahydrofuran, and the filtrate is concentrated in vacuo. The residue is taken up in methylene chloride, washed with 0.5 N HCl, dried over magnesium sulfate and concentrated by evaporation. After recrystallization from MTB ether/n-hexane, 20.4 g (≙73% of theory) of the compound shown above are obtained, of melting point 108° C.

EXAMPLE II-2

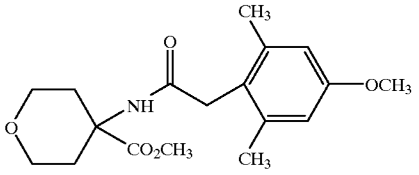

47.7 g (0.158 mol) of N-(2,6-dimethyl-4-methoxy-phenylacetyl)-4-amino-pyran-4-carbonitrile suspended in 320 ml of anhydrous methylene chloride are added dropwise at from 30 to 40° C. to 77.4 g (0.79 mol) of concentrated sulfuric acid. The mixture is stirred for 2 h at 40° C., 109 ml of anhydrous methanol are added dropwise, and the mixture is heated for 6 h at a bath temperature of from 40 to 70° C. The reaction mixture is poured onto 0.8 kg of ice and extracted with methylene chloride, the organic phases are combined and washed with sodium hydrogen carbonate solution and dried over magnesium sulfate, and the solvent is evaporated off in vacuo. After recrystallization from MTB ether/n-hexane, 37.7 g (≙71% of theory) of the compound shown above are obtained, of melting point 168° C.

The substances of the formula II listed in Table 11 below are obtained analogously:

TABLE 11

(II)

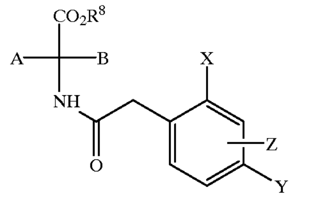

| Ex. No. | X | Y | Z | A | B | $R^8$ | Isomer | m.p. ° C. |
|---|---|---|---|---|---|---|---|---|
| II-3 | $CH_3$ | $OCH_3$ | 6-$CH_3$ | 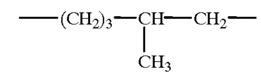 | | $CH_3$ | β | oil |
| II-4 | $CH_3$ | $OCH_3$ | 6-$CH_3$ | $-(CH_2)_5-$ | | $CH_3$ | — | 174 |
| II-5 | $CH_3$ | $OCH_3$ | 6-$CH_3$ | i-$C_3H_7$ | $CH_3$ | $CH_3$ | α | 112 |
| II-6 | $CH_3$ | $OCH_3$ | H | 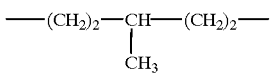 | | $CH_3$ | β | 108 |
| II-7 | $CH_3$ | $OCH_3$ | 6-$CH_3$ | 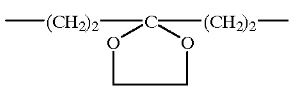 | | $CH_3$ | — | 134 |
| II-8 | $CH_3$ | $OCH_3$ | H | 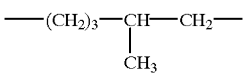 | | $CH_3$ | β | 122 |
| II-9 | $CH_3$ | $CH_3$ | 6-$OCH_3$ | 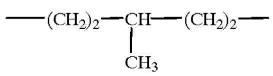 | | $CH_3$ | β | 163 |
| II-10 | $OCH_3$ | $CH_3$ | H | $-(CH_2)_2-CHCH_3-(CH_2)_2-$ | | $CH_3$ | β | 136 |
| II-11 | $OCH_3$ | $CH_3$ | H | $-(CH_2)_3-CHCH_3-CH_2-$ | | $CH_3$ | β | 121 |
| II-12 | $CH_3$ | H | 6-$OCH_3$ | $-(CH_2)_2-CHCH_3-(CH_2)_2-$ | | $CH_3$ | β | 138 |

EXAMPLE XVII-1

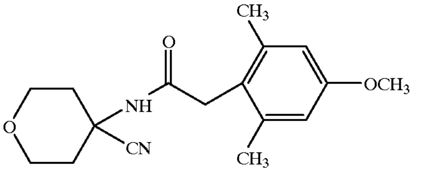

38.6 g (0.2 mol) of 2,6-dimethyl-4-methoxy-phenylacetic acid are heated at 50 to 60° C. with 29.3 ml (0.4 mol) of thionyl chloride until the evolution of gas has come to an end. The excess thionyl chloride is distilled off in vacuo, the residue is taken up in 100 ml of anhydrous tetrahydrofuran and this solution is added dropwise at 0 to 10° C. to a solution of 25.2 g (0.2 mol) of 4-aminopyran-4-carbonitrile and 28 ml (0.2 mol) of triethylamine in 400 ml of anhydrous tetrahydrofuran, and the mixture is subsequently stirred at room temperature for 1 h. The reaction mixture is poured into a mixture of 900 ml of water and 100 ml of 2 N hydrochloric acid, and the precipitate is filtered off with suction, dried and recrystallized from MTB ether/n-hexane. 47 g (≙79% of theory) of the compound shown above are obtained, of melting point 156° C.

The compounds of the formula (XVII) listed in Table 12 were obtained in analogy to Example XVII-1.

TABLE 12

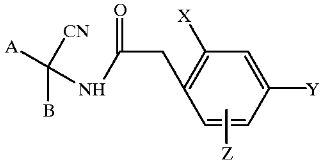

| Ex. No. | X | Y | Z | A | B | m.p. ° C. |
|---|---|---|---|---|---|---|
| XVII-2 | $CH_3$ | $OCH_3$ | 6-$CH_3$ | i-$C_3H_7$ | $CH_3$ | 186 |
| XVII-3 | $CH_3$ | $OCH_3$ | H | $-(CH_2)_2-O-(CH_2)_2-$ | | 116 |

Use Examples

Example A

Myzus test

Solvent: 7 parts by weight of dimethylformamide

Emulsifier: 1 part by weight of alkylaryl polyglycol ether

To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by the peach aphid (*Myzus persicae*) are treated by being dipped into the active compound preparation of the desired concentration.

After the desired time the destruction in % is determined. In this context, 100% means that all of the aphids have been killed; 0% means that none of the aphids has been killed.

In this test, for example, the compounds according to Preparation Examples Ia-1, Ia-2, Ia-6 and Ic-1, at an exemplary active compound concentration of 0.1%, brought about a destruction of at least 80% after 6 days.

Example B

Pre-emergence test

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, for example, the compound according to Preparation Example Ia-6, at an exemplary active compound concentration of 0.01%, brought about a destruction of 98% after 7 days.

What is claimed is:

1. A compound of the formula (II)

(II)

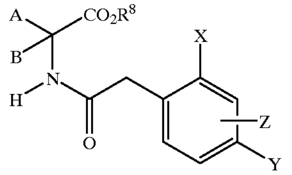

in which

A represents hydrogen, in each case optionally halogeno-substituted alkyl, alkenyl, alkoxyalkyl, polyalkoxyalkyl or alkylthioalkyl, cycloalkyl, which is optionally interrupted by at least one heteroatom and optionally substituted, or represents in each case optionally halogen-, alkyl-, halogenoalkyl-, alkoxy- or nitro-substituted aryl, arylalkyl or hetaryl, B represents alkyl or alkoxyalkyl, or

TABLE

| Pre-emergence test | | | | | |
|---|---|---|---|---|---|
| Active compound | g/ha | Beta vulgaris | Alopecurus myosuroides | Avena fetus | Cynodon dactylon |
| (Ic-1) 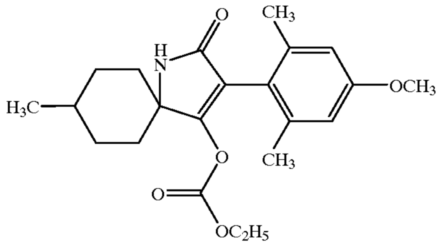 | 250 | 0 | 100 | 70 | 100 |

Example C

Tetranychus test (OP-resistant/spray treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested with all stages of the red spider mite (*Tetranychus urticae*) are sprayed with a preparation of the active compound of the desired concentration.

After the desired time, the effect in % is determined. 100% means that all the spider mites have been killed; 0% means that none of the spider mites has been killed.

A and B together with the carbon atom to which they are attached represent a saturated or unsaturated, unsubstituted or substituted ring which is optionally interrupted by at least one heteroatom, X represents alkyl or alkoxy, Y represents hydrogen, alkyl or alkoxy, Z represents hydrogen, alkyl or alkoxy, with the proviso that at least one of Y and Z represents alkoxy if X represents alkyl, and $R^8$ represents alkyl.

2. A process for the preparation of an acyl-amino acid esters of the formula (II) as claimed in claim 1, wherein an amino acid derivative of the formula (XIV)

(XIV)

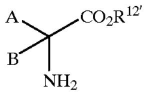

in which $R^{12'}$ represents hydrogen (XIVa) or alkyl (XIVb)

and

A and B have the meaning given in claim 1, is acylated with a phenylacetyl halide of the formula (XV)

(XV)

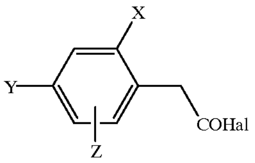

in which

X, Y, and Z have the meaning given in claim 1,

Hal represents chlorine or bromine, or wherein an acylamino acid of the formula (IIa)

(IIa)

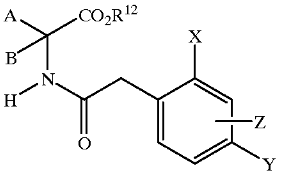

in which

A, B, X, Y and Z have the meaning given above and $R^{12}$ represents hydrogen is esterified or wherein an aminonitrile of the formula (XVI)

(XVI)

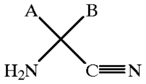

in which

A and B have the meaning given above is reacted with phenylacetyl halide of the formula (XV)

(XV)

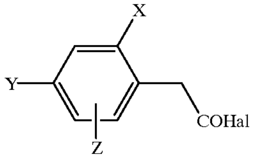

in which

X, Y and Z have the meaning given above and

Hal represents chlorine or bromine, to give a compound of the formula (XVII)

(XVII)

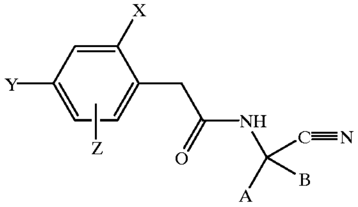

in which

A, B, X, Y and Z have the meaning given above and this compound is subsequently subjected to alcoholysis in the presence of sulfuric acid.

* * * * *